(12) United States Patent
Weiss et al.

(10) Patent No.: US 12,209,250 B2
(45) Date of Patent: Jan. 28, 2025

(54) ENGINEERED HERPES SIMPLEX VIRUS-1 (HSV-1) VECTORS AND USES THEREOF

(71) Applicant: Massachusetts Institute of Technology, Cambridge, MA (US)

(72) Inventors: Ron Weiss, Newton, MA (US); Maria Hottelet Foley, Cambridge, MA (US); Jin Huh, Watertown, MA (US); Ross D. Jones, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 483 days.

(21) Appl. No.: 16/741,827

(22) Filed: Jan. 14, 2020

(65) Prior Publication Data
US 2020/0291428 A1    Sep. 17, 2020

Related U.S. Application Data

(60) Provisional application No. 62/818,464, filed on Mar. 14, 2019.

(51) Int. Cl.
| | |
|---|---|
| *C12N 15/86* | (2006.01) |
| *A61K 35/76* | (2015.01) |
| *A61K 48/00* | (2006.01) |
| *C12N 7/00* | (2006.01) |
| *C12N 15/113* | (2010.01) |

(52) U.S. Cl.
CPC .............. *C12N 15/86* (2013.01); *A61K 35/76* (2013.01); *A61K 48/005* (2013.01); *C12N 7/00* (2013.01); *C12N 15/113* (2013.01); *C12N 2710/16643* (2013.01); *C12N 2800/10* (2013.01)

(58) Field of Classification Search
CPC ........ C12N 15/86; C12N 7/00; C12N 15/113; C12N 2710/16643; C12N 2800/10; C12N 2710/16621; C12N 2710/16662; A61K 35/76; A61K 48/005; A61K 2039/5254; A61K 2039/5256; A61K 35/763
See application file for complete search history.

(56) References Cited

U.S. PATENT DOCUMENTS

| | | | |
|---|---|---|---|
| 4,683,202 A | 7/1987 | Mullis | |
| 5,837,532 A * | 11/1998 | Preston | A61P 31/22 |
| | | | 435/320.1 |
| 5,928,906 A | 7/1999 | Köster et al. | |
| 6,319,703 B1 * | 11/2001 | Speck | A61P 43/00 |
| | | | 435/235.1 |
| 10,174,341 B2 * | 1/2019 | Glorioso, III | A61P 29/02 |
| 10,391,164 B2 * | 8/2019 | Dubensky, Jr. | A61P 31/20 |
| 2007/0003571 A1 * | 1/2007 | Coffin | C12N 15/86 |
| | | | 424/130.1 |
| 2016/0008458 A1 * | 1/2016 | Mahalingam | A61K 39/12 |
| | | | 435/236 |
| 2017/0073685 A1 * | 3/2017 | Maeder | C12N 15/85 |
| 2020/0224220 A1 * | 7/2020 | Finer | C12N 15/63 |

FOREIGN PATENT DOCUMENTS

| | | | |
|---|---|---|---|
| WO | WO 1998/15637 A1 | 4/1998 | |
| WO | WO 2001/046449 A1 | 6/2001 | |
| WO | WO 2015/009952 A1 | 1/2015 | |
| WO | WO 2016/040395 A1 | 3/2016 | |
| WO | WO-2017132552 A1 * | 8/2017 | ........... A61K 35/763 |
| WO | WO 2019/027414 A1 | 2/2019 | |

OTHER PUBLICATIONS

Thompson RL, Preston CM, Sawtell NM. De novo synthesis of VP16 coordinates the exit from HSV latency in vivo. PLoS Pathog. Mar. 2009;5(3):e1000352. doi: 10.1371/journal.ppat.1000352. Epub Mar. 27, 2009. (Year: 2009).*
Lam Q, Smibert CA, Koop KE, Lavery C, Capone JP, Weinheimer SP, Smiley JR. Herpes simplex virus VP16 rescues viral mRNA from destruction by the virion host shutoff function. EMBO J. May 15, 1996;15(10):2575-81. (Year: 1996).*
Preston CM, Nicholl MJ. Repression of gene expression upon infection of cells with herpes simplex virus type 1 mutants impaired for immediate-early protein synthesis. J Virol. Oct. 1997;71(10):7807-13. (Year: 1997).*
Yao F, Schaffer PA. An activity specified by the osteosarcoma line U2OS can substitute functionally for ICP0, a major regulatory protein of herpes simplex virus type 1. J Virol. Oct. 1995;69(10):6249-58. (Year: 1995).*
Preston CM, Mabbs R, Nicholl MJ. Construction and characterization of herpes simplex virus type 1 mutants with conditional defects in immediate early gene expression. Virology. Mar. 3, 1997;229(1):228-39.*
Lim F. "HSV-1 as a Model for Emerging Gene Delivery Vehicles", International Scholarly Research Notices, vol. 2013, Article ID 397243, 12 pages, 2013. (Year: 2013).*
Smiley JR, Duncan J. Truncation of the C-terminal acidic transcriptional activation domain of herpes simplex virus VP16 produces a phenotype similar to that of the in1814 linker insertion mutation. J Virol. Aug. 1997;71(8):6191-3. (Year: 1997).*
Preston CM, Mabbs R, Nicholl MJ. Construction and characterization of herpes simplex virus type 1 mutants with conditional defects in immediate early gene expression. Virology. Mar. 3, 1997;229(1):228-39. (Year: 1997).*
Grant K. "Production and Purification of Highly Replication Defective HSV-1 Based Gene Therapy Vectors". PhD Dissertation, University of Pittsburgh, 2008. (Year: 2008).*
International Search Report and Written Opinion for PCT/US2013/073062, mailed on May 20, 2014.

(Continued)

*Primary Examiner* — Rachel B Gill
(74) *Attorney, Agent, or Firm* — Wolf, Greenfield & Sacks, P.C.

(57) ABSTRACT

Provided herein are engineered HSV-1 vectors comprising a modified HSV-1 genome. The engineered HSV-1 vectors can be used to deliver genetic circuits (e.g., up to 100 kb) to cells in vitro or in vivo. Methods of treating or diagnosing a disease (e.g., cancer) using the engineered HSV-1 vectors described herein are also provided.

19 Claims, 8 Drawing Sheets
Specification includes a Sequence Listing.

(56) References Cited

OTHER PUBLICATIONS

International Preliminary Report on Patentability for PCT/US2013/073062, mailed on Jun. 9, 2015.
Enk et al., HSV1 MicroRNA Modulation of GPI Anchoring and Downstream Immune Evasion. Cell Rep. Oct. 18, 2016;17(4):949-956. doi: 10.1016/j.celrep.2016.09.077. PMID: 27760325; PMCID: PMC5081403.
Fu et al., Incorporation of the B18R gene of vaccinia virus into an oncolytic herpes simplex virus improves antitumor activity. Mol Ther. Oct. 2012;20(10):1871-81. doi: 10.1038/mt.2012.113. Epub Jun. 12, 2012. PMID: 22692498; PMCID: PMC3464635.
Lim, HSV-1 as a Model for Emerging Gene Delivery Vehicles. International Scholarly Research Notices. 2013;2013: Article ID 397243, 12.
Marshall et al., Long-term transgene expression in mice infected with a herpes simplex virus type 1 mutant severely impaired for immediate-early gene expression. J Virol. Jan. 2000;74(2):956-64. doi: 10.1128/jvi.74.2.956-964.2000. PMID: 10623758; PMCID: PMC111616.
Peters et al., Designing Herpes Viruses as Oncolytics. Mol Ther Oncolytics. 2015;2:15010-. doi: 10.1038/mto.2015.10. Epub Jul. 22, 2015. PMID: 26462293; PMCID: PMC4599707.
Smiley et al., Truncation of the C-terminal acidic transcriptional activation domain of herpes simplex virus VP16 produces a phenotype similar to that of the in1814 linker insertion mutation. J Virol. Aug. 1997;71(8):6191-3. doi: 10.1128/JVI.71.8.6191-6193.1997. PMID: 9223515; PMCID: PMC191881.
Agarwalla et al., Oncolytic herpes simplex virus engineering and preparation. Methods Mol Biol. 2012;797:1-19.
Bartel, MicroRNAs: target recognition and regulatory functions. Cell. Jan. 23, 2009;136(2):215-33.
Berger et al., Expression of herpes simplex virus ICP47 and human cytomegalovirus US11 prevents recognition of transgene products by CD8(+) cytotoxic T lymphocytes. J Virol. May 2000;74(10):4465-73.
Chen et al., ICP27 recruits Aly/REF but not TAP/NXF1 to herpes simplex virus type 1 transcription sites although TAP/NXF1 is required for ICP27 export. J Virol. Apr. 2005;79(7):3949-61.
Chen et al., ICP27 interacts with the RNA export factor Aly/REF to direct herpes simplex virus type 1 intronless mRNAs to the TAP export pathway. J Virol. Dec. 2002;76(24):12877-89.
Corbin-Lickfett et al., The HSV-1 ICP27 RGG box specifically binds flexible, GC-rich sequences but not G-quartet structures. Nucleic Acids Res. Nov. 2009;37(21):7290-301.
Dai-Ju et al., ICP27 interacts with the C-terminal domain of RNA polymerase II and facilitates its recruitment to herpes simplex virus 1 transcription sites, where it undergoes proteasomal degradation during infection. J Virol. Apr. 2006;80(7):3567-81.
Demuth et al., Polymer multilayer tattooing for enhanced DNA vaccination. Nat Mater 2013; 12:367-6.
Deshmane et al., During latency, herpes simplex virus type 1 DNA is associated with nucleosomes in a chromatin structure. J Virol. Feb. 1989;63(2):943-7.
Ellison et al., Control of VP16 translation by the herpes simplex virus type 1 immediate-early protein ICP27. J Virol. Apr. 2005;79(7):4120-31.
Fontaine-Rodriguez et al., Proteomics of herpes simplex virus infected cell protein 27: association with translation initiation factors. Virology. Dec. 20, 2004;330(2):487-92.
Garcia-Sastre. Ten Strategies of Interferon Evasion by Viruses. Cell Host Microbe. Aug. 9, 2017;22(2):176-184.
Goldsmith et al., Infected cell protein (ICP)47 enhances herpes simplex virus neurovirulence by blocking the CD8+ T cell response. J Exp Med. Feb. 2, 1998;187(3):341-8.
Griffiths-Jones. The microRNA Registry. Nucleic Acids Res. Jan. 1, 2004;32(Database issue):D109-11.
Griffiths-Jones et al., miRBase: microRNA sequences, targets and gene nomenclature. Nucleic Acids Res. Jan. 1, 2006;34(Database issue):D140-4.
Griffiths-Jones et al., miRBase: tools for microRNA genomics. Nucleic Acids Res. Jan. 2008;36(Database issue):D154-8. doi: 10.1093/nar/gkm952. Epub Nov. 8, 2007.
Gu et al., Components of the REST/CoREST/histone deacetylase repressor complex are disrupted, modified, and translocated in HSV-1-infected cells. Proc Natl Acad Sci U S A. May 24, 2005;102(21):7571-6. doi: 10.1073/pnas.0502658102. Epub May 16, 2005.
Herrlinger et al., HSV-1 infected cell proteins influence tetracycline-regulated transgene expression. J Gene Med. Sep.-Oct. 2000;2(5):379-89.
Honess et al., Proteins specified by herpes simplex virus. XI. Identification and relative molar rates of synthesis of structural and nonstructural herpes virus polypeptides in the infected cell. J Virol. Dec. 1973;12(6):1347-65.
Kozomara et al., miRBase: annotating high confidence microRNAs using deep sequencing data. Nucleic Acids Res. Jan. 2014;42(Database issue):D68-73. doi: 10.1093/nar/gkt1181. Epub Nov. 25, 2013.
Kozomara et al., miRBase: integrating microRNA annotation and deep-sequencing data. Nucleic Acids Res. Jan. 2011;39(Database issue):D152-7. doi: 10.1093/nar/gkq1027. Epub Oct. 30, 2010.
Medzhitov et al., Innate immunity: impact on the adaptive immune response. Curr Opin Immunol. Feb. 1997;9(1):4-9.
Miki et al., Efficient Detection and Purification of Cell Populations Using Synthetic MicroRNA Switches. Cell Stem Cell. Jun. 4, 2015;16(6):699-711.
Netea et al., Trained Immunity: An Ancient Way of Remembering. Cell Host Microbe. Mar. 8, 2017;21(3):297-300.
Olesky et al., Evidence for a direct interaction between HSV-1 ICP27 and ICP8 proteins. Virology. Jan. 5, 2005;331(1):94-105.
Pinnoji et al., Repressor element-1 silencing transcription factor/neuronal restrictive silencer factor (REST/NRSF) can regulate HSV-1 immediate-early transcription via histone modification. Virol J. Jun. 7, 2007;4:56.
Re, Synthetic Gene Expression Circuits for Designing Precision Tools in Oncology. Front Cell Dev Biol. Aug. 28, 2017;5:77.
Rivella et al., The cHS4 insulator increases the probability of retroviral expression at random chromosomal integration sites. J Virol. May 2000;74(10):4679-87. doi: 10.1128/jvi.74.10.4679-4687.2000.
Roizman et al., The first 30 minutes in the life of a virus: unREST in the nucleus. Cell Cycle. Aug. 2005;4(8):1019-21. doi: 10.4161/cc.4.8.1902. Epub Aug. 7, 2005.
Sandri-Goldin, ICP27 mediates HSV RNA export by shuttling through a leucine-rich nuclear export signal and binding viral intronless RNAs through an RGG motif. Genes Dev. Mar. 15, 1998;12(6):868-79.
Sciabica et al., ICP27 interacts with SRPK1 to mediate HSV splicing inhibition by altering SR protein phosphorylation. EMBO J. Apr. 1, 2003;22(7):1608-19.
Sedlackova et al., Herpes simplex virus type 1 immediate-early protein ICP27 is required for efficient incorporation of ICP0 and ICP4 into virions. J Virol. Jan. 2008;82(1):268-77. doi: 10.1128/JVI.01588-07. Epub Oct. 24, 2007.
Souki et al., Arginine methylation of the ICP27 RGG box regulates the functional interactions of ICP27 with SRPK1 and Aly/REF during herpes simplex virus 1 infection. J Virol. Sep. 2009;83(17):8970-5. doi: 10.1128/JVI.00801-09. Epub Jun. 24, 2009.
Van Craenenbroeck et al., Episomal vectors for gene expression in mammalian cells. Eur J Biochem. Sep. 2000;267(18):5665-78.
West et al., Insulators: many functions, many mechanisms. Genes Dev. Feb. 1, 2002;16(3):271-88.
Xie et al., Multi-input RNAi-based logic circuit for identification of specific cancer cells. Science. Sep. 2, 2011;333(6047):1307-11.
Yao et al., An activity specified by the osteosarcoma line U2OS can substitute functionally for ICP0, a major regulatory protein of herpes simplex virus type 1. J Virol. Oct. 1995;69(10):6249-58.
Zhou et al., Association of herpes simplex virus type 1 ICP8 and ICP27 proteins with cellular RNA polymerase II holoenzyme. J Virol. Jun. 2002;76(12):5893-904.

* cited by examiner

MD405

MD406

MD409

MD410

MD306

MD412

MD417

ENGINEERED HERPES SIMPLEX VIRUS-1 (HSV-1) VECTORS AND USES THEREOF

RELATED APPLICATION

This application claims priority under 35 U.S.C. § 119(e) to U.S. Provisional Application Ser. No. 62/818,464, filed Mar. 14, 2019, the entire contents of which are incorporated by reference herein.

GOVERNMENT SUPPORT

This invention was made with Government support under Grant No. P50 GM098792 awarded by the National Institutes of Health. The Government has certain rights in the invention.

BACKGROUND

Viral vectors have been used to delivery transgenes in vitro and/or in vivo. However, viral vectors may induce toxicity, interfere with transgene expression, and/or are limited in the size of the transgene that can be delivered.

SUMMARY

Provided herein, in some aspects, are engineered Herpes Simplex Virus-1 (HSV-1) vectors comprising a modified HSV-1 genome. The HSV-1 genome is modified to attenuated the virus such that they are not toxic to transduced cells but are not so severely attenuated so that high titer viral particles can be obtained in appropriate packaging cell lines and robust transgene expression can be achieved. The engineered HSV-1 vectors described herein can be used to deliver complex genetic circuits (e.g., genetic circuits of up to 100 kb in length). Also provided herein are packaging cells for producing HSV-1 viral particles comprising the engineered HSV-1 vectors. The HSV-1 viral particles may be used for various applications (e.g., therapeutic or diagnostic applications).

Accordingly, some aspects of the present disclosure provide engineered Herpes Simplex Virus-1 (HSV-1) vectors containing a modified HSV-1 genome containing deletions in genes encoding Infected Cell Protein 4 (ICP4), Infected Cell Protein 0 (ICP0), and Virion Protein 16 (VP16).

In some embodiments, both copies of ICP4 are deleted from the modified HSV-1 genome. In some embodiments, the deletion in the gene encoding VP16 results in a truncation of VP16 protein at amino acid 422. In some embodiments, both copies of ICP0 are deleted from the modified HSV-1 genome.

In some embodiments, the modified HSV-1 genome further includes deletions in one or more genes encoding γ34.5, Latency-Associated Transcript (LAT), ICP6, ICP8, ICP27, ICP22, and ICP47.

In some embodiments, the modified HSV-1 genome further includes deletions in LAT and γ34.5.

In some embodiments, the modified HSV-1 genome includes deletions in both copies of ICP4, both copies of ICP0, a deletion in in the gene encoding VP16 that results in a truncation of VP16 protein at amino acid 422, and deletions in one copy of LAT and γ34.5.

In some embodiments, the modified HSV-1 genome includes the nucleotide sequence of SEQ ID NO: 1.

In some embodiments, the deletions render one or more of ICP4, ICP0, VP16, γ34.5, LAT, ICP27, ICP22, and ICP47 non-functional.

In some embodiments, the modified HSV-1 genome is from HSV-1 strains F, 17, or KOS.

In some embodiments, the modified HSV-1 genome further includes one or more genetic circuits. In some embodiments, the genetic circuit is up to 150 kb in length. In some embodiments, the genetic circuit encodes an output molecule.

In some embodiments, the output molecule is an HSV-1 protein. In some embodiments, the HSV-1 protein is selected from: VP16, ICP0, ICP27, ICP22, ICP47, ICP6, ICP8, γ34.5.

In some embodiments, the output molecule is a therapeutic molecule. In some embodiments, the therapeutic molecule is an anti-cancer agent.

In some embodiments, the output molecule is a diagnostic molecule.

In some embodiments, the output molecule is a functional molecule.

In some embodiments, the output molecule is an inhibitor of innate immune response.

In some embodiments, the inhibitor of innate immune response is an RNA interference (RNAi) molecule that targets an innate immune response component.

In some embodiments, the inhibitor of innate immune response is Vaccinia B18R protein.

In some embodiments, the engineered HSV-1 vector is a plasmid.

Other aspects of the present disclosure provide packaging cells containing the engineered HSV-1 vector described herein.

In some embodiments, the engineered HSV-1 vector is integrated into the genome of the packaging cell. In some embodiments, the packaging cell further includes nucleic acids encoding one or more HSV-1 viral genes. In some embodiments, the one or more HSV-1 viral genes encode VP16, ICP0, ICP27, ICP4, ICP22, ICP47, ICP6, ICP8, γ34.5. In some embodiments, the packaging cell further includes nucleic acids encoding an inhibitor of innate immune response. In some embodiments, the inhibitor of innate immune response is an RNA interference (RNAi) molecule that targets an innate immune response component. In some embodiments, the inhibitor of innate immune response is Vaccinia B18R protein. In some embodiments, the packaging cell produces at least 1 plaque forming units of HSV-1 viral particles. In some embodiments, the packaging cell is a U2OS cell.

Other aspects of the present disclosure provide engineered HSV-1 viral particles containing the engineered HSV-1 vector or produced by the packaging cell line described herein.

Further provided herein are methods of treating a disease, the method containing administering an effective amount of the engineered HSV-1 viral particle described herein to a subject in need thereof, wherein the engineered HSV-1 vector includes a genetic circuit encoding a therapeutic molecule.

Further provided herein are methods of diagnosing a disease, the method containing administering an effective amount of the engineered HSV-1 viral particle described herein to a subject in need thereof, wherein the engineered HSV-1 vector includes a genetic circuit encoding a diagnostic molecule.

In some embodiments, the engineered HSV-1 viral particle does not induce an immune response in the subject or induces a lower immune response compared to a natural HSV-1 particle in the subject. In some embodiments, the engineered HSV-1 vector infects cells in the subject and delivers the genetic circuit into cells in the subject. In some embodiments, the engineered HSV-1 viral particle is administered systemically or locally. In some embodiments, the engineered HSV-1 viral particle is administered via injection. In some embodiments, the disease is cancer. In some embodiments, the cancer is breast cancer, glioblastoma, pancreatic cancer, prostate cancer, or lung cancer. In some embodiments, the disease is cachexia.

In some embodiments, the subject is a mammal. In some embodiments, the mammal is human. In some embodiments, the mammal is a non-human primate. In some embodiments, the mammal is a rodent.

Other aspects of the present disclosure provide methods of delivering a genetic circuit into a cell, containing contacting the cell with the HSV-1 vector, or the engineered HSV-1 viral particle described herein, wherein the engineered HSV-1 vector includes a genetic circuit. In some embodiments, the contacting is in vitro. In some embodiments, the contacting is in vivo. In some embodiments, the contacting is ex vivo.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. For purposes of clarity, not every component may be labeled in every drawing.

(FIG. 1A) Schematics of exemplary engineered HSV-1 vectors with deletions in various HSV-1 genes. (FIG. 1B) A graph showing the in vitro delivery of a cell state classifier by the engineered HSV-1 vectors.

(FIG. 2A) The packaging cell line expresses HSV-1 viral genes to complement the deletions in HSV-1 genome. Several different packaging cell lines were constructed using the U2OS cell line. (FIG. 2B) A microRNA sensor is integrated into an engineered HSV-1 vector. (FIG. 2C) Virus production in the packaging cell line.

FIGS. 5A-5C. Anti-cancer activity of therapeutics delivered by the engineered HSV-1 vector described herein in mouse cancer model. The logic functions of the genetic circuit delivered by the engineered HSV-1 vector classifies cancer cells based on high mir-21, low mir-112a, low mir-138, and low mir-199a. (FIG. 5A) Tumor size was monitored over 15 days post injection by imaging firefly luciferase (Fluc). (FIG. 5B) Conditionally replicating engineered HSV-1 vector delivering genetic circuits improves survival rate more than 2-fold. (FIG. 5C) Metastasis was measured at different time points. Blood metastasis correlated with early time death of the mice.

DETAILED DESCRIPTION OF CERTAIN EMBODIMENTS

Figure 1A:
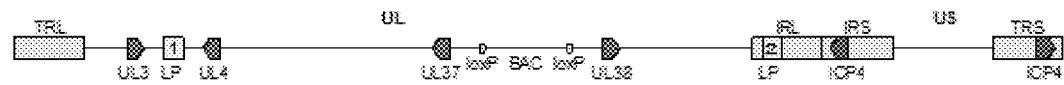
FIGS. 1A-1B. Engineered HSV-1 vectors and activity in delivering genetic circuits.
Figure 1A:
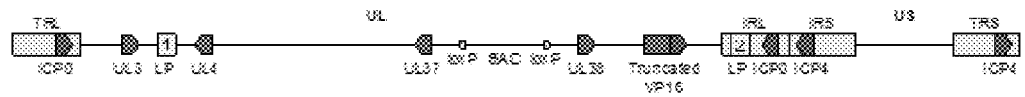
Figure 1A:
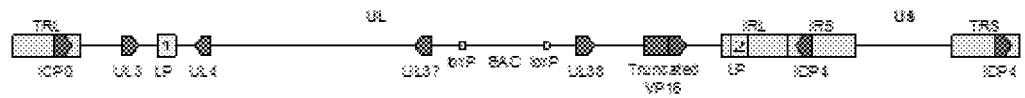
Figure 1A:
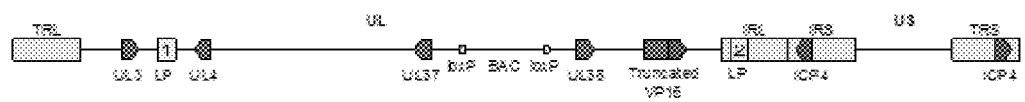
Figure 1A:
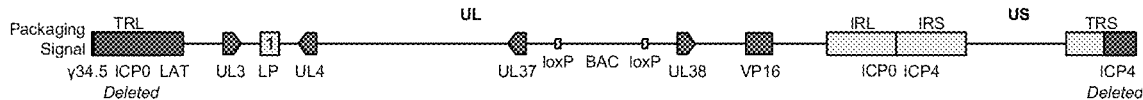
Figure 1A:
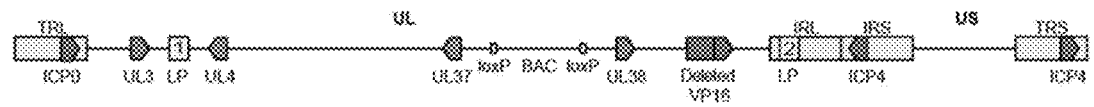
Figure 1A:
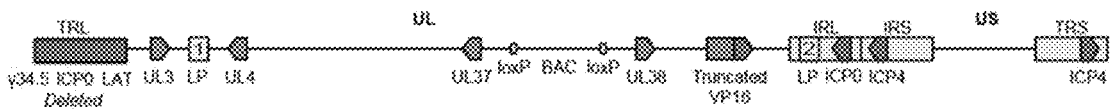
Figure 1B:
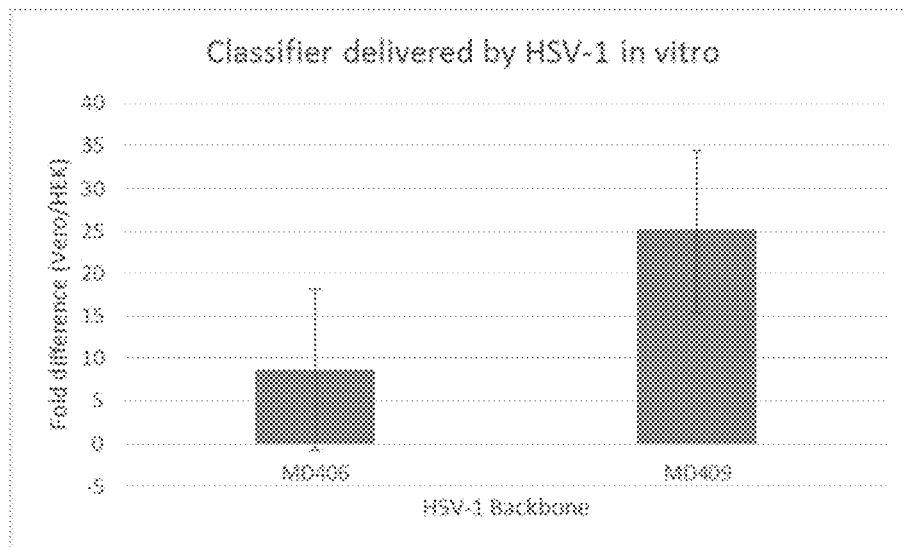
Figure 2A:
FIGS. 2A-2C. Packaging cell lines.
Figure 2B:
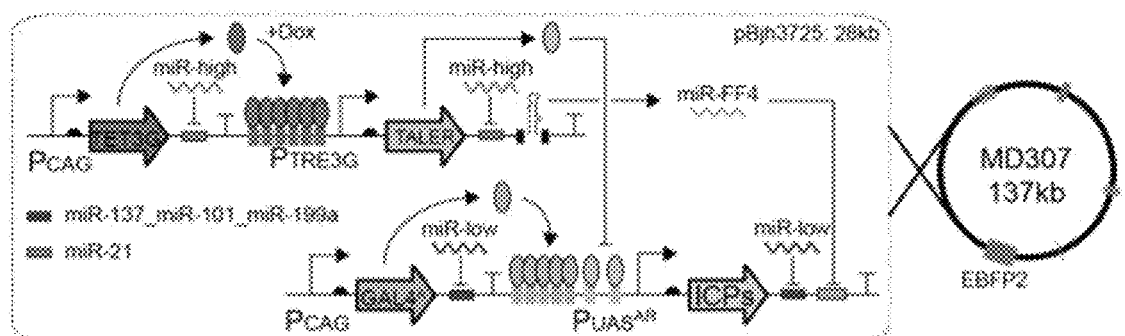
Figure 2C:
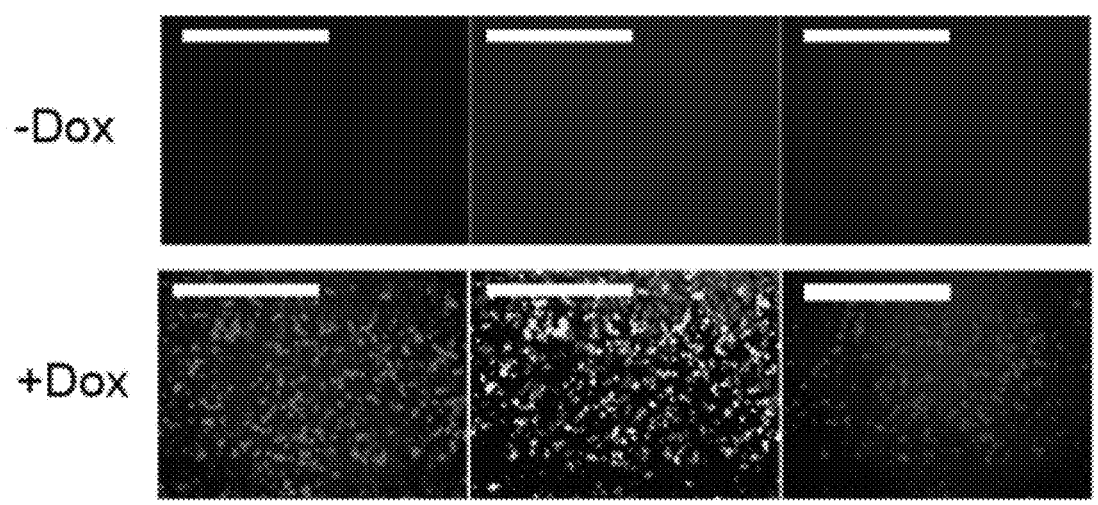

Viral vectors have been widely used in transgene delivery. Issues associated with viral vectors include virus-induced toxicity, viral vector-interference with transgene expression, and/or difficulties in high titer viral particle production. To reduce virus-induced toxicity or viral interference with transgene expression, the virus can be engineered to obtain an attenuated variant. However, attenuation may also affect transgene expression and viral particle packaging. Different virus strains may also lead to different performance of viral vectors.

The present disclosure, in some aspects, relates to engineered Herpes Simplex Virus-1 (HSV-1) vectors comprising a modified HSV-1 genome. The engineered HSV-1 vectors can be used to deliver complex genetic circuits that, in some embodiments, encode transgenes. The modified HSV-1 genome contains all necessary viral components to enhance virus production and transgene production, but have low level interference with circuit performance. Packaging cell lines that allow high titer viral particles to be produced are also provided. In some embodiments, the engineered HSV-1 vectors or the packaging cell lines also have features that reduce innate immune response by host cells. Large numbers of HSV-1 variants comprising different modifications to its genome were screened for the identification of variants that meet the desired criteria. These variants can be used for a number of in vitro and in vivo applications.

Herpes simplex viruses (HSV) are double-stranded linear DNA viruses in the Herpesviridae family. Two members of the herpes simplex virus family infect humans—known as HSV-1 and HSV-2. HSV-1 strains suitable for use in accordance with the present disclosure include, without limitation, F, 17, and KOS.

The structure of HSVs consists of a relatively large, double-stranded, linear DNA genome encased within an icosahedral protein cage called the capsid, which is wrapped in a lipid bilayer called the envelope. The envelope is joined to the capsid by means of a tegument. The complete viral particle is known as the virion (the terms "viral particle" and "virion" are used interchangeably herein).

The genomes of HSVs (e.g., HSV-1) are complex and contain two unique regions called the long unique region (UL) and the short unique region (US) and contain genes encode a variety of proteins involved in forming the capsid, tegument and envelope of the virus, as well as controlling the replication and infectivity of the virus. The HSV-1 genome contains about 85 open reading frames, which encode 4 major classes of proteins: (1) those associated with the outermost external lipid bilayer of HSV (the envelope), (2) the internal protein coat (the capsid), (3) an intermediate complex connecting the envelope with the capsid coat (the tegument), and (4) proteins responsible for replication and infection.

Transcription of HSV genes is catalyzed by RNA polymerase II of the infected host. Immediate early genes, which encode proteins that regulate the expression of early and late viral genes, are the first to be expressed following infection. Early gene expression follows, to allow the synthesis of enzymes involved in DNA replication and the production of certain envelope glycoproteins. Expression of late genes occurs last; this group of genes predominantly encode proteins that form the virion.

HSV (e.g., HSV-1) produces at least 49 infected cell proteins (ICPs) ranging in molecular weight from 15 to 280 kDa (e.g., as described in Honess et al., *Journal of Virology*, Vol. 12, No. 6, 1347-1365, 1973, incorporated herein by reference). The ICPs may be structural proteins or non-structural proteins. Non-limiting, exemplary ICPs that may be deleted from the modified HSV-1 genome described herein include: ICP0, ICP4, ICP6, ICP8, ICP22, ICP27, γ34.5 (also termed ICP34.5 herein), and ICP47.

"Infected Cell Protein 0 (ICP0)" is produced during the earliest stage of infection, when the virus has recently entered the host cell, a stage known as the immediate-early or a phase of viral gene expression. During these early stages of infection, ICP0 protein is synthesized and transported to the nucleus of the infected host cell. ICP0 promotes transcription from viral genes and alters the expression of host and viral genes in combination with a neuron specific protein (e.g., as described in Gu et al., *Proc. Natl. Acad. Sci. U.S.A.* 102 (21): 7571-6, 2005; and Pinnoji et al., *Virol. J.* 4: 56. doi: 10.1186/1743-422X-4-56, 2007, incorporated herein by reference). At later stages of cellular infection, ICP0 relocates to the cell cytoplasm to be incorporated into new virions (e.g., as described in Sedlackova et al., *Journal of Virology.* 82 (1): 268-77, 2008, incorporated herein by reference). ICP0 acts synergistically with HSV-1 immediate early (IE) protein, ICP4, and is essential for reactivation of latent herpes virus and viral replication. During latent infection a viral RNA transcript inhibits expression of the herpes virus ICP0 gene via an antisense RNA mechanism. The RNA transcript is produced by the virus and accumulates in host cells during latent infection; it is known as Latency Associated Transcript (LAT). There are two copies of ICP0 in the HSV-1 genome.

"Infected Cell Protein 4 (ICP4)" is an important transactivator of genes associated with lytic infection in HSV-1 (e.g., as described in Pinnoji et al., *Virol. J.* 4: 56. doi: 10.1186/1743-422X-4-56, 2007, incorporated herein by reference). Elements surrounding the gene for ICP4 bind a protein known as the human neuronal protein neuronal restrictive silencing factor (NRSF) or human repressor element silencing transcription factor (REST). When bound to the viral DNA elements, histone deacetylation occurs atop the ICP4 gene sequence to prevent initiation of transcription from this gene, thereby preventing transcription of other viral genes involved in the lytic cycle. ICP0 dissociates NRSF from the ICP4 gene and thus prevents silencing of the viral DNA (e.g., in Roizman et al., *Cell Cycle.* 4 (8): 1019-21, 2005, incorporated herein by reference). There are two copies of ICP4 in the HSV-1 genome.

"Infected Cell Protein 6 (ICP6)" is a viral ribonucleotide reductase (vRR) that functions to allow replication of wild-type HSV to occur even in quiescent cells, such as the neurons that are infected during encephalitis caused by wild-type HSV-1. Without this function, HSV replication is severely curtailed in quiescent cells (e.g., as described in Goldstein et al., *Virology* 166: 41-51, 1988, incorporated herein by reference).

"Infected Cell Protein 8 (ICP8)" is required for HSV-1 DNA replication. It is able to anneal to single-stranded DNA (ssDNA) as well as melt small fragments of dsDNA. Its role is to destabilize duplex DNA during initiation of replication. It differs from helicases because it is $ATP^-$ and $Mg^{2+}$-independent. In cells infected with HSV-1, the DNA in those cells become colocalized with ICP8. ICP8 is required in late gene transcription, and has found to be associated with cellular RNA polymerase II holoenzyme.

"Infected Cell Protein 22 (ICP22)" functions as a general transcriptional regulator of cellular and viral mRNAs mainly by mediating changes on the host RNA polymerase II. One change, which is UL13 independent, is the rapid loss of Pol II forms bearing Ser-2 phosphorylation. A second change, which is UL13 dependent, is the appearance of an intermediate form of Pol II that differs from the normal hypo- and hyperphosphorylated forms. These Pol II modifications immediately inhibit host genome transcription, leading to cell cycle deregulation and loss of efficient antiviral response. ICP22 also recruits cellular transcription elongation factors to viral genomes for efficient transcription elongation of viral genes.

"Infected Cell Protein 27 (ICP27)" is a multifunctional regulatory protein that is required for HSV-1 infection. At early times after infection, ICP27 interacts with a splicing protein-specific kinase, SRPK1, and recruits this predominantly cytoplasmic kinase to the nucleus, where ICP27 then interacts with members of a conserved family of splicing factors termed SR proteins (e.g., as described in Sciabica et al., *EMBO J.* 22:1608-1619, 2003; and Souki et al., *J. Virol.* 83:8970-8975, incorporated herein by reference). Through these interactions, ICP27 mediates the aberrant phosphorylation of SR proteins, which, as a consequence, are unable to perform their roles in spliceosome assembly, resulting in an inhibition of host cell splicing. Also at early times after infection, ICP27 interacts with cellular RNA polymerase II (RNAP II) through the C-terminal domain (CTD) and helps to recruit RNAP II to viral transcription/replication sites (e.g., as described in Zhou et al., *J. Virol.* 76:5893-5904, 2002; and Dai-ju et al., *J. Virol.* 80:3567-3581, 2006, incorporated herein by reference). As infection progresses, ICP27 disassociates from splicing speckles and interacts with the TREX complex mRNA export adaptor protein Aly/REF and recruits Aly/REF to viral replication compartments (e.g., as described in Chen et al., *J. Virol.* 79:3949-3961, 2005; and Chen et al., *J. Virol.* 76:12877-12889, 2002, incorporated herein by reference). While associated with replication compartments, ICP27 binds viral RNA and escorts its bound RNA cargo through the nuclear pore complex to the cytoplasm (e.g., as described in Corbin-Lickfett et al., *Nucleic Acids Res.* 37:7290-7301, 2009; and Sandri-Goldin et al., *Genes Dev.* 12:868-879, 1998, incorporated herein by reference). In the cytoplasm, ICP27 enhances the translation initiation of some viral mRNAs by an interaction with translation initiation factors (e.g., as described in Ellison et al., *J. Virol.* 79:4120-4131, 2005; and Fontaine-Rodriguez et al., *Virology* 330:487-492, 2004, incorporated herein by reference). ICP27 also has been shown to interact with ICP8 when it is associated with RNAP II (e.g., as described in Olesky et al., *Virology* 331:94-105, 2005, incorporated herein by reference).

"Infected Cell Protein 47 (ICP47)" is a protein that functions in allowing invading HSV to evade the human immune system's CD8 T-cell response (e.g., as described in Goldsmith et al., *The Journal of Experimental Medicine.* 187 (3): 341-8, 1998; and Berger et al., *Journal of Virology.* 74 (10): 4465-73, 2000, incorporated herein by reference).

Infected cell protein 34.5 (ICP34.5) is a protein encoded by the γ34.5 gene, and it blocks a cellular stress response to viral infection (e.g., as described in Agarwalla et al., *Methods in Molecular Biology.* 797: 1-19, incorporated herein by reference). When a cell is infected by HSV, protein kinase R is activated by the virus' double-stranded RNA. Protein kinase R then phosphorylates a protein called eukaryotic initiation factor-2A (eIF-2A), which inactivates eIF-2A. EIF-2A is required for translation so by shutting down eIF-2A, the cell prevents the virus from hijacking its own protein-making machinery. Viruses in turn evolved ICP34.5 to defeat the defense; it activates protein phosphatase-1A which dephosphorylates eIF-2A, allowing translation to occur again. HSV lacking the γ34.5 gene will not be able to replicate in normal cells because it cannot make proteins.

Virion Protein 16 (VP16) serves multiple functions during HSV infection, including transcriptional activation of viral immediate early genes and downregulation of the virion host shutoff protein. Furthermore, VP16 is involved in some aspects of virus assembly and/or maturation.

"Latency-associated transcript (LAT)" is the only region of the HSV genome that shows active transcription after HSV establishes latent infections in sensory neurons as a circular episome associated with histones (e.g., as described in Deshmane et al., *J. Virol.* 63:943-947, 1989, incorporated herein by reference). The LAT region carries an 8.3-kb polyadenylated RNA that is spliced to yield a 2.0-kb stable intron that accumulates abundantly in a subset of the sensory neurons. This 2.0-kb intron can be alternatively spliced in some neurons to yield a 1.5-kb intron. While the LAT region has not been shown to encode any proteins, this region has been implicated in a number of pathogenic functions, including neuronal survival and antiapoptosis, virulence, suppression of latent transcription, establishment of latency, and reactivation from latency.

Other non-limiting examples of HSV proteins include envelope proteins such as UL1 (gL), UL10 (gM), UL20, UL22, UL27 (gB), UL43, UL44 (gC), UL45, UL49A, UL53 (gK), US4 (gG), US5 (gJ), US6 (gD), US7 (gI), US8 (gE), and US10; capsid proteins such as UL6, UL18, UL19, UL35, and UL38; tegument proteins such as UL11, UL13, UL21, UL36, UL37, UL41, UL45, UL46, UL47, UL48, UL49, US9, and US10; and other proteins such as UL2, UL3, UL4, UL5, UL7, UL8, UL9, UL12, UL14, UL15, UL16, UL17, UL23, UL24, UL25, UL26, UL26.5, UL28, UL29, UL30, UL31, UL32, UL33, UL34, UL39, UL40, UL42, UL50, UL51, UL52, UL54, UL55, UL56, US1, US2, US3, US81, US11, and US12.

The accession numbers of exemplary HSV-1 genes and proteins that are deleted in the modified HSV-1 genome described herein are provided in Table 1.

TABLE 1

HSV-1 genes

| Gene Name | Gene Accession No. | Protein Accession No. |
| --- | --- | --- |
| ICP0 | 2703389 | YP_009137074.1 |
| ICP4 | 2703392 | YP_009137135.1 |
| ICP6 | 2703361 | YP_009137114.1 |
| ICP8 | 2703458 | YP_009137104.1 |
| ICP22 | 2703435 | YP_009137136.1 |
| ICP27 | 24271474 | YP_009137130.1 |
| ICP47 | 2703441 | YP_009137148.1 |
| γ34.5 (ICP34.5) | 2703395 | YP_009137073.1 |
| VP16 | 2703413 | YP_009137121.1 |
| LAT | 24271498 | N/A |

VP16 amino acid sequence, full length
(SEQ ID NO: 2)
MQRRTRGASSLRLARCLTPANLIRGDNAGVPERRIFGGCLLPTPEGLLSA

AVGALRQRSDDAQPAFLTCTDRSVRLAARQHNTVPESLIVDGLASDPHYE

YIRHYASAATQALGEVELPGGQLSRAILTQYWKYLQTVVPSGLDVPEDPV

GDCDPSLHVLLRPTLAPKLLARTPFKSGAVAAKYAATVAGLRDALHRIQQ

YMFFMRPADPSRPSTDTALRLNELLAYVSVLYRWASWMLWTTDKHVCHRL

SPSNRRFLPLGGSPEAPAETFARHLDRGPSGTTGSMQCMALRAAVSDVLG

HLTRLANLWQTGKRSGGTYGTVDTVVSTVEVLSIVHHHAQYIINATLTGY

GVWATDSLNNEYLRAAVDSQERFCRTTAPLFPTMTAPSWARMELSIKAWF

-continued

GAALAADLLRNGAPSLHYESILRLVASRRTTWSAGPPPDDMASGPGGHRA

GGGTCREKIQRARRDNEPPPLPRPRLHSTPASTRRFRRRRADGAGPPLPD

ANDPVAEPPAAATQPATYYTHMGEVPPRLPARNVAGPDRRPPAATCPLLV

RRASLGSLDRPRVWGPAPEGEPDQMEATYLTADDDDDARRKATHAASAR

ERHAPYEDDESIYETVSEDGGRVYEEIPWMRVYENVCVNTANAAPASPYI

EAENPLYDWGGSALFSPPGRTGPPPPPLSPSPVLARHRANALTNDGPTNV

AALSALLTKLKREGRRSR

VP16 amino acid sequence, truncated at amino acid 422
(SEQ ID NO: 3)
MQRRTRGASSLRLARCLTPANLIRGDNAGVPERRIFGGCLLPTPEGLLSA

AVGALRQRSDDAQPAFLTCTDRSVRLAARQHNTVPESLIVDGLASDPHYE

YIRHYASAATQALGEVELPGGQLSRAILTQYWKYLQTVVPSGLDVPEDPV

GDCDPSLHVLLRPTLAPKLLARTPFKSGAVAAKYAATVAGLRDALHRIQQ

YMFFMRPADPSRPSTDTALRLNELLAYVSVLYRWASWMLWTTDKHVCHRL

SPSNRRFLPLGGSPEAPAETFARHLDRGPSGTTGSMQCMALRAAVSDVLG

HLTRLANLWQTGKRSGGTYGTVDTVVSTVEVLSIVHHHAQYIINATLTGY

GVWATDSLNNEYLRAAVDSQERFCRTTAPLFPTMTAPSWARMELSIKAWF

GAALAADLLRNGAPSLHYESIL

In some embodiments, the modified HSV-1 genome described herein comprises deletions in genes encoding one or more (e.g., 1, 2, 3, 4, 5, 6, 7, 8, 9, 10, or more) of the ICPs (e.g., ICP0, ICP4, ICP6, ICP8, ICP22, ICP27, ICP47, and γ34.5 (ICP34.5), VP16, and LAT). A "deletion" in a gene means part or all of the gene is removed from the modified HSV-1 genome. For example, at least 10% (e.g., at least 10%, at least 20%, at least 30%, at least 40%, at least 50%, at least 60%, at least 70%, at least 80%, at least 90%, or 100%) of the gene may be removed. For example, in some embodiments, a deletion in VP16 means a complete deletion of the gene encoding VP16. In some embodiments, a deletion in VP16 gene is a partial deletion that results in a truncation of VP16 protein (SEQ ID NO: 2) at amino acid 422. Typically, a complete deletion completely removes the gene product (encoded protein) function, while a partial deletion may result in a complete loss or a reduction (e.g., by at least 20%, at least 30%, at least 40%, at least 50%, at least 60%, at least 70%, at least 80%, least 90%, or at least 95%, or at least 99%) of the gene product function. In some embodiments, the deletions render the deleted genes (e.g., one or more of ICP4, ICP0, ICP8, ICP6, VP16, γ34.5 (ICP34.5), LAT, ICP27, ICP22, and ICP47) non-functional. In the case of VP16, the partial deletion results in a truncated VP16 that lacks the transactivation domain but the truncated VP16 remains an essential structural component of the HSV-1 viral particle.

The deletion may be anywhere in the gene. There may be one deletion in one gene, or multiple deletions in one gene. In some embodiments, for genes that are present with multiple copies (e.g., 2 copies) in the HSV genome (e.g., ICP0, ICP4, γ34.5, and LAT), a "deletion" in such a gene, unless otherwise specified, means a deletion in one or both copies of the gene. If there are deletions in both copies of the gene, the deletions can be the same or different.

In some embodiments, the modified HSV-1 genome described herein comprises a deletion in one or more genes encoding ICP0, ICP4, γ34.5, VP16, and LAT. In some embodiments, the modified HSV-1 genome described herein comprises deletions in one or more of the gene encoding ICP0 (e.g., one or both copies), ICP4 (e.g., one or both copies), γ34.5 (e.g., one or both copies), LAT (e.g., one or both copies), and VP16. In some embodiments, when both copies of VP16 has deletions, one copy is completely deleted and the other copy comprises a deletion that results in a truncation of VP16 protein (SEQ ID NO: 2) at amino acid 422.

In some embodiments, the modified HSV-1 genome described herein comprises deletions in the genes encoding γ34.5 (e.g., one or both copies), LAT (e.g., one or both copies), and ICP0 (e.g., one or both copies), and a deletion in the gene encoding VP16 that results in a truncation of VP16 protein (SEQ ID NO: 2) at amino acid 422.

In some embodiments, the modified HSV-1 genome described herein comprises deletions in the genes encoding ICP4 (both copies), γ34.5 (both copies), LAT (both copies), and ICP0 (both copies), and a deletion in the gene encoding VP16 that results in a truncation of VP16 protein (SEQ ID NO: 2) at amino acid 422.

In some embodiments, the modified HSV-1 genome described herein comprises deletions in the genes encoding ICP4 (both copies), γ34.5 (one copy), LAT (one copy), and ICP0 (one copy), and a deletion in the gene encoding VP16 that results in a truncation of VP16 protein (SEQ ID NO: 2) at amino acid 422.

In some embodiments, the modified HSV-1 genome described herein comprises deletions in the genes encoding ICP4 (both copies), γ34.5 (one copy), LAT (one copy), ICP0 (one copy), and ICP27.

In some embodiments, the modified HSV-1 genome described herein comprises deletions in the genes encoding ICP4 (one copy), γ34.5 (one copy), LAT (one copy), and ICP0 (one copy).

In some embodiments, the modified HSV-1 genome described herein comprises deletions in the genes encoding ICP4 (both copies), γ34.5 (one copy), LAT (one copy), and ICP0 (one copy), and a complete deletion in the gene encoding VP16.

In some embodiments, the modified HSV-1 genome described herein comprises deletions in the genes encoding ICP4 (both copies), γ34.5 (one copy), LAT (one copy), and ICP0 (both copies), and a deletion in the gene encoding VP16 that results in in a truncation of VP16 protein (SEQ ID NO: 2) at amino acid 422.

In some embodiments, the modified HSV-1 genome described herein comprises deletions in the genes encoding ICP4 (both copies), γ34.5 (one copy), LAT (one copy), and ICP0 (one copy), and a deletion in the gene encoding VP16 that results in in a truncation of VP16 protein (SEQ ID NO: 2) at amino acid 422.

In some embodiments, the modified HSV-1 genome described herein comprises deletions in the genes encoding ICP4 (both copies), and a deletion in the gene encoding VP16 that results in in a truncation of VP16 protein (SEQ ID NO: 2) at amino acid 422.

In some embodiments, the modified HSV-1 genome described herein comprises deletions in the genes encoding ICP4 (both copies), ICP0 (one copy) and a deletion in the gene encoding VP16 that results in in a truncation of VP16 protein (SEQ ID NO: 2) at amino acid 422.

In some embodiments, the modified HSV-1 genome described herein comprises deletions in the genes encoding ICP4 (both copies), ICP0 (two copies) and a deletion in the gene encoding VP16 that results in in a truncation of VP16 protein (SEQ ID NO: 2) at amino acid 422.

In some embodiments, the modified HSV-1 genome described herein comprises deletions in the genes encoding ICP4 (both copies), a deletion in one copy of the gene encoding VP16 that results in in a truncation of VP16 protein (SEQ ID NO: 2) at amino acid 422, and a complete deletion of the second copy of gene encoding VP16.

In some embodiments, the modified HSV-1 genome described herein comprises deletions in the genes encoding ICP4 (both copies), ICP0 (one copy), a deletion in one copy of the gene encoding VP16 that results in in a truncation of VP16 protein (SEQ ID NO: 2) at amino acid 422, and a complete deletion of the second copy of gene encoding VP16.

In some embodiments, the modified HSV-1 genome described herein comprises deletions in the genes encoding ICP4 (both copies), ICP0 (both copies), a deletion in one copy of the gene encoding VP16 that results in in a truncation of VP16 protein (SEQ ID NO: 2) at amino acid 422, and a complete deletion of the second copy of gene encoding VP16. In some embodiments, the modified HSV-1 genome comprise deletions in both copies of ICP4, both copies of ICP0, a deletion in the gene encoding VP16 that results in a truncation of VP16 protein at amino acid 422, and deletions in one copy of LAT and one copy of γ34.5 (ICP34.5).

In some embodiments, the modified HSV-1 genome comprise deletions in both copies of ICP4, both copies of ICP0, a deletion in one copy of the gene encoding VP16 that results in a truncation of VP16 protein at amino acid 422, a complete deletion of the other copy of gene encoding VP16, and deletions in one copy of LAT and one copy of γ34.5 (ICP34.5).

In some embodiments, the modified HSV-1 genome comprise deletions in both copies of ICP4, both copies of ICP0, a deletion in in the gene encoding VP16 that results in a truncation of VP16 protein at amino acid 422, and deletions in one copy of LAT and one copy of γ34.5 (ICP34.5).

In some embodiments, the modified HSV-1 genome described herein comprises a nucleotide sequence that is at least 70% identical to the nucleotide sequence of SEQ ID NO: 1. For example, the modified HSV-1 genome may be at least 70%, at least 80%, at least 90%, at least 95%, or at least 99% identical to the nucleotide sequence of SEQ ID NO: 1. In some embodiments, the modified HSV-1 genome is 70%, 80%, 90%, 95%, or 99% identical to the nucleotide sequence of SEQ ID NO: 1. In some embodiments, the modified HSV-1 genome comprises the nucleotide sequence of SEQ ID NO: 1.

The modified HSV-1 genome may be incorporated into vectors. A "vector" refers to a nucleic acid (e.g., DNA) used as a vehicle to artificially carry genetic material (e.g., a genetic circuit) into a cell where, for example, it can be replicated and/or expressed. In some embodiments, a vector is an episomal vector (see, e.g., Van Craenenbroeck K. et al. *Eur. J. Biochem.* 267, 5665, 2000, incorporated by reference herein). A non-limiting example of a vector is a plasmid. Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. In some embodiments, the vector is a bacterial artificial chromosome (BAC). A bacterial artificial chromosome (BAC) is a DNA construct, based on a functional fertility plasmid (or F-plasmid), used for transforming and cloning in bacteria, usually *E. coli*.

In some embodiments, the engineered HSV-1 vector further comprises one or more (e.g., 1, 2, 3, 4, 5 or more) genetic circuits. A "genetic circuit," as used herein, refers to an engineered nucleic acid molecule (typically DNA) that exerts one or more functions. Such functions include, without limitation: sensing input signals, producing output molecules, producing control signals, functioning as logic gates, or regulating the signals sensed or produced by other genetic circuits. In some embodiments, the genetic circuit exerts one of the functions described herein. In some embodiments, the genetic circuit exerts multiple functions. For example, one genetic circuit may sense an input signal and produce an output signal in response.

In some embodiments, the engineered HSV-1 vector described herein comprises one genetic circuit, e.g., a genetic circuit that responds to a signal such as an environmental cue or an artificially supplied signal and expresses an output molecule. In some embodiments, the signal is a small molecule. In one non-limiting example, such a genetic circuit comprises a promoter (e.g., an inducible promoter) operably linked to a nucleotide sequence encoding an output molecule. The signal could be a signal that represses or activates the inducible promoter.

In some embodiments, the engineered HSV-1 vector described herein comprises multiple genetic circuits, wherein the multiple genetic circuits are components of a more complex genetic system including various layers of transcriptional or translation control of the expression of an output molecule. In such complex genetic systems, different types of genetic circuits are used, e.g., without limitation, sensor circuits, signal circuits, control circuits, and/or regulatory circuits. In some embodiments, the engineered HSV-1 vector described herein comprises part of the genetic system (some of the genetic circuits in the genetic system) or all of the genetic system (all of the genetic circuits in the genetic system). The engineered HSV-1 vector comprises a genetic circuit, broadly refers to all the situations described herein, e.g., it comprises one genetic circuit or multiple genetic circuits that are part or all of a genetic system.

A sensor circuit typically comprises a region that detects an input signal (e.g., a binding site for a small molecule signal or a target site for a microRNA signal). In some embodiments, the sensor circuit further comprises a promoter operably linked to a nucleotide sequence encoding a regulator (e.g., a transcriptional regulator such as a transcriptional repressor or activator) for the other circuits in the system. Sensing the input signal leads to the expression or non-expression of the regulator, thus affecting the behavior of the downstream circuits. In some embodiments, different types of sensor circuits are used for detecting different signals simultaneously.

A signal circuit responds to the sensor circuit (e.g., to the regulator produced by the sensor circuit) and in turn produces an output molecule. In some embodiments, the signal circuit comprises an activatable/repressible promoter operably linked to a nucleotide sequence encoding the output molecule. An "activatable/repressible" promoter is a promoter that can be activated (e.g., by a transcriptional activator) to drive the expression of the nucleotide sequence that it is operably linked to, and can be repressed (e.g., by a transcriptional repressor) to repress the expression of the nucleotide sequence that it is operably linked to. In some embodiments, more than one signal circuits are used in the genetic system.

In some embodiments, the genetic system further comprises additional regulatory elements to enhance its performance (e.g., sensitivity, specificity, and/or robustness). In some embodiments, such regulatory elements may be feed-forward and/or feed-back transcriptional regulation loops. For example, in some embodiments, the signal circuit further comprises a nucleotide sequence encoding a regulator that regulates the behavior of the sensor circuit, thus creating a feedback loop. In some embodiments, additional regulatory circuits are included in the genetic system, further fine-tuning the communication between the sensor circuit and the signal circuit via transcriptional and/or translational control.

A control circuit produces a constant signal independent of the input signal and may be used to control for variations caused by other factors other than the microRNA profile, e.g., transfection, cellular health, etc. In some embodiments, The control circuit comprises a constitutive promoter operably linked to a nucleotide sequence encoding a control signal that is different from output signals. The control signal is typically a detectable molecule such as a fluorescent molecule.

The engineered HSV-1 vector of the present disclosure may be used to deliver genetic circuits of up to 100 kb in length. For example, the genetic circuit may be up to 100 kb, up to 90 kb, up to 80 kb, up to 70 kb, up to 60 kb, up to 50 kb, up to 40 kb, up to 30 kb, up to 20 kb, up to 10 kb, up to 5 kb, up to 2 kb, or up to 1 kb in length. In some embodiments, the genetic circuit is 1-100, 1-90, 1-80, 1-70, 1-60, 1-50, 1-40, 1-30, 1-20, 1-10, 10-100, 10-90, 10-80, 10-70, 10-60, 10-50, 10-40, 10-30, 10-20, 20-100, 20-90, 20-80, 20-70, 20-60, 20-50, 20-40, 20-30, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70, 70-100, 70-90, 70-80, 80-100, 80-90, or 90-100 kb in length. In some embodiments, the genetic circuit is about 1, 2, 5, 10, 15, 20, 25, 30, 35, 40, 45, 60, 65, 70, 75, 80, 85, 90, 95, or 100 kb in length. In some embodiments, the genetic circuit is up to 33 kb in length.

Complex systems that comprise multiple genetic circuits have been described in the art. A non-limiting example is the cell state classifier that senses the presence or absence of microRNAs as described in International Application No. PCT/US2017/044643 and International Application Publication No. WO 20116/040395, incorporated herein by reference. Other non-limiting examples of genetic circuits of systems that may be used in accordance with the present disclosure include, those described in Xie et al, *Science*, Vol. 333, Issue 6047, pp. 1307-1311, 2011; Miki et al., *Cell Stem Cell*, Vol. 16, issue 6, pp. 699-711, 2015; Sayeg et al., *ACS Synth. Biol.*, 4 (7), pp 788-795, 2015; and in Ra et al., *Front Cell Dev Biol.* 2017; 5: 77, 2017).

The genetic circuits are constructed by combining different genetic elements. A genetic element refers to a particular nucleotide sequence that has a role in nucleic acid expression (e.g., promoter, enhancer, terminator, genomic insulator, microRNA target site, or a polyadenylation signal) or encodes a discrete product of a genetic circuit (e.g., an activator, a repressor, a microRNA, or an output molecule).

A "microRNA" or "miRNA" is a small non-coding RNA molecule that functions in RNA silencing and post-transcriptional regulation of gene expression (e.g., as described in Ambros et al., *Nature* 431 (7006): 350-5, 2004; and Bartel et al., *Cell*. 136 (2): 215-33, 2004). A microRNA may be 15-30 nucleotides in length. For example, a microRNA may be 15-30, 15-25, 15-20, 20-30, 20-25, or 25-30 nucleotides in length. In some embodiments, a microRNA may be 16-24 nucleotides in length. In some embodiments, a microRNA may be 20-24 nucleotides in length. In some embodiments, a microRNA may be 15, 16, 17, 18, 19, 20, 21, 22, 23, 24, 25, 26, 27, 28, 29, or 30 nucleotides in length.

A "microRNA target site" is a nucleotide sequence that is complementary to the nucleotide sequence of the microRNA. Naturally, microRNA targeting sites exist in messenger RNAs (mRNA), typically in the 3' untranslated regions of mRNAs. Binding of the microRNA to its target site in via sequence complementarity leads to silencing of an output molecule either via degrading the mRNA or suppressing translation of the mRNA (e.g., as described in Bartel et al., *Cell* 136 (2): 215-33 (2009), incorporated herein by reference) containing the microRNA binding sites. Herein, when microRNA target sites are referred in the context of the genetic circuits (i.e., in a context of DNA), it means the nucleotide sequence that encodes the microRNA target sites in the mRNA that is produced from the genetic circuit.

Information about the sequences, origins, and functions of known microRNAs maybe found in publically available databases (e.g., mirbase.org/, all versions, as described in Kozomara et al., *Nucleic Acids Res* 2014 42:D68-D73; Kozomara et al., *Nucleic Acids Res* 2011 39:D152-D157; Griffiths-Jones et al., Nucleic Acids Res 2008 36:D154-D158; Griffiths-Jones et al., *Nucleic Acids Res* 2006 34:D140-D144; and Griffiths-Jones et al., *Nucleic Acids Res* 2004 32:D109-D111, including the most recently released version miRBase 21, which contains "high confidence" microRNAs).

An "activator," as used herein, refers to a transcriptional activator. The terms "activator" or "transcriptional activator" are used interchangeably herein. A transcriptional activator is a protein that increases gene transcription of a gene or set of genes. Most activators function by binding sequence-specifically to a DNA site located in or near a promoter and making protein-protein interactions with the general transcription machinery (RNA polymerase and general transcription factors), thereby facilitating the binding of the general transcription machinery to the promoter.

A "repressor," as used herein, refers to a transcriptional repressor. The terms "repressor" or "transcriptional repressor" are used interchangeably herein. A transcriptional repressor is a DNA- or RNA-binding protein that inhibits the expression of one or more genes by binding to the operator or associated silencers. A DNA-binding repressor blocks the attachment of RNA polymerase to the promoter, thus preventing transcription of the genes into messenger RNA. An RNA-binding repressor binds to the mRNA and prevents translation of the mRNA into protein.

One skilled in the art is able to choose the transcriptional activators or repressors for use in accordance with the present disclosure. Public databases are available for known or predicted transcriptional regulators, e.g., transcriptionfactor.org.

A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof. A promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. In some embodiments, a coding nucleic acid sequence may be positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter. In some embodiments, using inducible promoters in the genetic circuits results in the conditional expression or a "delayed" expression of a gene product.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, an inducer signal is anhydrotetracycline (aTc), which is a derivative of tetracycline that exhibits no antibiotic activity and is designed for use with tetracycline-controlled gene expression systems, for example, in bacteria.

In some embodiments, an inducer signal is isopropyl β-D-1-thiogalactopyranoside (IPTG), which is a molecular mimic of allolactose, a lactose metabolite that triggers transcription of the lac operon, and it is therefore used to induce protein expression where the gene is under the control of the lac operator. IPTG binds to the lac repressor and releases the tetrameric repressor from the lac operator in an allosteric manner, thereby allowing the transcription of genes in the lac operon, such as the gene coding for beta-galactosidase, a hydrolase enzyme that catalyzes the hydrolysis of β-galactosides into monosaccharides. The sulfur (S) atom creates a chemical bond which is non-hydrolyzable by the cell, preventing the cell from metabolizing or degrading the inducer. IPTG is an effective inducer of protein expression, for example, in the concentration range of 100 μM to 1.0 mM. Concentration used depends on the strength of induction required, as well as the genotype of cells or plasmid used. If lacIq, a mutant that over-produces the lac repressor, is present, then a higher concentration of IPTG may be necessary. In blue-white screen, IPTG is used together with X-gal. Blue-white screen allows colonies that have been transformed with the recombinant plasmid rather than a non-recombinant one to be identified in cloning experiments.

Other inducible promoter systems are known in the art and may be used in accordance with the present disclosure. Examples of inducible promoters include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated E. coli promoters such as positively regulated σ70 promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rhl), Pu, FecA, pRE, cadC, hns, pLas, pLux), σS promoters (e.g., Pdps), σ32 promoters (e.g., heat shock) and σ54 promoters (e.g., glnAp2); negatively regulated E. coli promoters such as negatively regulated σ70 promoters (e.g., Promoter (PRM+), modified lamdba Prm promoter, TetR-TetR-4C P(Las) TetO, P(Las) CIO, P(Lac) IQ, RecA_DlexO_D-LacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), σS promoters (e.g., Lutz-Bujard LacO with alternative sigma factor σ38), σ32 promoters (e.g., Lutz-Bujard LacO with alternative sigma factor σ32), and σ54 promoters (e.g., glnAp2); negatively regulated B. subtilis promoters such as repressible B. subtilis σA promoters (e.g., Gram-positive IPTG-inducible, Xyl, hyper-spank) and σB promoters. Other inducible microbial promoters may be used in accordance with the present disclosure.

In some embodiments, inducible promoters of the present disclosure function in eukaryotic cells (e.g., mammalian cells). Examples of inducible promoters for use eukaryotic cells include, without limitation, chemically-regulated promoters (e.g., alcohol-regulated promoters, tetracycline-regulated promoters, steroid-regulated promoters, metal-regulated promoters, and pathogenesis-related (PR) promoters) and physically-regulated promoters (e.g., temperature-regulated promoters and light-regulated promoters).

A "genomic insulator" refers to a class of DNA sequence elements that possess a common ability to protect genes from inappropriate signals (e.g., enhancing signal or repression signal) emanating from their surrounding environment, i.e., establishing boundaries for gene expression. In some embodiments, a genomic insulator has one or more proteins associated with the DNA sequence elements when exerting its function (e.g., as described in Yang et al., *Adv Cancer Res.* 2011; 110: 43-76; and in West et al., *Genes & Development* 16:271-288, 2002, incorporated herein by reference). Certain genomic insulators, e.g., chicken HS4 insulator (cHS4) have been shown to enhance the expression of a transgene integrated into the chromosome by a retroviral vector (e.g., as described in Revilla et al., *J. Virol.* May 2000 vol. 74 no. 10 4679-4687, incorporated herein by reference). Genomic insulators that may be used in accordance with the present disclosure may be from different organisms, e.g., *Saccharomyces cerevisiae, Drosophila melanogaster*, or a vertebrate such as a chicken or a mammal. In some embodiments, the mammal is human. Various genomic insulators that may be used in accordance with the present disclosure are described in West et al., *Genes & Development* 16:271-288, 2002, incorporated herein by reference).

An "enhancer," as used herein, refers to a transcriptional enhancer. The terms "enhancer" and "transcriptional enhancer" are used interchangeably herein. An enhancer is a short (50-1500 bp) region of DNA that can be bound by activators to increase the likelihood that transcription of a particular gene will occur. Enhancers are cis-acting and can be located up to 1 Mbp (1,000,000 bp) away from the gene, upstream or downstream from the transcription start site. Enhancers are found both in prokaryotes and eukaryotes. There are hundreds of thousands of enhancers in the human genome.

An "operator," as used herein, refers to a segment of DNA to which a repressor binds to regulate gene expression by repressing it. In the lac operon, an operator is defined as a segment between the promoter and the genes of the operon. When bound by a repressor, the repressor protein physically obstructs the RNA polymerase from transcribing the genes, thus repressing transcription of the gene.

A "polyadenylation signal," as used herein, refers to a sequence motif recognized by the RNA cleavage complex that cleaves the 3'-most part of a newly produced RNA and polyadenylates the end produced by this cleavage. The sequence of the polyadenylation signal varies between groups of eukaryotes. Most human polyadenylation sites contain the AAUAAA sequence.

A transcriptional terminator typically occurs after a polyadenylation signal in any of the genetic circuit of the present disclosure. A "transcriptional terminator" is a nucleic acid sequence that causes transcription to stop. A terminator may be unidirectional or bidirectional. It is comprised of a DNA sequence involved in specific termination of an RNA transcript by an RNA polymerase. A terminator sequence prevents transcriptional activation of downstream nucleic acid sequences by upstream promoters. Thus, in certain embodiments, inclusion in the various nucleic acid constructs and circuits described herein of a terminator that ends the production of an RNA transcript is contemplated. A terminator may be necessary in vivo to achieve desirable output expression levels (e.g., low output levels) or to avoid transcription of certain sequences.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided, which usually cause transcription to terminate on both the forward and reverse strand. In some embodiments, reverse transcriptional terminators are provided, which usually terminate transcription on the reverse strand only.

In prokaryotic systems, terminators usually fall into two categories (1) rho-independent terminators and (2) rho-dependent terminators. Rho-independent terminators are generally composed of palindromic sequence that forms a stem loop rich in G-C base pairs followed by several T bases. Without wishing to be bound by theory, the conventional model of transcriptional termination is that the stem loop causes RNA polymerase to pause, and transcription of the poly-A tail causes the RNA:DNA duplex to unwind and dissociate from RNA polymerase.

In eukaryotic systems, the terminator region may comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in some embodiments involving eukaryotes, a terminator may comprise a signal for the cleavage of the RNA. In some embodiments, the terminator signal promotes polyadenylation of the message. The terminator and/or polyadenylation site elements may serve to enhance output nucleic acid levels and/or to minimize read through between nucleic acids.

Terminators for use in accordance with the present disclosure include any terminator of transcription described herein or known to one of ordinary skill in the art. Examples of terminators include, without limitation, the termination sequences of genes such as, for example, the bovine growth hormone terminator, and viral termination sequences such as, for example, the SV40 terminator, spy, yejM, secG-leuU, thrLABC, rrnB T1, hisLGDCBHAFI, metZWV, rrnC, xapR, aspA and arcA terminator. In some embodiments, the termination signal may be a sequence that cannot be transcribed or translated, such as those resulting from a sequence truncation.

A large number of different genetic circuits may be constructed using different genetic elements. The different genetic circuits of a genetic system may be included in one or more (e.g., 2, 3, 4, 5, 6, 7, 8, 9, 10, or more) nucleic acid molecules (e.g., HSV-1 vectors) and introduced into a cell. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., *Green and Sambrook, Molecular Cloning*, A Laboratory Manual, 2012, Cold Spring Harbor Press).

In some embodiments, the genetic circuits are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

In some embodiments, the genetic circuit encodes an output molecule. An "output molecule" is a molecule that is produced by the genetic circuit in response to the detection of a specific input signal. The output molecule may be, e.g., without limitation, a detectable molecule, a therapeutic molecule, a diagnostic molecule, a functional molecule, a HSV-1 viral protein, or a molecule that inhibits innate immune response (also referred to herein as "an inhibitor of innate immune response").

A "detectable molecule" refers to a molecule that has a signal that can be detected. In some embodiments, a detectable molecule is a fluorescent molecule, e.g., is a fluorescent protein or fluorescent RNA. A fluorescent protein is a protein that emits a fluorescent light when exposed to a light source at an appropriate wavelength (e.g., light in the blue or ultraviolet range). Suitable fluorescent proteins that may be used in accordance with the present disclosure include, without limitation, eGFP, eYFP, eCFP, mKate2, mCherry, mPlum, mGrape2, mRaspberry, mGrape1, mStrawberry, mTangerine, mBanana, and mHoneydew. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used as an output molecule in the sensor circuit of the present disclosure include, without limitation, Spinach and Broccoli (e.g., as described in Paige et al., *Science* Vol. 333, Issue 6042, pp. 642-646, 2011, incorporated herein by reference). In some embodiments, a detectable molecule is an enzyme that hydrolyzes an substrate to produce a detectable signal (e.g., a chemiluminescent signal). Such enzymes include, without limitation, beta-galactosidase (encoded by LacZ), horseradish peroxidase, or luciferase. In some embodiments, the output molecule is a fluorescent RNA. Detectable molecules may be used for diagnostic purposes and these detectable molecules are also referred to as "diagnostic molecules."

In some embodiments, the output molecule is a therapeutic molecule. A "therapeutic molecule" is a molecule that has therapeutic effects on a disease or condition, and may be used to treat a diseases or condition. Therapeutic molecules of the present disclosure may be nucleic acid-based or protein or polypeptide-based.

In some embodiments, nucleic acid-based therapeutic molecule may be an RNA interference (RNAi) molecule (e.g., a microRNA, siRNA, or shRNA) or an nucleic acid enzyme (e.g., a ribozyme). An "RNA interference (RNAi) is a biological process in which RNA molecules inhibit gene expression or translation, by neutralizing targeted mRNA molecules. In some embodiments, the output molecule is a microRNA, a small interfering RNA (siRNA), or a short hairpin RNA (shRNA) that inhibits the expression of a component of the innate immune response. A "microRNA" is a small non-coding RNA molecule (containing about 22 nucleotides) that functions in RNA silencing and post-transcriptional regulation of gene expression. A "siRNA" is a commonly used RNA interference (RNAi) tool for inducing short-term silencing of protein coding genes. siRNA is a synthetic RNA duplex designed to specifically target a particular mRNA for degradation. A "shRNA" an artificial RNA molecule with a tight hairpin turn that can be used to silence target gene expression via RNA interference (RNAi).

RNAi molecules and there use in silencing gene expression are familiar to those skilled in the art. In some embodiments, the RNAi molecule targets an oncogene. An oncogene is a gene that in certain circumstances can transform a cell into a tumor cell. An oncogene may be a gene encoding a growth factor or mitogen (e.g., c-Sis), a receptor tyrosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPase (e.g., Ras), or a transcription factor (e.g., Myc). One skilled in the art is familiar with genes that may be targeted for the treatment of cancer.

In some embodiments, nucleic acid-based therapeutic molecule may be a guide RNA (gRNA). A "guide RNA" herein refers to a fusion of a CRISPR-targeting RNA (crRNA) and a trans-activation crRNA (tracrRNA), providing both targeting specificity and scaffolding/binding ability for Cas9 nuclease. A "crRNA" is a bacterial RNA that confers target specificity and requires tracrRNA to bind to Cas9. A "tracrRNA" is a bacterial RNA that links the crRNA to the Cas9 nuclease and typically can bind any crRNA. The sequence specificity of a Cas DNA-binding protein is determined by gRNAs, which have nucleotide base-pairing complementarity to target DNA sequences. The native gRNA comprises a 20 nucleotide (nt) Specificity Determining Sequence (SDS), which specifies the DNA sequence to be targeted, and is immediately followed by a 80 nt scaffold sequence, which associates the gRNA with Cas9. In some embodiments, an SDS of the present disclosure has a length of 15 to 100 nucleotides, or more. For example, an SDS may have a length of 15 to 90, 15 to 85, 15 to 80, 15 to 75, 15 to 70, 15 to 65, 15 to 60, 15 to 55, 15 to 50, 15 to 45, 15 to 40, 15 to 35, 15 to 30, or 15 to 20 nucleotides. In some embodiments, the SDS is 20 nucleotides long. For example, the SDS may be 15, 16, 17, 18, 19, 20, 21, 22, 23, 24, or 25 nucleotides long. Guide RNAs are used in conjunction with RNA-guided nucleases (e.g., Cas9 nuclease and its orthologues) to target the RNA-guided nuclease to a target site. As such, when the nucleic acid-based therapeutic molecule is a gRNA, the RNA-guided nuclease is also provided (e.g., also encoded by the genetic circuit, or provided on a co-transfected plasmid).

Non-limiting examples of protein or polypeptide-based therapeutic molecules include enzymes, regulatory proteins (e.g., immuno-regulatory proteins), antigens, antibodies or antibody fragments, and structural proteins. In some embodiments, the protein or polypeptide-based therapeutic molecules are for cancer therapy.

Suitable enzymes (for operably linking to a synthetic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase,), esterases (e.g. sterol esterase), disaccharidases (e.g., sucrase, lactase, beta-galactosidase, maltase, isomaltase), DNases, and RNases.

Non-limiting examples of antibodies and fragments thereof include: bevacizumab (AVASTIN®), trastuzumab (HERCEPTIN®), alemtuzumab (CAMPATH®, indicated for B cell chronic lymphocytic leukemia,), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-C5, IOR-T6 (anti-CD1), IOR EGF/R3, celogovab (ONCOSCINT® OV103), epratuzumab (LYMPHOCIDE®), pemtumomab (THERAGYN®), Gliomab-H (indicated for brain cancer, melanoma). In some embodiments, the antibody is an antibody that inhibits an immune check point protein, e.g., an anti-PD-1 antibody such as pembrolizumab (KEYTRUDA®) or nivolumab (OPDIVO®), or an anti-CTLA-4 antibody such as ipilimumab (YERVOY®). Other antibodies and antibody fragments may be operably linked to a synthetic promoter, as provided herein.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1. Other transcription factors may be operably linked to a synthetic promoter, as provided herein.

As used herein, an immunoregulatory protein is a protein that regulates an immune response. Non-limiting examples of immunoregulatory include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunoregulatory proteins may be operably linked to a synthetic promoter, as provided herein.

As used herein, an antigen is a molecule or part of a molecule that is bound by the antigen-binding site of an antibody. In some embodiments, an antigen is a molecule or moiety that, when administered to or expression in the cells of a subject, activates or increases the production of antibodies that specifically bind the antigen. Antigens of pathogens are well known to those of skill in the art and include, but are not limited to parts (e.g., coats, capsules, cell walls, flagella, fimbriae, and toxins) of bacteria, viruses, and other microorganisms. Examples of antigens that may be used in accordance with the disclosure include, without limitation, cancer antigens, self-antigens, microbial antigens, allergens and environmental antigens. Other antigens may be operably linked to a synthetic promoter, as provided herein.

In some embodiments, the antigen of the present disclosure is a cancer antigen. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-C5. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS 1, α-fetoprotein, E-cadherin, α-catenin, β-catenin, γ-catenin, p120ctn, gp100Pmel117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, Imp-1, P1A, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, CD20 and c-erbB-2. Other cancer antigens may be operably linked to a synthetic promoter, as provided herein.

In some embodiments, the therapeutic molecule is an anti-cancer agent. In some embodiments, the anti-cancer agent is an oligonucleotide (e.g., therapeutic RNAi, antagomir, etc.) or a polypeptide (e.g., an antibody). Antibodies that are used for treating cancer are known to those skilled in the art. For example, the anti-cancer agent may be an immune checkpoint inhibitor. An "immune checkpoint" is a protein in the immune system that either enhances an immune response signal (co-stimulatory molecules) or reduces an immune response signal. Many cancers protect themselves from the immune system by exploiting the inhibitory immune checkpoint proteins to inhibit the T cell signal. Exemplary inhibitory checkpoint proteins include, without limitation, Cytotoxic T-Lymphocyte-Associated protein 4 (CTLA-4), Programmed Death 1 receptor (PD-1), T-cell Immunoglobulin domain and Mucin domain 3 (TIM3), Lymphocyte Activation Gene-3 (LAG3), V-set domain-containing T-cell activation inhibitor 1 (VTVN1 or B7-H4), Cluster of Differentiation 276 (CD276 or B7-H3), B and T Lymphocyte Attenuator (BTLA), Galectin-9 (GAL9), Checkpoint kinase 1 (Chk1), Adenosine A2A receptor (A2aR), Indoleamine 2,3-dioxygenase (IDO), Killer-cell Immunoglobulin-like Receptor (KIR), Lymphocyte Activation Gene-3 (LAG3), and V-domain Ig suppressor of T cell activation (VISTA).

Some of these immune checkpoint proteins need their cognate binding partners, or ligands, for their immune inhibitory activity. For example, A2AR is the receptor of adenosine A2A and binding of A2A to A2AR activates a negative immune feedback loop. As another example, PD-1 associates with its two ligands, PD-L1 and PD-L2, to down regulate the immune system by preventing the activation of T-cells. PD-1 promotes the programmed cell death of antigen specific T-cells in lymph nodes and simultaneously reduces programmed cell death of suppressor T cells, thus achieving its immune inhibitory function. As yet another example, CTLA4 is present on the surface of T cells, and when bound to its binding partner CD80 or CD86 on the surface of antigen-present cells (APCs), it transmits an inhibitory signal to T cells, thereby reducing the immune response.

An "immune checkpoint inhibitor" is a molecule that prevents or weakens the activity of an immune checkpoint protein, For example, an immune checkpoint inhibitor may inhibit the binding of the immune checkpoint protein to its cognate binding partner, e.g., PD-1, CTLA-4, or A2aR. In some embodiments, the immune checkpoint inhibitor is a small molecule. In some embodiments, the immune checkpoint inhibitors is a nucleic acid aptamer (e.g., a siRNA targeting any one of the immune checkpoint proteins). In some embodiments, the immune checkpoint inhibitor is a recombinant protein. In some embodiments, the immune checkpoint inhibitor is an antibody. In some embodiments, the antibody comprises an anti-CTLA-4, anti-PD-1, anti-PD-L, anti-TIM3, anti-LAG3, anti-B7-H3, anti-B7-H4, anti-BTLA, anti-GAL9, anti-Chk, anti-A2aR, anti-IDO, anti-KIR, anti-LAG3, anti-VISTA antibody, or a combination of any two or more of the foregoing antibodies. In some embodiments, the immune checkpoint inhibitor is a monoclonal antibody. In some embodiments, the immune checkpoint inhibitor comprises anti-PD1, anti-PD-L1, anti-CTLA-4, or a combination of any two or more of the foregoing antibodies. For example, the anti-PD-1 antibody is pembrolizumab (KEYTRUDA®) or nivolumab (OPDIVO®) and the anti-CTLA-4 antibody is ipilimumab (YERVOY®). Thus, in some embodiments, the immune checkpoint inhibitor comprises pembrolizumab, nivolumab, ipilimumab, or any combination of two or more of the foregoing antibodies.

In some embodiments, a protein or polypeptide-based therapeutic molecule is a fusion protein. A fusion protein is a protein comprising two heterologous proteins, protein domains, or protein fragments, that are covalently bound to each other, either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

In some embodiments, the output molecule is a functional molecule. A "function molecule" refers to a molecule that is able to interact with other molecules or circuits to exert a function (e.g., transcription regulation, DNA or RNA cleavage, or any enzymatic activities). Exemplary functional molecules include, without limitation, enzymes (e.g., without limitation, nucleases), transcriptional regulators (e.g., without limitation, activators and repressors), RNAi molecules (e.g., without limitation, siRNA, miRNA, shRNA), and antibodies. In some embodiments, the functional molecule is a nuclease (e.g., a site-specific nuclease).

In some embodiments, the output molecule is an HSV-1 viral protein. In some embodiments, the HSV-1 viral protein can be those that are deleted from the modified HSV-1 genome. Their conditional expression from the genetic circuit complements the deletions but would confer less toxicity. In some embodiments, the HSV-1 viral protein is a viral protein that promotes viral DNA replication and viral particle production. While these genes are not deleted, it may be desirable to further provide these proteins in trans to increase the effective concentration of these proteins. Non-limiting examples of HSV-1 viral proteins that may be used as the output molecule include: VP16, ICP0, ICP27, ICP22, ICP47, ICP6, ICP8, and γ34.5 (ICP34.5).

In some embodiments, the output molecule is an inhibitor of innate immune response. For example, the output molecule may be an RNAi molecule that targets an innate immune response component. An "innate immune response" refers to the response by the innate immune system. The innate immune system uses a set of germline-encoded receptors ("pattern recognition receptor" or "PRR") for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism. In some embodiments, the innate immune response elicited by the composition described herein confers heterologous ("non-specific") immunity to a broad range of pathogenic microbes by enhancing innate immune responses to subsequent stimuli, a phenomenon known as "trained immunity", a form of innate memory, e.g., as described in Netea et al. (Trained Immunity: An Ancient Way of Remembering. *Cell Host Microbe.* 2017 Mar. 8; 21(3):297-300, incorporated herein by reference).

The receptors of the innate immune system that recognize PAMPs are called Pattern Recognition Receptors (PRRs). (Janeway et al. (1989) *Cold Spring Harb. Symp. Quant. Biol.* 54: 1-13; Medzhitov et al. (1997) *Curr. Opin. Immunol.* 94: 4-9, incorporated herein by reference). PRRs vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: 1) humoral receptors circulating in the plasma; 2) endocytic receptors expressed on immune-cell surfaces, and 3) signaling receptors that can be expressed either on the cell surface or intracellularly. (Medzhitov et al. (1997) *Curr. Opin. Immunol.* 94: 4-9; Fearon et al. (1996) *Science* 272: 50-3, incorporated herein by reference). Non-limiting examples of PRRs include: toll-like receptors (e.g., TLR2), NOD1/2, RIG-1/MDA-5, C-type lectins, and STING.

Cellular PRRs are expressed on effector cells of the innate immune system, including cells that function as professional antigen-presenting cells (APC) in adaptive immunity. Such effector cells include, but are not limited to, macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, including, without limitation: chemokines, interferons, interleukins, lymphokines, and tumour necrosis factors. This latter function allows efficient mobilization of effector forces to combat the invaders.

Thus, components of the innate immune system that may be targeted include, without limitation, PRRs, chemokines, interferons, interleukins, lymphokines, and tumour necrosis factors. Inhibiting the expression of the components of the innate immune system dampens innate immune response (e.g., by at least 20%, at least 30%, at least 40%, at least 50%, at least 60%, at least 70%, at least 80%, at least 90%, or more).

In some embodiments, the inhibitor of innate immune response is a known viral protein that functions in immune evasion of certain infectious viruses. One non-limiting example of such protein is the Vaccinia B18R protein. Certain miRNA expressed from HSV-1 has also been shown to downregulate the innate immune system. Any known viral proteins that play a role in the immune evasion of viruses may be used in accordance with the present disclosure, e.g., those described in Garcia-Sastre et al., *Cell Host & Microbe*, VOLUME 22, ISSUE 2, P176-184, 2017, incorporated herein by reference).

Other aspects of the present disclosure provide packaging cells comprising the engineered HSV-1 vector described herein. Engineered HSV-1 viral particles are packaged in the packaging cells. For viral particle packaging, the engineered HSV-1 vector is delivered to the packaging cell, e.g., via any methods known to those skilled in the art, such as transfection or electroporation. In some embodiments, the engineered HSV-1 vector is integrated into the genome of the packaging cell (e.g., via recombination).

In some embodiments, the packaging cell is engineered such that it expresses (e.g., transiently or constitutively) a HSV-1 viral protein that is deleted from the modified HSV-1 genome or a HSV-1 viral protein that enhances viral replication and viral particle packaging. For example, plasmids comprising nucleotide sequence encoding these HSV-1 viral proteins can be co-transfected with the engineered HSV-1 vector and the expression of the HSV-1 viral proteins can be placed under the control of inducible promoters. Non-limiting examples of HSV-1 viral proteins that may be used as the output molecule include: VP16, ICP0, ICP27, ICP22, ICP47, ICP6, ICP8, and γ34.5 (ICP34.5). In some embodiments, the packaging cell is engineered such that it expresses (e.g., transiently or constitutively) an inhibitor of the innate immune response. Any of the inhibitors of the innate immune response described herein or known in the art can be used.

In some embodiments, the packaging cell produces at least 1 plaque forming units (pfu) of HSV-1 viral particles. For example, the packaging cell may produce at least 1, at least 10, at least 100, at least 1000, at least $10^4$, at least $10^5$, or more pfu of HSV-1 viral particles. In some embodiments, the packaging cell produces about 1, about 10, about 100, about 1000, about $10^4$, about $10^5$, or more pfu of HSV-1 viral particles. "About" means within 3%, e.g., 3% more or 3% less.

Any cells suitable for viral particle packaging may be used as the packaging cell of the present disclosure. In some embodiments, the packaging cell is an eukaryotic cell. Examples of eukaryotic cells for use in accordance with the invention include, without limitation, mammalian cells, insect cells, yeast cells (e.g., *Saccharomyces cerevisiae*) and plant cells. In some embodiments, the eukaryotic cells are from a vertebrate animal. In some embodiments, the cell is a mammalian cell. In some embodiments, the cell is a human cell. In some embodiments, the cell is from a rodent, such as a mouse or a rat. Examples of vertebrate cells for use in accordance with the present disclosure include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used. Typically, it is preferably to use cell lines that have high transfection efficiency and low innate immune response for high viral titer production. In some embodiments, the packaging cell is a U2OS cell (ATCC® HTB-96™).

The engineered HSV-1 viral particle comprising the engineered HSV-1 vector described herein or produced by the packaging cell described herein are also provided. The engineered HSV-1 particle can be used in various applications, e.g., for delivering a genetic circuit into a cell and for other therapeutic and diagnostic purposes. Thus, methods of delivering a genetic circuit into a cell are provided, the method comprising contacting the cell with the HSV-1 vector or the engineered HSV-1 viral particle described herein, wherein the engineered HSV-1 vector comprises a genetic circuit. The contacting may be in vitro, in vivo, or ex vivo. The cell may be an eukaryotic cell. In some embodiments, the cell is a mammalian cell such as a human cell. The cell may be isolated from a human subject and contacting may be in vitro or ex vivo. The cell may be in a human subject and the contacting is in vivo.

Other aspects of the present disclosure provide methods of treating a disease, the method comprising administering an effective amount of the engineered HSV-1 viral particle a subject in need thereof, wherein the engineered HSV-1 vector comprises a genetic circuit encoding a therapeutic molecule. Methods of diagnosing a disease are also provided, the method comprising administering an effective amount of the engineered HSV-1 viral particle to a subject in need thereof, wherein the engineered HSV-1 vector comprises a genetic circuit encoding a diagnostic molecule.

In some embodiments, the engineered HSV-1 viral particle does not induce an immune response in the subject or induces a lower immune response (e.g., at least 20%, at least 30%, at least 40%, at least 50%, at least 60%, at least 70%, at least 80%, at least 90%, at least 95%, or at least 99% lower), compared to a natural HSV-1 particle in the subject. An immune response may be measured by any methods known in the art, e.g., by measuring the antibody titers against the engineered HSV-1 viral particle, measuring cytokine production or T cell activation in the subject upon administering the engineered HSV-1 viral particle.

In some embodiments, the engineered HSV-1 infects cells in the subject and delivers the genetic circuit to cells in the subject. Depending on the type of genetic circuit that is delivered and the state of the cell (e.g., gene expression profile, such as microRNA profile) in the subject, the output molecule (e.g., diagnostic molecule or therapeutic molecule) may be produced, indicating a disease state or providing therapy to the subject having a disease.

In some embodiments, the engineered HSV-1 viral particle may be formulated in a composition for administering to a subject. In some embodiments, the composition is a pharmaceutical composition. In some embodiments, the composition further comprises additional agents (e.g. for specific delivery, increasing half-life, or other therapeutic agents). In some embodiments, the composition further comprises a pharmaceutically acceptable carrier. The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" is a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

Some examples of materials which can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as peptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

An "effective amount" refers to the amount of the engineered HSV-1 viral particle or composition comprising such required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a disorder. Alternatively, sustained continuous release formulations of agent may be appropriate. Various formulations and devices for achieving sustained release are known in the art.

An effective amount of the engineered HSV-1 viral particle or composition comprising such may be administered repeatedly to a subject (e.g., 2, 3, 4, 5, 6, 7, 8, 9, 10 times or more). In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the agents used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the agent (such as the half-life of the agent, and other considerations well known in the art).

For the purpose of the present disclosure, the appropriate dosage of the engineered HSV-1 viral particle or compositions comprising such as described herein will depend on the specific agent (or compositions thereof) employed, the formulation and route of administration, the type and severity of the disorder, previous therapy, the subject's clinical history and response to the agents, and the discretion of the attending physician. Typically the clinician will administer an agent until a dosage is reached that achieves the desired result. Administration can be continuous or intermittent, depending, for example, upon the recipient's physiological condition, and other factors known to skilled practitioners. The administration of an agent may be essentially continuous over a preselected period of time or may be in a series of spaced dose, e.g., either before, during, or after developing a disorder.

A "subject" refers to human and non-human animals, such as apes, monkeys, horses, cattle, sheep, goats, dogs, cats, rabbits, guinea pigs, rodents (e.g., rats, and mice). In one embodiment, the subject is human. In some embodiments, the subject is an experimental animal or animal substitute as a disease model. A "subject in need thereof" refers to a subject who has or is at risk of a disease or disorder (e.g., cancer).

The engineered HSV-1 viral particle or a composition comprising such may be delivered to a subject (e.g., a mammalian subject, such as a human subject) by any in vivo delivery method known in the art. For example, the engineered HSV-1 viral particle or a composition comprising such may be delivered intravenously. In some embodiments, engineered nucleic acids are delivered in a delivery vehicle (e.g., non-liposomal nanoparticle or liposome). In some embodiments, the engineered HSV-1 viral particle or a composition comprise such is delivered systemically to a subject having a cancer or other disease and produces a therapeutic molecule specifically in cancer cells or diseased cells of the subject. In some embodiments, the engineered HSV-1 viral particle or a composition comprising such is delivered locally to a site of the disease or disorder (e.g., site of cancer).

Various diseases may be treated using the compositions and methods described herein. In some embodiments, the disease is a disease that can be treated by gene therapy. One skilled in the art is familiar with such diseases. In some embodiments, the disease is cancer. In some embodiments, the disease is cachexia.

Non-limiting examples of cancers that may be treated using the compositions and methods described herein include: premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer.

In some embodiments, the tumor is a melanoma, carcinoma, sarcoma, or lymphoma. In some embodiments, the cancer is breast cancer, glioblastoma, pancreatic cancer, prostate cancer, or lung cancer.

EXAMPLES

Viral agents have a plethora of therapeutic and biotechnology applications. Traditional molecular biology techniques have expanded the utility of viruses by introducing modifications for therapeutic gene delivery, increased safety, and tropism for target cells. To date, modified viruses based on adenovirus, vaccinia, and herpesvirus (HSV-1) have been approved for use in humans.

However, delivery of complex genetic circuits remain a challenge. Described herein are engineered Herpes Simplex Virus-1 (HSV-1) vectors suitable for delivery of large (e.g., up to 100 kb), complex genetic circuits both in vitro and in vivo. The delivery platform was designed to utilize a library of standardized genetic elements and a workflow based on efficient molecular biology methods for rapid and modular construction of prototypes. The library includes therapeutic genes, promoters and repressors for transcriptional control, insulators, polyA sequences, and biosensors (including microRNAs and environment-sensitive promoters) for construction of transcription units capable of constitutive or conditional gene expression. Circuits are built by incorporating multiple transcription units into the platform with layered cascades of transcriptional regulation to achieve logic-based control of an output. As demonstrated herein, a multiple miRNA input classifier that is capable of sensing four miRNAs (1 high and 3 low), processing information, and conditionally expressing an output was successfully delivered using the engineered HSV-1 vector.

Example 1. Engineered HSV-1 Vectors

HSV-1 proteins are known to upregulate minimal CMV promoter, which is one of several minimal promoters used in engineered promoters (e.g., as described in Herrlinger et al., J Gene Med. 2000 September-October; 2(5):379-89, incorporated herein by reference). HSV-1 proteins are also known to cause cell death. HSV-1 deletion mutants were generated in order to identify mutants that have less circuit interference and less toxicity. HSV-1 Strains F, 17, and KOS were used for the study. Whose genome of selected HSV-1 strains are cloned into bacterial artificial chromosome (BAC) and modified by lambda red recombination. Their replication efficiency was measured in a prototype packaging cell line. Top candidates were selected and a classifier circuit was integrated to characterize circuit behavior as well as cytotoxicity.

TABLE 2

List of HSV-1 variants (41 variants, Strain F variants not listed here)

| Clone | Helper plasmid used for modification | Description of helper plasmid | Description of modification |
|---|---|---|---|
| MD301 | pBjh3763 | SKI-attB-attP21-UL3/4 for KOS | Insertion of attBxB1 and attP21 Double LP between UL3 and UL4 |
| MD302 | pBjh3776 | SKI-attP21-UL3/4 for KOS | Insertion of attP21 LP between UL3 and UL4 |
| MD303 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
| MD305 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
| MD306 | pBjh3776 | SKI-attP21-UL3/4 for KOS | Insertion of attP21 LP between UL3 and UL4 |
|  | pBjh3791 | SKI-beginning KOS | Deletion of γ34.5, LAT, ICP0 |
| MD307 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
| MD308 | pBjh3776 | SKI-attP21-UL3/4 for KOS | Insertion of attP21 LP between UL3 and UL4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
| MD309 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
| MD310 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |

TABLE 2-continued

List of HSV-1 variants (41 variants, Strain F variants not listed here)

| Clone | Helper plasmid used for modification | Description of helper plasmid | Description of modification |
|---|---|---|---|
| MD311 | pBjh3776 | SKI-attP21-UL3/4 for KOS | Insertion of attP21 LP between UL3 and UL4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |
| MD312 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |
| MD313 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3808 | SKI-V422 | Truncation of VP16 at $422^{nd}$ amino acid |
| MD314 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3792 | SKI-ICP27 KOS | Deletion of ICP27 |
| MD316 | pBjh3776 | SKI-attP21-UL3/4 for KOS | Insertion of attP21 LP between UL3 and UL4 |
|  | pBjh3791 | SKI-beginning KOS | Deletion of γ34.5, LAT, ICP0 |
|  | pBjh3788 | SKI-ICP4 KOS | Deletion of ICP4 |
| MD317 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3787 | SKI-VP16 KOS | Deletion of VP16 |
| MD318 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |
|  | pBjh4,010 | SKI_UL37 | Deletion of all except pac, oriS, BAC (first half) |
| MD319 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |
|  | pBjh4,010 | SKI_UL37 | Insertion of 10 attB LP array and deletion of all except pac, oriS, BAC (first half) |
|  | pBjh4,009 | SKI_UL38 | Insertion of 10 attB LP array and deletion of all except pac, oriS, BAC (second half) |
| MD320 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh4025 | SKI_SynPolyAFWD-attB2-4arrayREV-SV40PAREV-UL4 | Replacement of attP21 LP with attB2, attB3, and attB4 triple LPs between UL3 and UL4 |

TABLE 2-continued

List of HSV-1 variants (41 variants, Strain F variants not listed here)

| Clone | Helper plasmid used for modification | Description of helper plasmid | Description of modification |
|---|---|---|---|
| MD322 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |
|  | pBjh4025 | SKI_SynPolyAFWD-attB2-4arrayREV-SV40PAREV-UL4 | Replacement of attP21 LP with attB2, attB3, and attB4 triple LPs between UL3 and UL4 |
| MD323 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3808 | SKI-V422 | Truncation of VP16 at $422^{nd}$ amino acid |
|  | pBjh4025 | SKI_SynPolyAFWD-attB2-4arrayREV-SV40PAREV-UL4 | Replacement of attP21 LP with attB2, attB3, and attB4 triple LPs between UL3 and UL4 |
| MD325 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |
|  | pBjh5143 | SKI_synthPA_attB2_PhiC31attB (from pBjh4010) |  |
| MD326 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3789 | SKI-IR v2 KOS | Deletion of γ34.5, LAT, ICP0 |
|  | pBjh3808 | SKI-V422 | Truncation of VP16 at $422^{nd}$ amino acid |
|  | pBjh5143 | SKI_synthPA_attB2_PhiC31attB (from pBjh4010) | Replacing 10 attB LP array with attB2 single LP and LoxP sites with PhiC31 attB/P (first half) |
|  | pBjh5144 | SKI_synthPA_PhiC31attP (from pBjh4009) | Replacing 10 attB LP array with attB2 single LP and LoxP sites with PhiC31 attB/P (second half) |
| MD327 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh5243 | JH751F_attB2_attP13_SpecR_attB13 in S1-2 | Insertion of attB2 LP between CTRL1 and CTRL2 |
| MD328 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3808 | SKI-V422 | Truncation of VP16 at $422^{nd}$ amino acid |
|  | pBjh5243 | JH751F_attB2_attP13_SpecR_attB13 in S1-2 | Insertion of attB2 LP between CTRL1 and CTRL2 |
| MD329 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh5243 | JH751F_attB2_attP13_SpecR_attB13 in S1-2 | Insertion of attB2 LP between CTRL1 and CTRL2 |
| MD330 | pBjh3763 | SKI-attB-attP21-UL3/4 for KOS | Insertion of attBxB1 and attP21 Double LP between UL3 and UL4 |
|  | pBjh3788 | SKI-ICP4 KOS | Deletion of ICP4 |
|  | pBjh3788 | SKI-ICP4 KOS | Deletion of ICP4 |
|  | pBjh3791 | SKI-beginning KOS | Deletion of γ34.5, LAT, ICP0 |
|  | pBjh3808 | SKI-V422 | Truncation of VP16 at $422^{nd}$ amino acid |
|  | pBjh5243 | JH751F_attB2_attP13_SpecR_attB13 in S1-2 | Insertion of attB2 LP between CTRL1 and CTRL2 |
|  | pBjh5311 | ICP0 only | Deletion of ICP0 |

TABLE 2-continued

List of HSV-1 variants (41 variants, Strain F variants not listed here)

| Clone | Helper plasmid used for modification | Description of helper plasmid | Description of modification |
|---|---|---|---|
| MD331 | pBjh3763 | SKI-attB-attP21-UL3/4 for KOS | Insertion of attBxB1 and attP21 Double LP between UL3 and UL4 |
| | pBjh3788 | SKI-ICP4 KOS | Deletion of ICP4 |
| | pBjh3788 | SKI-ICP4 KOS | Deletion of ICP4 |
| | pBjh3791 | SKI-beginning KOS | Deletion of γ34.5, LAT, ICP0 |
| | pBjh5243 | JH751F__attB2__attP13__SpecR__attB13 in S1-2 | Insertion of attB2 LP between CTRL1 and CTRL2 |
| | pBjh3808 | SKI-V422 | Truncation of VP16 at 422$^{nd}$ amino acid |
| MD332 | pBjh3763 | SKI-attB-attP21-UL3/4 for KOS | Insertion of attBxB1 and attP21 Double LP between UL3 and UL4 |
| | pBjh3788 | SKI-ICP4 KOS | Deletion of ICP4 |
| | pBjh3788 | SKI-ICP4 KOS | Deletion of ICP4 |
| | pBjh5243 | JH751F__attB2__attP13__SpecR__attB13 in S1-2 | Insertion of attB2 LP between CTRL1 and CTRL2 |
| | pBjh3808 | SKI-V422 | Truncation of VP16 at 422$^{nd}$ amino acid |
| MD333 | pBjh3763 | SKI-attB-attP21-UL3/4 for KOS | Insertion of attBxB1 and attP21 Double LP between UL3 and UL4 |
| | pBjh3788 | SKI-ICP4 KOS | Deletion of ICP4 |
| | pBjh3788 | SKI-ICP4 KOS | Deletion of ICP4 |
| | pBjh5243 | JH751F__attB2__attP13__SpecR__attB13 in S1-2 | Insertion of attB2 LP between CTRL1 and CTRL2 |
| | pBjh3808 | SKI-V422 | Truncation of VP16 at 422$^{nd}$ amino acid |
| | pBjh5311 | ICP0 only | Deletion of ICP0 |
| MD334 | pBjh3763 | SKI-attB-attP21-UL3/4 for KOS | Insertion of attBxB1 and attP21 Double LP between UL3 and UL4 |
| | pBjh3788 | SKI-ICP4 KOS | Deletion of ICP4 |
| | pBjh3788 | SKI-ICP4 KOS | Deletion of ICP4 |
| | pBjh5243 | JH751F__attB2__attP13__SpecR__attB13 in S1-2 | Insertion of attB2 LP between CTRL1 and CTRL2 |
| | pBjh3808 | SKI-V422 | Truncation of VP16 at 422$^{nd}$ amino acid |
| | pBjh5311 | ICP0 only | Deletion of ICP0 |
| | pBjh5357 | ICP0 only | Deletion of ICP0 |
| MD101 | pBjh3754 | SKI-attB-attP21-UL3/4 for 17 | Insertion of attBxB1 and attP21 Double LP between UL3 and UL4 |
| MD401 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| MD402 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| | pBjh3760 | SKI-ICP4 from strain 17 | Deletion of ICP4 |
| MD403 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| | pBjh3760 | SKI-ICP4 from strain 17 | Deletion of ICP4 |
| | pBjh3927 | SKI_Beginning Strain 17 | Deletion of γ34.5, LAT, ICP0 |
| MD404 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| | pBjh3760 | SKI-ICP4 from strain 17 | Deletion of ICP4 |
| | pBjh3927 | SKI_Beginning Strain 17 | Deletion of γ34.5, LAT, ICP0 |
| | pBjh5243 | JH751F__attB2__attP13__SpecR__attB13 in S1-2 | Insertion of attB2 LP between CTRL1 and CTRL2 |
| MD405 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| | pBjh3760 | SKI-ICP4 from strain 17 | Deletion of ICP4 |
| | pBjh5243 | JH751F__attB2__attP13__SpecR__attB13 in S1-2 | Insertion of attB2 LP between CTRL1 and CTRL2 |
| MD406 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| | pBjh3760 | SKI-ICP4 from strain 17 | Deletion of ICP4 |
| | pBjh5243 | JH751F__attB2__attP13__SpecR__attB13 in S1-2 | Insertion of attB2 LP between CTRL1 and CTRL2 |
| | pBjh3808 | SKI-V422 | Truncation of VP16 at 422$^{nd}$ amino acid |
| MD407 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| | pBjh3760 | SKI-ICP4 from strain 17 | Deletion of ICP4 |
| | pBjh3927 | SKI_Beginning Strain 17 | Deletion of γ34.5, LAT, ICP0 |
| | pBjh5243 | JH751F__attB2__attP13__SpecR__attB13 in S1-2 | Insertion of attB2 LP between CTRL1 and CTRL2 |
| | pBjh3808 | SKI-V422 | Truncation of VP16 at 422$^{nd}$ amino acid |

TABLE 2-continued

List of HSV-1 variants (41 variants, Strain F variants not listed here)

| Clone | Helper plasmid used for modification | Description of helper plasmid | Description of modification |
|---|---|---|---|
| MD408 | pBjh3754 | SKI-attB-attP21-UL3/4 for 17 | Insertion of attBxB1 and attP21 Double LP between UL3 and UL4 |
|  | pBjh3760 | SKI-ICP4 from strain 17 | Deletion of ICP4 |
|  | pBjh3760 | SKI-ICP4 from strain 17 | Deletion of ICP4 |
|  | pBjh3927 | SKI_Beginning Strain 17 | Deletion of γ34.5, LAT, ICP0 |
|  | pBjh5243 | JH751F_attB2_attP13_SpecR_attB13 in S1-2 | Insertion of attB2 LP between CTRL1 and CTRL2 |
|  | pBjh3808 | SKI-V422 | Truncation of VP16 at $422^{nd}$ amino acid |
|  | pBjh5311 | ICP0 only | Deletion of ICP0 |
| MD409 | pBjh3754 | SKI-attB-attP21-UL3/4 for 17 | Insertion of attBxB1 and attP21 Double LP between UL3 and UL4 |
|  | pBjh3760 | SKI-ICP4 from strain 17 | Deletion of ICP4 |
|  | pBjh3760 | SKI-ICP4 from strain 17 | Deletion of ICP4 |
|  | pBjh5243 | JH751F_attB2_attP13_SpecR_attB13 in S1-2 | Insertion of attB2 LP between CTRL1 and CTRL2 |
|  | pBjh3808 | SKI-V422 | Truncation of VP16 at $422^{nd}$ amino acid |
|  | pBjh5311 | ICP0 only | Deletion of ICP0 |
| MD410 | pBjh3754 | SKI-attB-attP21-UL3/4 for 17 | Insertion of attBxB1 and attP21 Double LP between UL3 and UL4 |
|  | pBjh3760 | SKI-ICP4 from strain 17 | Deletion of ICP4 |
|  | pBjh3760 | SKI-ICP4 from strain 17 | Deletion of ICP4 |
|  | pBjh5243 | JH751F_attB2_attP13_SpecR_attB13 in S1-2 | Insertion of attB2 LP between CTRL1 and CTRL2 |
|  | pBjh3808 | SKI-V422 | Truncation of VP16 at $422^{nd}$ amino acid |
|  | pBjh5311 | ICP0 only | Deletion of ICP0 |
|  | pBjh5357 | ICP0 only | Deletion of ICP0 |
| MD411 | pBjh3754 | SKI-attB-attP21-UL3/4 for 17 | Insertion of attBxB1 and attP21 Double LP between UL3 and UL4 |
|  | pBjh3760 | SKI-ICP4 from strain 17 | Deletion of ICP4 |
|  | pBjh3760 | SKI-ICP4 from strain 17 | Deletion of ICP4 |
|  | pBjh5243 | JH751F_attB2_attP13_SpecR_attB13 in S1-2 | Insertion of attB2 LP between CTRL1 and CTRL2 |
|  | pBjh3808 | SKI-V422 | Truncation of VP16 at $422^{nd}$ amino acid |
|  | pBjh5525 | SKI_deleting VP16 | Deletion of VP16 |
| MD412 | pBjh3754 | SKI-attB-attP21-UL3/4 for 17 | Insertion of attBxB1 and attP21 Double LP between UL3 and UL4 |
|  | pBjh3760 | SKI-ICP4 from strain 17 | Deletion of ICP4 |
|  | pBjh3760 | SKI-ICP4 from strain 17 | Deletion of ICP4 |
|  | pBjh5243 | JH751F_attB2_attP13_SpecR_attB13 in S1-2 | Insertion of attB2 LP between CTRL1 and CTRL2 |
|  | pBjh3808 | SKI-V422 | Truncation of VP16 at $422^{nd}$ amino acid |
|  | pBjh5311 | ICP0 only | Deletion of ICP0 |
|  | pBjh5525 | SKI_deleting VP16 | Deletion of VP16 |
| MD413 | pBjh3754 | SKI-attB-attP21-UL3/4 for 17 | Insertion of attBxB1 and attP21 Double LP between UL3 and UL4 |
|  | pBjh3760 | SKI-ICP4 from strain 17 | Deletion of ICP4 |
|  | pBjh3760 | SKI-ICP4 from strain 17 | Deletion of ICP4 |
|  | pBjh5243 | JH751F_attB2_attP13_SpecR_attB13 in S1-2 | Insertion of attB2 LP between CTRL1 and CTRL2 |
|  | pBjh3808 | SKI-V422 | Truncation of VP16 at $422^{nd}$ amino acid |
|  | pBjh5311 | ICP0 only | Deletion of ICP0 |
|  | pBjh5357 | ICP0 only | Deletion of ICP0 |
|  | pBjh5525 | SKI_deleting VP16 | Deletion of VP16 |
| MD417* | pBjh3754 | SKI-attB-attP21-UL3/4 for 17 | Insertion of attBxB1 and attP21 Double LP between UL3 and UL4 |
|  | pBjh3760 | SKI-ICP4 from strain 17 | Deletion of ICP4 |
|  | pBjh3760 | SKI-ICP4 from strain 17 | Deletion of ICP4 |
|  | pBjh5243 | JH751F_attB2_attP13_SpecR_attB13 in S1-2 | Insertion of attB2 LP between CTRL1 and CTRL2 |
|  | pBjh3808 | SKI-V422 | Truncation of VP16 at $422^{nd}$ amino acid |
|  | pBjh5311 | ICP0 only | Deletion of ICP0 |
|  | pBjh5357 | ICP0 only | Deletion of ICP0 |
|  | pBjh5357 | ICP0 only | Deletion of LAT and ICP34.5 (one copy each) |

TABLE 2-continued

List of HSV-1 variants (41 variants, Strain F variants not listed here)

| Clone | Helper plasmid used for modification | Description of helper plasmid | Description of modification |
|---|---|---|---|
| MD418 | pBjh3754 | SKI-attB-attP21-UL3/4 for 17 | Insertion of attBxB1 and attP21 Double LP between UL3 and UL4 |
| | pBjh3760 | SKI-ICP4 from strain 17 | Deletion of ICP4 |
| | pBjh3760 | SKI-ICP4 from strain 17 | Deletion of ICP4 |
| | pBjh5243 | JH751F_attB2_attP13_SpecR_attB13 in S1-2 | Insertion of attB2 LP between CTRL1 and CTRL2 |
| | pBjh3808 | SKI-V422 | Truncation of VP16 at $422^{nd}$ amino acid |
| | pBjh5311 | ICP0 only | Deletion of ICP0 |
| | pBjh5357 | ICP0 only | Deletion of ICP0 |
| | pBjh5525 | SKI_deleting VP16 | Deletion of VP16 |
| | pBjh5357 | ICP0 only | Deletion of LAT and ICP34.5 (one copy each) |

*MD300 series: Strain KOS
*MD101 and 400 series: Strain 17

Nucleotide sequence of MD417

(SEQ ID NO: 1)

```
gcccgccgccgccgctttaaagggccgcgcgcgaccccgggggggtgtgttttgggggggcccgttttcggggtctggccgctcctcccc ccgctcctcccccgctcctcccccgctcctcccccgctcctcccccgctcctcccccgctcctcccccgctcctcccccgctcc tcccccgctcctcccccgctcctcccccgctcctcccccgctcctcccccgctcctcccccgctcctcccccgctcctcccccc gctcctcccccgctcctcccccgctcccgcggccccgccccccacgcccgccgcgcgcgcacgccgcccggaccgccgcccgcctttt tttgcgcgcgcgcgcccgcgggggcccgggctgccacaggtgaaaccaacagagcacggcgcactccgcacgtcacacgtcacgtcat ccaccacacctgcccaacaacacaactcacagcgacaactcaccgcgcaacaactcctgttcctcatccacacgtcaccgcgcacctcccg ctcctccagacgtaccccggcgcaacacaccgctcctgctacacaccaccgcccctcccagccccagccctccccggcccagccctccc cggcccagccctccccggcccagccctccccggcccagccctccccggcccagccctccccggcccagccctccccggcccagcc ctccccggccgcgtcccgcgctccctcggggggttcgggcatctctacctcagtgccgccaatctcaggtcagagatccaaaccctccgg gggcgcccgcgcaccaccaccgcccctcgcccctcccgcccctcgcccctcccgcccctcgcccctcccgcccctcgcccctcccgc ccctcgcccctcccgcccctcgcccctcccgcccctcgcccctcccgcccctcgcccctcccgcccctcgcccctcccgcccctcg ccccctcccgcccctcgcccctcccgcccctcgcccctcccgcccctcgcccctcccgcccctcgcccctcccgcccctcgcccct cccgcccctcgcccctcccgcccctcgcccctcccgcccctcgcccctcccgcccctcgcccctcccgcccctcgaataaacaacgc tactgcaaaacttaatcaggttgttgccgtttattgcgtcttcgggtctcacaagcgccccgccccgtcccggcccgttaCTCACGTTAAG GGATTTTGGgcttgttctccgacgccatcgccgatgcggggcgatcctccggggatacggctgcgacggcggacgtagcacggtaggtcac ctacggactctcgatgggggggaggggcgagacccacggaccccgacgaccccgccgtcgacgcggaactagcgcggaccggtcgatgct tgggtgggaaaaaggacagggacggccgatcccctcccgcgcttcgtccgcgtatcggcgtcccggcgcggcgagcgtctgacggtctgt ctctggcggtcccgcgtcggtcgtggatccgtgtcggcagccgcgctccgtgtggacgatcggggcgtcctcgggctcatatagtcccag gggccggcgggaaggaggagcagcggaggccgccggccccccgccccccggcgggccacccgaacggaattccattatgcacgacccc gccccgacgccggcacgccgggggcccgtggccgcggcccgttggtcgaaccccggccccgcccatccgcgccatctgccatgggcgggg cgcgagggcgggtgggtccgcgccccgccccgcatggcatctcattaccccgatccggcggtttccgcttccgttccgcatgctaacga ggaacgggcaggggggcgggccccgggccccgacttcccggttcggcggtaatgagatacgagcccgcgcgcccgttggccgtcccggc ccccggtcccgcccgccggacgccgggaccaacgggacggcgggcggcccaagggccgcccgccttgccgcccccccattggccggcggg cgggaccgccccaagggggcggggccgccgggtaaaagaagtgagaacgcgaagcgttcgcacttcgtcccaatatatatatattagg gcgaagtgcgagcactggcgccgtgcccgactccgcgccggccccgggggcgggcccggcggcgggggcgggtctctccggcgcacata aaggcccggcgcgaccgacgcccgcagacggcgccggccacgaacgacgggagcggctgcggagcacgcggaccgggagcgggagtcgcag agggccgtcggagcggacgcgtcggcatcgcgacgccccggctcgggatcgggatcgcatcggaaagggacacgcggacgcgggggggaa
```

-continued

```
agacccgcccaccccacccacgaaacacaggggacgcaccccggggggcctccgacgacagaaacccaccggtccgccttttttgcacgggt aagcaccttgggtgggcggaggagggggggacgcgggggcggaggagggggggacgcgggggcggaggagggggggacgcgggggcggaggag gggggacgcgggggcggaggaggggggacgcgggggcggaggagggggctcacccgcgttcgtgccttcccgcaggaggaacgtcctcgtc gaggcgaccggcggcgaccgttgcgtggaccgcttcctgctcgtcggggggggagcatgtcgtgggccctggaaatggcggacaccttcctg gacaccatgcgggtttgggcccaggacgtacgccgacgtacgcgatgagatcaataaaaggggggcgtgaggaccgggaggcggccagaaccg ccgtgcacgacccggagcgtccccttgctgcgctctcccgggctgctgcccgaaatcgcccccaacgcatccttgggtgtggcacatcgaag aaccggcgggaccgtgaccgacagtccccgtaatccggtaacccgttgagtcccgggtacgaccatcacccgagtctctgggcggagggtg gttccccccgtggctctcgagatgagccagacccaacccccggcccccagttgggcgggcgacccagatgtttacttaaaaggcgtgccg tccgccggcatgcaccccagaggtgttcacgcacctcgaggacacccgcgcatgatctccggaccccccgcaacggggtgataatgatcaag cggcggggcaatgtggagattcggtctactacgagtcggtgcggacactacgatctcgaagccatctgaagccgtccgaccgccaacaat ccccaggacaccgcgtgttccccgggagcccccgggttccgcgaccaccccgagaacctagggaacccagagtaccgcgagctcccagagac cccagggtaccgcgtgaccccagggatccacgacaacccggtctcccaggagccccggtctcccgggagccccggtctcccgggagc cccggaccccacgcaccccccgcgaaccacgtacggctcgcgggtctgtatagccccgggcaagtatgccccctggcgagcccagacccct tctcccacaacatggagcatacgctcgggccccgcgtcgggatccacaccgcggttcgcgtcccgcccaccggaagcccaacccacacgca cttgcggcaagacccgggcgatgagccaacctcggatgactcagggctctaccctctggacgcccgggcgcttgcgcacctggtgatgttg cccgcggaccaccgggccttctttcgaaccgtggtcgaggtgtctcgcatgtgcgctgcaaacgtgcgcgatccccgcccccggctacag gggccatgttgggccgccacgcgcggctggtccacacccagtggctccgggccaaccaagagacgtcgcccctgtgccctggcggacggc ggccattaactttatcaccaccatggccccccgcgtccaaacccaccgacacatgcacgacctgttgatggcctgtgctttctggtgctgt ctgacacacgcatcgacgtgttcgtacgcggggctgtactcgacccactgcctgcatctgtttggtgcgtttgggtgtggggacccggccc taaccccaccccttgtgctagggcaatttgtacccttaataaattttacaaacagattttatcgcatcgtgtcttattgcggggagaaaac cgatgtcggcatagaaaaccgccatgattctaagacgtccgaacgcgagtgggtggggaacaacccataccggacagatgccgatgagcca cccgcaccccttgggtgcgggtggtacggggtggtttgttcatcctatggttccgaccccacaaacagcccccagagtcggtttgggtatgg ttacattttctgtctggtggtcgggcttgtttcttccttgccactccccacccaccccactccccacccaccccactccccacccaccccactc cccacccaccccactccccacccaccccactccccacccaccccactccccacccaccccactccccacccaccccactccccacccaccccactcc ccacccaccccaaaaatcaaccgggagacaacattgccaatcgaacccaatttaatgtagttaaaggctgggtgcaaattgcgggtgatgg gggggaagagagacgacaagaaggacgcgcgtgtcgatgcggtcttttagcggagcagccacatcaggagcgccccaaatccgcccgacag aacggccacgaggagacaggcgatcaccatgccgacgcagcgggtgcgtctgcgtcgacgccttaataccgactgttggcggcccatgcgt acgaggaagtcgttggccgcctcgtcttcgctttccgagtagtaggcttcgaccgaaactggcgaggccgtgggataaagcggcacggaca tgtcggatcgcgctgaggagttgggatcggagagccgggacgtcatcgaggccgaagaaagctccgggtgggaagttgcggtcgctgtga ctcacgatttttaatttgctgcggctaggcggaccaccggcccctttatgcgcctcgggcaattgacgtcacataccacgcaatcccacaca ggacggcccccaggccggaagcccccggagccaccgagcggccagccaggcgacaaacagggaggggcgtcgacagcctggagggccat cggggagacaacggccgtgtagcccggggggtcgcgggtgtggcgagggcgcggtcgacgtggcgagggcgggcggtcatgtcgggggggt ccgcgttcgtcggaaatcgcgattagctcgtctccgacgtccacctcgccgcggtcgcccagttcggcgaccgacgtgggggcctcgggat ggggcgccttaccagaagacggacgaatcggaggcctgggagtaacggcgatcgggccttccggatccaaaggttgtgagctggcggcgag attgatgcccatcgctacgggggtatacagacggagccgttggtgataagatctcaaagccggatccattggtggagggagagtcgggtct ctccgggggggccagccacgggacctggtcgcgttctccctcgctgtccgagctccagtccgcgtacagctcgctgtcggccacgcgaatg tacgtgggcccttacccgaggccctgcttttaaccgcccgccaggcacgcctgcgccaacaggtcatacacgcccacaccgacaaccca gtgcagacagcagcagggcggcccccatcaccgcccctaaccgcagggcgccgtgggttgggggcgcgtggggaggggcccgacgtgcgg gtgggtgggctcggccaaatccgcgccgcgctgtgggaggggctgttccaccaccgcgttccggtactgcgccgcggtgctgatggtaatg tggccccaggcgtgaatatggtcgttgacgtacaccacacagatacaggccgagtgttgtggggacgcgtcccggaactccagattga cggaggccgcctgccacgccagccccgggacgggctccatgtgagcctcggccgaacagcgcggtggggggtttgttctggaacaccccgc
```

-continued gtagctgcggacggccaggcgagacgtccacgtactcgcggcgcacggcgcgtcggccggggacagacattctgggagctgcgggtgatac agacacgattcgtatattcgcatctcggcacacgaggtcggcacgtcgaacctcaaccagacgacgtccatggagtaggtctggtcgtcgt gggcgatggcatggatggagacgttcgtgctgaacgtctccccgggggaaaacaggatagcttccggagtctccatacgcacggtcaccccc acgcacatgtgagacttcggggggcgctgggccaagacctcgggggggcgggggaggcgggagccggggggtcccgctggcgggagtgccg gcgagactttcgtcctcgccctcgtcattgtcatcctcgtcgtaatcggctggggtcggggtggggtcggaactggggccggttgcacca ccaggaccaccgaggccacttggcgagccgggtcctttatgtcgcccacggacagggtatacaggccgctgtccgtctctcggaccccgtg aataaccagactccggttaaccacggccgcgcgctcctgccacacgaagtccgttcgtagaccccggtcgcagatggggccgggggggcg tacgccatcgccagcgggaccggagcgcgcatgcacgccgcatccacgaccgtctcgggcacctgcttgggggcatcagcgagacccacg acgggtgtaaggggccgcacccatccaggggttccacggcccatagtagtttctgggtcgggccgcgccccgtaggccccggagctggaag caacgaaacgtcctcgccgacactcacccgtctccaggacgttttgggcgttcccgccaagcacgatacaacacaaacaccgagaagaaac cccaccaccgccccgcgatccatgtcccggggatagcagccgatcttcgggtaaaatgggagcccaacaaacagcaccgcaccaacccgcc agaagaggcaaagtcaacacaacaacgccttaaatgcgccgcgggccctctccccggcttcctgaactcctcccatccattctttgcttcc ttctttggtttccggggagggggggaaagaaatcgacatacacggatataggtaaataataccggtttattcccaactcagggactgcggt cggttatgtggtgctcccggccagtggccgtggacctataccaacaggggaggcgttgggtgggtgtcgtggggtccacgggggcgtcg gaagcccagccgccccagcgggctccgactcttcggcgatggccgtcagggagggcattggcgtgcgtgacgaccggcgccgggatttggg gggggtgctcggatgcgatttgagctcggctccgaggcgggccatggccgcttcgttcaccgcgcatgagatgcccgtgggcatctgggggg ctgtaaatcgggcgacgggagcgtcggtagcggcgttgacatctgtgtataaagcaaatacagctccccagaaacaccagggctatgatgg acgcggggatggctatctggattatctgggtcaccgttagcgcgtatcgcgagtcgcgggtcgctcgcgtggcattagatgggggttcgtg gttgaccccggggaggttgtggttttggatctcccgtggggaagggcgtggtcgatgcttggggagcggggatggtggtcgagggagcgggg atggtggtcgagggggtggaggtggtggtcgaggggggtggaggcctggttaggggcgggttggtatacgctcgccggggccagacgcgggg ccgaagacggaagcagtttcgggtcgcaggagccataggccgagccgttgtacgccagagtcccttcggcggctatggccatccccaggac aaacaggctggcgtttggcgcgtcaccgacccatacgcgtaacacgtacaccccggcatagtcccgcgttgccctctggacccgcaaaagc ggctgtgggccagattgagctccaggtgggatatgcggggctgtgagtgctgtcggtcgcgcgacacagggcgaatgccacggcggggc gacgtgggcacgcggtcaccgtgacgacatgcacgacccgtgggcatttgtgtcccatggggtagtgccacagctctacgcccccatcgta gtaggtggtgtgggggacctggtcccccacaaagcgaagctcccgagaataagcaggtcttcctccactacgccgtcgggcccaaggcc ccggcgtccacaaatgagtttgataccagactgaccgtggggccacggacaaccaggctggtggcacagacccagaggcccacgagcacca ggccctgcaacgggcggcacggcatcccggaacgggacggttcgcaaaaaaagctgtgggtgcgacaggcggaacaggtgcgcgtcccccg ctaccgacttatcgactgtccacctttccccccttccagactcgctttatatggagttaaggtcccatcccaaccccgcagacctgacccc cccgcacccattaaggggggtatctagtaaaacaagggctggtgcgaggacggctggtcgtcttcccggatgtgggggaggcgtatgcgc tttggggcttttttgagtgtggcggcgcatccagtacacaattccgcaaatgaccagggctgccaggagactgccgcccaccgcgccggcga tcaggcccatgttgttcggggtggccggggatggtaaggcgtcgcggcgtcctggatcgacggtatgtgccagtttggtgggatttgcgg cgccaccgtccccacggggtcctccaagagggccgaatcctcggggtcttccggggcgagttctggctgcgtggcgttgggggtctcggac agctccgggggcagcagggtgctcgtgtatgggccttgggcccgtgccacccggcgatcttcaagctgtatacggcgacggtgcgctggt tctcggggatgaagcggggcagcatcccgatgctgtccaccgtcacccctgctggtaggcctgggggagaggcaggctgacgggggat gcgcagcggagggcgtacttacaggagcccttggctcggtgctccaggataaactgtgtaatctccgtccagtcgtttatcttcacgagc cgcaggtacgtgccggcggtctcaaacgcggggcgtgcatcaggaaccccaggttatcctcgctgacggcgctgaagctgtcatagtagt tccagcggggctgcgttcggatgggacaggcccccagagacttgttgtaggagcattcggtgtactccatgaccgtgatggggatagcaca gttgcctcccatccgaaaccaagcgatggtcaggttgtagggttgtttccggacgtcttcggaggccccgcggacaatctgggggggcctcc gacggtgcgtttaggagcacgctgcggcaggcgcgctccaacacggcgtagtaaaccgtgatcgggaggctggggggctggaacgggtccg gtaggcccgcctggatgtggtacacgcgccggaccccggagggtcggtcagctggtccaggaccggaaggtctttgccgcgaaagcgatt -continued

```
ggggtcggccatcttgagagaggcatccaccaaggcatatttgccgcggaccccatggaggcccactatgacgacaaacaaaatcacggcc cccaacctggcggcagcccccccataccggaacgcaccacacaaaagagaccttaaggataactgatgatcggggtagttggtcgttcgc gctgaagcttatgaccgaacaactccctaacccctgcttttaaagacagactttgttataccccctcctcctcgtaaaatggcccctcccc cttggggattcgtcggtgtggtcggtatggacgatagtgtcacacggccgggctaccgcgatctttattgggggccggggccacggattt cctggttagcccggtgttgttgggtgccctccgcattcgccccccatcccctgccggacatggtttgggggcgcaccggtgatttata ccatgccagctggtggtgtcgggagtttggacccgacatcacccacgcggagaaggggggggggggggaaattatacgacaactgggtcc atgtagggatggtaacgccccacccgcggcacgtacgacgcaggagctcaagcagacatgccgcccccaggactacggcgcacagcccac cgactacgaggggggacggcaaagcccccaggggctggggtgagggggacactgggcgtgcgttaaggggtccgttgtgttggccgcagg tccccgatgggtggcggcaagaacagccccacgaggcttcccaaaagcccagatgccagactgcgcgcagagacatcgcgacacacaga acgccaagtcgtgtgctgtttctccggatagccaggcctggctcagacgtccgttggccgtttcgggtggttctgaggcccggaagtcgc gcatgcttcatgggtcccgggcatgtatttaactgcaccccgtccaatgaccgccccgcgtccgccacaccccaaaaacaccagagatgc atatcaactagataccaccgcctttattgttcttgctttccgcatgtgggctctcccatccccgcccataccctacccgcgttcggac ggcaggcacacgtaacgcacgctagggtgtgtgcgtcgcccgcgtctggaccaaccgccacacaggtgtgtcgccatcgcaccaatacaca aaaacgataaggtgtggatgacggtgctgacgacgaagagggtgtccagggcggggaggcagtgaggaacgagaacagcggggtatgttg aggcgtcggaaccaagggtcgtccctttgaggtgagtcgggtcgtggggcgagttgccagcggcccgataatggtgggggtgtcttcggg cgactggtctcggggcgcgcggggagttgttgggatcggggatggggactacgggacggttgggtttgtccttctcgacgtcctcagcca acgggaaggctgggcccggggactggggtagggtgtcacgggtcccatctccccctcaagatgttcgccgtccccggcccctcctcctc ttcctcctcctccagtccaatacttggcatgggggggtgtgtggtcgggcgtggtaaggctgatggcggtgggagagtcggtggtgccggtc tgggtcatgttgggggcttcatgcgagggacgaccggtggtctggagttgggggttgggtggtggaggagacgttggtgggaaccccgata caccgacaagaaccaaaaggaatgggataatgggaacaacggcacgcatggcgccctgcgacatgatgccaaaaacaccacagacgcggat cggggtcttttttgtgccaacccgcaaacagcaccgcccccagggggcggtcatttctgttgaaacagcggcaaacaaagcagctctgcggc gctggggcgaagcgcgccgtcgaaggtgagggcttttgcaaaccagatattcgacgtctatgtccatcttgtagtagcgggtccaggccggt cgggtgtacggcgggcgattgttcccggccgcgcgggagcggtagcgcgaggtgaggcgcgattctggatgcggggaaaactcgtcaacgt ggacctgggcctgtcggatgatgcgggtgatctgactgtcgcacgggcccctttgggccgcgggggggccgagaacaaggacgcgttgtg gacgcagtctcgaagatcaccagaccggcgctccaaatgtcgacggtcgtggtatacggatccccggccaggacctcggggggcgttggtg tcgatggttccggcgattccgtaggggaaggggcttgatcgggaaccctgcacgaagcacgcggcgccaaagtcccccaggcaaatgtcct cgggggtgttaataaaaatatttttcggtcttaatgtcgcggtggataatgccctggcggtgaatgtagtcaacggcgcttaggagctgccg ggagaccgctgcgatctgcgggcgtcccagtgggttcaggcgcctactcagataggtatacaggtcggcctggtacttggggaggaccaga cacgtgaccccggagacgacatgcaggtccaggaggggcaggatcgccgggtggtccagtcgcctcagcagtcgcgcctcgtggctcgtgc tcgtgtaccaccccgccttcacgattacccgttgggggtaatctggatggctgctgtcaaagacacaccccctccgatcctggggtgagcgc tccgtggatcgtaaagcccatgccagtcaccagcttggccatggtcgagggggcttgccgccgcggctgatggctcgagccgcctccctg tccatggcgtccagctcttccgcggtaaatcccgtggccccaatctcatcccggctgcgtcgtcgtataccgggggggagatgcgccacacg ggggagggatggtcgttggccccgataaggggaccggtcgcgtcccgggcagaaaaagctcctctgcgtattcctccggataggccac gtcgtccggggcgtcctcgtcgacatcgtccgcggcatccgcgctggggtcgtcctctatggggtagtcctggtttccgtacatctgggca aggatctcctgcagatgacacaggcgctcggcctcgctgggtggtgtggtgtgggaaggtttgggggtctccgggggcggggagtccaggc acgcgtcctcggctggggtataaaaggggccatgaggaaacaccccgggacggctttgtctccggcgggacggcctcctcttcctcctgcc ctgtcccccgtaaacgcgacaaaacttacgacaggccattcgccgcaccgtgagtgccaaccaacgagcaccccgaacgacgggcccggg gttttaaggagcggcagtttgacgaccacccctgacctaccccccgtaaatcaccctcccctcccccggacgcctccgctgccggtcg ctccaagggccccccggggaaggcgggtctgtggaccgtagggcccttaaattttttagagcagccccgcgtcggcctgtctccccgccgt gcgtggccttacaaatctgcaagtgccccaaatcggacacgggcctgtaatataccaacatgggcgttgttgtcgtcaacgtaatgaccct ccttgaccagaacaacgccctgccccggacttccgtcgacgcaagcccggccctgtggagcttcctgcttaggcagtgccgcattttggca
```

-continued

```
tcagaacccctgggtacccggtcgtcgttcgtccggccaaccttcgacggttggccgagccgctgatggacttacccaaacccacccgcc
cgatcgtgcgcactaggtcctgtcgctgcccccaaacaccaccacgggcctgtttgcggaggacagccccttggagagcaccgaggtcgt
ggacgccgtggcgtgcttccgactgctgcaccgagaccaacccagccccctcgcctctaccacttgtgggtggtaggcgcggcggatctg
tgtgtgccgtttctcgaatacgcccaaaaaatccggctcggggtaagatttatcgccatcaagaccccagacgcgtgggtgggagaaccgt
gggccgtgccgactcggttttttgcccgagtggaccgtggcgtggacccgttccccgcggccccaaccaccccctggagaccctgctcag
ccggtacgaataccagtacggcgtggtactgcccgggacaaacgacgggagcgcgattgtatgcgctggctgcggtccctgattgctctg
cacaaaccccacccagctaccccaggccccttacgacgtcccatccggtgcggcgtccgtgttgtgcgtgtatgggcatgcccgaggtcc
cagacgagcaacccacatcgccgggccgtggtccgcaagaaactgaccctctgatcgccgttcgcggcgaacggccccgacttcctcacat
ctgctatccggttaccacccttagccccggtgccaataaaccccaaacaccccccatgtccgcgtggtctgtttctctccgcccttcc
cgccattaagacgctgggacaaacgctttgattttggtcttttattttggggacatacaagggggtcggggcgaccggactcacggccgga
gaaacgtgtcgctgcacggatagggcaggcggtggagaagcgcattttccggcagccgtccagacacttgcggtcttctgcggcgcgacc
cgccccagaatcggatgggcccgggcgttccacggagctggtatcggccacgaccgcagacagccagggctgggagccctcctgggggtc
cagtcaaactccccaaactcatcctccagacgcacagcgagggacccgcggggttctggggtttccagcgtaacggggagggggcatcct
ccgtgtcggactgggacgcgagcgtgtggtccgaaccggcggcctccagatcggtggcatcggagatttcatcatcgcttgtcgcgctgag
atgaatctcgagattactaagatcacactccgggccgtaccgtctggtctccaaacaaggaagcttgcacacgggttccgcggtggcgtcg
aatcgagcctccacctcccgtatggtgttgcgcaggtgcatgccccaggttccgccggacacctgcagcaaacggcaccacgtgcgcgggg
ccagacgggctcggcagtatcccatcaggtaacagtcgcgtatcaggtggcgcaggcggttggcactgccgtgggggtcccgggcgacccg
caggacccgaaacagctgattgatacactggcgcatgtagcccaggtcggggtccatcgtgcgctgctccgcctctgggcctggcgcacc
gagcgccgtagcattgcatttgggcttggggccgacggggtgggggcccggggctgcgtttcccgggtagaccggacccgccccatcttag
gaaaaataaccccatcccgccgatcgggagagctcgtgagccgcaggtttacccgggcccgcttgggtcgtgggggaatgtcgtcataaga
ccagtcggacgtgtcgtcggggtcgtccgacaccgacgcatccgtttccgtccccgtggtggattccgccgacatgtccagaaaaaaccgc
cccccaagcctccgggggggccctacggccaccgatgcgggggcttcatcctggtcccagactcggtcgaatccgatgctgtctcggatt
cgacctcagactccaaggctgtatcggattctacctcagactccgatgagaggggcgggaagggcgcttgcgcttgcgcgtgcccagggg
cggggatcggagagcgggacgccgcgcttttacacaaggcgcaaaagcgcctggggaaatgtcggccatccagaaaacgtcccggaggacc
acagtggcttccccccgcccgacgagcaggaagcggtccacgcaacggtcgccgccggtcgcctcgacgaggacgttcctcctgcgggaag
gcacgaacgcgggtgagcccctcctccgccccgcgtccccctcctccgccccgcgtcccctcctccgccccgcgtccccctcc
tccgccccgcgtcccctcctccgccccgcgtcccccctcctccgcccacccaaggtgcttacccgtgcaaaaaaggcggaccggtg
ggtttctgtcgtcggaggccccggggtgcgtcccctgtgtttcgtgggtggggtgggcgggtctttccccccgcgtccgcgtgtccctt
tccgatgcgatcccgatcccgagccggggcgtcgcgatgccgacgccgtccgctccgacggccctctgcgactcccgctcccggtccgcgt
gctccgcagccgctcccgtcgttcgtggccggcgccgtctgcgggcgtcggtcgcgccgggccttttatgtgcgccggagagacccgccccc
cgccgcccgggcccgccccggggccggcgcgagtcgggcacggcgccagtgctcgcacttcgccctaataatatatatatattgggacg
aagtgcgaacgcttcgcgttctcacttcttttacccggcggccccgccccttggggcggtcccgcccgccggccaatgggggggcggcaa
ggcgggcggcccttgggccgcccgccgtcccgttggtcccggcgtccggcggcgggaccggggggcccggggacggccaacgggcgcgcg
gggctcgtatctcattaccgccgaaccggaagtcggggcccgggccccgcccctgcccgttcctcgttagcatgcggaacggaagcgga
aaccgccggatcggcggtaatgagatgccatgcggggcgggcgcggacccacccgccctcgcccccgcccatgcagatggcgcggat
gggcggggccgggggttcgaccaacgggccgcgcggccacgggccccggcgtgccggcgtcgggcgggtcgtgcataatggaattccgtt
cggggtgggcccgccgggggggcgggggccggcggcctccgctgctcctccttcccgccggcccctgggactatatgagcccgaggacgc
cccgatcgtccacacggagcgcggctgccgacacggatccacgacccgacgcgggaccgccagagacagaccgtcagacgctcgccgcgcc
gggacgccgatacgcggacgaagcgcgggaggggggatcggccgtccctgtccttttttcccacccaagcatcgaccggtccgcgctagttcc
gcgtcgacggcgggggtcgtcggggtccgtgggtctcgcccctcccccatcgagagtccgtaggtgacctaccgtgctacgtccgccgt
```

-continued

```
cgcagccgtatccccggaggatcgccccgcatcggcgatggcgtcggagaacaagcCCAAAATCCCTTAACGTGAGtaacgggccgggacg
gggcggggcgcttgtgagacccgaagacgcaataaacggcaacaacctgattaagttttgcagtagcgttgtttattcgaggggcgggagg
gggcgaggggcgggaggggcgaggggcgggaggggcgagggcgggaggggcgagggcgggaggggcgagggcgggaggggcga
ggggcgggaggggcgagggcgggaggggcgagggcgggaggggcgagggcgggaggggcgagggcgggaggggcgagggcg
ggaggggcgagggcgggaggggcgagggcgggaggggcgagggcgggaggggcgagggcgggaggggcgagggcgggaggg
ggcgagggcgggaggggcgagggcgggaggggcgagggcggtggtggtgcgcgggcgcccccggagggtttggatctctgacctga
gattggcggcactgaggtagagatgcccgaaccccccgagggagcgcgggacgcggccggggagggctggggccggggagggctggggcc
ggggagggctggggccggggagggctggggccggggagggctggggccggggagggctggggccggggagggctggggccggggagggctg
gggctggggagggcggtggtgtgtagcaggagcggtgtgttgcgccggggtacgtctggaggagcgggaggtgcgcggtgacgtgtggat
gaggaacaggagttgttgcgcggtgagttgtcgctgtgagttgtgttgttgggcaggtgtggtggatgacgtgacgtgtgacgtgcggagt
gcgccgtgctctgttggtttcacctgtggcagcccggccccccgcgggcgcgcgcgcgcaaaaaaggcgggcggcggtccgggcggcg
tgcgcgcgcggcgggcgtggggggcggggccgcgggagcgggggaggagcgggggaggagcgggggaggagcgggggaggagcgg
ggggaggagcgggggaggagcgggggaggagcgggggaggagcgggggaggagcgggggaggagcgggggaggagcgggggagg
agcgggggaggagcgggggaggagcgggggaggagcgggggaggagcgggggaggagcgggggaggagcggccagaccccgaaaa
cgggccccccaaaacacaccccggggtcgcgcgcggcccttaaagcggcggcggcgggcagcccgggccccccgcggccgagact
agcgagttagacaggcaagcactactcgcctctgcacgcacatgcttgcctgtcaaactctaccaccccggcacgctctctgtctccatgg
cccgccgccgccatcgcggccccgccgccccggccgcccgggcccacgggcgccgtcccaaccgcacagtcccaggtaacCTCACG
TTAAGGGATTTTGGAGTTGAAATATGTTTACTAATAAGACTTTATGGGTAGGGGCATCTGGGAATCTGCAAAATCCATCTCAGATCCTTCC
GTATTTAcagccgttctgcgtgtctgttcttgcgtgtggctgggggcttatatgtgggtcccggggcgggatggggtttagcggcgggg
ggcggcgcgccggacggggcgctggagataacggcccccggggaacggggggaccggggctgggtatcccgaggtgggtgggtgggcggcgg
tggccgggccgggccgggccgggccgggccggtgggcgggtttggaaaaacgaggaggaggaggagaaggcggggggggggagacggg
gggaaagcaaggacacggcccgggggggtgggagcgcgggccgggccgctcgtaagagccgcgacccggccgccggggagcgttgtcgccgt
cggtctgccggccccgtccctccctttttttgaccaaccagcgccccccccctcaccaccattcctactaccaccaccaccaccac
cgacacctcccgcgcaccccgcccacatccccccccaacccgcaccaccagcacgggttgggggtagcaggggatcaagggggggcaaag
ccggcggggcggttcggggggggggggggggcgggagaccaagtaggcccgcccatccgcggcccctcccggcagccacgccccagcg
tcgggtgtcacggggaaagagcagaggggagaggggagagggggggagaggggagagggggggagaggggagagggggggagaggggagag
ggggggagaggggagagggggggagaggggagaggggggagaggggagagggggggagaggggagagggggggagaggggagaggggggg
agagggagagggggggagagggagccagttagattgcatgtgatcgttgggaatgaccccgggggttataaaaggcgcgtcccgtggac
gcggccctcggttgggcgacgcatgccagcccaacaaaatccgccggggtgccagtcccattcccgaaggcgtagcccgttaacttggctg
gcttggatggggagtagggccttttccattaccccaaggacctagcgcgcgggagtcgtggctttggggcgcatccatgcttcggaggcg
gcgcaacccgacgcgggtttatggagcgcggggaacgcgtttgctgatccccgcccccctacgatagcttgtctggtaggaacgaggggc
cgtttgtcgttattgatctggacaccccacggacccacctccaccgtactctgctgggcccctgttgtccgtgccaattccgccaacctc
ctccggagagggcgaggcgtcggagcggggccgctcacgccaagccgcccagcgagccgctcggcgcgcccggcgccgcgccgaacgacgt
gcgcagcgccggagttttggccctggcgggttattggcaaccccctgtttcttccggaaaccaggcttgtggccccacccgacatcacaa
gggacctcttgtcgggcctcccgacgtacgccgaggctatgtcggaccaccccccaacctatgccactgtcgtggccgttcgttcgaccga
acagccgtccggggctttggcgcccgacgaccagcgacgaacgcaaaactcgggcgcgtggcggcctcctagggtcaattcgcgcgagctg
tacagggcccaacgcgcggcgcgcggctcgtctgatcatgccccataccggcgacagggctgttgtggcgtggtgtggcgccatgctgtat
ttggggtggtcgcgattgtggtggtcattattctggtattcctgtggcggtaagcgcccctgtgagttaataaataaaagtatcacggtcc
atactggcctgtcgcgttgtctctgagggctttgggtccacaaactcacaccacgcctggtttggttgggttacggctctttatttttttg
ggggggggttacacacattcatgggggggttggagatcacgccttaattttaatcttgacgcgtcgatgctctgccgcgcgggcggccatgc
cgctggagctgatggagcgcaggtgctgtagggccgcggaggcccccatccagcatgttttttgagaacggataccgacagtggcagtggta
```

-continued cacgatcccgtttatcgtgtactctcccgccgaggacgcgccggacccagagacgtccttaatcgtcccgacgctaaacggccgcgcacac cgcagccgcaccccgcgcttatcctccagttcgcgtaggaccggcgggtggttaaccaggtccgcaaagttgcggagctcggtaatcagcg gagggtgtggtgggtgtccttgtataccgcaaagaaaaagcagtggattgtgccgctggtctcacaggaggcgcggaccaggtaactccg cacggccacgcaagcggagtccgttttgctggtgtgcatggccgtttcggcctgccaggtggcgttgaggcagtaagggggggcacgtgg gttatgtccggggcccgtaagaacaggttggtgagggggtcgctgtcatagtgcaaaggggggatgcgcccgggcgggaagctcctaag ggcactatgacaccggccttggaacggggacggatttatacgttgggttagttccctccgcccacccaggccgtacgccgggcccacccc gccatctgccgtgacccacgccccgccggccatgagcaaagaaggacaacacgaggggcgatttgtttgaaatgttttgttttattgtac ctaaaacagggagttgcaataaaaatatttgccgtgcacgtacgggggggcgacgatgtgactggccgtcaactcgcagacacgactcgaa cactcctggcggtgcgtgtctaggatttcgatcaggcccgccatgcaggccccggggaggtagaaatgcatcttctctccgaccccgacac caagggtcgcgtagtcgatctccgcgacgccacgctcgacgcggttggcgagcctggccagaatgacaaacacgaaggatgcaatgtcctt aatgtccgccagacgccgccgcgaacacagttcgtccaggccgcacaggcctcgcgccttcaggtagcactggagaaagggccgcaggcgc gtggcgaggttatccagcacagccgcggccgtcccgataatgggtcctgggggcgcagcggcaggttgtggtggatgcacatcttgcacc acggccagcgtctcgtcggcggaggccagcgcctcgatgaaattttcttggcgcagcacgcagtcgcgcatggccttggcggtcgatgcggc ccgaggattgccggcaaaagtgcgatagaggctcgggccgtgggcgaccaaggtttcccaggagaccgtctggtctcggcgtcaaaggggc cctccttggcccgccagcaccggggcccaggggctattcgcggcgggaaacggctgccccccaaagggggtcgtgcatgacctgtgcgctgc ggccaaagctctcgctgatgcggtcgaccgccgcgcgctcggagatggagcgcaggaccaaccgcgtggtggcgtcgatggtgtcggcggc gggcgcctttcgctccggggccggggcgcggggtccgcgggcggggggcaatcgccagcgtcattagcggggggggtgcttggcgcacg ccccgtgtccgctggcctccgggtgggtcgggctgctcactgccgcgccacgcctcgccatgggggcgccggggccgtccgtccacccccg ccccggggcggggtcccccaggggttgcgattggttctgggggcacgccggcggggtccgacaaaccatcggcagccccgggaccaccgcg accccgaccccctgcgacgcccacggcgtccgccgcgggcaggctgggctttggtcggtgggggttggaggcgggccaccttgccccgtgc tgctcgggggagcaagacggtcgccgggccccgaggcgcgaccacacactgtggggcgctggttgaggatcgttgggccctgccgctccg tcggacgaggcgtctgggtgctgggtacgccgggtcttctggacgagacgggcggaccgccgggcgagcggcgtcgagtatcggctccgg tccgtcctctccgtgggggtcttccatgtcctcgtccgacgaggaacactccccgctgctgtccgattccaggtcgtcgcggcggctctcc gccggctcggggggtcctcgtccagatcgctgtcggagaggtccaggccgaggtcaattagcatatcaatgtcagtcgccatgaccgggc tgtcggctgccgtcggggctggggtgtcggatatggcctctggtggtggcgcaccggtagcgagcgaccgggcccgaatcggggagaggca ccgaagcgtgaccgtggttggaacacggctgcacaccaccaccggccgggtggtggatgtccttatacccgtggtgccggggccggctctc ccaaacccctcctcgttccgccccccgggcgggccccgccccacctccggcacagacaaggaccaatcagacaccataagtacgtggca tgtatttaattagcatatcacataccccgttccgcttccgcggggacccgggcggggtggatacgctggctgggttggtcttggtaacgg gacggccaattgggacccatgggcggggtcgttgggatccaggctacacgtggcctcgggggaccgattttcatttgcatatgacgcgtcg ggtgggtgggccccaagacaggacagtttccaatttgcatatgccgttacggtttccgccggcctggatgtgacgtcatacatcaaacagg cgcctctggatctcctgctcgtagtgaagcgccacgagcaccaccccggccaccacggcgatataacacaatcgcactgcgatcccgaga ggatgatggaacagcagcgcccgcagacgcccgacagccccttggatcgccccggggcggcggccttgtctgcgttcttgggggccgggcc ccgccgcagaatacaatacagctctgtcaggccgatggtggagacaaaacaccaggtggtgatggtcagaaacaggggtatgtgatcgca catgcccccgggatatgaaagcggtgccgacgatgagacccacggccacaaagcgtagcatcaactcgcagcctacgatgaccccgatgg cggggcggtggtacaagaaggtgaccgggtccgtctcaaacaactgaaccaggttttgccgctggaccgacagctcgcagagcaggcgggt aattttcgtgtaggggtactgcaggaacacgctcgatacgatgcggcctgcgtagttcaagaggtaggtggccggggccaccatcttgtgg gcgggactcacgacgccaaacatacatcggcgttggtggagggcgacgaacgccagatacaggaaccaccctacgaccaccagacgcaccc gtgtgtaccatagggtctccagacagttaactgcctcgtggacgttcatgatccgacgattcatggcgtcaggtgggacctggaagggcac gacccctacccgcgataagattggcgtagcagatatgggcgtggttgcgcagccccgttgggggggtgcgtcggggcccccagaaacaat agggtctggttcattttcatccacacgagggcggtgtcgttgttggtgccggtggggcgtaccgcgtaaatacatcggtgcagcggactgg -continued

```
caccgaagacggtgtaccacacgagcacgaggccgtacgccgttatcaagacgacggttgagaggtgctgcagggaacggacggcgagcat
ggcgtgccggccgtcaatggtaaacagcgtgtgcaggcggttgctgtcgcatttggcggcaaagcactgctgacacaaggacacgcacaggc
ggttgttggccccgacgctcagcgcgacgaatgtccgcgccgtggcgcgactcgcccggccgtgcttaaagcgcagacacgacaggctttg
ctgcagggtaccgcgaacgggactagctgtaggaggacccagtcgtccttactgacggcccgccggacggatacggcctgatattcgccg
gcgtgttcgggaaagtgggtttcgatgcacgcgactatccgccccagcagttccgatgcgaacccctcgacggtccccccgcatccggct
gtacgttgtaccgacccaggacctccgtcagggtctcgcgtcgcccaaagtgttccagcgcgttgcgggacgccttcctttcaaagaagct
cacatagtccccacccaggctgtgcaggacacggatctcccgggggaagcgagataggtgggcgggcgtgaaaatggaagcgccgcggg
tcggcgtgcgcggcgacaaacgccggaacgtctttgcaggcgggggggatcacaaacactggcagcagccttccgcacgcaggcccgtcgg
gggcgattttggcaaaatacggcaagcgcaggctgtggccgtgggcgtacaccccgtatcgatcaacaggaagtttttttacgtagctccc
gatggcctccacaaaatctcggtccaacagcaccgcctgctggatgacccgtgccacccccgcatcgttagagaaccgtggacgacgtac
ggggcggggacgggcatgcacacccgcagtccgatcttgtcggtgcaggaacacacggggcgaatccgtttcgcgaggttccgccgtgggc
cgacttcgtggcacaggtcaaagtaggcaacctcgtcgtccgggggatcgtgggatgtgtccatggcgcccgggtcctccgcccactcctc
atcaccggcgtcgtcgtagcagggaaaccagtccccgtcgtcgtcgttgccgagtccgctgccggaacccacggacgccgggccgggccga
catgcgcttttgaaaaaataacagggatatgcgtcggggtccacgcgggccgcgggaaacaggagctgaaccgcagccagagccccgcgcc
taaagtggcccagggcctcgtggagccggcgaaaggggacgggctccttcagggcgatgtcgagatccaggatgatgtttgtgattgccag
cgcgccgttgaatatctcgttgcgattcacgtacatctgcccccggcatccaggccgccaggggcatcacggggccctgggcgcggatg
cgatccgtgagccgcctgcccagcgcgccgtggtcggggtgcgccgccgcttcggcggacacgaccgcttcggccaggcgagcgtcccgcg
ttatgcgggcccagtcgtcccaggccagcgcggcaaatgcctgtcccgtggggaccatggatatccggtagacgggcaggggagtctgcac
cgccgcattacggataagcgccgcgatcgccgggggtgtgggcctgctgttccgtggcggccagtctcaggaggcgcttgacaattccg
caggtctgtggggcggcgtgccgccgccgtgtcctccccgggactggcgggcgcaaacgcgggccacccgcggggaccaggagctttt
cggcgtccgccaaacgcccatcattttggtggcggagtccacgccccgcaatacgcggggcgggcgtcagggccccgggcgcgtacgt
gcgagcgcgcaggtaggccttggccgtatcgccatccaggacggtctcccgggggtcacgttgtgtttgacgtactccccgatattcagt
tgggcgcgcacgtgacaaaaaaattgttccacgcctccctgcccaggggcgagggctgctccgtgctggccgcggggttgggtcgtggg
tcgtcacggcccgaagatgcgtggctaggcgcggggggctgaaacactcaaaatgggccaggtagatgtacgtaatgaattcacggtcgga
cacgcgcaggcaactgcgatcgtgggttatgaacttctccagcgcactggtctcgcggacgtcggccgcaatacggcgctccacgtaaagc
ggaaacccggccgccgcggccccgcgggcgtactggctcgtgcaacagaaccgcgtgatggcggcaaacgaggtcagggacgcagcgctga
cggtgtcggggcggggggcgtgggaatcgcgtaggtggcgcagatgtccttgatggcctgcaggtcgtacgtggccccgcgcccccag
acgctgggcctgaagcaggtagtaccgagtggtgagcaccaggcttttttcgtccggcccgaatttgctaagaaaccagaagggactctgc
gcgcttccataatacgccctgcggtacgcggcaagcacgcgcacctcgtggtggacgtatagcgtggtaaggccgcgttgtcccagggacg
tgcgccccacgagcgagcgtagggacgcgccctgatcatactgcgccgcggcggcgtcgcgtccggtgcgggggctggcgttgttgatggc
cacggtgagagccaggatcatgttcgcatgcagcgcgaacgtggcctccgcgtccagggtggcggcgatgtggtccggttgtagcggggtc
ccgtgcgccagggcgtcctgtagcgcggcgacgtcgtccgctcgctcgaagcgacagacgaacatgggtcgggttcgcccgcgggcctggt
gggtcccacccacttccgtccccaataaacaaaaggttactcggaaggagtcgccatttagcccgcccgacgcttggtagagcgcccgact
ctcttcgaacctgtcttgctccgtgggcccgtcggcacgccatcgtgcgtgtatgcgtcgtagctgaatatataaaccggctcggccccc
agtagagagtttgtgagaagggcgatcgaagaggtaataacgcaccgtcggtcgcataaagcgcggtcacctccacgggagtcccggccg
cccgcctctccccgcggttcccgtcttcctgccccattgcgtccgcgcgcccaagggccagtacccgcccgcgatggcttctcttctcggg
gctatatgtggctggggagcgcgccccgaggaacaatatgagatgatccgcgcggccgttccgccctcggaggcggagccgcggctgcagg
aggccctggcggtcgttaacgcgctacttcccgcccccatcacgctcgatgacgccctggggtccctggacgacacccgacgcctcgtgaa
ggccccgcgccttggcccgcacgtaccacgcctgcatggtgaacctagaacgactggcgcgccaccaccccgggctcgaggccccacgatc
gacggggccgtggcggcccatcaggacaagatgcggcgcctggcggacacgtgtatggccaccatcctgcagatgtacatgtccgtgggg
cggctgacaagtccgcggatgtgctcgtctcccaggctattcggagcatggccgagagtgacgtggtcatggaggatgtggccatcgccga
```

-continued

```
acgggcccttggcctctccgccttcggggttgccggggggaacccggtcggggggggattggggtgaccgaggcgccctccttggggcacccc
cacacgccgcccccggaggttacgctggcgcctgccgcccgaaacggcgacgccctcccggaccccaaaccggaatcgtgtcccgcgtgt
ccgttcccagacctacagcctccccaaccgcacctcgccctggcccatctcgagcagctccgtgtgttttgggtcaataaatgcgtgtttt
catccaacccgtgtgttttgtgtttgtgggatggaggggcgggtgtgatagacccacaggcatccaacataaacaactacacacaggaaag
atgcgatacaaacgttttttattgcccggaacgaacccaaagctgtgggctaaataccggtagagccaaaaccccggtcccgcgctcgct
cggggggggcctccgcgtcaaactcgttcgtaaacaccaggagcggcgggttcctgggttcggcggttgagtccggaacacccctggggtag
tttcgaagcgctttggtcccgtgaaagttgtccgggggggatccaaggaagagcgtccgcccccgcaaccaggagctgggcgaccttggcgc
cggcctcgagggtcacaggaaccccgtaaggttgtaaacaacaaacgcacatacgtgcccggggagccagcgcgtaggaacgaccaggag
gccgcgggcgttgagcgacgaccgccccaacacatagcaggccgcgggcccggcgtccgcgtggagcatgcggagggatggctgcacgacc
gtggtgccgtttgccgggacggtgaccgggcgacggacgacaatgtcgaaaccggcatcctcctcgcgttttggaaggaaggcgatggctt
ctcgtacgccgtccccgtgttccgtctgaaccggcgtcagctcgccggcatagacgagggaccgccctcggcgtcgcgccggtagggccgt
agtcacgcttggggccccgagcgcccccctccaaccaaggatcttcgcgtatcccggcccggttggagggggggcgccagttgcgggaac
tgccgcagggaaatcggctcggtgagggccggggggtcgccaggatgtccaggaacgtcacgtcgacccgcagggtcccgggggcaaatt
cccgcgtccttttaggcgctacgaccacggccataacggttccgcggtaccccgagtcgataagacccagtattacgtggtgcccggggct
ggctagcgcgggggcgtgaataatcgcgcaaaagtcagccggcatagccattcgcaggtccagagagacgcgcccgacggcccatccggag
tccccgctaaccttcggcataaaagccaccgcgcgcctgttgaccaggttcagttgcacgactccgcccccgcgagtagcgacggccgtgt
gccagtcgccatcgtaccccccgacccaagctgtccggctggacaaggatcgccccggatccccactgactcatcttcctgttagggacgat
gggcccccccagaagggtctgtcgggcgggcctgttgtttgtcttgctcgtcgccttagcggcgggagacgcgggcccgcgcggggagccg
cccggcgaggagggcgggcgcgatgggatcgggggcgcgcggtgcgagacccaaaacactggccaaatgtctgccccgggggccctggtgc
cctttatgtaggcatggcctcgatgggcgtgtgtattatcgcacacgtctgtcagatctgccagaggctactggctgccgggcacgcctg
aacccgccctgtgtggggtgaggggtggggtggagggtgtcccaggacttccccttcctcgcggaaaccgagaccgtttggggcgtgtct
gtttcttggcccctggggattggttagacccatggggttgtggttatatgcacttcctataagactctcccccaccgcccacagagggccac
tcacgcatcccccagtgggttttgcggaccctctcttctctcccgggccgcccctatcgctcgacctctccacacctgcaccaccccgccg
tccgaacccaggcctaattgtccgcgcatccgaccctagcgtgttcgtggaaccatgacctctcgccgctccgtgaagtcgggtccgcggg
aggttccgcgcgatgagtacgaggatctgtactacaccccgtcttcaggtatggcgagtcccgatagtccgcctgacacctcccgccgtgg
cgccctacagacacgctcgcgccagaggggcgaggtccgtttcgtccagtacgacgagtcggattatgccctctacggggggctcgtcatcc
gaagacgacgaacaccggaggtcccccgacgcggcgtcccgtttccggggcggttttgtccggcccggggcctgcgcgggcgcctccgc
cacccgctgggtccggaggggccggacgcacacccaccaccgcccccgggccccccgaacccagcgggtggcgactaaggccccgcggc
cccggcggcggagaccaccgcggcaggaaatcggcccagccagaatccgccgcactcccagacgccccgcgtcgacggcgccaacccga
tccaagacaccgcgcaggggctggccagaaagctgcactttagcaccgcccccccaaacccgacgcgccatggaccccccgggtggccg
gctttaacaagcgcgtcttctgcgccgcggtcgggcgcctggcggccatgcatgcccggatggcggcggtccagctctgggacatgtcgcg
tccgcgcacagacgaagacctcaacgaactccttggcatcaccaccatccgcgtgacggtctgcgagggcaaaaacctgcttcagcgcgcc
aacgagttggtgaatccagacgtggtgcaggacgtcgacgcggccacggcgactcgagggcgttctgcgcgtcgcgcccccaccgagcgac
ctcgagcccagcccgctccgcttctcgcccagacggcccgtcgagtgaaaacttccgtacccagacaataaagcaccaacaggggttca
ttcggtgttggcgttgcgtgcctttgtttcccaatccgacggggaccgggactgggtggcggggggtgggttggacagccgcctcggttc
gccttcacgtgacaggagccaatgtggggggaagtcacgaggtacggggcggccgtgcgggttgcttaaatgcgtggtggcgaccacggg
ctgtcattcctcggaacggacggggttcccgctgcccacttcccccataaggtccgtccggtcctctaacgcgtttggggttttctct
tcccgcgccgtcgggcgtcccacactctctgggcgggcgggacgatcgcatcaaaagcccgatatcgtctttcccgtatcaaccccaccc
aatggacctcttggtcgacgagctgttttgccgacatgaacgcggacggcgcttcgccaccgcccccgcccggccgggggtcccaaaaac
accccggcggccccccgctgtacgcaacggggcgcctgagccaggcccagctcatgccctcccacccatgcccgtcccccccgccgccc
```

-continued

```
tctttaaccgtctcctcgacgacttgggctttagcgcggggccccgcgctatgtaccatgctcgatacctggaacgaggatctgttttcggc
gctaccgaccaacgccgacctgtaccgggagtgtaaattcctatcaacgctgcccagcgatgtggtggaatgggggacgcgtacgtcccc
gaacgcacccaaatcgacattcgcgcccacggcgacgtggccttccctacgcttccggccacccgcgacggcctcgggctctactacgaag
cgctctctcgtttcttccacgccgagctacgggcgcggggaggagagctatcgaaccgtgttggccaacttctgctcggccctgtaccggta
cctgcgcgccagcgtccggcagctgcaccgccaggcgcacatgcgcggacgcgatcgcgacctgggagaaatgctgcgcgccacgatcgcg
gacaggtactaccgagagaccgctcgtctggcgcgtgttttgttttttgcatttgtatctatttttgacccgcgagatcctatgggccgcgt
acgccgagcagatgatgcggcccgacctgtttgactgcctctgttgcgacctggagagctggcgtcagttggcgggtctgttccagccctt
catgttcgtcaacggagcgctcaccgtccggggagtgccaatcgaggcccgccggctgcgggagctaaaccacattcgcgagcacctaaac
ctcccgctggtgcgcagcgcggctacggaggagccaggggcgccgttgacgaccctcccaccctgcatggcaaccaggcccgcgcctctg
ggtactttatggtgttgattcgggcgaagttggactcgtattccagcttcacgacctcgccctcgaggcggtcatgcgggaacacgcgta
cagccgcgcgcgtacgaaaaacaattacgggtctaccatcgagggcctgctcgatctcccggacgacgacgcccccgaagaggcggggctg
gcggctccgcgcctgtcctttctccccgcgggacacacgcgcagactgtcgacggccccccgaccgatgtcagcctggggactagggg
cgcgaccggacccgcatccccgtctggttttcccctcccgtcaccggttcgtatccacaataaaacacgagcacatacattacaaaacct
gcggttgtcgtctgattatttggtggtggggaaagaactagccaggagacgggaccgcgcaaccaacccactgggtctgggttgccggc
gtgtgtgttagccgcgtctgcgggcctgtcgtgtagattcgaaaccacggacgggtgattgtgtcgcagggcggcccgcgtataaaggcga
gagcgcgggaccgtttccgcatttggccgggggctggggcggcgggtagccttcgcgggagatactgcgtttttttgcgccggccccgtcg
ctcccgtccattcccatcgcgaggggtccggcggcacctaccccggcctccatccgcgctgtgggtctttttcttttttgggggtagc
ggacatccgataaccccgcgtctatcgccaccatgtcggctcgcgaacccgcggggcgcaggaggcgcgcatccaccgcccccgcgcctcg
cccgtggcggacgagccagcgggcgatggggtggggttcatgggtacctgcgtgcggtgttccgcgggatgacgacagcgagctagagg
ctctggaggagatggcgggcgacgagccgcccgtgcgccgtcgacgggaaggcccgcgagcccgacgacggcgcgcgtcggaagccccgcc
cacatcccatcgccgagcgtcccggcagcgccccgggcccgatgcggcccgtagccagtcggtgcgcggtcgcctggacgatgatgatgag
gttccccgcggtcctccgcaggcccggcagggggatacctgggtcccgtcgacgcgcgggctattttgggggcgggtcggcggttcgcggg
tggcgccgtcgccgctgttcctagaggagctgcagtacgaggaggacgactaccggaagccgtcgggccggaggacggcggcggggcccg
ttccccgcccaaggtggaggttctggagggacgcgtgccgggcccggagctccgggcggcattcccgttggatcgactggcccctcaggtt
gccgtgtgggacgagtccgtgcgctccgccctagccctggggcatccggccgggttttaccgtgtccggatagcgcgttcgggttatcgc
gcgtgggggtcatgcacttcgcctcccccgacaacccccgcggtgttttccgccaaaccctgcagcagggcgaggcgttggcctggtatat
cacgggcgatgggattcttgacctgacggatcgtcgaacaaaaaccagccccgcccaggcgatgagctttttggcggatgccgtcgtgcgg
ctggccatcaacgggtgggtgtgcgggacgcgccttcacgcggaggcgcgcgggtctgacctggacgacagggcggccgagctgaggcggc
agttcgcgagcctcacggcgttgcgtcccgtcggggccgcggccgtgccgttactgagcgcgggggggttagtgtcccccccaatccggccc
cgacgccgcggtgttccgcagctcgctggggtccctgctgtactggcccggggtgcgcgcgctgctggaccgcgactgtcgcgtggccgcc
cgctatgccggccgcatgacgtacctggccaccggggccctgctcgcccgcttcaatcccgacgccgtccggtgcgttttgacgcgggagg
ccgccttcctggggcgcgtgctggatgtgctggccggtgatggcggagcagacggtccagtggctctcggtggtcgtgggggcgcgcctgca
cccgcacgtgcaccaccccgcctttgcggacgtggcgcgggaggagctgtttcgcgccctgcccctgggaagccccgcggtcgtgggggcc
gagcacgaggcgctgggcgacaccgcagcgcgccggctgctcgccaacagcgggctcaacgccgtgctgggcgctgcggtgtacgcgctgc
acacggccctggcgaccgtgaccttaaagtacgcccgggcgtgcggggacgcgcaccggcgccgggacgacgcggcggccacgcgcgccat
tctggccgccgggctcgtcctgcagcggctgctgggctttgccgacaccgtggtggcgtgcgtgacactggccgcgtttgacgggggattc
acggcccccgaggtgggcacgtacaccccccctgcgctacgcgtgcgtcctccgagcgacccagcccctgtacgcgcgcaccaccccgcca
agttctgggcggacgtccgcgcggccgcggagcacgtggatctgcgccccgcctcctcagcgccccgggccccgtgtccgggacggcaga
ccccgcctttcttctcaaggacctggagccctttccccccgccccgtaagcggcgggtccgtgttgggccgcgggtccgcgtggtggac
atcatgtcccagtttaggaaactgctgatgggagacgaggggccgccgccctgcgggcgcacgtgtcgggaggcgcgcgaccgggctgg
gaggcccgccacgcccataagctcctcccgataaaaagcgccccgatggccctggacgcggcataactccgaccggcgggtcccgaccgaa
```

-continued cgggcgtcaccatgcagcgccggacgcgcggcgcgagctccctgcggctggcgcggtgcctgacgcctgccaacctgatccgcggcgacaa cgcgggcgttcccgagcggcgcatcttcggcgggtgtctgctccccaccccggaggggctccttagcgcggccgtgggcgccttgcggcag cgctccgacgacgcgcagccggcgtttctgacctgcaccgatcgcagcgtccggttggccgcgcggcaacacaacacggttcccgagagtt tgatcgtggacgggctcgccagcgacccgcactacgagtacatccggcactacgcttcggccgccacccaggcgctgggcgaggtggagct gcccggcggccagttgagccgcgccatcctcacgcagtactggaagtacctgcagacggtggtgcccagcggcctggacgtccccgaggac cccgtgggcgactgcgaccccagccttcacgtgctgctgcggcccaccctggcgccaaagctgctggcgcgcaccccgttcaagagcgggg ccgtggcggccaagtacgccgccaccgtggccggcctgcgcgacgccctccatcggattcagcagtacatgttctttatgcgcccggcgga cccaagccgccccagcaccgacaccgcactgcggctcaacgagctcctggcctacgtctccgtgctgtaccggtgggcgtcctggatgctg tggacgacggacaagcacgtatgtcaccggctgagtccctccaatcgccggttcctcccgctcggcggcagcccggaggcgcccgcggaaa cgttcgcgcgccatctggaccggggtcccagcggcacgaccggctccatgcagtgcatggcgctcagggcggcggtcagcgacgtcctggg ccacctgacgcgcctagccaacctgtggcagaccggcaagcggagcggcggtacgtacgggaccgtggataccgtcgtatccacggtggag gttctgtcgatcgtccatcaccacgcccagtatatcatcaacgcgaccctcaccgggtacggcgtctgggcaccgacagcctgaacaacg agtatctgcgggccgcggtggacagccaggagcgtttctgtcggaccaccgcccccctgttcccacgatgaccgcccccagctgggcccg gatggagttgagcatcaaggcttggttcggggccgccctggccgcggatctgctccgcaacggggcgccgtcgctccactacgagtccatc ctgcggctcgtggcgtctcgccggacgacgtggtccgcggggcctcccccggacgacatggccagcggcccggggggggcatcgcgcggggg gtgggacctgtcgggaaaagattcagcggggcgcggcgcgacaacgagcccccgccctccccgacctcgcctacactcgacccccgcgtc cacccggaggttccggaggcgccgcgcggacggcgcggggccccgcttccggatgcgaacgacccggtcgccgagcccccgctgcggcc acacagccggccacgtattacacgcacatgggggaggtgcccccgcgcctcccggcccgtaacgtcgcgggacccgacaggcgaccgccgg cggcgacgtgccccctcctcgtccggcgcgcgtctctggggagcctcgatcggccacgggtgtggggacccgccccggagggagaacccga ccagatggaagccacgtatctgacggccgacgacgacgacgacgacgcccgccgaaagccaccacgccgcctcggcccgcgaacggcac gcccctacgaggacgacgagtcaatatacgagacggtgagcgaggacgggggggcgtgtctacgaggaaataccatggatgcgggtctacg aaaacgtctgcgtgaacacggcgaatgcagcgccggcctcccgtacattgaggcggaaaatcccctgtacgactgggggggatccgccct attttccccccgggccgcaccgggccccgccccgccgttgagcccctcgcccgtcctcgcccgccatcgagccaacgccctgaccaac gacgcccgaccaacgtcgccgccctgagcgccctcctgaccaagcttaaacgcgaaggacgccggagccggtgaacgcctccgcccgtgc tgccgtcgctagaccacgccccctttccccctgtttgtcgacgagatttaataaaaataaccaaaaacaccacaggggaccgcgtgttctttt ttatcgcacgtgattgtgtgtttattattttgggtccgtgccggaccccccaaccctcgttgaccggtgtgatcctgggatgcggagggg gagggaaggggagaagaggagacgagacagaccgcagtacacgcgcctcacggcagcccagcgcgttgcgggtcgaagttacaaactgaa caaagcccccgggactgcggggatagtagcatatgcgaagggcgggctcctcgcaaaactggtcaataccgccgacgccgtcgacgagccg caggcaggcccgaatgccgtctccgctcacccaccagtagcccgaggatcttgccgactggacgcgtgcgacggcggccagctgtttggca gccgcgcgggggatcagggtcgccggggcgctacagccgccgaccgcctgctcgtgctccatgggggtcggatcccaggatatgcacccga ggttgaactcgtgccatccgctgtcgcatgggggaaagtgcccacgagccccgcgagggcacgaggaccaacgcggcaatgatcacaactcc cccgatgatggtcccgacgccaacccaggccgcggcggggagccgagcccgcatgggggggtgtcccggggcccaggggccggtaggcgtgt tccgatgcccgcagaggcatgccgttgtgttggtaggaaagcggctcaggggggaggcgttttgctccacgccgtgtgtcgttcgggatcga ccaaggatgacctgagggaagagagggtggcggctttatagcgcccagcggtgggcgggatagaggggggaccaaactatatagatattaa aaaggtaacggggggtcttgcgttaccgccgatgacgctgccgcgactgtgatgtgcggacgacgtacacgattgccgttacgaccagga cccccgccgcgagaaccccgattccaatccccacccactcgatcgcctcgatcacctgccgctcggtggggtccctgggtgggggctggtg actgccgtggtgttctagaacgggaatcccggccggatatccggtcaaccgacagatgtactcgctgtagtcgtacgaaatgggcagggtg gaccggaccgtagccagcccggggtggtcgcacgactcctgggccgtaacggccgacttagccgccggtgaggggtcgtcccccaggaacc aggcaaacgtcacgccctcggggacgcagccggccgtgcagaccacatgccggaccccaaattccatggtgatggttggccgcggcagcac cagggccagcccggtggcattgcgtcgcgagaacgtcacggagtcgcgatgccacgtcatctggcaggtgaaggtccgcgggggggacctgg -continued

```
ccgccgacagcctcggaggtcacggtagagactgtggtgaacccgtcggggtgctcgtgcgtctgcgtgtcgatctggcccgggttaaaca
cctggtggtcgtcctcgaaccagacaaactccacggggttacgcgggtagtaggcggcggccgtgcacgtcgccttgaacggctgaccctc
catcaccgcgtggggctggagggtcagagacggggggcggaacatgcggacgcgcacccacgtcccgtactcgtgcgggctgtccatccgg
ccccaggccaagtaatacattccctgggtcgcggggcgtcacctcgccgataatcagccgctgggtcggcagcggcccggtgacagaataca
acggagggtcggcgcccgggccggccccctccgcccagagcacgtgggggtccgttaggttggggggcgctgtcgtacaccaggagtccccc
gggtggggcggtgatgttcgtcaggacctcctctaggtcgggagccggagcgattgggggggacggaccccatggagtaacgccatatctgg
aggcggaactccatgcgggtggaattccgaaaccggcatcggatctgcacccgcgagccgtaccgggccaatgggtcgcggcggtcgcacc
acacgggcccgggggggtttagtggggcggcccgacttggcggggggtggtgttgttctttgggtttgggtcggggggtggacgtgggggggct
tttgggcgtggaggtgggcttgggggttgttgggggggctggccggctcggtgggggtggttttgttttgtgtgacattgttgggggtttggg
gtcgatgtgggggtgacctccgggctggcggctgacccgggggaccccgatgtgggggcctcgctcgcgttcgtcaccgctcccgcggtga
tcgtgggcccggtggaggcagtttccgagcccccggacaccccgccccgagccacaacaggctccacaggaccacggcaaggcccacccg
ccccggggccatgcccgacgcctcccctcgcgagggatcggctagcgttcccggcaaagcgagaccgggcactgaaaacgacctccacac
ggaccaccgatgggggtgtgcgttcgatgcggcctcccgaccaagcgccctcgatagtgagggtagcccgtgtccccttccggaatttat
acccgggccccatccggggtttgggtgttatggcgaaatcatcacacaccggcggtcttcgggactaatgccttttattgaaaaatatatc
aatcgcccgaccgcccgcccgttgaccccggagggcacagcagcaccccacccaaaacccagcgcgtacacggagaagaagaggccccg
aagcgtcgccgccaaccgggccccgtccccgggtccttcctgtgcaggcgacgccggagcccagcacctgcgccaacgaaatccacacg
gcacccctagcgccgcatacacgacaacctcggaaaaccgaaacaccaacccgaggttgatgacctgcagtccggcgtgaacaaacagca
gcgggtccgtaaggtcccagggcgcaagcgcctgacacagctccgtcagggccaccgccacatggcctccgagaaacacctgggccacag
cggcaggcccgggccggcgttccccgggcatgttctcgcaccgtcttgacggcaagcgcgcccgcccccagaaaggtgaccacgggcacc
cagacgttttcgggccgcgcgaccctggccggtgcgacctcatcggccggcggcccgtgggatcgttgggggggtcgggggggacgggggcc
cgggaacccgggctcgctctgggtcctccggggggcggcgggaaagagactcgcctgcggtgatgacacagacgcggcggtggtcggggca
agccctggaaaagcagtccctggcggtggtcgcccccgggcccgccaacaccgccgcggccagggcggccgcggcgggcccaccgatccac
cagtagcgcgcgctgcctccgatcgtcagcccgccgacgaccatccccagggtgccgacgaacaggggcccggggcgaggagaaagagcg
gatagacgtcatcggcgagcaccaggagcgccgcataggcggcgcccagcgccaggcactgggtggccgggcccggggccggggccccgg
ctgcgtgccgggctccccgagactccacagaacaagggccgctccaccggccgccagtttgagccaggcgtatatccgcgcggtgggccgc
gcgaggggagggggtgcgcgcataaagcccagcacggcgcacccgacggcgaacgccccagacgcggcattcgcgtacggcccgcgcgaca
taacgaccgatcccgcaaaacccagcgtggcggcctgaagccagatatgcatgaaccccgcgcagggcccccacgcacgcgaggtgtgg
ccgtccgtcgtcgacccgtccctggccgtcctccggggacacggcccggtggctgtcgttgcggagcatcccgcgccttggccgtgatggc
acgcggggtggttccgtcagcgccccacatacgcttttataaggacagggaaaggaaatacacgaaacccgaggtgggggcgccaggcac
acacatgaaccacacgcgacacgcgggaaagtgttgggcaataccaagtttatttacattaacccgggatggtgcgagagttgggcggccg
ccaaggccccgcccgtcagggaatccaaaaccatacggggtttggggccccccggaaggcggagaaggcgccggggcttgcttctcc
ggtcgggaggtcgcgaaagtaacacgcgtaacggcttccgctccgggcgtctggagcggcgggacgggccgccgtcccgtccgccgcatcg
gagtcgtcctccgtgtccaggggactggatctgcgggcgggggtgcggtgggcgacccgtcttaggttctttagggcgtgtccgcgc
gcgcatcctcgcccccgagcgcccccgcttggtcgtgggagtgacccgcgtggtcgacgacggcatcggacaggcatgcaaggcccccgc
ctctcccgcccgggcagcgccatcgaggtcttccggatcgccgtggctgaccgcgtccgacgcggagtcctggctgtctgttggctcgctc
ccagaggcccggaggccgagctcccggctgaaggagacccctggctatgacccagccagtccaggcaaatcttctgggggtttcaggagaa
ataccgccgataccgcgttgggaccggtggcggtgacgcacagactggggacgggggtcgtgaggaagaacttgagggtgccccgccgac
ctgcagtcgccggagcaccgcccgcatgctgcaatcgtcgacgaccacagagaaggtgcgatgggtatttttcccgtacaccgtcttggcg
ttggcggccgcctggcccgccttggtgagcgcgttggacaggatctggacctgggtgctggtgctggacgacacgccctcctcgcgggcag
caaaggtgacgcaggtactcgtggtgaacacggaaaatttgccgttaaccccgagctcgaacgtggtgggcgtggcactatcggcccgt
cgcgttaaggaccttggtgagctgcggcctcgtcaggcgcaactgaacgtcgggggttccctggggaaccagcaccacaaagctcgtcagt
```

-continued

```
tcgcgcttcatcagcgtctcgctggctagctcaacggcctcgccgtcggacgtcgtcgtccatatgcgctgaaccagcgtgcgaaacggggg
cctggcccgtgatcgccaactccaccgacgtaggtccgggtactggttggcgcgaaacacgctcaggagggagcgcttctggtccacgag
agacaggaacgccgccgtgggtccgcgccagcgataccgactgaattgcgagtgttccaggggcaggaacacctgctccccaaagatcgtg
ttatggataaggatgccccggtcgcccataaccagaagcgagtccagaaggctcgtgcgcagcggggcaaacgcctgtaggattccattaa
gttcggcgccctgcaggaccacctggcagggcgcccctcctccggctgcccgagggacgcgtccgacgcgtcctccacggggggaggcggg
ggccacaccgccaggggaatccgtcatcccaacgcgggctgggaacaccccacagtgacgaggtgggcttcggtggtgagggcagccgggc
cggggtctcgggtgcgggacgcggaggggggcgtatgccgctgcgagggtggggttttgatggcagccaggggacccaagcaaccggaccgt
cgctcaccgagccagaaactacggcaggcccgccgcgctagcctgattaaatacgccccagctcgttaggccacaccccttttggaagagg
caatgagcggggggaaggttggcccgcaccggcgcatgcagggtgctgcaccaatccgcgtggagttgggccatcgaaattataaagagcg
tccccctaacggattattgtcctcttgtgtcggtgttgttgtctgggtcaccatacacagagagacaggctcgggtgtcccggaccgtcgca
ccaaccacgccttagttaggccgatccgcagttacaattgacctgacatgggtttgttcgggatgatgaagtttgcccacacacaccatct
ggtcaagcgccggggccttggggcccccggccgggtacttcaccccccattgccgtggacctgtggaacgtcatgtacacgttggtggtcaaa
tatcagcgccgatacccccagttacgaccgcgaggccattacgctacactgcctctgtcgcttattaaaggtgtttacccaaaagtcccttt
tccccatcttcgttaccgatcgcggggtcaattgtatggagccggttgtgtttggagccaaggccatcctggcccgcacgacggcccagtg
ccggacggacgaggaggccagtgacgtggacgcctctccaccgccttcccccatcaccgactccagacccagctctgccttttccaacatg
cgccggcgcggcacctctctggcctcggggacccggggggacggccgggtccggagccgcgctgccgtccgccgcgccctcgaagccggccc
tgcgtctggcgcatctgttctgtattcgcgttctccgggccctggggtacgcctacattaactcgggtcagctggaggcggacgatgcctg
cgccaacctctatcacaccaacacggtcgcgtacgtgtacaccacggacactgacctcctgttgatgggctgtgatattgtgttggatatt
agcgcctgctacattcccacgatcaactgtcgcgatatactaaagtactttaagatgagctaccccccagttcctggccctctttgtccgct
gccacaccgacctccatcccaataacacctacgcctccgtggaggatgtgctgcgcgaatgtcactggacccccccgagtcgctctcagac
ccggcgggccatccgccgggaacacaccagctcgcgctccacggaaaccaggcccctctgccgccggccgccgcggcaccgagacgcgc
gtctcgtggaccgaaattctaaaccaacagatcgccggcggatacgaagacgacgaggacctccccctggatccccgggacgttaccgggg
gccacccggccccaggtcgtcctcctcggagatactcaccccgcccgagctcgtccaggtcccgaacgcgcagctgctggaagagcaccg
cagttatgtggccaaccggcgacgccacgtcatccacgacgccccagagtccctggactggctcccgatcccatgaccatcaccgagctg
gtggaacaccgctacattaagtacgtcatatcgcttatcggccccaaggagcgggggccgtggactcttctgaaacgcctgcctatctacc
aggacatccgcgacgaaaacctggcgcgatctatcgtgaccggcatatcacggcccctgatatcgccgacaggtttctggagcagttgcg
gacccaggccccccacccgcgttctacaaggacgtcctggccaaattctgggacgagtagcccaaacgtcagacgagcgcgcttgtcccc
gaacaaacgacccaccaataaaattatggtatcctatgcccgcagaatctggacggacctggttactgcttttttgcgccgccttttatcct
ctcccacccccgcgtccctgacaagaatcacaatgagacccaaagtttggttcagaggtttattatgggcaaacacgggtagaagcgcgcc
gcgacactcacagatcgttgacgaccgccccggcgtaggaggtgctgcgacactcgaaaaaattggtgtgtttgtcggtggacatgaggct
cagcggaaagctggcgtcgggggtgggcggaaaacagtggcttcatgtggataaggcccaacaggcgatccgcgctgaatcgcacgtag
ttttcgatggccgccagcgccgccgggctcaggatatggctgtccgtcggcgcctgggatcggataaatccgatctcgatctcgaccgcct
ggcggaacagcccgtacacgcggtcgggcgggggcttggcgtgcccgccgaggtagttgttgtagatgtaacacgaggccgtcgtgtgcac
ggcctcgtcccggctgatgaggtcgtttgactggcaggtgacccgcagaaggttgttggtgcgaaggtaggcgatggcggcaaacgaggcg
gcaaaaagatgccctcgatgaggatcatgagaatgaacttttccggaacggaggcgcattcccgcacccgcgcttccaaccagtccacct
tggcgcggatggccgggtggttgatggtaccggccacgtactcgcggcgcgcctggtcgttgttgtggaaaagcaccagctggatgatgtt
gtacacgcgcgagtgtacgacttcgatgcattcctgctccacgtagtagtggagaatgtccttctgctcaaacaggccggagaggccgccc
aggttttccgtaaccaggtcgtcggcggccgacaggaaagcgaagaggaagcggtaaaagctgagctcgccctcggaaagcttggagacgt
cctcctcgtcccccacgaaaacaagctcggtttccagccagcggttaaggatgctgagggagcgcaggtggttaatgtcgggacactggga
ggtgtagaagtacctctcggggtcggggcactttggaatctggatcgccaggtccgccgtcgcgctctggcccgtaagggccgtcagagcg
```

-continued ggggagagggctggggccgcggaatccatggcagcaggggagagcgtgggacggcgacgacagtggcggcgggcctggcgcggaggggtt tgtcggtcacagcgcgcagctcatgcagacaatgttgtcgtcgccgccaaagacccgctgttggtcgccttgcgaaccttgcagtagtac atccctgtttttagtccgcgcttatatgcgtggaccagaaggcggaccagggtggaggctgggagggtcccgtccgccttctccgtgacat acagggtcatggattggctatggtcgacgtagggggcgcggtccgcacacaggtcgatcagcaacttctggtcgtagtcaaacgcggtctt gaatcgccggaggggtgggtgggctccaggcacgggagcgcctgcgccacggaccactgcttggcgtcgagactgtccatcacctccagg aggcgcttcccgctaaacgtgcgttccagttcctttagcaggagcgtgttggggcgcagcgtctcgccgtcccgggtcacctggctgaaca ggttggtgaacaggggggcaaagccctcgctgacgtccgagatctgcgccgaggcggcggtgggcatcagcgcgacaaactggctgttgcg caggccgtgtttcatcatgctctggcgtagcatctcccactcgccctcgtaccgcggccgggcgtccggaaagcgctcccagtgaaagcgg ccggcgcgatacatgctgcgcttaaagtggttgaaggacgggccccgcaacgcacagcgcgttgctggtcttcatcgccgacagcagca tcacctcggcgatgtgtttgttcaggtcctgaaattcggcagactccagatccagccccagcttcaggcaggccgtgtgcaggcctgcat gccgattcccatggaccgcaggttgtcgttgccgcgggtgcactggggcgtgggttgtagcgtgctgtcgatcatgatgttcaccatcagc acgcacgcctgcacggcgtcgcggagccgcccaaagtcaaacgtctgcctggagacgcatcgggccagattcacgcttcccaggttgcaga ccccactggatcgcttggaggccgatggacgatctcggtgcagaggttggagccggcgatggccgcccctgggtgtcgtagatgtagtg gcggttcaccgcgtctttgaacatgacgaaggggctcccggtcgtggccgcactgcgcacaatgccataggccagctcctggatgggtatc tgctcgccaacccatgacctcgaggtgctggtagagcttctcgaactcctccccgtgaaagtcggcgagcgacatgctggtgtcccggt cgaacagggtccatgtgacgttcttctcgccgtccaggtggcgaatcaggcgcttgaaaaacaggtctggcatccagagggcgctgaagat attgtcgcagcgctgggcctcttcgccggcgaggaccccttcatccggagcacggcccgcacgtcggtgtgccacggctccaggtacacg cacgcgccggtcggacgcgcgctctctttgttgtgcgccgccaccagcgagtcaaggaccttgagggcgggcatgacgctggcggtcccgg ggccggagtcgttaaacgcctgcacgcatagcccgatgcccccgttgcgggcgaggatggcactgacgttgctggtgatggcccgcaggt cgccttgtttgtggtggcctgggggtttaccaggtagcagctggaggtgtagtagttgcgggtcccaggttcagcatggcgggggtcgac ggtacgatctggtggtcgtagaggcggtggaaaaagaacttgaacatttcccaccacgacccctctcgcccagggcgatgtggcgcatgc cgcgcgtggcccggcaggccaaaaagccggcgatgcgggtgtacatctggaagacggactccatgtagtgcccgccaaaacgctttaggta aaactcctcatacttcagggccgattgcagccccgctcgaccagcgtgtgcggtgtgctgtggatcagacagtcgtaatggtccagagcc tgggccaggatcaccagctgggcttcgtgctcgcgaagcctttccgtcaggccaaaatccagggccacttccttggatcgcagccactcct caaaggaggcctcccgggtccggatccgcaggtgcaccagaaccccaggatgcggtaaaggcgagcggaccggctcaccagcggcttgaa cccgttgaccagccgcgtcacatactccctgagataataagggcatgtatgcgttcggcgggaccggaggaacgtccagacacaggcgctgc atctccacgagcgcgtagttgagaagcccaaagtcgtcctccgtgaggcgagggggggctgccgaatgtcctgggggggacacgcttggttt cctcgcgggcgcaccggcaaaagtactccagcatgagcgcggggttcgcggttcacggcatctcccagaaagcgcgccacggcctccgcgtt ctcgggcgtgagttccaggggacggggtaggccgtgcccgttcccagacgtggccgggggtccgaaagcccctccgcgtcgtcccgggcc acggcgggatcggccgcaagaccagcgccggcctctggcgtcggcgcgtgtgggtctaccgctgagggaccaccggcgtcggcgcccgggc cggggggtcccggggcaaacatccaggggcgcggtgtcattgctccacgggcgacacacggggccatctatctgcagggagtcatccgatga cgaatcggagtcaagggcgtcgtcgtacgtggccccgccggacacgtccgaggaggcgtgtgacagcgtctccgagtccgtgtcctccgag tcatccgagtcggaatcggacgaccggtcgtccgagacgaactccgcggggccgactggatcccctccccccgaataccgcagagcggc gccgtgtgtcgcgacaggaacaacagccgccacccaggtgaagcggggaggaggagggggccccaagggcctcggtggggacgtcggc cgtctgggtaccggtagacgtccccgccgagcgacgtggggttccccgaatgccacgacggcggtcccgccgtcgctgccggctccgatg tttgtcaccgcaacgaagggagcggggatgccgcggccccgggtcctgggggcgcccgcgcaccacgtctccgtcgatgatcatggtgc agttggaaccacattggacaaagttgctatcgctgatgcggtaggacgcggacccgggcgtcttgtcggaaagcaccatcacgccattgac tcgctggcagtacacgtggtggccgtgggcgagaggggccccggcggcctcccctgggtggctgcgctggggccgccggcctcctgtccc ccaaccggggcccgcgcttcgacgggagaggatgcggctgggcggctggccatttcaacagacgcggcgggtttcggcgggctcgagaggg gacgtcggcgggtccggcgagtggtggggtcgagattcgacaaggccgctgcctgacgaatcgcaccgagagccaaagaagataggcgaga gcaggtccggaaggcgggagcgcaaaggaaaccggggagggacgcaagctcacaggagcacggcgaccggcaagtttccaaagcacccacc -continued

```
tgtggtaccctaaaccacccgcgctggcttttatccacatcgcgcaggggtggggcgcgggccagtttcagtgaaacccaaaaggacaca ccgatgtcctgagtcacggggqtgtgttccttccatgtatcccatttgcattttgtggcttcctcccgcccaaaggacgttacaacactcg cgtttcgggtttcagtggctttatttggcggacgcccgggtcaacgaacaacgagtgacagcggggaaggggttgggggcggagcgttgtg tgggcggggcgtttgctacgctcacgcgcatgcccgccactcgccggggcgccacaccacgccttccagaatgacaacgggacgctgacc gccccaaagcgctcggtgcggtgcaggcagcggggactatcctcgggcatcatgccgagctctgcaaaggcggcgtacgtacaggtgcgtg cggtggggcgccccgcaggtccggctgccagcggtacagcctgtcggcgaactgggggttcgtgacctggccagccgagcaacgcgggt ttggggattggcggccaggcccgcgagggggaagtcgggqtttcggtttggggccgggggcgtcatgtcctcggtgccgtgaatcgtgttg gtgatccggaggcgcccaaacagccgctccagggccggctccaacccgcgcggggggagctggctcttgatcacgtacacacaacacagct cctggtcccggcgctggcggtaagtgaataccaggtacagaaacgccgcgcccgggcccccagccccagctcggcgtccaggtccacgaa cgcacatgccgggaggatcacggccgagcggggccggcccgggtggccggtgtgcgccgcctcctggggcccggcgcacacggcggtgacg ctcgctagctcgtcctgggtgacccacgacaccagcccccgaaaaaccgcatgacctcgtggggaagacgtgcgtgtgaaccatggcgc gcagacactcggaaaaacgatccaggcgcgccccaccccgcgtcccgcggtagttggccgtgacgtgggcccgtaccgcatcggcggcgtc gcgcgcgtcgtacgaggcggcacacgccgccaccaggaagttaaacgacactaggcccgcgcgcgtgcaccgctctcggctcgccccgac cccagggcggtcgcctccatcagctggccccaggcctcgcccagccgctcggtctgccggcctggcggggcgcgctggtgggccaggtgag gcaggtcggcggggtgccgcagcgccagaagcagcgtcccagcacgatccgcgttgggttggcacagatccgtcaggatcacttggcgggt tagatgatggcgcggggagccgatcagggccgccccccgcgcatggtgcccgcaggatcttgtccagggcctgttcggtatcgtcgttg ggggtcagcgccccaggggqcgcgtctgtgccgtccaggccaagcaaccacagcgtgctggccgccctccggggtcccgaccccctggga gccctgggccgtcgcggcgagagatcggggggcgcaggacgcgccgaagcaggccctgtcccgcggtatcgcgtgttgtgggggggagttc cacggtactcccgccccacacggaagggqttgcgggtagcggattggtcttcattgcgacccagatcgcgacctagcaagaccggggga gggagggggggggggtcgaaaggacactcacgcaaggcggaaccacccaccccacagccaaacgcggctaccgcctccggtgggttgtgt tggccgactggcccggcgcgtccgtatacacacgtttaaagggccatttgggccgccccgcagaaagtccgcaacccacgccgtccgggct gcccgcacatccggacaatcccccgggcctgggtccgcgaacgggatgccgggacttaagtggccgtataacaccccgcgaagacgcgggg tactcgcaacgcctgcggggtcctggagggccgcggggatcgataattcgccgctccctacagcgcacgacagtcattcccgcccggtc tcgtcgttggtctacgctgtccccacccacgcgagccgggcgtcatggcagaccgcggtctcccgtccgaggccccccgtcgtcacgacct cacccgccggtccgccctcggacggacctatgcagcgcctattggcgagcctagccggccttcgccaaccgccaaccccacggccgagac ggcaaacggggcggacgacccggcgtttctggccacggccaagctgcgcgccgccatggcggcgtttctgttgtcgggaacggccatcgcc ccggcagacgcgcgggcatgctggcggccgctgctggaacacctgtgcgcgctccaccgggcccacgggcttccggagacgcgctcttgg ccgagaacctcccgggttgctcgtacaccgcttggtggtggctctccccgaggccccgaccaggccttccgggagatggaggtcatcaa ggacaccatcctcgcggtcaccggctccgacacgtcccatgcgctggattccgccggcctgcgcaccgcggcggccctggggccggtccgc gtccgccagtgcgccgtggagtggatagaccgctggcaaaccgtcaccaagagctgcttggccatgagcccgcggacctccatcgaggccc ttggggagacgtcgctcaagatggcgccggtcccgttggggcagcccagcgcgaaccttaccaccccggcgtacagcctgctcttccccgc cccgttcgtgcaagagggcctccggttcttggccctggtgagtaatcgggtgacgctgttctcggcgcacctccagcgcatagacgacgcg accctcactcccctcacacgggccctctttacgttggccctggtggacgagtacctgacgaccccgagcggggggctgtggtcccgccgc ccctgttggcgcagtttcagcacaccgtgcgggagatcgacccggccataatgattccgccgctcgaggccaacaagatggttcgcagccg cgaggaggtgcgcgtgtcgacggccctcagccgcgtcagcccgcgctcggcctgtgcgccccggggacgctaatggcgcgcgtgcggacg gacgtggccgtgtttgatcccgacgtgccgttcctgagttcgtcggcactggcagtcttccagcctgccgtctccagcctgctgcagctcg gggagcagccctccgccggcgcccagcagcggctgctggctctgctgcagcagacgtggacgttgatccagaataccaattcgccctccgt ggtgatcaacaccctgatcgacgctgggttcacgccctcgcactgcacgcactacctttcggccctggaggggtttctggcggcgggcgtc cccgcgcggacgccaccggccacggactcggcgaagtccagcagctctttgggtgcattgccctcgcggggtcgaacgtgtttgggttgg cgcgggaatacgggtactatgccaactacgtaaaaactttcaggcgggtccaggcgccagcgagcacacgcacgggcggctctgcgaggc
```

-continued

```
ggtcggcctgtcgggggcgttctaagccagacgctggcgcgtatcatgggtccggccgtgccgacggaacatctggcgagcctgcggcgg gcgctcgtgggggagtttgagacggccgagcgccgctttagttccggtcaacccagccttctccgcgagacggcgctcatctggatcgacg tgtatggtcagacccactgggacatcaccccaccaccccggccacgccgctgtccgcgcttctccccgtcgggcagcccagccacgcccc ctctgtccacctggccgcggcgacccagatccgcttccccgccctcgagggcattcaccccaacgtcctcgccgacccgggcttcgtcccc tacgttctggccctggtggtcggggacgcgctgagggccacgtgagcgcggcctaccttccccgcccggtcgagttcgcctgcgtgtgt tggcctgggcccgggactttgggctggctatctccccacggttgagggccatcgcaccaaactgggcgcgctgatcaccctcctcgaacc ggccgccggggcggcctcggccccactatgcagatggccgacaacatagagcagctgctccgggagctgtacgtgatctccaggggtgcc gtcgagcagctgcggccctggtccagctgcagcccccccgcccccgaggtgggcaccagcctcctgttgattagcatgtacgccctgg ccgcccgggggtgctgcaggacctcgccgagcgcgcagacccctgattcgccaactggaggacgccatcgtgctgctgcggctgcacat gcgcacgctctccgcctttttcgagtgtcggttcgagagcgacgggcgccgcctgtatgcggtggtcggggacacgcccgaccgcctgggg ccctggcccccgaggccatggggacgcggtgagtcagtactgcagcatgtatcacgacgccaagcgcgcgctggtcgcgtccctcgcga gcctgcgttccgtcatcaccgaaaccacggcgcacctgggggtgtgcgacgagctggcggcccaggtgtcgcacgaggacaacgtgctggc cgtggtccggcgcgaaattcacgggtttctgtccgtcgtgtccggcattcacgcccgggcgtcgaagctgctgtcgggagaccaggtcccc gggttttgcttcatgggtcagtttctagcgcgctggcggcgtctgtcggcctgctatcaagccgcgcgcgcggccgcgggacccgagcccg tggccgagtttgtccaggaactccacgacacgtggaagggcctgcagacggagcgcgccgtggtcgtggcgcccttggtcagctcggccga ccagcgcgccgcggccatccgagaggtaatggcgcatgcgcccgaggacgcccccccgcaaagcccgcggccgaccgcgtcgtgcttacg agccgtcgcgacctaggggcctgggggactacagcctcggcccctgggccagacgaccgcggttccggactccgtggatctgtctcgcc aggggctggccgttacgctgagtatggattggttactgatgaacgagctcctgcgggtcaccgacggcgtgtttcgcgcttccgcgtttcg tccgttagccggaccggagtctcccagggacctggaggtccgcgacgccggaaacagtctccccgcgcctatgcccatggacgcacagaag ccggaggcctatgggcacggcccacgccaggcggaccgcgagggggcgcctcattccaacaccccgtcgaggacgacgagatgatcccgg aggacaccgtcgcgccacccacggacttgccgttaactagttaccaataaagctttattatgttacgccacccccgtgtgttgttctcgg tgttatggtgtgcgggcgggcggggggggggtggaagaccaagacagacaaacgcagctcggttttgggaagcgatcaccgcgactcgt agcctaatcaggggaaccggggccatggtacgggggcatgggtggcggaaacaacactaaccccgggggtccggtccataaacaggccggg tctctggccagcagggcacatatgatcgcgggcaccccaccgcactccacgatggaacgcggggggatcgcgacatcgtggtcaccggtg ctcggaaccagttcgcgcccgacctggagccgggggggtcggtatcgtgcatgcgctcgtcgctgtcctttctcagcctcatatttgatgt gggccctcgcgacgtcctgtccgcggaggccatcgagggatgtttggtcgaggggggcgagtggacgcgcgcgaccgcgggccctgggccg ccgcgcatgtgttcgatcgtcgagctccccaacttcctcgagtacccaggggcgcgcggcggactgcgctgtgtcttctcgcgcgtatacg gcgaggtgggcttcttcggggagcccgcggcgggcctgctggagacacaatgccccgcacacacgttcttcgccggcccgtgggccctgcg ccccctgtcgtacacgctcctaaccattggccccctagggatggggctgttcagggacggcgacaccgcatacctttttgacccgcacggc cttccggagggcaccccgcgttcatcgccaaagtgcgggcggggacatgtatccatacctgacgtattacacccgcgatcgcccggacg tacggtgggcgggagccatggtgttttcgtgccgtcgggcccggaacccgcggctcctgcggacttgacggccgcggctctgcatctttta cggggccagcgagacttacctgcaggacgaagcgttcagcgaacggcgcgtggccatcacgcaccccctgcggggcgagatcgcgggcctg ggggagccctgcgtcggcgtgggccccgggaggggtaggggcccggggccacacccgcccacagccgcccagtcgccgccaccgaccc gggccgtcgcgacgacagggcctccgagacatcccggggacgcgccggtccgtcggcaaaaccagaggccaagcgcccgaatcgggcgcc cgacgatgtatggcggtggccctgaagggtaccccacccacgatccccctccgccgacccaccctccgccgacccaccctccgcgatc ccaccaccgcctccctccgcccccaagaccccgccgcagaggcggccgaagaagatgacgacgacatgcgggtcctggagatgggcgtcg tcccggttggtcggcaccgggcacgctactcggccggccttcccaagcgccgccgacccacctggactccgccttccagcgtcgaagacct gacttcgggggagaaaacgaaacgctcggccccccctgccaaaaccaagaagaaatccacccccaaaggcaaaacccccgtcggggccgcg gtcccgcctccgttccggagcctgtcctcgcctcggcacccccgaccggcggcgcgcggtcgccgaggcgggcgaggacgacgggc ccacggttccggcgtcctcacaggccctcgaggcgctgaagactcgccgctcgcccgagcccccgggcgcagacctcgcccagctgttcga ggcccacccaaacgtggccgccacggcggttaagttcaccgcgtgctccgccgccctggcccgcgaggtcgccgcgtgttcgcggctcacc
```

-continued

```
atcagcgccttacggtcgccgtatccggcctctccggggctgctggagctctgtgttattttttttctttgaacgcgtcctcgcctttctca tcgagaacgggccccggacgcacacccaggccggggtggccggcccggccgccgccctgctggagtttaccctgaacatgctgccctggaa aacggccgtgggggactttctggcctccacgcgcctgagcctggccgacgtggccgcccatctgcccctcgtccagcacgtgctggacgaa aactctctgatcggtcgcctggcgctggcgaagctgatccttgtggctagggatgtcattcgggagacggacgccttttacggggaactcg cggacctggagctgcagcttcgcgcggccccgccggccaatctgtatacacgcctcggcgagtggcttctggagcgctcgcaggcccaccc ggacaccctttttgcccccgccaccccgacgcacccagaaccgcttctgtatagagtccaggctctggccaaatttgcccgtggcgaagag attagggtggaggcggaggatcgccagatgcgcgaggccctcgacgccctcgctcgcgggtcgacgcggtctcacagcacgccgggcccc tcggcgtaatgcccgccccggccggggcggccccgcagggggctccgcgccacccccctgggccccgaggccgttcaggttcggctgga ggaggtgcggacccaggcccgtcgggcgatcgagggcgcggttaaggagtacttttaccgggggccgtatacagcgccaaggctctacag gccagcgacaacaacgaccgccggtttcacgtggcttcggccgccgtcgtgcccgtggtccagctgctcgagtccctgcctgtcttcgacc agcacacgcgggacatcgcgcagcgcgccgccattcccgccccgccccgatcgcgaccagccccacggccatcctgttgcgggatctgat ccagcggggccagacgctggacgcccccgaggacctggcggcctggctctccgtcctgacggacgccgccaaccaagggctgatagaacgc aagccactggacgagctggcgcgcagcatccgcgacattaacgaccaacaggcgcgccgcagctcgggtctggccgagctgcggcgcttcg acgccctagatgcggccctgggccagcagctggacagcgacgcggcctttgttcctgcgcccggcgcgtcgccctacccgacgacggcgg gctgtcgccagaggccacgcgcatggccgaggaagcgctgcggcaggcgcgggccatggatgccgccaagctgacggcagagctcgccccc gatgcgcgtgcccgtttgcgggagcgcgcgcgctccctggaggcaatgctcgagggagcgcgggagcgggcgaaggtggcccgcgacgccc gggagaagttcttgcacaaactccagggggtcctgcgccccctccctgactttgtggggctaaaggcctgtccggccgtcctggcgaccct gcgggcctccctgccggcgggctggtcggacctccccgaggccgttcggggggcgcccctgaggttacggcggcgctgcgggcggacatg tgggggctgctggggcagtaccgagatgccctggagcacccgactccggacacggcgacggctctgtctggcttgcatcccagcttcgtgg tggtgctgaagaacctgttcgccgacgccccagagactccgtttctcttgcagttcttcgccgatcacgccccgatcatagcccacgccgt ctcgaacgccatcaacgccggcagcgccgccgtcgcaacggcagaccctgcgtcgacggtggatgcggccgtgcgggcgcaccgcgtcctg gtcgacgcggtgacggccctgggcgcggccgccagcgacccggcctcccccctggccttcctagcggccatggccgacagccgccgcggat acgtcaaggcgactcggttggccctggacgcgcgggtggccatcgcccagctcacgaccttagggtcggctgccgccgaccttgtcgtcca ggtgcgccgggccgccaaccaaccggagggagagcatgcctccctgatccaggccgcgacgcgcgcgaccaccggcgcgcgggaaagcctc gcgggccacgagggcaggttcgggggcctgttgcacgccgaagggacggccggggaccactcccccagcgggcgcgccctgcaggagctgg gaaaggtcatcggcgccacgcgacgccgcgccgacgaacttgaggccgccaccgccgacctcagagagaagatggcggcccagcgcgcccg cagtagccacgagcgctgggccgccgacgtggaggccgtgctggaccgcgtggaaagcggtgccgagtttgacgtggtcgagctccgtcgc ctgcaggcgctggcggggcacgcacggctacaaccccgggacttccgaaagcgggccgaacaggcgctgggaaccaacgccaaggcggtga cccttgccctggagacggcccttgcgtttaacccatacaccccccgagaaccagcgccacccatgctcccccgctcgcagccattcaccg catcgactggagcgcggccttcgggcgcgcggccgacacgtacgccgacatgtttcggtggacaccgagccctggcgcggcttctgcgg ctggcggggggggctgctggagcgggcccaggcgaacgacgggtttatcgactaccacgaggccgtcctacacctgtcggaagacttgggggg gcgtgccggccctgcgccagtacgtgccgttttttcaaaagggctacgccgagtacgtggatatccgcgatcgcctggacgccctccgggc cgacgcgcggcgcgatcggaagcgtggcgctggacctggccgccgccgcgaggagatatccgcggtgcgcaacgacccggcggcggcc gccgagcttgtccgggcaggggtcaccctgccctgcccgagcgaggacgcgctggtggcgtgcgtggcggcgctggagcgcgtggaccaga gccccgtgaaggacacggcgtacgccgactacgtcgcattcgtgacccgacaggacctggccgataccaaggacgccgtggtgcgcgccaa acagcagcgcgccgaagccaccgagcgggtcacgcgcgggctgcgggaggtgctggccgcgcgcgagcgccgggcccagctcgaggccgag ggtctggccaatctgaagaccctgctgaaggtggtcgccgtcccggcgaccgtggccaagacgctggaccaggcgcgctcggcggaggaga tcgcggatcaggtcgaaattctggtggaccagacggagaaggcgcgcgagctcgacgtgcaggcggtcgcctggttggaacatgcccagcg tacctttgagacgcacccgctaagcgcggccagcggcgacggcccgggcctcctgacgcgacagggcgcgcgcctgcaggcgctcttcgac acccgtcgccgcgtcgaggccctgcggaggtctctcgaggaggccgaggcggagtgggacgaggtatggggtcgcttcggccgcgttcgcg
```

-continued

```
gggggggcctggaaatcgcccgagggatttcgcgcggcatgcgagcagcttcgcgccctgcaggacaccaccaacactgtgtcggggctgcg
agcccagcgggactacgagcgccttcccgccaagtaccagggcgtcctgggcgcaagagcgccgagcgggccggggccgtggaggagctc
gggggggcgcgtggcccaacacgccgacctgagcgcccggctgcgggacgaggtggtgccaagggtggcctgggagatgaactttgacaccc
tggggggcctgttggcggaattcgacgcggtggccggggacctggcccatgggcggtggaggagttccggggcgcgcgggagctcatcca
acgccgcatgggcttatatagcgcgtacgccaaggccacaggccagacgggcgcgggcgcggcggccgcgcccgcgccctgctcgtggat
cttcgcgccctagacgcccgcgcccgggcgtccgccccaccggccaagaggccgacccgcagatgctgcgccgccggggcgaggcgtacc
tgcgagtgagcggaggcccggggcccctggtgctgcgcgaggccaccagtacgctggatcggccgttcgcccccagcttttggtcccgga
tggaacgccactgcagtacgcgctctgcttcccggccgtgaccgacaagctcggcgcgctgctgatgtgtcccgaggcggcatgcattcgc
ccccgcttccgacggacaccctggagtcggcctcgaccgtcacggccatgtacgtcctcaccgtcatcaaccggcttcagctggccctca
gcgacgcccaggccgccaactttcagctcttcggacgctttgtgcgccaccgccaggcgagatggggggcctcgatggatgcggcggccga
gctctacgtcgcccctcgtcgcgaccactctcacgcgcgagtttgggtgtcgctgggcccagctggaatggggggtgacgcggcggccccg
gggccgccgctcggaccccagagctccactaggcaccgcgtttcctttaacgagaacgacgtgctggtggcgctggtggccagctcccgg
aacacatttacacctttggcgcctggatctggttcgccaacacgagtacatgcatctcaccctccccgtgcgtttcagaacgcagcaga
ttccatgctattcgtgcagcgcctgaccccgcatccagacgcccgcatccgcgtgctgccagcgttttcggccggaggccctccgacccgg
ggcctcatgttcggcacgcggctggcagactggcgccgcggcaagttgtccgaaaccgacccctggcgccctggcgctcggtcccgagc
tgggaaccgagcgcggcgccgcgctgggaaagctgagtcccgcccaggcgctggcggcggtgagcgtcctcgggcgcatgtgtctcccaag
caccgctctggtcgctctttggacctgcatgtttccggacgactacacagagtatgacagtttcgacgcccttctgaccgcgcgtctggaa
tctgggcagacgctgagcccctcggggggggcgcgaggcgtcaccccccgctcccccaacgccctctaccggcccacgggccagcacgtcg
ccgtgccggccgccgccacccaccgcaccccccgcggcgcgcgttacggccatggacctggtgctggcggcagtgctcctgggcgcgcccgt
cgtcgtggcgctccgcaacaccacggccttttcccgcgagtcggagctggagctgtgtctcacgctgtttgactcacgcgctcgcgggccg
gacgccgccttgcgcgatgccgtgtcgtccgacatcgagacgtgggccgtccgcctcctgcacgccgacctgaacccgatcgaaaacgcgt
gtctggcggcacagctcccgcgcctgtccgcgctcatcgccgagcggcccctcgcccggggcccgccgtgtctggtgctcgtggacatctc
catgaccccggtcgcggtgttgtgggaaaacccggacccccccgccccccccgacgtgcggtttgttggcagcgaggccaccgaggagctc
ccgtttgtggcgggcggcgaggacgtcctcgccgccagcgccaccgacgaggacccccttcctcgcgcgagctatcctcgggcggccgttcg
acgcctccctcctgtcggggggagctattcccggggcatccggtgtaccagcgcgccccgacgaccagagcccctcggtcccgaacccgac
ccccggccctgtggaccttgttggggcggagggctcgttggggcccggaagcctggccccacgctattcaccgacgccaccccccggcgag
cccgtccccccctcgcatgtgggcatggattcacggcctggaggagctcgcgtctgacgactccggcggccccgcgcccctccttgccccgg
acccccttttcgcccaccgccgatcagtccgtcccccacgtcccagtgtgcaccgcggcccccctgggccggcagtcacggctcgcgaagcacg
accgggcgtcccggccgaaagcacgcggccggcgcccgtgggccccccgcgacgacttccggcgcttgccgtcccccccaaagttcccgggcg
cccccgatgccaccgcccccccgccccccgcctcctcccgcgcttctgccgcttcttcgtccgggtcgcgcgcgcgccgacaccgccggg
cacgctccctggcgcgcgccacccaggcttccgcgaccacccagggttggcggccgcctgccctccccgacacggtcgcccggttaccga
tttcgcgcgccccccggcccctcccaaaccccagagccagcgccccacgctttggtgtctggtgtgcccctcccgctcgggcccaggcc
gccggccaggcttctcccgctctccctatcgatcccgttccgccccggtcgcaaccggcacggttttgccggggggcgaaaaccgccgcc
ccccgctaacctcgggtcccgcgccaaccccccccagggttcccgtaggcgggccgcagcggcgccttacgcgccccgctgtcgcgtcgct
gtccgaatcgcgggaatccctcccttcaccctgggaccccgccgaccccacggccctgttttaggccgcaacccggccgagccgacctca
tcctctcccgcaggtccctctcccccgcctcccgcggtccaacccgtcgcccccgccccgacgtcaggcccgcccccacatacttgacgc
tggagggcggtgttgcgcccggaggcccggtttccgccgccccactacacggcagccggtggccacgccaccacatctgcgcgccccg
ggggcatttgaccgtcagccgcctgtccgcgcccaaccccagcccagcccagcccagcccagcccagcccagcccagcccagcccagcccag
cccagcccagcccagcccagcccagcccagcccagcccagcccaacccaacccagcccaacccagcccaacccagcccaacccagcccaac
cccagcccaacccagcccaacccagcccaaccccagcccaaccccagcccaaaacgggcatgtagcacccggggagtatccggc
ggttcggttccgggcaccgcaaaaccgcccatccgtcccggcttccgcgtcttccacaaatccacgcacgggcagctccttgtctggggtg
```

-continued

```
tcttcgtgggcatcctccctcgcgctacacatcgacgctaccccccgcccgtgtcgctgcttcagaccctgtatgtctctgacgacgaag actccgacgccacctcgttgttcctctcggattccgaggccgaggcgctcgacccactccctggggaaccacactcccccataaccaacga accattcagtgcgttatccgccgatgactcccaagaggtgacgcgcttacaattcggccccccgcccgtatcggcaaacgcagttctgtcg cgacgctacgtgcaacgcaccggtcgtagcgcctggcggtactgatccgcgcctgttaccgcctacaacagcagttacagcggacccgcc gggcgctgcttcatcacagcgacgccgtgctgaccagcctacatcacgtgcgcatgttactgggctagacgcgctcgattatttggtgtgt taagtttcgaaccgtcgaaccctatcccactcccttgaataaacacgacattaaacgcaaggctcgtgcgttggtgtggtcttttattgat taaaacaccccagaaggaactccccgggcctcacggggtcccgggcgtcgaaggttctcgaacgacaaacggtgaataggtgcgccgcagg ccaaacgcgggccgcaaccaggcggccggggcgtcgcccgcgaacataggctgcggggtaaacgtgttgtttgcgtgggccagaccaaggt ccgtcagcgccgccgcctgaccgcggagaaactcccgcacggccccttgggtgccctgggggtgcgggtggttgttatccatgataaactg agagttattggtggccaagacgagcccgcgcatgccaagcgcccggacgctatcggtggtaacggtgctggggcggtgaaattgcgggacg gccatcgggaccggaggtcgggaagcgatatgggggtgtcggtcgggaggctgtgtggggcgaaggcgtccggaacgcactggcgattag ggcggcggtgcgtcctttttttataggcgcgcgccagcaccaaccacccaccaaatagcggccccaggacgagtcccgccgccaaaacgag cgcggggggggccaatccgtaggtgcttaagaccccgcagggcctggtgccacgggcgggagggcccttgggttaacaaggggagcgggcca aaaccgtcccccctggcccggaaaccgttccggccaccccagcccggcctcggccccgtacgcctcccgggaccgccgggttcggcggc gacgggtaatagcctgctcggcggcgcggcacaggatccgtctcgtccgtccggcatcttcggggcccatgaaccgaaacgcgagctgcac gcggggcatgcgcacaaagcagctgatccacatgctggccatcatcggccgggcatccaggccgagccgcccttgatggtgtccaggtcg ccgagggacagccccgtcgtctcggtggagcccaggatcacattggtccgctctggcgtaatcgcgccccggggggcgttgtgtgggcgat gaaaaaaccctgaaacagcaccgacacgccggtgttctgtatgcgcaggtaagggttgcacgggacctcggcccagtcgttcataagccg cagtacatactcgatgggaaacgactcgtcggacccgtcatggccatgaaactgaaaggcgcacctggaggggaggctggagggagagtag gggcccgcctccccgtcccgccccgcaacgtagatgggacgataagccgaattcgctgaacgagacccttcgaaggcgtcacctgggtggc cggtgtagggcttgcccagtcccgccatggcgcccgcgatgggagcgtgcgtgcccgcgtaaacccaccaaagggttcgcgaaccgtcccg cccaacagcacgcgcgtcagccccgcagaatctggtgcaggtccaggaaccggttaatgaccgccgcgaatcttcccgcttgcgggcgag cagctcgccgtgcacacacgcggtgtccggggtctgcggggcggcggcgtcgtcgggcgcttttataggcccggcgtacgtcaggagggag gccagccgctgcgtccgcgacaggtagttcagcttggcgtccgtagtcgggaagacaacctccagctcggcgggggtcatatcctcgaacc agacggccgcgtcatgcgcgccgtctcgcgagacgtagcgcgcgtctagactctccagggtctgggaccgcagcgcgcagtcggggattgt gtcccgtaaagttcgctggcgcgtgcgcccctcccgcccagccatggcaacttcgcccccggggtcctggcgagcgtcgcggtgtgcgaa gagtcccccggcagcagctggaaggcgggggcgttcgagcgcgcgtatgtggccttcgatcccagcctcctggctcttaacgaggctctct gcgccgagctcctgacggccagtcacgtgataggtgtgccgcccgtcggtacgctcgacgaggacgtcgccgccgacgtggtcaccgcccc ctcaagggcccgcggggggggcgggcgacgaggggggttcggcggggcgcggaggaccccgcaacccgccccggatccctgtggggagggg cttttggacaccgggccttttccgcggcggccatcgacaccttcgcgctggaccggccctgtctggtctgccgcaccatcgagctgtaca agcaaacctaccgcctctcgcctcagtgggtggccgattacgcgtttctctgtgccaaatgcctgggggcgcccccactgcgccgctagcat cttcgtggccgcgttcgagtttgtgtacgtcatggaccgccactttctgcgcaccaagaaggcgaccctggtcggctccttcgcacgcttt gccctcaccataaacgacatccaccggcacttttttctccactgctgcttccgtaccgacggcggggtgcccgggcggcatgcccagaagc aacccaagccctcgccctcccgggagccgccaaggtgcagtactccaactactcgttcctggcgcagtctgccacccgggccctcatcgg aaccttggcctccggggcgaggaggggcgggtcggcggcgggatccggcacgcagccgtcgctcaccaccgcgctgatgaactggaag gattgcgcccgtctcctggactgcacggagggtcggcgcggggcggggacagctgctgtactcgcgccgccgctcgcaacggggaattcg agacggtcgccggggaccgcgagccggaggagtcgccggatacgtgggcgtacgcggatctggtcctgttgctcctcgccggcaccccgc cgtctgggagtcggggcccccagctgcgcgctgccgcgaggcccgtcgcgccacggtccgccagtcctgggaagcgcatcgcggggcacgc acgcgcgacgtggctccgcgctttgcgcagtttaccgaacccgatgcccagcccgacctcgacctgggccctctgatggccaccgtgctga aacacggccgggggcgcgggcgcaccggcggagaatgcctgctgtgtaacctgttactggtgcgtgcttactggctggccctgcgcagact
```

-continued

```
ccgggcctccgtggtccgctactcggaaaacaacacgagcctcttcgactgtatcgtacccgtcgtcgaccagctcgaggctgaccccgag
acgcagcccggggacggggccggtttgtgagcctgcttcgggccgcggggcccgaggccatctttaagcacatgttctgtgaccccatgt
gcgccattacggagatggaggttgacccctgggttctgttcggccatcccccgccacccatcccgacgagctgctgctccacaaggccaa
gctggcctgcgggaacgagttcgaggggcgtgtctgcatagcgttgcgtgccctcatctacaccttcaagacgtatcaggtatttgtacca
aagcccaccgcgctcgccacatttgtccgtgaggcgggcgcgctgcttagacgccactcgatctcgctcctgtccctggagcacaccctgt
gtacctatgtatgacaccgaccccatcgccgcggctcccggccccgggccctatcacggcaaggagcgccggcggtcgcgctcctctgcgg
ccggcgggactctgggcgtggtgcgtcgggcctcccggaagagcctgccgcctcacgcccgcaaacaggagctgtgtttacacgagcgcca
gcgctatcggggccttttcgccgccctcgcccagacgccctccgaggagatcgccatcgtgcgctcgctctcggtgccctggtgaagacc
actcccgtctcgctgcccttctgtctggaccagaccgtggccgacaactgcctgaccctctccgggatgggctactacctaggcatcgggg
gttgctgtcccgcgtgcaacgcgggagacgggcggttcgccgccaccagccgcgaggccctaatcctggccttcgtgcagcagatcaacac
gatattcgagcatcgcgccttcctggcctccttggtcgtgttggccgaccgccacaacgccccctccaggacctcttggccgggattctt
ggccaacccgagctttttttcgtccacacgatcctgcgcggaggcggggcgtgcgacccgcggctgttgttttacccggaccccacttacg
ggggccacatgctgtacgtcatctttcccggcacgtccgcccacctgcactaccggctcatagaccggatgctcaccgcgtgcccggggta
ccggttcgtcgcccacgtgtggcagagcacgtttgtgctcgtggtccggcgcaacgcagagaaacccacggacgcggagattccgaccgtg
tcggccgcagacatttattgtaaaatgagggacatcagcttcgacgggggctcatgctagagtatcaaaggctctatgcaacattcgacg
agtttcctccgccgtagcgccggcacccaccgccccgaaccctgcggtccggagccgcgcggccacgtcgtccgggggtgccacacttcg
ggaataaaccttttaacagactctcggtgatcttggcgttattcccaaacagggccttgaatgtcacgcacgccgcccccaacaggtggg
agaagtaatagtccgtgttcagggcgacgccgtgggcaatggcgtatgcgggatcctcggccagctcggacaccagcagcttgcggggctt
ggacgcgcctcccgggggtcggcaggcgacggcgtctcccggggcgcttggccggggagggcagggccgcggggggggcgggctcgtcc
cctggggcggcggcgtctagctcgcggagggcggccagccgcgcgaccgtctcctctacctcgcgggtctgggccacgatcacgtacggga
tccggtccttgatggacgggacctgccgcgcggcgggccatgagcttgtaataccaccgtcaggtgggccaggcgcttgttggtgtacgcgcg
cgggtgtctgctcagttcggcggtgaggacaaagtcctggatgtccctctccgggtcggtgatgcgccgatgggcgtctacgaggacggcc
ccgaacgcctgcagtccctcgggcaggggtcgcgccagccactcctccgcgggggcgctcggctaacgcggcggccgctccggagacggtat
cgtcgtaaaacagcaggtcgaccagggccctggaggtgcggttgataaacgcgcagttgttttttgcgcaccagatccacgcccttgatgag
catcttaccccccgtagatgacgccgatgtacttttttcttggcgatcagcagcagcttggtgaacgtcttttcgcactcgagtttgatgggg
ggcagaaacagcgcgcgcgagatgtggctcgccatcttgtcgcccacggccgtcagcccggcggccgtgaggccgcggcacagcacaaaga
tggagtccgtgtccccgtagatgatgcgcatggaataggggcccggggggcgcgcatgtcggccgcctccgggaaatcggccaggagctgttc
gaaggccgcccagcgcgcgtggacgtactcgcgggtcgcgagcagcatctcgcggccgatggtcgtcaccgtcgcggcaacgtgcaggcac
ggcaggagtccgtgctgcactcccgtgaacccgtacaccgagttacacacgaccttgatggcggcctgctgcttgtccaggagcacggcct
cctcggggctgctctggggaatccgcgagcggatctgctttcgcatggcgagccagtcccgcaggaggatgctgaggaggctctctcgcac
gtgagccttgacgaagaacagccgtcgccccccacctcgatctccaggtagtccttgcccgcctccaggtcgccactgcgtcggccctc
agggagagcgtgctgaagcacaggttgtgggcctggatgatgctggggtacaggctggcaaagtcgaacaccaccacggggttcacgtgaa
acccggaagtggggtcaaggaccctggccccctggtaccccacgtgcctgccggcggtctccgcgcgccctccggctcccgctcgccccc
gccctcctcgcgttcgtcctcgtcctccccctcctcctctggccgctcctcgtcctcccgggctgcggcggacgcttgggcgcctccccc
ccggcgcccctaaatcgcccctgggtgtccggcagaataaagcccttctggtcggccaggcgcagcaggcacgtaaagacgcggatctgct
ggccgtcgtagatggtgcgggtgatgttaatacccgccaagcgcgcgacggccgagagctccagatggggcaaaaacttaaaaaacagctg
gcccaccagcagggaatcctgtatgcagtactcgccgatcacccgcgttgcgcgggcccggcggcgtagtaggcggggatgtcgcgatag
ctcaggtccttcttcttgtccttcaggacggcttcggccacggcgttgagcttgtagctcgagagcttgatcttgtcggttataatcccgt
acatgtcgatgttcaccatgccgttcacctttatcttgctgcgcttctggaagtggctctggcctatgtcccacacgcgaaacacgccccg
gccgttcatgcggccgtacccgtccagggggacctgtaaatgtccgtcagcttggccagcaagaagggccagtcgaagttgatgatgttg
tacccggtcacgaactcggggccgtactgtttcacaagggtcatgaaggccaacagcatctcgaattcgctgtcgaattccagaaccacgg
```

-continued gcgtgggcaggccctggccgccagctcgttcaggtgggattcggggaggtcgcaggaaccgagcgaaaacaggaggacgtgctccagggc
ggtggtggacaggtcgtagagcagacaggatatctggatgaccaggtcctccgggtgcccggccaccggaaaggccagctcgtcctccccc
cccgccttgcattcgatatcgaagcacatgagcttgtatgccggtaggtcgctcatgccccctcgatggccaggttgtccgccgtacagt
taaactcgacgtcgctggatgtcccgaaggccatcggggcccgcggctgggctagcgtgttgttccggcccggtttgagacggtaccagcc
gaaggtgacgaacccggggttgtccaggatgaaccgggtggtggcgtcgaccccaccctcgtacttcttgatggccgggcagaagttgtcg
cacaggtacgacagcacgcgcccgcttcggacgtagacgcggtaaaacagagcggggcgcgtctcgtagtagtacacgtcggtgcgctcca
ccacctccgcctcgaagtggtccgcggagatgccgcggaacgacgcgcccggggactcgcgcagggccgcggccatgcgctcgcagagatc
tcgtggggcgcggcattgtaggtgcctgtcgacctcctccttgttcatgtaaaagtactgccgcgtgccgtaaacgtgaacggccacccgg
tggccttccggagtcaggcccaggagcgtgatgacggtccccgtcggtgtgatggcgtccataaaccgcgcgtggaactgggccgcgcgca
tgccgtacgcgtgctccacgttctccaggatgtcgtacacgtgaaagacggtgacggtgggttgaaccccgccggggcgtggtccacgcc
gccccacaggcgcgagcgccgcggccagaagccgcccgacccgacgcggaggacgtcgcgctcgtccccccgcagtacaccttggggcg
cgcttgaggtgaccgtcgtgcaccccggcgcgcttctccgggggggcatcctcgtccagcacccgcggggcgatgaatcgaaattcatcgc
attcgctatagtacgtatggcgctgggttggcccggtcggcttctgttgcgtcccgactggggcgaggtagggggttgtaaaagttttgcct
caaacaaggcggggtccccggctggctccgcgagggccggcgggcgcaaaaaaccggacgccgccctggccgccgactttcctccgggg
gacagcgggccgccgccaccggaaaacatcgcggttgttcccacccgaacccctaaagaggggaatgtggggagggggaagagaaaaacc
caaaagccgcttgggtgggatggcaaaattaccggaccccaggctcgcccgggccggcatgtgcaagggccttgtttgtctggcggatc
cgggcggcgagctgctgcgcggcgccccggccggcggcccggtttattcgcgtcggcccggccgggcttatggaccgccggcggccg
acaggagagtgacgtagccggtgggcgtggccgctattataaaaaaagtgagaacgcgaagcgttcgcactttgtcctaataatatatata
ttattaggacaaagtgcgaacgcttcgcgttctcactttttttataatagcggccacgcccaccggctgatgacgcgcggggcgtgggagg
ggctggggcggaccggcacgccccaggtaaagtgtacatataccaaccgcataccagacgcacccgacccggagcacctgaccgtaagca
tctgtgcctctcgcagggacccgcgttgccggccgccggggttcatcggcacccgtggttacccgggggggttgtcggtgaaggggaggg
attcattccccaaccccggtctccaaccctccccttgaccgtcgccgccccccccggattttgacgctcgggagacataccttgtcggc
gtccgtcgtcgtgccgggattacctccgttcgcgaccgattgacaaaaggacatggagacaaagcccaagacggcaaccaccatcaaggt
ccccccgggccctgggatacgtgtacgctcgcgcgtgtccgtccgaaggcatcgagcttctggcgttactgtcggcacgcagcggcgat
tccgacgtcgccgtggcgcccctggtcgtgggcctgaccgtggagagcggctttgaggccaacgtggccgtggtcgtgggttctcgcacga
cggggctcgggggtaccgcggtgtccctgaaactgacgccctcgcactacagctcgtccgtgtacgtctttcacggcggccggcacctgga
ccccagcacccaggccccgaacctgacgcgactttgcgagcgggcacgccgccattttggcttttcggactacaccccccggcccggcgac
ctcaaacacgagacgacggggggaggcgctgtgtgagcgcctcggcctggacccggaccgcgccctcctgtatctggtcgttaccgagggct
tcaaggaggccgtgtgcatcaacaacaccctttctgcacctgggaggctcggacaaggtaaccataggcggggcggaggtgcaccgcatacc
cgtgtacccgttgcagctgttcatgccggatttagccgtgtcatcgcagagccgttcaacgccaaccaccgatcgatcggggagaattttt
acctaccgcttccgttttttaaccgcccctcaaccgcctcctgttcgaggcggtcgtgggacccgccgccgtggcactgcgatgccgaa
acgtggacgccgtggcccgcgcggccgcccacctggcgtttgacgaaaaccacgagggcgccgccctccccgccgacattacgttcacggc
cttcgaagccagccaggtaagaccccgcggggcgggcgcgacggcggcggcaagggccggcgggcgggttcgaacagcgcctggcctcc
gtcatggccggagacgccgccctggccctcgagtctatcgtgtcgatggccgtctttgacgagccgcccaccgacatctccgcgtggccgc
tgttcgagggccaggacacggccgcggcccgcgccaacgccgtcggggcgtacctggcgcgcgccgcgggactcgtgggggccatggtatt
tagcaccaactcggccctccatctcaccgaggtggacgacgccggcccggcggacccaaaggaccacagcaaaccctccttttaccgcttc
ttcctcgtgcccgggacccacgtggcggccaacccacaggtggaccgcgagggacacgtggtgcccgggttcgagggtcggcccaccgcgc
ccctcgtcggcggaacccaggaatttgccggcgagcacctggccatgctgtgtgggttttccccggcgctgctggccaagatgctgtttta
cctggagcgctgcgacggcggcgtgatcgtcgggcgccaggagtggacgtgtttcgatacgtcgcggactccaaccagaccgacgtgccc
tgtaacctatgcaccttcgacacgcgccacgcctgcgtacacacgacgctcatgcgcctccgggcgcgccatccaaagttcgccagcgccg -continued

```
cccgcggagccatcggcgtcttcgggaccatgaacagcatgtacagcgactgcgacgtgctgggaaactacgccgccttctcggccctgaa gcgcgcggacggatccgagaccgcccggaccatcatgcaggagacgtaccgcgcggcgaccgagcgcgtcatggccgaactcgagaccctg cagtacgtggaccaggcggtccccacggccatggggcggctggagaccatcatcaccaaccgcgaggccctgcatacggtggtgaacaacg tcaggcaggtcgtggaccgcgaggtggagcagctgatgcgcaacctggtggaggggaggaacttcaagtttcgcgacggtctgggcgaggc caaccacgccatgtccctgacgctggacccgtacgcgtgcgggccgtgcccctgcttcagcttctcgggcggcgatccaacctcgccgtg taccaggacctggccctgagtcagtgccacggggtgttcgccgggcagtcggtcgaggggcgcaactttcgcaatcaattccaaccggtgc tgcggcggcgcgtgatggacatgtttaacaacgggtttctgtcggccaaaacgctgacggtcgcgctctcggaggggcggctatctgcgc ccccagcctaacgccggccagacggcccccgccgagagcagcttcgagggcgacgttgcccgcgtgaccctgggggtttcccaaggagctg cgcgtcaagagccgcgtgttgttcgcgggcgcgagcgccaacgcgtccgaggccgccaaggcgcgggtcgccagcctccagagcgcctacc agaagcccgacaagcgcgtggacatcctcctcggaccgctgggctttctgctgaagcagttccacgcggccatcttccccaacggcaagcc cccggggtccaaccagccgaacccgcagtggtgtctggacggccctccaacgcaaccagcttcccgcccggctcctgtcgcgcgaggacatc gagaccatcgcgttcattaaaaagttttcccctggactacggcgcgataaactttattaacctggccccccaacaacgtgagcgagctggcga tgtactacatggcaaaccagattctgcggtactgcgatcactcgacatacttcatcaacacccttacggccatcatcgcggggtcccgccg tcccccagcgtgcaggctgcggccgcgtggtccgcgcagggcggggcgggcctggaggccggggcccgcgcgctgatggacgccgtggac gcgcatccgggcgcgtggacgtccatgttcgccagctgcaacctgctgcggcccgtcatggcggcgcgcccatggtcgtgttggggttga gcatcagcaagtactacggcatggccggcaacgaccgtgtgtttcaggccgggaactgggccagcctgatgggcggcaaaaacgcgtgccc gctccttattttgaccgcacccgcaagttcgtcctggcctgtcccgggccgggtttgtgtgcgcggcctcaagcctcggcggcggagcg cacgaaagctcgctgtgcgagcagctccggggcattatctccgagggcggggcggccgtcgccagtagcgtgttcgtggcgaccgtgaaaa gcctggggcccgcacccagcagctgcagatcgaggactggctggcgctcctggaggacgagtacctaagcgaggagatgatggagctgac cgcgcgtgccctggagcgcggcaacggcgagtggtcgacggacgcggccctggaggtggcgcacgaggccgaggccctagtcagccaactc ggcaacgccggggaggtgtttaactttggggattttggctgcgaggacgacaacgcgacgccgttcggcggcccgggggccccgggaccgg catttgccggccgcaaacgggcgttccacggggatgacccgtttggggaggggccccccgacaaaaagggagacctgacgttggatatgct gtgagggggtggggggtgggggaacctagggcggggcgggaatgtgtgtaaaataaattattgctacgacatccgtgcttgtttgtgttc cgtgtctatatctctgggcgggccgtgattcctctccgcggtgtctgggaatagagcagaaacgcacgcgccgccgactcccggcttgccg gtcggcgggcccgcggggaggccgccccgaagaggggggaccccgggggctcagccagacgccgggtagcgtacggaccgcctcggtccaccgc atactccggccgcggtacagatcggcgccgcgagatggccgccccggtgtccgagcccaccgtggcccgtcaaaagttgttagccctgctc gggcaggtgcagacctatgtgtttcagatagagctgctccggcggtgcgaccccacatcggacgggggaagctcccccaactgaagctga acgcgcttcaggtgcgggcgctgcggcgtcgtctgaggccgggcctggaggcccaggccggggcctttctcaccccgctgtcggtcaccct ggagttgctgctagagtacgcgtggcgcgagggcgagcggctcctgggcagcctggagacgttcgcgaccgcggagacgtcgcggcgttt ttcacggagaccatgggcctggcccgaccctgtccgtatcaccaacgggtcaggctggatacgtatggcgggaccgtccatatggagctgt gtttcctgcacgacgtcgagaactttctaaagcagctaaactactgccacctcatcaccccctcgcgcggcgccaccgccgcgctggagcg cgttcgggagtttatggtggggggcggtgggtcgggccttatcgtccccccggagcttagcgacccgtcccacccctgcgcggtctgtttc gaggaactgtgtgtgacggcgaaccaggggggcgacgatcgcccgccgcctggcggaccgtatctgtaaccacgtcacccagcaggcgcagg tgcggctggacgccaacgagctgcggcggtacctgccccacgccgccgggctgtcggacgccgaccgcgcgggcgctctccgtgttgga ccatgcgctggcccggaccgcggggggcgacgggcagccccacccgtcgcccgagaacgactcggtccgcaaggaggccgacgccctgctg gaggcgcacgacgtgtttcaggccaccacgcccgcctgtacgccatcagcgaattgcgattctggctcgcgtccggcgaccgcgccggcc agaccaccatggacgcgtttgccagcaacctgaccgcgctggcgcggcgcgagttgcagcaggagaccgccgcggtggccgtggaactggc gctgttcgggcggcgggcgagcatttcgatcgcgcgttcggagccacctggcggcgctggatatggtggacgcctaataatcggcggt caggccacgtcacccgacgatcagatcgaggcgctcatccgcgcgtgctacgaccaccacctgacgacgccgctcttgcggcgcctcgtca gccccgaacagtgcgacgaggaggcgctgcgtcgcgtgctggcgcgcatgggggcgggggcgcggcggacgcgcccaagggcggcgcggg ccccgacgacgacggggaccgtgtcgccgtagaggaaggggcacggggggttgggagctcccggggcgggggcgaggacgaagaccgtcgc
```

-continued cgcgggcccgggggggcaggggcccgagacgtgggggacatcgccacgcaagcggccgcggacgtgcgggagcgacggcggctgtacgcgg accgcctgacgaagcggtcgttggccagcctggggcgctgcgtccgcgagcagcgcggggagctcgagaagatgctgcgggtcagcgtcca cggcgaggtgctgcccgcgacgttcgccgcggtcgccaacggctttgcggcgcgcgcgcgcttctgcgccctgacggcgggcgcgggcacg gtcatcgacaaccgctcggcgccgggcgtgttcgacgcgcaccggttcatgcgagcgtctctcctgcgacaccaggtggacccggccctgc tccccagcatcacccatcgcttcttcgagctcgtcaacgggcccctctttgatcactccacccacagcttcgcccagcccccaacaccgc gctgtattacagcgtcgagaacgtggggctcctgccgcacctgaaggaggagctcgcccggttcatcatgggggcggggggctcgggtgct gattgggccgtcagcgaatttcagaggttttactgttttgacggcatttccggaataacgcccactcagcgcgccgcctggcgatatattc gcgagctgattatcgccaccacactctttgcctcggtctaccggtgcggggagctcgagttgcgccgcccggactgcagccgcccgacctc cgaaggtcgttaccgttacccgcccggcgtatatctcacgtacgactccgactgtccgctggtggccatcgtcgagagcgcccccgacggc tgtatcggccccggtcggtcgtggtctacgaccgagacgttttctcgatcctctactcggtcctccagcacctcgcccccaggctacctg acgggggggcacgacgggcccccgtagtcccgccatgcgccagggcgcccccgcgcggggggcgccggtggttcgtcgtatgggcgctcttgg ggttgacgctggggtcctggtggcgtcggcggctccgagttcccccggcacgcctgggtcgcggccgcgacccaggcggcgaacgggg ccctgccactccggcgccgcccgccctggcgccccccaacggggggaccccgaaaccgaagaagaacaaaaaaccgaaccccccaaagccg ccgcgccccgccggcgacaacgcgaccgtcgccgcgggccacgccaccctgcgcgagcacctgcgggacatcaaggcggagaacaccgatg caaacttttacgtgtgcccacccccacgggcgccacggtggtgcagttcgagcagccgcgccgctgcccgacccggcccgagggtcagaa ctacacggagggcatcgcggtggtcttcaaggagaacatcgcccccgtacaagttcaaggccaccatgtactacaaagacgtcaccgtttcg caggtgtggttcggccaccgctactcccagtttatggggatctttgaggaccgcgcccccgtccccttcgaggaggtgatcgacaagatca acgccaagggggtctgtcggtccacggccaagtacgtgcgcaacaacctggagaccaccgcgtttcaccgggacgaccacgagaccgacat ggagctgaaaccggccaacgccgcgacccgcacgagccggggctggcacaccaccgacctcaagtacaacccctcgcgggtggaggcgttc caccggtacgggacgacggtaaactgcatcgtcgaggaggtggacgcgcgctcggtgtaccgtacgacgagtttgtgttggcgactggcg actttgtgtacatgtccccgttttacggctaccggggaggggtcgcacaccgaacacaccagctacgccgccgaccgcttcaagcaggtcga cggcttctacgcgcgcgacctcaccaccaaggcccgggcacgcgcgccgaccacccggaacctgctcacgacccccaagttcaccgtggcc tgggactgggtgccaaagcgcccgtcggtctgcaccatgaccaagtggcaggaggtggacgagatgctgcgctccgagtacggcggctcct tccgattctcttccgacgccatatccaccaccttcaccaccaacctgaccgagtacccgctctcgcgcgtggacctgggggactgcatcgg caaggacgcccgcgacgccatggaccgcatcttcgcccgcaggtacaacgcgacgcacatcaaggtgggccagccgcagtactacctggcc aatgggggctttctgatcgcgtaccagccccttctcagcaacacgctcgcggagctgtacgtgcgggaacacctccgcgagcagagccgca agccccccaaaccccacgcccccgccgcccggggcagcgccaacgcgtccgtggagcgcatcaagaccacctcctccatcgagttcgccag gctgcagtttacgtacaaccacatacagcgccatgtcaacgatatgttgggccgcgttgccatcgcgtggtgcgagctgcagaatcacgag ctgaccctgtggaacgaggcccgcaagctgaaccccaacgccatcgcctcggccaccgtgggccggcgggtgagcgcgcggatgctcggcg acgtgatggccgtctccacgtgcgtgccggtcgccgcggacaacgtgatcgtccaaaactcgatgcgcatcagctcgcggcccggggcctg ctacagccgccccctggtcagctttcggtacgaagaccagggccccgttggtcgaggggcagctggggagaacaacgagctgcggctgacg cgcgatgcgatcgagccgtgcaccgtgggacaccggcgctacttcaccttcggtgggggctacgtgtacttcgaggagtacgcgtactccc accagctgagccgcgccgacatcaccaccgtcagcaccttcatcgacctcaacatcaccatgctggaggatcacgagtttgtcccccctgga ggtgtacacccgccacgagatcaaggacagcggcctgctggactacacggaggtccagcgccgcaaccagctgcacgacctgcgcttcgcc gacatcgacacggtcatccacgccgacgccaacgccgccatgtttgcgggcctgggcgcgttcttcgaggggatgggcgacctgggcgcgcg cggtcggcaaggtggtgatgggcatcgtgggcggcgtggtatcggccgtgtcgggcgtgtcctccttcatgtccaacccctttgggggcgct ggccgtgggtctgttggtcctggccggcctggcggcggccttcttcgcctttcgctacgtcatgcggctgcagagcaacccccatgaaggcc ctgtacccgctaaccaccaaggagctcaagaaccccaccaacccggacgcgtccggggagggcgaggagggcggcgactttgacgaggcca agctagccgaggcccgggagatgatacggtacatggccctggtgtctgccatggagcgcacggaacacaaggccaagaagaagggcacgag cgcgctgctcagcgccaaggtcaccgacatggtcatgcgcaagcgccgcaacaccaactacacccaagttcccaacaaagacggtgacgcc -continued

```
gacgaggacgacctgtgatgggggggtttgttgtaaataaaaaccacgggtgttaaaccgcatgtgcatcttttggtttgtttgtttggtac
gccttttgtgtgtgtgggaagaaagaaaagggaacacaaactcccccgggtgtccgcggcctgtttcctctttcctttcccgtgacaaaac
ggaccccttggtcagtgccgattccccccccccacgccttcctccacgtcgaaggcttttgcattgtaaagctaccgcctacccgcg
cctcccaataaaaaaagaacatacaccaatgggtcttatttggtattacctggtttatttaaaaagatatacagtaagacatcccatggta
ccaaagaccggggcgaatcagcgggcccccatcatctgagagacgaacaaatcggcggcgcgggccgtgtcaacgtccacgtgtgctgcgc
tgctggcgttgacaagggcccggcctccgcgttggatgcctccggttgggatccggtggcggcggggggaacgcgggctccgtcggtag
aggggcgcgcgtctgggtggaaggacatgggggcggtggcgggcctggcgggcaggcagctggggcatacgggggagtgggggcatgggac
gccggaccctggggaggaccgtaggggggcgctgtgtggtgggggggcgatacacggcctccggggacaaagggccgggtgggtcgttgttg
gttccggctcccccacctgagggcgatagtgcgccaccggcgtgtacattccatagggggcgctggtccgagcccgcatgtgcgccagttc
ctgctgcagagacgtcaccgcccccatcagcgccgtgatggtctcgttggtcccgggagaatggcgggccgcgcgccgggagtcgaccccg
cgcggccccgcctcgagcctccccggggtagtacgggtagtccgcgtccggttcgtcctggtcgcagtaggactccgacggccccgcctcgt
accggcgacgctttcccgaccccggaccccagggtctcccgcggccggctgaccgcccgcctggcggtccgcggctatggccccaccaa
cgcggctatctgcgcctcgagtgggctgggtcccgagaacagcaccccgggatactgatgggcgacgtggggagggtaatgctgggaaaga
cccgcaccgtgaggcccataggccacggaccccgccgcagccgggaaaccaaacgcggaatgcggctgggttggggcgcggcatggccgg
cgacgagctggttgtaatgggaggccgggatccacaggtagctcccgtcgccgggcggcgcggggccgggtgcccgatgtcggaacggg
gttcatggggggcagtaccggggacaaggcgaccccgcgctgacggacgattgggcaccggtcaccctgcggcgcggcagcgatcgagccg
ggcggtatgtccgtggactccggggccccgttcttataccgcgcgccggcgcggaaacaggctccgccccccacattttgaattttcgc
tcgcctggaggtaggtgtgtccggcgatcccggcctgccgccgccgctcggccaccaggctccagcggtcccgcagcatcatgttgttaac
ggcggtggaaagcagcgtgtgggtcagcgcctccacgccgggcgcccaggtgcgcccggacagcgcgagctcggcctcggcggccagtcgc
cgcgcccctcgcgagacgccggcgacaggtggcgaaagggcgcgatggcggcgtcgagaccggtgtcgtaggtgacgatagtgccgaggc
gccgcccgatcgcgcacagcgcgacgtgcgcgaacagcgtgcgatcggggtgcgcctcgcccccaggcgttttgtggccagggagaccga
gggcaggtagttggtgatcaggtacaacaggcgctcctcccgggagagcggcggcccgcggcgctcgaaaatcgcagcgctggcggccgtc
tcgaggacgcgctccagctgcacgcaggcgatcagccccacaaaaaacggcccgcggggtcgtcgaccacggccagcacccgccccacct
cgcagccagcgcggtggtccacgttaatcgggagtgggttatccggaggcagggccgcccgcaccgtatccggatccaatgccaactcgcc
cgagtccccgctgtcatacagggccaaaaacccagccacgtaaatgggcacggcctgtcgggcaggggctcctccatccggtctcccggg
gcatcggctgccatgcgcgcacccacagagactttggtggacgaaaaaaaaaaggcgcaacggtcgggggcgggcggaaaggcgagagc
gaatgctaaactaaacgctaacccagctcccgccgttgcgttcacgccaaccgccgggccgggactggagcccgccgtttacggggtatga
ccttttgagtacaggcacaaagaaaacccaacggaggctcttgttctttctccctaatgcccctcccccctcgcccaccacccactaaac
cgccgacaggtactgtggaatgaaccccagacataaaagtacaacatgtcgtagtcgctgctaacgttgaacgcggagaaacgcttggtg
ttggagcccaagccaatgcgtgcctgctgcgccagcaggccaagcccctgttcgtattggatcgccagggcgtcgtgggcgtggataacct
cccccacaggggtggggtttgtgcgggtgcggttgatgagttccagggcggtgaggcgcaccagcgccgcctggcgggccccgatgacat
atccaccacccgccgcgtcgacccgaccggccgccccgcctgggcgtcaagacacagggcggccaggccgggaaacagctgggtcagctcg
accgccgggtcggcccggtacagcggaagcacgtaattggcacatagcgcctccagattgttgtctccgctcttgatggccccgagtcgg
acccggaggcccacgggcgatggcctccgaagggacggctccggggatcagcatgcccagctgcaggcggttgttgaggcggtccgcgta
cacgttgccgttcgcgaggagccgctggataacgcccagggccgttatggtgttcgcggttgcccgcagcagagtctggtcctcccacagg
aataggttgtggccccggctgaggaacgcggcggcggcgcggtttatgtcgtcgtggtgcgccacgccgtcggggttaacgtgggtactcg
cgtcccggggacgtccccgggcgccggggagcacccgtggtgcatcagcgtggcgatcacgatgtgcgacgccagcgctccgtgttc
gtagcggccccgccggccgcgaactgcgtcttggggagcttgtcgtcgcggtagcggtactgtggccggccgccctcggtcccgatcacc
gcggccaggcacgccaggtagcggggcagccggcccagcagatcccgaacgtgaccggagcgcggtcgctatcgtcggcggccccgtgcg
tgtttcggtacagcaggtagagacacaacacggcgcactcgaaggcggaatagtggcgctggcccacatacagccggccgcacgcctgcag
ggacagtaccagcgccgtcatgaaggtcttggacatacggccgtcccgaaagtcggcactgcgggtggtcaggggaaagtccgtgatggtg
```

-continued

```
cggtcctggatagtgcggtaccaggtcccgaacaccaccccgacgagccggtcgccccgcggcccgcgtacaccatgtgtagcagatcca
cggggaggttggtgtcgtatcgtagcggcgggtcgttgcgcacgatctggacctccatctccgcgacggccagacccgggggcgcccccc
gtcgccccacccgccggctcatcccgcgcgcggcatccgcctcttcggcggcggccgccgccgtctccagcgcctccagggcgcctgcg
atctcgtgcacgttccgttcgatcgggcgtaaccggcgctcgatatcgacggggagctcggccgcctgcatggcggcgttctccagggcag
cggcagccgctgtgcgctgggcctgtaggacgaccacctgctccgccgccgtctcccgggggaggttaaagacgggcgacatccaaaagtc
ccggggaactcggggtgatgaagtttcgggaatcggcgactatgaagcgcctgtgttcccagacgtccagagcgtcaaatgggcagtac
gggtccatctgcgagaggcggagagcgaaaataacacacgagaactgcggtcgttgtcctaactaccagaccttgttttatttggggacaa
gatgggggtgggatgaggggcgcgatggcacagcggaccggcgtctggcgtgggaaacccgggggctgttgtcgggtggctcccgccg
gatccaaatgagtcttcggacctcgcgggggccgcttaagcggtggttagggtttgtctgacgcgggggaggggaaggaacgaaacact
ctcattcggaggcggctcggggtttggtcttggtggccacgggcacgcagaagagccgccgcgatcctcttaagcacccccccgccctccgt
ggaggcgggggtttggtcggcgggtggtaactggcgggccgctgactcgggcgggtcgcgcgccccagagtgtgaccttttcggtctgctc
gcagaccccgggcggcgccgccgcggcggcgacgggctcgctgggtcctaggctcaatggggaccgtatacgtggacaggctctggagca
tccgcacgactgcggtgatattaccggagaccttctgcgggacgagccgggtcacgcggctgacgcggagcgtccgttgggcgacaaacac
caggacggggcacaggtacactatcttgtcaccggaggcgcgagggactgcaggagcttcagggagtggcgcagctgcttcatcccgtg
gcccgttgctcgcgtttgctggcggtgtcccggaagaaatatatttgcatgtctttagttctatgatgacacaaacccgcccagcgtct
tgtcattggcgaattcgaacacgcagatgcagtcggggcggcgcggtcccaggtccacttcgcatattaaggtgacgcgtgtggcctcgaa
taccgagcgaccctgcagcgacccgcttaacagcgtcaacagcgtgccgcagatcttggtggcgtgaaactcccgcacctcttcggccagc
gccttgtagaagcgcgtatggcttcgtacccctgccatcaacacgcgtctgcgttcgaccaggctgcgcgttctcgcggccataacaaccg
acgtacggcgttgcgccctcgccggcagcaaaaagccacggaagtccgcctggagcagaaaatgccacgctactgcgggtttatatagac
ggtccccacgggatggggaaaaccaccaccacgcaactgctggtggccctgggttcgcgcgacgatatcgtctacgtacccgagccgatga
cttactggcgggtgttgggggcttccgagacaatcgcgaacatctacaccacacaacaccgcctcgaccagggtgagatatcggccgggga
cgcggcggtggtaatgacaagcgcccagataacaatgggcatgccttatgccgtgaccgacgccgttctggctcctcatatcggggggag
gctgggagctcacatgccccgcccccggccctcaccctcatcttcgaccgccatccatcgccgcctcctgtgctaccggccgcgcgat
acctatgggcagcatgaccccccaggccgtgctggcgttcgtggccctcatcccgccgaccttgcccggcacaaacatcgtgttggggc
ccttccggaggacagacacatcgaccgcctggccaaacgccagcgccccggcgagcggcttgacctggctatgctggccgcgattcgccgc
gtttatgggctgcttgccaatacggtgcggtatctgcagggcggcgggtcgtggcgggaggattggggacagctttcggggcggccgtgc
cgccccaggtgccgagccccagagcaacgcgggcccacgaccccatatcggggacacgttatttaccctgtttcgggccccgagttgct
ggcccccaacggcgacctgtataacgtgtttgcctgggctttggacgtcttggccaaacgcctccgtcccatgcacgtctttatcctggat
tacgaccaatcgcccgccggctgccgggacgccctgctgcaacttacctccgggatggtccagacccacgtcaccacccaggctccatac
cgacgatctgcgacctggcgcgcacgtttgcccgggagatgggggaggctaactgaaacacggaaggagacaataccggaaggaacccgcg
ctatgacggcaataaaaagacagaataaaacgcacgggtgttgggtcgtttgttcataaacgcggggttcggtcccagggctggcactctg
tcgataccccaccgagaccccattgggaccaatacgcccgcgtttcttccttttccccaccccaaccccaagttcgggtgaaggcccagg
gctcgcagccaacgtcggggcggcaagccctgccatagccacgggccccgtgggttagggacggggtcccccatggggaatggtttatggt
tcgtggggttattattttgggcgttgcgtggggtcaggtccacgactggactgagcagacagacccatggttttggatggcctgggcat
ggaccgcatgtactggcgcgacacgaacaccgggcgtctgtggctgccaaacaccccgaccccaaaaaccaccgcgcggatttctggcg
ccgccggacgaactaaacctgactacggcatctctgccccttcttcgctggtacgaggagcgcttttgttttgtattggtcaccacggccg
agtttccgcggggaccccggccagctgctttacatcccgaagacctacctgctcggccggccccgaacgcgagcctgcccgcccccaccac
ggtcgagccgaccgcccagcctccccctcggtcgcccccttaagggtctcttgcacaatccagccgcctccgtgttgctgcgttcccgg
gcctgggtaacgttttcggccgtccctgaccccgagccctgacgttccgcggggagacaacgtggcgacggcgagccacccgagcgggc
cgcgtgatacaccgccccccgaccgccggttggggcccggcggcacccgacgacggagctggacatcacgcacctgcacaacgcgtccac
```

-continued

```
gacctggttggccacccggggcctgttgagatccccaggtaggtacgtgtatttctccccgtcggcctcgacgtggcccgtgggcatctgg acgacggggagctggtgctcgggtgcgatgccgcgctggtgcgcgcgcgctacgggcgggaattcatgggctcgtgatatccatgcacg acagccctccggtggaagtgatggtggtccccgcgggccagacgctagatcgggtcggggaccccgcggacgaaaaccccccggggctct tcccgggcccccggcggccccggtatcgggtcttgtcctagggtccctgacgcgggccgacaacggctccgcgctggacgccctccgc cgcgtgggcggctaccggaggagggcacgaactacgcccagttcctgtcgcgggcatacgcggagttttctcgggggacgcgggcgccg agcagggcccgcgcccccctctcttctggcgcctaacggggctgctcgcgacgtcgggttttgctttcgtgaacgccgcccacgcaaacgg cgcggtctgcctctccgacctgctaggcttttggcccactcgcgcgcgcttgccgggttggccgcccgcggggccgcgggctgtgccgcg gattctgtgtttttaatgtgtcagtcttggatcccacggcccgcctgcagctagaggctcggctccagcacctggtggccgagattctgg agcgcgaacagagcttggcattacacgcgctgggctatcagctggccttcgtgctggatagcccctcggcgtacgacgcagtggcgcccag cgcagcccatctcatcgacgccctgtatgccgagtttctagggggccgcgtgctgaccaccccggtcgtccaccgggcgctatttttacgcc tcggctgtcctccggcagccgttcttggctggcgtcccctcggcggtgcagcgggaacgcgcccgccggagccttctgatagcctcggccc tgtgtacgtccgacgtcgccgcagcgaccaacgccgacctccggaccgcgctggcccgggccgaccaccagaaaaccctcttttggcttcc ggaccacttttcgccatgcgcggcctccctgcgctttgatctagacgagagcgtgtttatcctggacgcgctggctcaagccacccgatcc gagaccccggtcgaagtcctggcccagcagacccacggcctcgcctcgaccctgacgcgttgggcacactacaacgccctgatccgcgcct tcgtccctgaggcctcacatcggtgcgggggcagtctgccaacgtcgagccacggatcctggtacccatcacccacaacgccagctacgt cgtcacccactcccctctgccccgggggatcggctacaagctcaccggcgtcgacgtccgacgcccactgttcctaacctacctcaccgcg acatgcgaaggctccacccgggatatcgagtccaagcggctggtgcgcacccaaaaccagcgcgacctgggcctcgtgggggccgtgttta tgcgctacaccccggccggggaggtcatgtctgtgttgctggtggatacggacaacacacagcagcaaatcgccgccgggccgacggaggg cgccccaagcgtgttttcgagcgacgtgccgtccacggccttgttgctatttccaaacggaaccgtcattcatttgctagcctttgacacg cagcccgtggccgcaattgcgcccgggtttctggccgcctctgcgctgggcgtggttatgattaccgccgccctggctggcatcctaaagg ttctccggacaagtgtcccgttttttttggagacgcgaataaagtgggcgtggcttcggccgtttctccgcccgaccgaataaactgtaacc gtgtctgtggtttgtttgttcaggccccggtggtgccgctccccagcccctcttttgctttccctccccccccccggagaggcgtccatt gacacacaagggtgtagtagcgatatacgtttattgggtcttttacacagactgtccgtgttgggagcgagcgagacgaacggtaagaag cacatccaggtacccggcggcccgcgtgcggctggccgcgcccgccgctccgcggtcaaacgcggaaagacggtccacgtcacccaccgct agcaccaggaggtcacccctgtcagccgcgcggtgtgcgtggctgcggacatgcgcccgcggccagcgtacagcacgctcaggaacgcac caaggtacgcgacgtgctcgggggagatcaccccccgggacggcgagacgttgcgattctataaagcgcagcagagcggtgctgtcggc ctgcacgtcgcttccaccggcacgtcctttgggggagaaggtcgaacatgaggagctgctcggctgtggttccggccgccagcgcgtcg cgaaacagcccgttgatggcatcggccaagactgggtcgtcgggccgagggacgtacaggccgtggcgctgtgtgtaccggcctacgagcc ggactagcgcggggaaggggacaggcgcctctctcggtggatgatatagtagtaaacggctagcttttggaggggggctcaggcccaacgc ggccccgataaacgcccgcggggcccccgcggagccaaacagtttccacgcctgctcccggaacccacgtacggcacgtacctcctcgcgg gtgaggccagagtcggcgcggggctcctccagcgcccggtctgcggcataaaacacccaccacagctcccttagcgtggggccgggcgggg cggaatcctgggccccgggcaccagggaactcgagtcggtgttgtttggcggaggcgccggcgaaacgccagcggggcccacgcggtcaat gtgtttgacttgcacgaactcgctgacggtggcccgcttggcgcccgcgccccccgacccccgccccgaccggcgatgggtcgtgggcg cggcggcccgtgataaccacatccgtgcgcgggttgtgggcgtcaagtggctggcgtggggcgggatgccgtcaaacaggccgctcacca gggcctccagcgagctcggagccggggaggtgcgcctgggccagggcgaacacgtatggggacggggtatacacaaagtgcgaggaaac gttgactatcgtttgggtgttcaaacaactcgatgattctgtcctgcgcccgcacgcgcagcccggatattagcacacccgggctggttcgc agcgaggtgcagtactcggccagacattcgtccagcacttccacgtcgttcgtgttaatcacatccagctcggagctcacgttcgggttta gaagacacacgctgtccagaaacacctcgtcctcccaatgggacgcacgtcctgcaggccgcgttgtcggagctcgcttcgtacatagtt ggcgaccacgcggtcgtctgggcctgtccctcgaacgaccagaccaaacttggcaatctcccggggctgcgaggcacacggccgccccacg gaataaacaccccccgcacacaaagtaggcccggtttcggtccgttgtgacgtaaaacacaacgtcccggtagtgcatggtggtggcgt agctaagctccatcgcgggcggcgacgtaacacggcccagaggccccctacggtggatgtgggcgtgggtatgggggaacaccgacaacag
```

-continued

```
aaactggagggcaacgcttggaacgccaataaagcacgcggactcgtcctcgtgcgtgccgcacgcggtgggggccgaaccggacacaggc
aaccccgacgtgcgttgcacaggcaggtctcgaatacaacgacggcttccgtagtatggaccctgccttttgaggacaaccccgggcgtgt
tcccgacacggcctactgggttttccgtttcctcccaccccattttttcccttggcctccaatgaactaaacgcaacgtcacacccacgg
gggggttacctacctcatcttgcgtgggcattggggcgtaggcgtaaattccgggttttgtggtcaacatcaaaggttatatcaaggcgcg
gaacggccttatcaaaacactcgcctccgcggatgcaacccgggtggtgtttgtgcaagaacccgggtgtctttgatctcgggatcctgct
gacgtaagcgacccttttgcggtttcggtctccccacctccaccgcacacccatgaccatgcgggatgaccttcctctggtggatcgagat
ctggtcgacgaggccgccttcggggggaggagggagaactgccgctggaggaacagttttcattgtcctcgtacggcacctctgattttt
ttgtcagttcggcatactcgcgtcttccgccccataccagccggtcttttcaaagcgcgtgattctgttcctttggtcgtttttggtcct
gaagccgttggagatggtggcagcgggcatgtattacgggctgaccggaagggtggtggcgccggcctgtatcctggccgccatcgtcggc
tactacgttacgtgggcggtgcgggcgctcctcctgtacgttaacatcaagagggatcgtctgccgttgtcggcgcccgtgttttggggga
tgtccgtgttttgggaggcacggccctgtgtgccttgttcgccgccgcccacgagacctcagtccggacgggcttttccactttatcgc
caccaaccaaatgctgccgcccaccgatcccctgcgcacacgggccctggggatagcctgcgcggccggggcctcgatgtgggtggcggcg
gcggacagctttgccgcctctgccaatttcttcctggcacgcttttggaccagggccatcttgaatgcaccgtcgcgttctaacgggggt
ggggcggggggggggtatataaggcctgggatcccacgtccccgggtctgttggggacactgggttctcctggaacgaggccgcagcctt
ctcccggtgcctttccccccgaccggcacccggcctctcacacagcatcccccgccttttgggtccgggcccgtcgtgtctttcggtgg
accttgggccgtcgggcacgtacacgggtggccgggcgttggggtggatcttagcctccccgggccaatatcgctagagacagccgatctc
cacgcgaccccatggccgctcccaaccgcgaccctccgggataccggtatgccgcggccatggtgccgaccgggtccctccttagcacgat
cgaggtggcgtcgcatcgacgcctgtttgattttttttcccgcgtgcgctccgatgcaaacagcctgtacgacgtcgagttcgacgcctg
ctggggtcgtattgcaacaccctgtcgctcgtgcgctttctggagctcgggttgtcggtggcgtgcgtgtgtaccaagtttccggagctgg
cctacatgaacgaggggcgcgtacagttcgaggtccaccagccgctgattgcccgcgacggcccgcaccccatcgagcaacccacacacaa
ttacatgaccaagattatcgaccgccgggccctgaacgccgccttcagcctggccaccgaggccatcgccctgctcacggggaggccctg
gacgggacgggtatcggcgcgcatcgccagttgcgcgccatccaacagctcgctcgcaacgtccaggccgtcctcggggcgtttgagcgcg
gcacggccgaccagatgctgcacgtgctgctggaaaaggcgccgcccctggctttgttgttgccgatgcaacgatacctggacaacggccg
cctggccaccagggtggcccgggcgaccctggtcgccgagctaaagcgaagcttctgcgagacgagcttttcctgggcaaggcgggccac
cgccggggaggccgtcgaggcctggctcgtggacctcaccacggccacgcagccctccgtggccgtgcccgtctgacgcatgccgacacgc
gcgggcggccggtcgacggggtgctcgtcaccaccgccccgatcaaacagcgcctcctgcagtccttcctgaaagtggaggacaccgaagc
cgacgtgccggtgacgtacggcgagatggtcctgaacggggccaacctggtcacggcgctcgtgatgggcaaggccgtgcgaagtctggac
gacgtgggccgccacctgctggagatgcaggaggagcagctcgacctgaaccggcagacgctggacgagctcgagagcgcccccagacga
cgcgcgtgcgcgcggatctggtgtccatcggcgagaagctggtctttctggaggccctggagaagcgcatctacgccgccaccaacgttcc
ctaccccctggtgggcgccatggacctgacgttcgtcctgcccctgggcctgttcaatccggtcatggaacggtttgccgcgcacgccggg
gacctagtcccgccccggccacccggatccccgcgccttcccgccccgccagctgttttttgggggaaggaccgccaggtgctgcgcc
tgtctctggaacacgcgatcgggaccgtgtgccaccttcgctgatgaacgttgacgcggcggtcggggccttaaccgcgacccccgtcga
agccgccaatccgtacggggcgtacgtggcggccccggccggccccgccgcagacatgcagcagctgttttttgaacgcctgggggcagcgc
ctggcccacgggcgggtccgatgggtcgcggaaggccagatgaccccggagcagtttatgcagcccgacaacgccaacctggctcttgagc
tgcaccccgcgttcgacttctttgtggggtggccgacgtggagctgccgggggggacgttccccggccggcccgggggagatccaggc
cacctggcgcgtggtgaacggcaacttgccctggcgctatgtccggcggcgttccgggacgcccggggcctggagctggggtgggacgc
cacgccatggccccgccaccatcgccgcgttcgcggggcgttcgacaccgcaactaccggcggtgttttacctgctgcaggccgcca
tacacggcagcgagcacgtcttctgcgccctggcccggctcgtggtccagtgcatcaccagctactggaacaacacgcggtgcgcggcgtt
cgtgaacgactactcgctggtctcgtacgtcgtgacctacctcggggagacctcccgaggagtgcatggccgtgtaccgggacctggtg
gcgcacgtcgaggccctggcccagctggttgatgactttaccctgaccggcccggagctgggcgggcaggcgcaagccgagctgaatcacc
```

-continued

```
taatgcgagacccggcgctgctgccacccctcgtgtgggactgtgacgccctgatgcggcgcgcggccctggaccgccatcgcgactgccg
ggttagcgcggggggccacgacccccgtgtacgcggcggcatgtaacgtggcgaccgcggacttcaaccgcaacgacggccagctgctgcac
aacacccaggcccgagccgcggacgccgcggatgaccggccgcaccgggggcggactggaccgtgcaccacaagatttactactacgtga
tggtgcccgccttctcgcggggccgctgctgcaccgcggggttcgcttcgaccgcgtatacgccaccctgcagaacatggtggtcccgga
gatcgcccccggcgaggagtgccccagcgaccccgtgacggacccccgcgcaccccctgcaccggccaatctggtggccaacacggtcaac
gccatgtttcacaacgggcgcgtggtagtggacgggcccgccatgctcacgctgcaggtgctggcccacaacatggccgaacgcacaacgg
cgctgctctgctcggcggcgcccgacgcgggcgccaacaccgcgtccaccaccaacatgcgcatattcgacggggcgttgcacgccggaat
cctgctgatggcccccagcatctggaccataccatccaaaatggcgactattttaccccctcccgtccacgcgctgttcgccggggcc
gaccacgtggcgaacgcgcccaattccccccggccctgcgcgacctgtcgcggcaggtcccctggtcccccggctctgggggccaact
acttttcgtcgatccgacagccgtcgtgcagcacgtccgcgagagcgcggccggggagaacgcgctgacctacgcgctcatggcggggta
cttcaagatcagtcccgtggccttgcatcatcagctcaagacgggcctccatcccgggtttggttcaccgtcgtccgacaggaccgcttt
gtgactgagaacgtgctgttctcggagcgcgcgtcggaggcgtacttcctgggccagctccaggtggcccggcacgaaactggcggggggg
taaacttcacgctcacccagccgcgcgggaacgtggacctgggcgtgggctacaccgccgtcgtggccacggcaaccgtccgcaaccccgt
caccgacatgggcaaccttccccaaaacttttacctgggccgcgggggctcccctctcctggacaacgcggcagccgtgtacctgcggaac
gcggtcgtggcgggaaaccgcctggggccggcccagcccgtcccgtgttcgggtgcgcccaggtgccgcggcgcgcagggatggaccacg
gccaggacgccgtgtgtgagtttatcgccacccccgtgtcgaccgacgtcaactacttccgccggccctgcaaccccggggacgcgccgc
cggggcgtttacgcggggacaaggaggggatgtcaccgccctcatgtacgaccacgccagagcgaccgtcccgggccttcgcggcc
acggccaacccgtgggcgtcgcagcgatttcgtacggggacctgctctataacggggcctaccacctcaacggggcctcgccggtgctca
gccctgctttaagttcttacgtcggccgacatcgccgccaaacatcgctgcctggagcgcctgatcgtggagacgggttcggcggtgtc
cacggccaccgccgccagcgacgtacagtttaagcgccccccggggtgccgcgaactcgtggaggacccgtgtggcctgtttcaggaggcc
tacccgctcacctgcgccagcgaccccgccctcctccgcagtgcccgcaacggggaagcccacgcgcgggagacccacttcgcgcagtatc
tcgtctatgacgcatccccgctcaagggactggctctgtaataaaccgcccgccttccttggggtagtgcgattcttttatcccacgcg
tcttctgtttccgcaagcccctagccccgccccctttgtcccgccgacaagccgcgattccgagggcgggccccataaaacccaagccg
ggactccgcggacggattcgctctcggtgcgtctgggcccgacagacctccccgcgcatgctctggggtccctgtcgcctcccaaccccct
aagacccacccccgtcctatgcgaggttggtcgcccgtctctgctacgccgctgaccccaccgcgctcctcccgccaccggaaccacca
ctgcactccctgccgcgtggatcggcgccatgctggcggacggctttgaaactgacatcgcgataccctcgggcatctcgcgccccgatgc
ggcggcgctgcagcgctgcgaagggcgggtggtattcctgccgaccatccgccggcaactgacgctggccgacgtggcgcacgaatccttc
gtctccggaggcgtcagtcccgacacgttggggttgttgctggcgtaccgaaggcgcttccccgcggtcatcacccgggtgcttcccacgc
gaatcgtcgcctgcccctggacgtgggcctcacccacgccggcaccgttaaccttcgcaacacctccccgtagatctctgtaacgggga
ccccatcagcctcgtcccgcccgtgttcgagggcaagcgacggacgtgcgcctggattcgctggacctcacgttgcggtttcccgttccg
cttccatcgcccctggcgcgcgaaatcgtggcgcggctcgtggccagggcatccgggacctgaaccccagcccagaaaccccggagggc
tgccagacctcaacgtgctgtactacaacgggagtcgcctctcgctgctggcggacgtccaacaactcggtcccgtaaacgccgagctgcg
atcgctggtccttaacatggtttactcgatcacggagggaaccaccatcatccttacgctaatccccggctctttgcgctaagtgcccag
gacgggtacgtgaacgctctactgcagatgcagagtgtcacgcgggaggccgcccagctcattcaccccgaagcccccggccctgatgcagg
atggagagcgaaggctgccgctttacgaggcgctcgtcgcctggctgacccacgcgggccaactaggagacaccttggccctggctcccgt
ggttcgggtgtgcacctttgacggcgcggccgttgtgcggtccgagacatggccccgttatacgctatccctaaggcccggctagaccc
acggggggtgggggtgggcatccagggagaaacccagcatacctaaataaataaaaacctaagaaattccaaaatatgcctgtgtgtcg
tatgtttatgggatttgggttgggttctgtgttcacagggggtggtactggtgccggtcgtgagagaatccccgtgttcccacgctt
cccgccaacacccccttcccccccccccttaacagacgacaccgtggtcgtgcgtagcatacctgggtgtgtttattgggcgctcacgag
acgcgtgtgataggagcgaatgtgtgcggaggtccggcctgggccgcgaggtagatggccataatgacggcgaccataaggtcatccgagg
cgccgttccgttttccggaatacgtacggacgtcagtgttgggggagacggtttcggtgaggttatttagctgctcgagcagatactcgac
```

-continued

```
cgggtcggtctgcaggcgcaccgtcgcggaaacgatctcctgggaggccatgacgccccggagttaaacttttaataaagtgttcaaag
gcgggcgtcttctgtttgttgagcaggaaaaggggtacagcaccgcgctcccgggaggctcgcagtggtagaagagaagctcggggcccg
agcccgcgtcggccccctccgaggccagtaggcggtgcatctctgtgtgcacgtgcgtggcgatggcgacggccgagtcctggctgctatt
tccctcgaccgccaccggacgccgcgaaacgccccgggatgcagggccaggacctgcgtcagactgtggacgacgcagcgggcgatgtcg
gcggggccgagcccgtgagcgcgcggagaaaaagtgctccagggcgaagatgatataatcgtcgcggtaccgcccgacgacagcgacgc
cggtcccggaggctcggtgttggccgtaacgcgggatccacgtacacgtacaaatcggggccatgaggccgctgttggtggtggtcga
ggggcggtacaacagaaaccgctcccccgcagacttggtcagaacgggccggtcgtcgccggtctccctggcctggccccgatgatctcc
tgcatgaaggaatcggccagaaacaaatcggcggtccggcgaaccgcccgtccatcgtgatgaaaacgggcttgttgaggatataacaag
aacaggccgtggcgtttgtgtgcgtcaccaccctcggcatgtgatcatcgcatatataggtcaccacgttgagaagctcgtctgcggcccc
gcggaggttgtacaaaaagctcgtactggcctcccggtgttggtggacgacacgaagataatcttgcagttggcctggttgagaaagccc
ataatcgtctggaccgcatccgggcgaataaagttggcctcgtcgacaaagagcaggttaaagtcctggcctcggattccctagagacaga
agaaacgcgccgcgcataagcacgcacgcctccgttggcgaatacgcatacgcgcgccaaacccacgcccttcccgcggactcggggacc
cgcatcgcctacacacccacacccaccccgaaccatgaacgcgcacttggccaacgaggtccagtacgatctcggccacggcccgggtcg
gccctcgtctttggttcacgtcatcatatccagcgagtgcctggcggccgcgggaatccctctggccgccctgatgcgcggccgccccgga
ctcgggacggccgcaaacttccaggtcgaaatccagactcgggctcatgccaccggcgactgtaccccgtggtgcacggcgtttgccgcct
acgtgcccgcgatgcggtgggggagcttctggcccccgtcgtgccggcacaccctggcctccttccgcgtgcgtccagcgccgggggtt
gttcgtctccctgcccgtggtgtgtgacgcgcagggcgtctatgacccgtacgccgtggcggcgctgcgccttgcgtggggctcggggcg
agctgtgccgcgtgattctgtttagttacgacgagctcgtcccccccaacacgcgctacgcggccgacagcacgcgcatcatgcgcgtct
gtcggcatttgtgccgctacgtcgctctgcttggcgccgccgccccgccggccgcgaaggaggctgcggcccacctgtccatgggtctggg
ggaaagcgcgtcccccgcgtccgcagcccttggccggccccacgcggggggcgcccgcagacccgcccatcgtcggggcgtccgaccccccc
atctccccggaggagcagctgacggccccccggcggcgacacgaccgcggcccaggacgtgtccatcgcacaggagaacgaggagatcctcg
cgttggttcagcgggcagtgcaggacgtcacccgccgccacccggtccgagcgcggaccgggcgtgcggcctgtggcgttgcatcggggct
acgccagggcgccctggttcaccaggccgtcagcggggcgccatgggggcggctgacgcagatgcggtgctggcgggtctggagcccccc
ggcgggggccgctttgtggccccagcgccccacgggcccggggcgaggacatcctgaacgacgttctaacccttaccctggtaccgcaa
agccgcggtcgctggtcgagtggttggatcgcggatgggaagccctggccggcggcgaccggccggactggctgtggagccgtcgttctat
ctccgtggtcctgcgccaccactacggaaccaagcagcgcttcgtcgtcgtctcctacgagaactccgtggcgtggggcgggcgacgcgcc
cgccctccgctgctgtcctcggcgctggccacggccctgaccgaggcctgcgccgcagaacgcgtcgtgcgcccccaccagctgtctcccg
ctgggcaggcggagctgctgctacgctttccgcgctcgaggtgcccctgcgccacccgcgccccgtcctgccgccctttgacatcgccgc
cgaggtcgcctttaccgcgcgcatacatctggcgtgcctccgggcctgggccaggccatccgggcgcgcgcttcagggcggcccgcgaatc
tcacagcgcctgcgctatgactttggccccgaccaacgcgcgtggttggggggaggtgaccaggcgcttcccccattctcctcgagaacctga
tgcgcgccgtcgaggggaccgcccccgacgccttttttcacaccgcgtatgccctggccgtcctggcacacctggggggacggggcggtcg
ggggcggcgggtcgtcccgctcggcgacgacctcccggcccgctttgccgactccgacggccattacgttttgactactacagcacaagc
ggagacacgctgcggcttaacaatcgtccaatcgccgtggcgatggatggtgacgtcagtaaacgcgagcagagtaaatgtcgcttcatgg
aggccgtcccctccacagccccacgcagggtctgcgagcaatacctgcccggggaaagctacgcctacctctgcctgggtttaatcgccg
cctctgtggcatagttgtctttcccgcgcgctttgcgttcaccattaacatcgcggcctaccttagcctctcggaccccgtcgcgcgggcc
gctgtccttaggttttgtcgcaaggtgtcgtccgggaacggccggtctcgctagcgggcgccttcccccggccacctcgcccacccactcc
tccccgcgccgttggccccgcctctgggttgccctccccccgccccggcatgcgcagctgggaccccggcggcccctggcgccgcc
tggtccccggggaccttgccccggccggattcccgggccggagctcgcggcacgcgcgatagagtcgacgacctggggacggacgtcgac
tctatcgcgcgcattgtcaactccgtctttgtgtggcgcgtcgttcgggcggacgagcggctcaagatcttccggtgtctaacggtcctca
ccgagcctctgtgtcaggtggcccttcctaacccagaccccgggcgcgccctcttctgcgagattttctgtatctgacgcgccccaaggc
```

-continued

```
gctgcggttgcccccgaacaccttctttgccctcttttcttaaccgcgagcgccgctactgcgcgatcgtccacctccggagcgtgacg
cacccctgaccccgctcctgtgcaccctcacgttcgcacgcatacgggcggccaccccccggaggaaaccccgacccaaccaccgaac
agctcgcggaggagccagtggtcggcgagctggatggcgcgtatctggtccccgcgaagaccccccggagccgggcgcgtgctgcgcctt
gggcccggggcctggtggcacctccccagcggccagatctactgctgggccatggacagcgacctggggtcgctctgtccaccgggaagc
agggcccgccatctgggatggctcctggccaggatcaccaaccacccggggggctgcgagtcctgcgccccgccgccccacatcgattccg
ccaacgcactgtggctctcctccgtcgtaacggagtcctgtcctgcgtcgcccgtgtctgtgggccaagatggccagtgtaccctggc
ggtccaggggatgctagcctgtgtccgcttctctttggccatcccgtggatacggtcaccctgctgcaggcccccgccgtccttgcatc
acggaccgtctgcaagaggtcgtcggggacggtgcggcgcggacaacatcccccgaccagcgccgggtggcgcctgtgtgtcttctctt
cgtacatcagtcgcctatttgctacgagttgccccaccgttgcccgggccgttgcccgggcctcctcaagcgatcccgaataaaatcagt
gcccacggggcagactttcctcccgcgtctggttgtgtgtgtatgtgggtgggtgggtgtgggtcggtcgacccggggcccttgggaga
gccatgcgaaagaaaagaggacttacgtttgtgttgtggctggaggcaaacacgatggtactgcgcgacccgtccggaaacgagaaggaga
tggtttcccctttaacgtggtccactcgggccgaaccgaaccagccccgcaggcaggcgtcgatctcctcaaacaccggctcggtcgcctt
gcggatgtgcgccgtgtagccgatcttgatccccgaaaggaggccagcgacagcgcgatgaggggcaccagaaaccaggtcttgccgtgg
cgccgggggacgagaaacacggtggcgcgctggcggaagtggcgcacggccgcgtcgctaaacagggggatctcaaacacgagacgcagga
acgtgttgacctgctccgcgtggtccccgaggagcacggcggccagaaagtaggtggcgtgcataaggatcattttttggaacagctccag
cgtgccgtacgtccggccgtgggtggccacgtccaccttggcccgttttttggggggcccgtggtctccgtgaggctggaggcccggaag
gaggttttgagcagctgggcaaagtcccgcacaaagtgcaccagctggcgaaaggcttcggagcggtggagggcctgaaacgtattcagaa
cgctatagtaggcgttacgctgaggcaccacgtccgccggcgcgcactccttaaaccgcagtcgcgccaccgcccgtaccaactcggggc
caggaattccagcttggccgtgtggtcgccccgaaatcacgcccctttagttgcgccggcaccaggctattaaacagcagccgccgcgcc
acggccgagaagagcggcgagtgctcgcagcagtcgtggagcgtcccgacgccagggaccacggtctggtggcgcttgggggtcgcggtcg
cgaaatctaaaagggcactcgtagggcatcgccgcccatggtgaggcccgccgacgcctcgtccgcgcccaccttaagttgcctctgttt
ctcgaggcgctccaggtactgctggacgtcggacgccagctgctgaccaaacatcgcgcacaccgggtggcgggtcgcggcggcgaagtac
cccgatcacgggccttgggcacgcgagactatcagagcacccccgggtcgcccgcagggtggcggaatggaccgagatgccgcccacgcg
gccctgcgccgacgcctggccgagacgcacctccgagccgagatttacaaggaccagaccctgcagctgcaccgggagggcgtcagcaccc
aagatcctcggtttgttggcgcctttatggctgcaaaggcggcccacttggaattggaggcgcggctaaagtcccgcgcgcgcttagagat
gatgcgacagcgcgcgacctgtgttaaaattcgcgtggaggagcaagcggcgcgtcgtgactttctaaccgcacaccgacggtacctcgat
ccggcgcttggtgagcgcctggacgccgtggacgatcgtcttgcggaccaggaggagcaactcgaggaagcagcgaccaacgcttctctgt
ggggagacggcgacctggccgaaggatggatgagtcccgcagacagcgacctgctggtcatgtggcagctaacctcagcccccaaggtgca
cgccaacggtccttcaaggattggctcgcatcctacgtacactccaaccccacggggcctccgggcgcccagcggcccctctctccagg
acgccgccgtctcccgctcctcccacgggtcccgccaccgatccggcctccgcgagcggcttcgcgcgggactatcccgatggcgaatgag
ccgctcgtctcatcgccgcgcgtcccccgagacgccggtacggcggccaaactgaaccgcccgcccctgcgcagatcccaggcggcgtta
accgcacccccctcgtccccctcgcacatcctcaccctcacgcgcatccgcaagctatgcagcccgtgttcgccatcaacccccgccctac
actacacgaccctcgagatccccggggcccgaagcttcgggggggtctggggggatacggtgacgtccaactgattcgcgaacataagcttgc
cgttaagaccataaaggaaaaggagtggtttgccgttgagctcatcgcgaccctgttggtcggggagtgcgttctacgcgccggccgcacc
cacaacatccgcggcttcatcgcgcccctcgggttctcgctgcaacaacgacagatagtgttccccgcgtacgacatggacctcggtaagt
atatcggccaactggcgtccctgcgcacaacaaaccctcggtctcgacggccctccaccagtgcttcacggagctggcccgcgccgttgt
gtttttaaacaccacctgcgggatcagccacctggatatcaagtgcgccaacatcctcgtcatgctgcggtcggacgccgtctcgctccgg
cgggccgtcctcgccgactttagcctcgtcaccctcaactccaactccacgatcgccggggcagttttgcctccaggagccggacctca
agtccccccggatgtttggcatgcccaccgccctaaccacagccaactttcacaccctggtgggtcacgggtataaccagcccccggagct
gttggtgaaataccttaacaacgaacgggccgaatttaccaaccaccgcctgaagcacgacgtcgggttagcggttgacctgtacgcctg
ggccagacgctgctggagttggtggttagcgtgtacgtcgccccgagcctgggcgtacccgtgacccggtttcccggttaccagtatttta
```

-continued

```
acaaccagctgtcgccggacttcgccctggccctgctcgcctatcgctgcgtgctgcacccagccctgtttgtcaactcggccgagaccaa cacccacggcctggcgtatgacgtcccagagggcatccggcgccacctccgcaatcccaagattcggcgcgcgtttacggatcggtgtata aattaccagcacacacacaaggcgatactgtcgtcggtggcgctgcctcccgagcttaagcctctcctggtgctggtgtcccgcctgtgtc acaccaaccgtgcgcgcggcacgcgctgtcgtgagaatcagcgttcacccggcggcgcgctcaaccaccgctcccccacgtcgtctcgg aaatggagtccacggtaggcccagcatgtccgccgggacgcaccgtgactaagcgtccctgggccctggccgaggacacccctcgtggccc cgacagcccccaagcgcccccgccctaacagtcttccgctgacaaccaccttccgtccctgcccccccaccccagacgacgtcagct gtggacccgagctcccattcgcccgttaaccccccacgtgatcagcacgccaccgacaccgcagacgaaaagccccgggccgcgtcgccgg cactttctgacgcctcagggcctccgaccccagacattccgctatctcctggggcacccacgcccgcgacccggacgccgatcccgactc cccggaccttgactctatgtggtcggcgtcggtgatccccaacgcgctgccctcccatatactagccgagacgttcgagcgccacctgcgc gggttgctgcgcggcgtccgcgcccctctggccatcggtcccctctgggcccgcctggattatctgtgttccctggccgtggtcctcgagg aggcgggtatggtggaccgcggactcggtcggcacctatggcgcctgacgcgccgcgggccccggccgccgcggacgccgtggcgccccg gcccctcatggggttttacgaggcggccacgcaaaaccaggccgactgccagctatgggccctgctccggcggggcctcacgaccgcatcc accctccgctggggccccagggtccgtgtttctcgccccagtggctgaagcacaacgccagcctgcggccggatgtacagtcttcggcgg tgatgttcgggcgggtgaacgagccgacggcccgaagcctgctgtttcgctactgcgtgggccgcgcggacgacggcggcgaggccggcgc cgacacgcggcgctttatcttccacgaacccagcgacctcgccgaagagaacgtgcatacgtgtggggtcctcatggacggtcacacgggg atggtcgggcgtccctggatattctcgtctgtcctcgggacattcacggctacctggccccagtccccaagaccccctggccttttacg aggtcaaatgccgggccaagtacgctttcgacccatggaccccagcgaccccacggcctccgcgtacgaggacttgatggcacaccggtc cccggaggcgttccgggcatttatccggtcgatcccgaagcccagcgtgcgatacttcgcgcccgggcgcgtccccggcccggaggaggct ctcgtcacgcaagaccaggcctggtcagaggcccacgcctcgggcgaaaaaaggcggtgctccgccgcgatcgggccttggtggagttaa atagcggcgttgtctcggaggtgcttctgtttggcgcccccgacctcggacgccacaccatctcccccgtgtcctggagctccggggatct ggtccgccgcgagcccgtcttcgcgaacccccgtcacccgaactttaagcagatcttggtgcagggctacgtgctcgacagccacttcccc gactgccccccccacccgcatctggtgacgtttatcggcaggcaccgcaccagcgcggagggaggcgtaacgttccgcctggaggacggcg ccggggctctcggggccgcaggacccagcaaggcgtccattctcccgaaccaggccgttccgatcgccctgatcattaccccgtccgcat cgatccggagatctataaggccatccagcgaagcagccgcctggcattcgacgacacgctcgccgagctatgggcctctcgttctccgggg cccggccctgctgctgccgaaacaacgtcctcatcaccgacgacggggaggtcgtctcgctgaccgcccacgactttgacgtcgtggatat cgagtccgaagaggaaggtaattctacgtgccccggatatgcgcggggttacgcgggccccggggagacagcgcctgcgttcatcggac ccccctcgcgccacactcaccggcggaccccgaggcgcctgccccgccaccagtttccaccccccatgtccgatagcgaataaaaac caaaacaatgttctgtatacggtcgcacgcgtgtcgttttaaaaaacccacaatcgccggggttgaggggggggggggacggtgatagt aacgggatcggacgccacacaccagacatacaccacggtcggttaaacacaaacggtttattaaaacggaaccaaacagctaccaacggc ggacggtgctgtacacggggtcctcggcgggctcggggtcgtaccccccaacggtgtcatagatgggatcgtcgtcgggcaggtgccgcgg gtgttgtatcttggcgtacaatacgtcggtttggtcgtccgccacctcgtcgtaaatcggctccccgtcggaatctccgtaccggtcgagc tggccgccgtatgagatcgcgtaggggtcttccgcatattcgggaatcccgggcgggctgccgggtgcgggcctgtggcggccgtctcgcg atccgcgcatggaactgctacgcgcttgagggcggaatgtgcgcggtgtcgcgtgtcgcgcatgcgcataaaaaatttggtgtggtgccg cctgtgatacagataggcgcgggtgcagcggagcacggccatgccgagggcaaaggcggcgaccagggcgagggcgacgcggactcccgtc tgagcccccggccactgcgtctccacaacgtagtagccgttggtgtaatagtgctcgcaggccaggccgacgatgcccgtggcggccacgg cccccaggtggggccaccaacacgcgcacgtagtgacacaacaccccctcgaccaccaacaacagcgatacgacgagaatggcgaacag cacggtcaggcagatgagcatgcccggggccgaaaaattaaagttgaacgcggcgatggtattcagggataccgcggcgtcggccgtgcac aggaagacgcccaacagcaaggcgtttgtcagcacggcgcgagccgggccgacgacgcgatgatgggtcggggccagctccatcaggccgt gcacctgacgcagatacgtcccgctcaggaccccctggtgcaaaaatgggccgcaaaatacaccagacacgcaaagtgcaggacgtaaac caggtgggccagctggctgatgcgatgggccagcaacaggacggtgatctgcagcaaccaagagcagacgtttccggcgatcagcgtggcg
```

-continued

```
tgcggcatggccatgcgggccgcagccagacggcggcccgcgtccagggcgcggtcgtagcgggaggtcacggcgccgaccacggcataca
cggccacggccaacaacaacacggccgtgattacataagtgcccacaaggctctgcgtgtccaacctgaggggcacggctacaccccccgcg
cacctcggccgtggagttcaccccggcataagagctcgccgtggcgtaaaagcagggaaaccgtgcccggaacacagaggccaggacgagg
agccccgtgacgcagaccgcagagaccacaaacgtcgccacctgcacacaccagacccaccacgccgtccgcgccccggtcatgcctttcg
tgggggcgcggagtcgggagatcctctgggggccgggcgtcccattgggacgacgagtgcgaacagtacacgtcgagcgtatcgctagc
gcggatgttgtacgggggggatttggccgaatgggtgccccgggttcacccgaaaacaacgatcgagcggcagcagcacggaccccgtcacc
ttccccaacgcgagcgcccgacggccaggtgcgtgactgtggtccgcgcgccaatggggtcgggaaaaactaccgcgctgatccgctggc
tgcgggaagcgatccactctccggacacgagtgtgctcgtcgtctcctgtcgtcggagttttacccagaccctagcgacgcggttcgctga
gtcaggcctggtcgactttgtcacctacttctcatccaccaattacattatgaacgaccgcccttccaccgacttatcgtccaggtggaa
agccttcatcgcgtgggccccaaccttctgaacaactacgacgtcctcgttctggacgaggttatgtcgacgctgggccagctctattcgc
caacgatgcagcaactgggccgcgtggatgcgttaatgctacgcctgctgcgcacctgtcctcggatcatcgccatggacgcaaccgccaa
cgcgcagttggtggacttcctgtgcggtctccggggcgaaaaaaacgtgcatgtggtggtcggcgagtacgccatgcccgggttttcggcg
cgccggtgcctgtttctcccgcgtctggggaccgagctcctgcaggctgcctgcgcccgccgggccgccgagcggcccgtctccggacg
cctctccggacgcccggggggccacgttctttggggagctggaagcgcgccttggcgggggcgataacatctgcattttttcgtcgacggt
ctccttcgcggagatcgtggcccggttctgccgtcagtttacggaccgcgtgctgttgcttcactcgctcacccccctcggggacgtgacc
acgtggggccaataccgcgtggttatatacacgacggtcgtaaccgtgggcctcagcttcgatcccctgcactttgatggcatgttcgcct
acgtgaaacccatgaactacgaccggacatggtgtccgtgtaccagtccctgggacgggtgcgcaccctccgcaagggggagctactgat
ttacatggacggctccggggcgcgctcggagcccgtctttacgcccatgctccttaatcacgtggtcagttcctgcggccagtggcccgcg
cagttctcccaggtcacaaacctgctgtgtcgccggttcaaggggcgctgtgacgcgtcggcatgcgacacgtcgctggggcgggggtcgc
gcatctacaacaaattccgttacaaacactactttgagagatgcacgctggcgtgtctctcggacagccttaacatccttcacatgctgct
gaccctaaactgcatacgcgtgcgcttctggggacacgacgatacccctgaccccaaaggacttctgtctgttttgcggggcgtacatttc
gacgccctcagggcccagcgcgatctacgggagctgcggtgccgggatcccgaggcgtcgctgccggcccaggccgccgagacggaggagg
tgggtcttttcgtcgaaaaatacctccggtccgatgtcgcgccggcggaaattgtcgcgctcatgcgcaacctcaacagcctgatgggacg
cacgcggtttatttacctggcgttgctggaggcctgtctccgcgttcccatggccaccgcagcagcgccatatttcggcggatctatgac
cactacgccacgggcgtcatccccacgatcaacgtcaccggagagctggagctcgtggcctgccccccaccctgaacgtaaccccgtct
gggagctgttgtgcctgtgcagcaccatggccgcgcgcctgcattgggactcggcggccgggggatctggaggaccttcggccccgatga
cgtgctggacctactgacccccactacgaccgctacatgcagctggtgttcgaactgggccactgtaacgtaaccgacggacttctgctc
tcggaggaagccgtcaagcgcgtcgccgacgccctaagcggctgtccccgcgcgggtccgttagcgagacggaccacgcggtggcgctgt
tcaagataatctggggcgaactgtttggcgtgcagatggccaaaagcacgcagacgtttcccggggcggggcgcgttaaaaacctcaccaa
acagacaatcgtggggttgttggacgcccaccacatcgaccacagcgcctgccggacccacaggcagctgtacgccctgcttatggcccac
aagcgggagtttgcgggcgcgcttcaagctacgcgtgcccgcgtggggcgctgtttgcgcacgcactcatccagcgccaaccccaacg
ctgacatcatcctggaggcggcgctgtcggagctccccaccgaggcctggcccatgatgcaggggcggtgaactttagcaccctataagt
ctcgggaccgcactcgttcggtacgtggtcgtccgcggaccggcggcgctgttgccggaacgcaccgaggggccaagttggcccccggacc
cgggccgtttcccaccccaccccaacccaaaaaccgcccccccccgtcaccggtttccgcgaccaccgggcccggccaggcacggca
gcatgggacccacagaccgcccgtgatccttaggggccgtgcgatggacaccgcagatatcgtgtgggtggaggagagcgtcagcgccatt
acccctttacgcggtatggctgccccccgcgctcgcgagtacttccacgccctggtgtattttgtatgtcgcaacgccgcaggggagggtc
gcgcgcgctttgcggaggtctccgtcaccgcgacggagctgcgggatttctacggctccgcggacgtctccgtccaggccgtcgtggcggc
cgcccgcgccgacgacgccggccgcctcccgctggagcccctggagaacccgactctgtggcgggcgctgtacgcgtgcgtcctggcg
gccctggagcgccagaccgggccggtggccctgttcgccccgctgcgtatcggctcggacccacgcacgggactggtggtgaaagttgaga
gagcgtcgtggggcccgcccgccgcccctcgcgccgctctcctggtcgcggaggccaacattgacatcgaccctatggccctggcggcgcg
cgttgccgagcatcccgacgcgcggctggcgtgggcgcgcctggcggccattcgcgacaccccccagtgcgcgtccgccgcttcgctgacc
```

-continued

```
gttaacatcaccaccggaaccgcgctatttgcgcgcgaataccagactcttgcgtttccgccgatcaagaaggagggcgcgttcgggacc tggtcgaggtgtgcgaggtgggcctgcggccacgcgggcacccgcaacgagtcacggcacgggtgctgctgccccgcgattacgactactt tgtaagcgccggcgagaagttctccgcgccggcgctcgtcgccttttccggcagtggcataccacggtccacgccgcccccggggccctg gccccgtctttgcctttctggggcccgagtttgaggtccgggggggacccgtcccgtactttgccgtcctggggttccggggttggccca cgttcaccgtgccggccacggccgagtcggcacgggacctggtgcgcggggccgcggccgcttacgccgcgctcctgggggcctggcccgc ggtggggccagggtcgtcctccccccgcgagcctggcccggcgtggcctcggcggcagccggatgcctcctgcccgcggtgcgggaggcg gtggcgcggtggcatcccgccactaaaatcatccaactgttagacccgcccgcggccgtcgggcccgtctggacggcgcggttttgcttcc ccggacttcgcgcccagctcctggcggccctggccgacctcggggggagcgggctggcggaccccacggccggacgggcctagcaagact ggacgcgctggtggtggccgctccctcagagccctgggccggggccgtcttggagcgcctggtcccggacacgtgcaacgcctgccctgcg ctgcggcagctcctgggtggggtaatggccgccgtctgcctgcagatcgaggagacggccagctcggtgaagttcgcggtctgcggggggcg atgggggtgcgttctggggtgtctttaacgtggaccccaagacgcggatgcggcttccggggtgatcgaggacgcccggcgggccatcga gacggccgtgggagccgtgcttagggccaacggcctccggctgcggcacccactgtgcctggccctcgagggcgtctacacccacgcagtc cctggagccaggcgggagtgtggttctggaactcccgcgacaacactgaccatcttgggggatttcctctccgcgggcccgcgtacaccac ggcggcaggggtcgtacgcgacacgctgcgacgggtcctgggcctgacaacggcatgcgtgccggaggaggacgcactcacggcccgggc cttatggaggacgcctgcgaccgccttatcttggacgcgtttaataaacggttggacgcggagtactggagcgttcgggtgtccccctttg aggccagcgacccctttgccccccactgccttccgcggcggcgccttgctggacgcagagcactactggcggcgcgtcgtgcgtgtctgtcc cggaggcggggagtcggtcggcgtccccgtcgatctataccgcggcccttgtgctccccccgtggactgcgctcatcacctgcgcgaa atcctgcgcgagattgagttggtgttaccggggtgctggcgggagtatgggcgagggggggaagtttgtgtatccctttgacgacaaga tgtcgtttctgtttgcctgagtttgaccaataaaaacattgccctgagacaagagcgctcccccgtgtgtgcttgagtctgtccgaatacg tgccgacttgccccccctccccgcacagatgggacgccatacacagccacccacccaccaagacggagtaaggacacgcgcatccgtcggga ggccacagaaacaaaaccgggtttatttcctaaaattcaacaaaactgataaaacagcgacgacgtctgtcgttttggggtctccgaaagc caccaatagaccagaggcgcgcgcacctcctccgacgcccagcagctccccatgatcccggcggggttataggccacgcagtcggagcggg ggggcggccccggcagccggaatgaggagctcgtcggggtggcacagaacagggccgagagaacgggggggcgggttgttggccagcaggta ccgggccatgtaccagtggggcaggacgaactcgtcgtcgaacggttttacgtgcaccatgaacatgagtgtgtttaggacccagtggcaa ctgcggaggaaaaggcagcgaacgcgttcgaatgggacgtgcggcgacccgcgaccccgagccacgccagaaccttggcaaaggtcgacg gggtggcgtggcttcgggggcagttctccaggtacatcagcagacaggcaagctcaaagtccaggaggtccctgggggttgaacagggagaa ccggtgcagcagaacgaggggggcacggccaggctgtgcacgtggtcctcgttggccgtcaggaccgccaccgcgaagccgcgataactg gactggccgcagcagcgcttaaagtaatcctccgacgtcacataggcgtcctcgggactcccgtccagaacgaaccgcaaccggcacccag gcgcgacgtcgacgcgcgcgatgctggtggcggtaaaccgcggctggcggtcgccgacctggcgcacctcgcaggccaggcggagcagcgt ctgctggctaatcgcctcggccgcctcgaccaggctgcggtccccggcgatggcctgcttgaggatggtggcggccgacccctcatcgtcg gccgtcgcggcggccatcccggtgcccgatgccccgccctggtccggcgcgcctcgcgcagttcttccgggcgaccgcgatctggaccgg ccccgcggggacgcgccgggccggaaatcggcgccgaccggggagggggcggggcagcgctgcgtgctggacgtccgcgacgaacaggg ccgcgatgtctgtcaggtacgtttgcaggcgggttttcttaaacaccgcatcccataactcctcctccccaggatgacatcggagcccgt gatgggcgcgcctacccgggggcccgaagcactgactcaaagtagggggcgacgaatgcggcgatcgccccgctggagtacgagatcgac gtctcttggccctggttgttgcggtgacacagaattttaaaacagcgcaccagctcgtgctcccagaggcgcgacaggcgctccaggtcct gggcgtacgaagggatgtacgggtgctgaaagctgttggcgacgtacgtgtcgtcgtccatggacttgctgacgtcgataatgtcatagtc ggcccggagcaggtccgccccgcagggcggctgccgcatccaccggtcacggactcggccgccaggtcggccgcgcgctgctggcgctcc agggccccgctgttgcgcgccggagctcgcggtcgcgctcctgcaattgggtcgccaggcccgcgttggtctcgcgcaggcgctcgatgg ttccaaacaggttatttatatagccctccaacacgccgttgatgttgttaaccacggccgtgcggaaggcctggcgaagctgcggcgcccg cccccccctggtcctggcccgcagaccgcggctgtttccgcccttgccgaatccagggagggtaccgtcgacggccggggcgtctatcagg
```

-continued

```
tgcccccggcctcgtcgaggtaggcacgcacggtgtcgttaatgtcgcctacgtggcgcatgcccttcatgttgatgataagccgcacga
ggcgcgaggcggccgacccggcttggtctcgtcgtcctccccaacaccttgttaacgacccgcgcggcaccggccaccccgcgctcgct
gtcgctcttgcgcccagcagcaccttgacggacgcggtattgcgcagccggcagacgtgcgcgtgttcccggagggagtgacacgcgacg
atctcgggaaacagccgctggacgggcgaatcgaagaccagacggtccccggtccacaaggggggccacagcaccagacattctccgcgct
gcccgctgatggggtctcgcacgagccagtcgccccggcggtggttgtagtagatatacacgcggtcgtagtccgccacgcgcgtggagtc
gaaggccagcgccagctcaaaaaaccggggccggcgcgctccgcggcctccgcgaccgtggccagctggcgggtcagcgggtgctgcttg
agaaacgccctcagaccctgcgtcacacccccttcttgtcgcttgcgtaatatggggaccagccccaggcacgtcagccagtcgatatatt
tggggaagcttgacgggccgctcgggccgcccggcgcaaagcaggcgaccaacccgtgggcaaagtccagcagcgtcgtcctaagcgtgtt
ccgccacgtgtcgaacaccgctcggccacccggcgatatccgcctcccgggcgttcctgtaccggcgaaccagccgttggggctgcaga
ccgcgggccgccacgtggccgagccagtccgcctcgaggtccccggtaagtggtggcgttgaggagcgcgtgaaagatcgccgcctgcagct
gccgggtggtcgcctcgctggaccggacgacgttgtacacccctggccctcggtataccccagctgcccgtggagaatctcgcggaacag
catcgtaccggggtggggtgaaccttacccagccgtcctcggggagcacagcgcttccgtgtcccccgcgcacgcgtagtgggggcc
cgcgagcgtggtgcggtcatggcggcggccggcggggagcgccagctagacggacagaaaccccggcccgccgccaccttcagcaacccgggg
accgaccagccgttccaggagggccgaggcctttttaaattttacgtctatgcacggggtgcagccaatccttaagcgcatccgagagct
ctcgcaacaacagctcgacggagcgcaagtgccccatctgcagtggttccgggacgtggcggccttagagtcccccgcaggcctgccccctc
agggagtttccgttcgcggtgtatcttatcaccggcaacgctggctccggaaagagcacgtgcgtgcagacaatcaacgaggtcttggact
gtgtggtgacgggcgccacgcgcattgcgcccaaaacatgtacgccaaactctcgggcgcctttctcagccgacccatcaacaccatctt
tcatgaatttgggtttcgcgggaatcacgtccaggcccaactgggacagtacccgtacaccctgaccagcaaccccgcctcgctggaggac
ctgcagcgacgagatctgacgtactactgggaggtgattttggacctcacgaagcgcgccctggccgcctccgggggcgaggagttgcgga
acgagtttcgcgccctggccgccctggaacggacccctggggttggccgagggcgccctgacgcggttggccccggccacccacggggcgct
gccggcctttacccgcagcaacgtgatcgtcatcgacgaggccgggctccttgggcgtcacctcctcacggccgtggtgtattgctggtgg
atgattaacgccctgtaccacaccccccagtacgcggcccgcctgcggcccgtgttggtgtgtgtgggctcgccgacgcagacggcgtccc
tggagtcgaccttcgagcaccagaaactgcggtgttccgtccgccagagcgagaacgtgctcacgtacctcatctgcaaccgcacgctgcg
cgagtacgcccgcctctcgtatagctgggccatttttattaacaacaaacggtgcgtcgagcacgagttcggtaacctcatgaaggtgctg
gagtacggcctgcccatcaccgaggagcacatgcagttcgtggatcgcttcgtcgtcccggaaaactacatcaccaaccccgccaacctcc
ccggctggacgcggctgttctcctcccacaaagaggtgagcgcgtacatggccaagctccacgcctacctgaaggtgacccgtgaggggga
gttcgtcgtgttcaccctcccgtgcttacgttcgtgtcggtcaaggagtttgacgaataccgacggctgacacaccagcccggcctgacg
attgaaaagtggctcacggccaacgccagccgcatcaccaactactcgcagagccaggaccaggacgcggggcacatgcgctgcgaggtgc
acagcaaacagcagctggtcgtggcccgcaacgacgtcacttacgtcctcaacagccagatcgcggtgaccgcgcgcctgcgaaaactggt
ttttgggtttagtgggacgttccgggccttcgaggcagtgttgcgtgacgacagctttgtaaagactcaggggggagacttcggtggagttt
gcctacaggttcctgtcgcggctcatatttagcgggcttatctccttttacaactttctgcagcgcccgggcctggatgcgacccagagga
ccctcgcctacgcccgcatgggagaactaacggcggagattctgtctctgcgccccaaatcttcgggggtgccgacgcaggcgtcggtaat
ggccgacgcaggcgcccccggcgagcgtgcgtttgattttaagcaactgggcgcgggacggggccggacgattttcccgacgacgac
ctcgacgttattttcgcggggctggacgaacaacagctcgacgtgttttactgccactacaccccggggaaccggagaccaccgccgccg
ttcacacccagtttgcgctgctgaagcgggccttcctcgggagattccgaatcctccaagagctcttcggggaggcatttgaagtcgccc
ctttagcacgtacgtggacaacgttatcttccggggctgcgagatgctgaccggctcgccgcgcgggggggctgatgtccgtcgccctgcag
acggacaattatacgctcatgggatacacgtacgcacgggtgtttgcctttgcggacgagctgcggaggcggcacgcgacggccaacgtgg
ccgagttactggaagaggcccccctgccttacgtggtcttgcgggaccaacacggcttcatgtccgtcgtcaacaccaacatcagcgagtt
tgtcgagtccattgactctacggagctggccatggccataaacgccgactacggcatcagctccaagcttgccatgaccatcacgcgctcc
cagggccttagcctggacaaggtcgccatctgctttacgcccggcaacctgcgcctcaacagcgcgtacgtggccatgtcccgcaccacct
cctccgaattccttcgcatgaacttaaatccgctccgggagcgccacgagcgcgatgacgtcattagtgagcacatactatcggctctgcg
```

-continued

```
cgatccgaacgtggtcattgtctattaacccgccgtcccttacagttccaccgaacccggcccggggggactcactacccaccgcgagatg tccaatccacagacgaccatcgcgtatagcctatgccacgccagggcctcgctgaccagcgcactgcccgacgccgcgcaggtggtgcatg tttttgagtacggcacccgcgcgatcatggtacggggccgggagcgccaggaccgcctgccgcgcggaggcgttgttatccagcacacccc cattgggctgttggtgattatcgactgtcgcgccgaattttgtgcctaccgctttataggccgggacagcaaccagaagctcgaacgcggg tgggacgcccatatgtacgcgtatccgttcgactcctgggtcagctcctcgcgcggcgaaagcgcccggagcgccacggccggcattttga ccgtggtctggaccgcggacaccatttacatcactgcaaccatttacgggtcgccccagaggagacgccaggcgcggcacacgggtggg cgccgcgcctccaccccgacaaccgcctgccccgggacggccgagtttctccagcccaccgcggacctgctggtagaggtgctgcgggag attcaactgagccccgccctggaatacgcagacaaacttttggggtcctaggatcccggccgatcgcgctcgtcacccgacactgaaatg cccccccccccttgcgggcggtccattaaagacaacaaacaaccagtagaactaccacctgaccggccagcctaccccaaaactaccgagg ggttttgataactttttttgataaaattttgataaccgttagcagcctaacaaaaaacaacgggagcgttacgctcccgttaataaattta acaaactacggcattacatgttttcgatgatcgcgtcaccaaactctgaacatttcagcagtttagcgccatccatcagacgctcgaagtc ataggttacggttttcgcgttgattgcgccttccatacctttaacaattaagtcagccgcttcggtccaacccatgtggcgcagcatcatc tcagcggagagaataatagagccaggatttactttgtcctgaccggcatatttcggcgcagtaccgtgggtggcttcaaacagggcgcatt cgtcaccgatgtttgcaccagggggcgataccgataccgccaacctgcgctgccagggcgtcagaaatgtagtcaccgttcaggttcataca ggcgatgggtttgtaccgtacaccactgagaccgcggtggttgaccagacaaaccacgacctatAGATCcCCAAAATCCCTTAACGTGAG ccaaatttatgtgttatttattaacatcaaacacgcgcgacgggcagtgagggtggcatggggggggggcggttactcggccccgaggcc agcatgacgttatctcggtggaggcgcattggctcggacgagacgaactcgtggacgaacacggggacggcggggcagagccgcccgtccg aagatcgcgtgtaatacttgcgcggcttgcgggactgaataacgacccgaagctgctctcgcactcgagcggcgtgggcgcgtttgcacaa cacaaacatctggaggcttttgttgctgcgcggcgcccgcgtgccgcgctggaacgccccgcgtctgtggtggcgcggggcgtttcccgaa aacgaggaggtcttggtgcacgcaatgctaaacttggccagcgacaaccgcaggtccttgcggatggtgtccgtgagctggcgacgcccta attcgtcgatcgacgacaccataaacagggtatcaaacgtcacgtagggcccgtcggtacagggcgggccgtcatccgcgcgcgttgggga gaaagacggcgctgtggcctcccgttccgggcccccgtgaaaggttggtcaggtgaggccacagcggcaccccgaatggaatctgcggga gtcgtatctggcgatatccccgactcgtgtttggcgtgtcgaacgtccagcccacgaggctagaatcgcaagcgcagagggaactccct ctcccccgacgcccgacatcaccgacccgtatgagaccagaggtttaaccattaaccgtctttattcatcggaaataccaaaagccccca ccgacaaaaaccccggacgtcgatgcctttcaaaccgaccagtcgatgggtgaaatcgaccgggtctcgaggtatcggttcgccacgagga aatgctggcaggttccgaacggaaccttggagaggggcgacgggtgcgaaaacttgaggacgcaatggacccgagggtccggcctgatggc attctgggcgtgtgtgcccagagcataaacaccaggccggggcggcgcgcggccaaccggcggataactccgcccacgaagcggtcccaa ccgattctagagtgggacgccgccgccccgcgcttgacggtcagggtcgtgtttagtaacaggacgccgtcccgcgcccactttccaggc aaccgtggccgctcatccgtgcctcgggataacagttcttgacggccgccaagacattccgaagactcggggaggcggcacgttcgcgcg cacgctaaacgcaagtccgtgcgcctggccggggtggtgatatgggtcctggccgatgataaccacgcgcacctcgtcggggtgcaataa cgagtccacgaaaacacatcctcccgcggcggcagcacctcttcggtctggcaccgacgattatattcggccaggaggtgggcggttaagg ggttcgccagctcaggctccatcaggggccgccacgcgtcgtcgatcagaaacacacgccgaaacgtggtccagtccagaggcgccgaggt cgccgcaggcgacacccccgtttgttaaatccatgggagggtcgggggcgcggacgaggaaaacgtcacaccagcgggacagcctcta gggcggcgaggagcgcccgccggccctgacgagcgacaggcggccggttcgcccccgaacccggacgggtttccgtcgaggcatcgttag aggcgccggagtggggtcgtcggcgtctgcttttgtggcggcgtcccgtcgcggggtggggtccgacgtggcgatgatgggcggcggcg tggtgaggggcttcggctgcaggcccgcttcatcgtccggcggcagaaccggggtccgtccagacgttccgttggtaggtcccaaatcctg tcgccctacacagcggcgggtgcgcgaatagtcaaagttcacacacccagccttcacaggtgtgtggctggcggcctgcttgcgactgtcc agcgcctggcgtatctctttataaagggccaagcgcgtttctgtttcctgggtgttggcaggaaacgcggggtaactcaagtcctccaaaa aacccgccacaaataaaaaggggttaacccaatatgccttctgggcatgcctatcccacaagaccgtgtccaatccgggacagtgataacg caaaaatataccgtctatcaaagcatagtttatagccgagggggtctcgtaacgccaatcaagatcgtcagacggggagcggcacacaaggc
```

-continued

```
acctttaatatatccccacctctcgagccacccgactccgaataacatattcggttgaaggcaagccccccgcacacacaaaaccccaa
cggcaataagcccgacccaacccaaaatccccatagcgcctagggtcggcacccacagaaacctacagtccccaagtgtttgcccagtaac
acaaccacgacgtcgtgccacacaagcccgtatccccgttcccgcgcttttcgttggtttatataccccctctccccccctctcccctct
ccccccctctccctctccccccctctccctctccccccctctccctctcccccctctccctctcccccctctccctctccctctccccc
ctctccctctccccccctctccctctccccctctccctctcccccctctccctctccctctgctctttcccgtgacacccga
cgctgggggcgtggctgccgggaggggccgcggatgggcgggcctacttggtctcccgcccccccccccccccccgaaccgccccgccgg
cttgtcccccctttgatccctgctaccccaacccgtgctggtggtgcgggttggggggggatgtgggcggggtgcgcgggaggtgtcg
gtggtggtggtggtggtggtagtaggaatggtggtgaggggggggggcgctggttggtcaaaaagggagggacggggggccggcagaccg
acggcgacaacgctccccggcggccgggtcgcggctcttacgagcggcccggcccgcgctccaccccccgggccgtgtccttgctttccc
cccgtctcccccccccccgccttctcctcctcctcctcgttttccaaacccgcccacccggcccggcccggcccggcccggcca
ccgccgccaccaccacctcgggatacccagccccggtccccgttcccgggggccgttatctccagcgcccgtccggcgcgccgcc
ccccgccgctaaacccatcccgccccgggaccccacatataagccccagccacacgcaagaacagacacgcagaacggctgtgtttat
ttaaataaaccaatgtcggaataaacaaacacaaacacccgcgacggggggacggaggggacggaggggagggggtgacggggacgggaac
agacacaaaacaaccacaaaaaacaacccaccgacaccccaccccagtctcctcgccttctcccacccaccccacgcccccactga
gcccggtcgatcgacgagcaccccgcccacgcccccgccctgccccggcgaccccgcccgcacgatcccgacaacaataacaacccc
aacggaaagcggcggggtgttggggaggcgaggaacaaccgaggggaacggggatggaaggacgggaagtggaagtcctgatacccatc
ctacaccccctgccttccaccctccggcccccgcgagtccacccgccggccggctaccgagaccgaacacggcggccgccgcagccgcc
gcagccgccgccgacaccgcagagccggcgcgcgcactcacaagcggcagaggcagaaaggcccagagtcattgtttatgtggccgcgggc
cagcagacggccccgcgacaccccccccccgcccgtgtgggtatccggccccccgccccgcgccggtccattaagggcgcgcgtgcccgcga
gatatcaatccgttaagtgctctgcagacaggggcaccgcgcccggaaatccattaggccgcagacgaggaaaataaaattacatcaccta
cccacgtggtgctgtggcctgtttttgctgcgtcatctcagcctttataaaagcgggggcgcggccgtgccgatcgcgggtggtgcgaaag
actttccgggcgcgtccgggtgccgcggctctccgggcccccctgcagccggggcggccaaggggcgtcggcgacatcctcccccctaagcg
ccggccggccgctggtctgtttttttcgttttcccgtttcggggtggtggggggttgcggttctgtttctttaacccgtctgggtgttt
ttcgttccgtcgccggaatgtttcgttcgtctgtcccctcacggggcgaaggccgcgtacggcccgggacgaggggccccgaccgcggcg
gtccgggccccgtccggacccgctcgccggcacgcgacgcgaaaaaggcccccggaggcttttccgggttcccggcccggggcctgagat
gaacactcggggttaccgccaacggccggccccgtggcggcccggcccggggcccggcggacccaaggggcccggcccggggcccac
aacggcccggccgcatgcgctgtggttttttttttcctcggtgttctgccgggctccatcgcctttcctgttctcgcttctccccccccctt
cttcaccccagtaccctcctccctccttcctccccgttatcccactcgtcgagggcgccccggtgtcgttcaacaaagacgccgcgtt
tccaggtaggttagacacctgcttctccccaatagagggggggaccccaaacgacaggggggcgcccagaggctaaggtcggccacgccac
tcgcgggtgggctcgtgttacagcacaccagcccgttcttttccccccctcccacccttagtcagactctgttacttaccgtccgaccac
caactgccccctttatctaagggccggctggaagaccgccaggggggtcggccggtgtcgctgtaacccccacgccaatgacccacgtactc
caagaaggcatgtgtcccaccccgcctgtgttttgtgcctggctctctatgcttgggtcttactgcctggggggggggagtgcgggggag
gggggtgtggaaggaaatgcacggcgcgtgtgtaccccccctaaagttgttcctaaagcgaggatacggaggagtggcgggtgccgggggg
accggggtgatctctggcacgcgggggtgggaaggtcggggagggggggatggagtaccggcccacctggccggcgcgggtgcgcgtgc
ctttgcacaccaacccacgtcccccggcggtctctaagaagcaccgccccccctccttcataccaccgagcatgcctgggtgtgggttgg
taaccaacacgcccatccctcgtctcctgtgattctctggctgcaccgcattcttgttttctaactatgttcctgtttctgtctccccc
ccccacccctccgcccacccccaacacccacgtctgtggtgtggccgacccccttttgggcgcccgtcccgcccgccacccctccc
atcctttgttgccctatagtgtagttaaccccccccgcccttttgtggcggccagaggccaggtcagtccgggcgggcaggcgctcgcggCT
CACGTTAAGGGATTTTGGGGACGGCGCAGAAGGGGAGTAGCTCTTCGCCGGACCGTCGACATACTGCTCAGCTCGTCCAATAACGGTTGTA
TTTGTAGAACTTGACCAGTTGGTCCTGTAAATATAAGCAATCCATGTGAGTCTCAGATCCTTCCGTATTTAaaacttaacacccacaccca
acccactgtggttctggctccatgccagtggcaggatgctttcggggatcggtggtcaggcagcccgggccgcggctctgtggttaacacc
```

-continued agagcctgTccaacatggcaccccactcccacgcaccccactcccacgcaccccactcccacgcaccccac tcccacgcaccccactcccacgcaccccacTCCCACGCACCCCACTCCCACGCACCCCATtcccacgcaccccactcccacgcacc cccactcccacgcatccccgcgatacatccaacacagacagggaaaagatacaaaagtaaacctttatttcccaacagacagcaaaaatcc cctgagttttttttattagggccaacacaaaagacccgctggtgtgtggtgcccgtgtctttcacttttcccctccccgacacggattgg ctggtgtagtgggcgcggccagagaccacccagcgcccgacccccccctccccacaaacacgggggcgtcccttaTAAATACGGAAGGAT CTGAGGTTCGTGGTAACTATGGGTGGTACAGGTGCCACCTAAATAGTGACACAACTGCTATTAAAATTTAACCAAAATCCCTTAACGTGAG gggggtcgtatgcggctggaggtcgcggacggagggtccctgggggtcgcaacgtaggcggggcttctgtggtgatgcggagaggggTg gcccgagtctgcctggctgctgcgtctcgctccgagtgccgaggtgcaaatgcgaccagactgtcgggccagggctaacttataccccacg cctttcccctccccaaaggggcggcagtgacgattcccccaatggccgcgcgtcccaggggaggcaggcccaccgcggggcggccccgtcc ccggggaccaacccggcgcccccaaagaatatcattagcatgcacggcccggccccgatttgggggcccaacccggtgtcccccaaagaa ccccattagcatgcccctcccgccgacgcaacaggggcttggcctgcgtcggtgccccggggcttcccgccttcccgaagaaactcattac catacccggaacccaggggaccaatgcgggttcattgagcgacccgcgggccaatgcgcgaggggccgtgtgttccgccaaaaaagcaat tagcataacccggaacccagggagtggttacgcgcggcgcgggaggcggggaataccggggttgcccattaagggccgcgggaattgcc ggaagcgggaagggcggccggggccgcccattaatgagtttctaattaccataccgggaagcggaacaaggcctcttgcaagtttttaatt accataccgggaagtgggcggcccggcccattgggcggtaactcccgcccaatgggccgggccccgaagactcggcggacgctggttggcc gggccccgccgcgctggcggccgccgattggccagtcccgcccccgaggcgggcccgccctgtgagggcgggctggctccaagcgtatata tgcgcggctcctgccatcgtctctccggagagcggcttggtgcggagctcccgggagctccgcggaagacccaggccgcctcgggtgtaac gttagaccgagttcgccgggccggctccgcgggccagggcccgggcacgggcctcgggccccaggcacggcccgatgaccgcctcggcctc cgccacccggcgccggaaccgagcccggtcggcccgctcgcgggcccacgagccgcggcgcgccaggcgggcggccgaggcccagaccacc aggtggcgcaccggacgtggggcgagaagcgcacccgcgcgggggtcgcgggggtcgcgggggtcgcggggtcgcgggggtcgcggggg gctccggcgcccccctcccgcccgcgcgtcgcaggcgcaggcgcgccaggtgctccgcggtgacgcgcaggcggagggcgaggcgcggcgg aaggcggaaggggcgcgagggggggtgggaggggtcagcccgcccccgggcccacgccgggcggtgggggccggggccggggggcggcg gcggtgggccgggcctctggcgccggctcgggcggggggctgtccggccagtcgtcgtcatcgtcgtcgtcggacgcggactcgggaacgt ggagccactggcgcagcagcagcgaacaagaaggcggggcccaccggcgggggcggcggcggggcggccgcgggcgcgctcctgaccgc gggttccgagttgggcgtggaggttacctgggactgtgcggttgggacggcgcccgtgggcccgggcggccggggcggcggggccgcga tggcggcggcgcgggccatggagacagagagcgtgccgggtggtagagtttgacaggcaagcatgtgcgtgcagaggcgagtagtgctt gcctgtctaactcgctagtctcggccgcggggggcccgggctgcccgccgccgccgctttaaagggccgcgcgcgaccccgggggtgtg ttttgggggggggcccgttttcggggtctggccgctcctcccccgctcctcccccgctcctcccccgctcctcccccgctcctccccc cgctcctcccccgctcctcccccgctcctcccccgctcctcccccgctcctcccccgctcctcccccgctcctcccccgctcct cccccgctcctcccccgctcctcccccgctcctcccccgctcctcccccgctcctcccccgctcccgcggcccgcccccacgc ccgccgcgcgcgcacgccgcccggaccgccgcccgcctttttgcgcgcgcgcgcccgcgggggcccgggct

Example 2. Packaging Cell Lines

In order to produce engineered HSV-1 in high titer, packaging cell lines that can complement deleted viral genes and support replication were constructed. Viral genes may be toxic to the cells, therefore their expression was put under control of doxycycline during viral 50 particle production. U2OS cell line was used to construct the packaging cell lines, because they can naturally complement VP16 and ICP0 to some degree (e.g., as described in Yao et al., *Journal of Virology*. 1995; 69(10):6249-6258, incorporated herein by reference) and withstand constitutive expression of ICP27.

Figure 3:
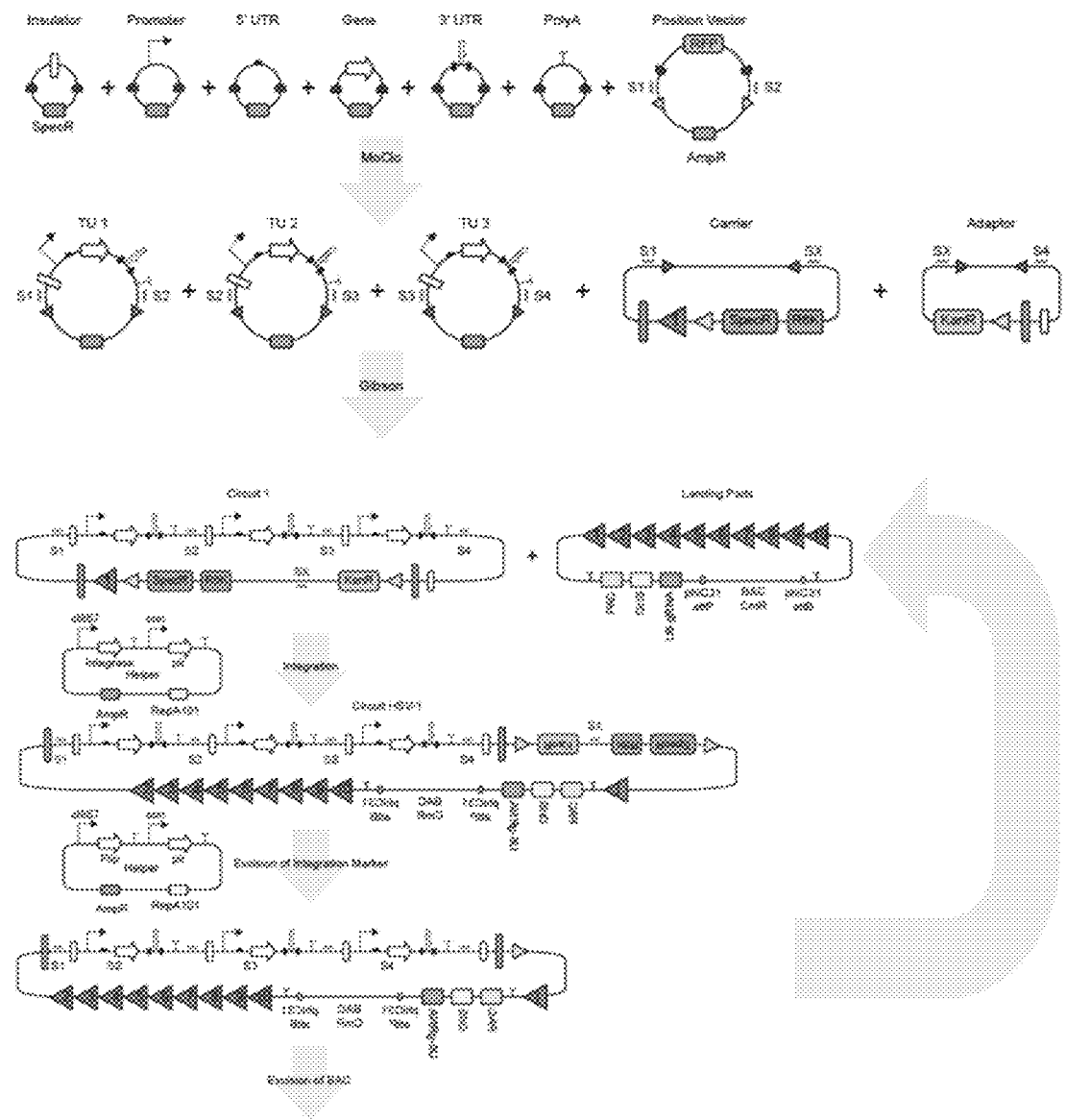
FIG. 3. Rapid, standardized assembly and integration of genetic circuits into HSV-1 backbone, virus production from the HSV-1 vector containing the genetic circuit, and use of the HSV-1 virus to treat metastatic breast cancer in a mouse model.
Figure 3:
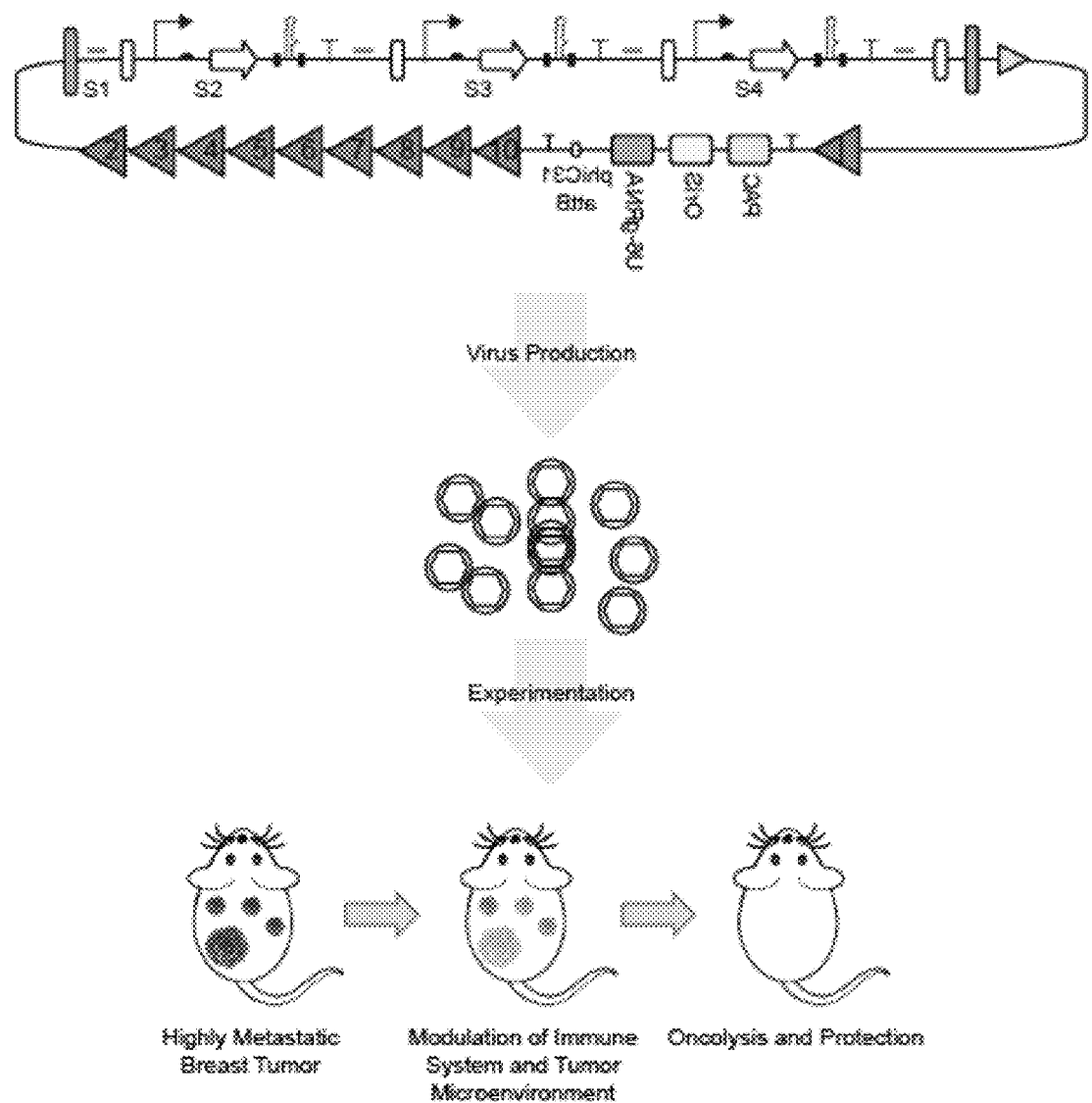

Example 3. Rapid, Standardized Assembly and Integration of Circuits into HSV-1 Backbone Rapid, standardized assembly and integration of circuits into HSV-1 backbone is depicted in FIG. 3. Individual parts including insulator, promoter, 5'UTR, gene, 3'UTR, and polyA are assembled with a position vector into a transcription unit by MoClo reaction using BsaI. These transcription units in different position vectors are then assembled with carrier and adaptor backbones into a circuit by Gibson assembly reaction. Using a helper plasmid which encodes an integrase under a temperature sensitive promoter, this circuit is integrated into HSV-1 backbone with a landing pad on genome. Using a helper plasmid which encodes Flp under a temperature sensitive promoter, integration marker is removed by Flp. Circuit HSV-1 DNA is then purified and co-transfected with a plasmid expressing Cre into packaging cells to reconstitute infectious circuit HSV-1. Reconstituted circuit HSV-1 can be tittered and injected into a mouse model for in vivo characterization of classified replication of HSV-1 as described in Example 4.

Example 4. In Vivo Characterization of Classified Replication of HSV-1

Figure 4:
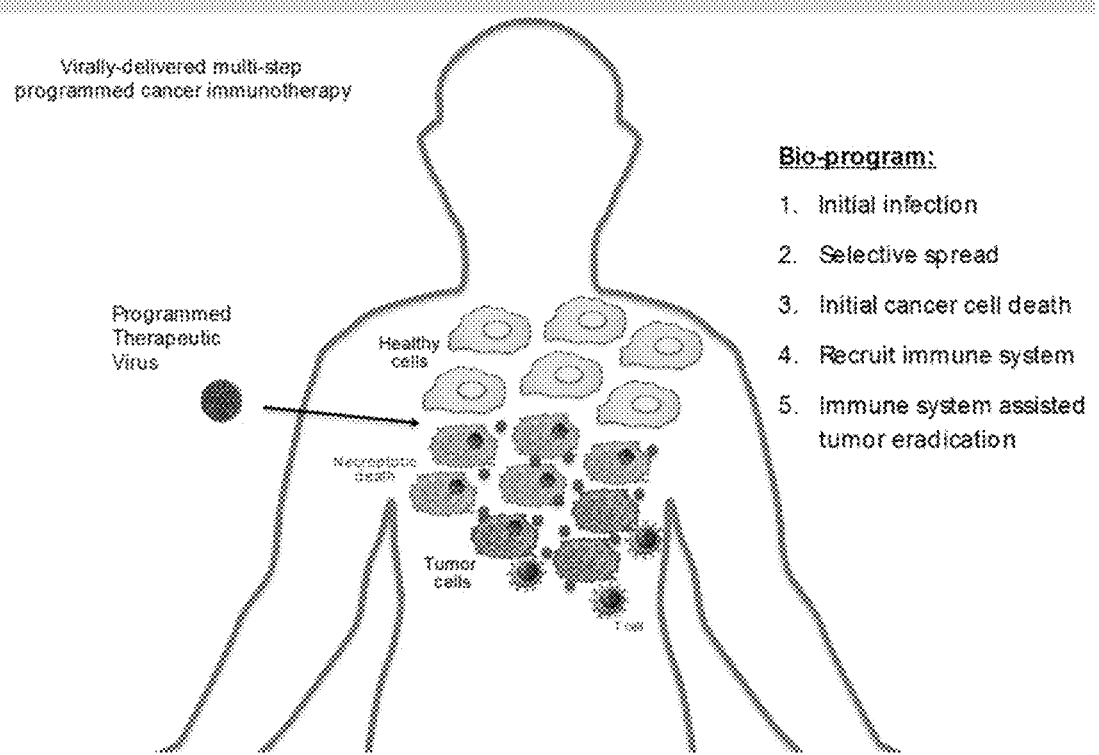
FIG. 4. Use of the Engineered HSV-1 vectors described herein for use in cancer therapy.

One of the applications is virally-delivered multi-step programmed cancer immunotherapy (FIG. 4). Programmed therapeutic virus is injected into primary tumor via intratumoral injection. The virus is selectively replicate and spread only in tumor cells and cause initial cell death of tumor cells followed by recruitment of immune system. The remaining tumor cells are removed by the immune system.

Figure 5A:
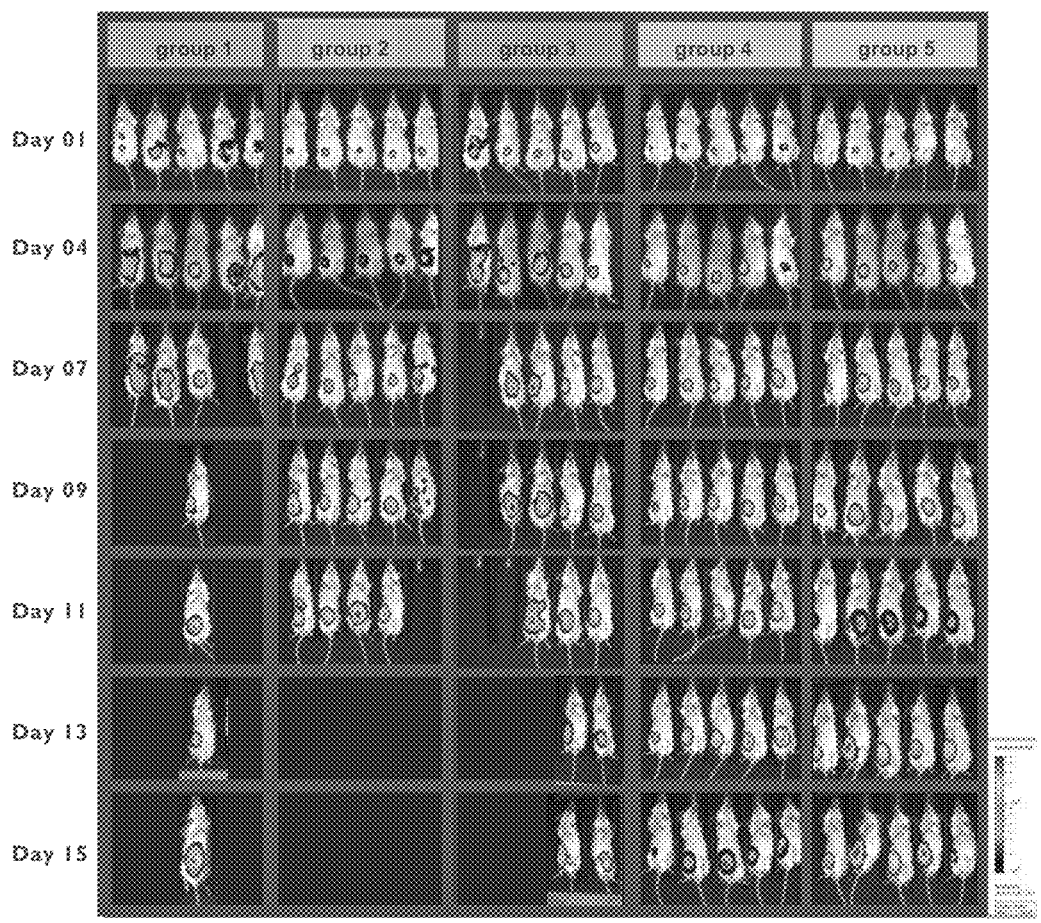
Figure 5B:
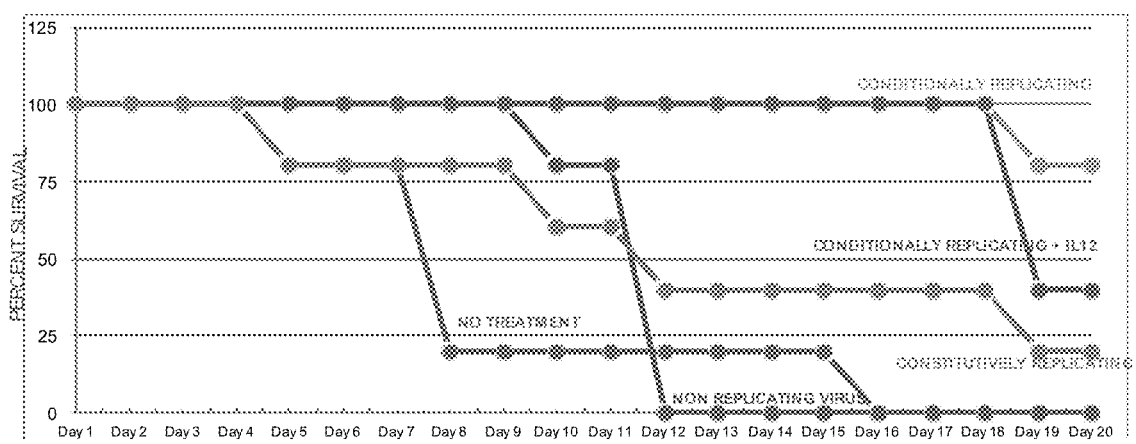

To study performance of conditionally replicating HSV-1, experiments were performed on groups of five mice. 10,000 4T1 cells expressing firefly luciferase (Fluc) were implanted in mouse mammary fat pad 7 days before injection of viruses. Each of five groups of mice was injected with PBS only (no treatment, group 1), non replicating virus (group 2), constitutively replicating virus (group 3), conditionally replicating virus (group 4), or conditionally replicating virus with IL-12 (group 5). Tumor size was monitored over 15 days post injection by imaging Fluc (FIG. 5A). The survival curve shows that the group treated with conditionally replicating virus survived longer than other groups (FIG. 5B).

Figure 5C:
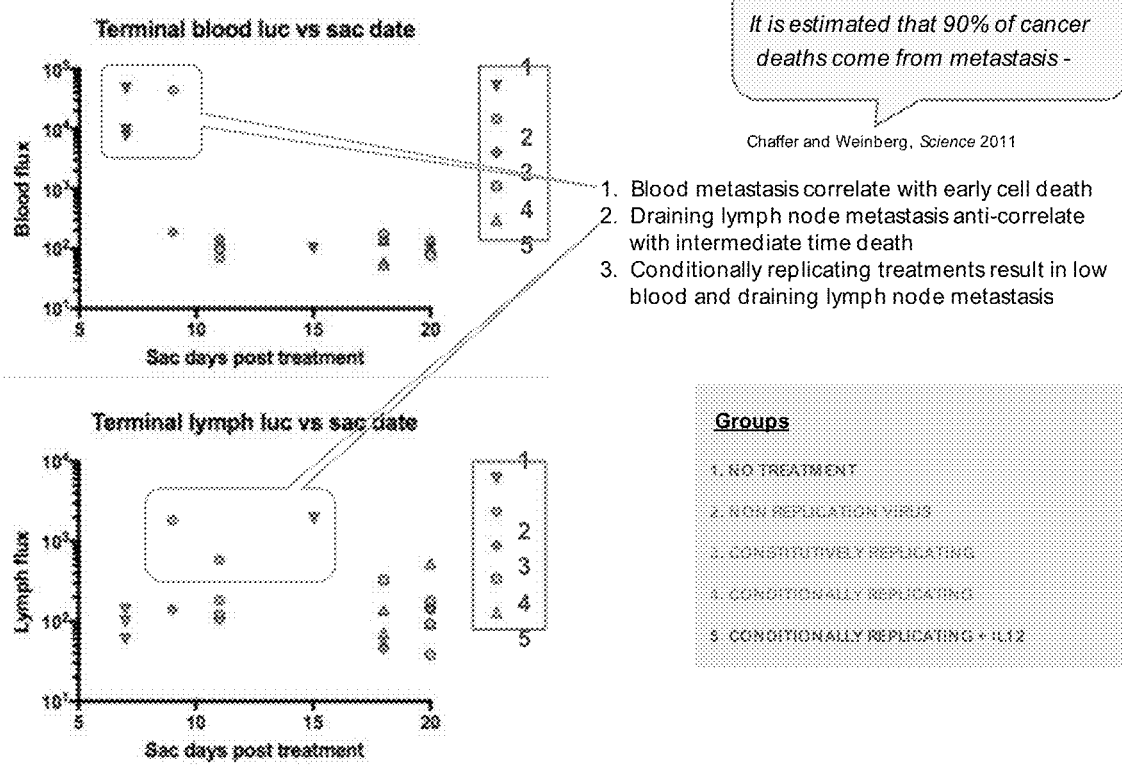

Interestingly, the group treated with conditionally replicating virus with IL-12 survived less than the group treated with conditionally replicating virus. Metastasis was measured by detecting Fluc signal in blood and draining lymph nodes at different time points (FIG. 5C). Blood metastasis correlated with early time death of the mice. Draining lymph node metastasis anti-correlated with intermediate time death. Conditionally replicating treatment resulted in low blood and draining lymph node metastasis.

Methods and Materials

TABLE 3

Helper plasmids

| Type of purpose | Plasmid ID | Description |
| --- | --- | --- |
| HSV-1 modification | pBjh3432 | pBjhSKI_cHS4-hEF1a-BFP-PA-cHS4_UL3-4_dSacB |
| HSV-1 modification | pBjh3433 | pBjhSKI_hEF1a-BFP-d34.5-UL4_dSacB |
| HSV-1 modification | pBjh3434 | pBjhSKI_glyL-hEF1a-BFP-d34.5-UL4_dSacB |
| HSV-1 modification | pBjh3435 | pBjhSKI_UL43-47_dSacB |
| HSV-1 modification | pBjh3511 | SKI_ICP47 |
| HSV-1 modification | pBjh3513 | SKI_1163GlyL |
| HSV-1 modification | pBjh3514 | SKI_ICP22-EYFP |
| HSV-1 modification | pBjh3540 | SKI_beginning |
| HSV-1 modification | pBjh3561 | SKI_dLuc |
| HSV-1 modification | pBjh3645 | SKI-3627 after ICP4 v2 |
| HSV-1 modification | pBjh3670 | SKI-IR v2 |
| HSV-1 modification | pBjh3754 | SKI-attB-attP21-UL3/4 for 17 |
| HSV-1 modification | pBjh3760 | SKI-ICP4 from strain 17 |
| HSV-1 modification | pBjh3763 | SKI-attB-attP21-UL3/4 for KOS |
| HSV-1 modification | pBjh3774 | SKI-attP21-UL3/4 for 17 |
| HSV-1 modification | pBjh3776 | SKI-attP21-UL3/4 for KOS |
| HSV-1 modification | pBjh3787 | SKI-VP16KOS |
| HSV-1 modification | pBjh3788 | SKI-ICP4 KOS |
| HSV-1 modification | pBjh3789 | SKI-IR v2 KOS |
| HSV-1 modification | pBjh3790 | SKI-ICP47 KOS |
| HSV-1 modification | pBjh3791 | SKI-beginning KOS |
| HSV-1 modification | pBjh3792 | SKI-ICP27 KOS |
| HSV-1 modification | pBjh3800 | SKI-ICP22 KOS |
| HSV-1 modification | pBjh3808 | SKI-V422 |
| HSV-1 modification | pBjh3809 | SKI-in14 |
| HSV-1 modification | pBjh4009 | SKI_UL38 |
| HSV-1 modification | pBjh4010 | SKI_UL37 |
| HSV-1 modification | pBjh4015 | SKI_P2A-tTA@vhs |
| HSV-1 modification | pBjh5058 | SKI_deleting U6-gRNA from MD319 |
| HSV-1 modification | pBjh5143 | SKI_synthPA_attB2_PhiC31attB (from pBjh4010) |
| HSV-1 modification | pBjh5144 | SKI_synthPA_PhiC31attP (from pBjh4009) |
| HSV-1 modification | pBjh5234 | SKI_inserting attB2 between LATP2 and CTRL2 in joint region |
| HSV-1 modification | pBjh5243 | JH751F_attB2_attP13_SpecR_attB13 in S1-2 |

TABLE 3-continued

Helper plasmids

| Type of purpose | Plasmid ID | Description |
|---|---|---|
| HSV-1 modification | pBjh5311 | JH751F_attP12_SpecR_attB12 in Sl-2 |
| HSV-1 modification | pBjh5357 | JH751F_attP11_SpecR_attB11 in S1-2 |
| Circuit integration into HSV-1 | pBjh3916 | pIntBxB1 |
| Circuit integration into HSV-1 | pBjh4022 | Flp in LC65 helper plasmid |
| Circuit integration into HSV-1 | pBjh4031 | pInt2 |
| Circuit integration into HSV-1 | pBjh4032 | pInt3 |
| Circuit integration into HSV-1 | pBjh4033 | pInt4 |
| Circuit integration into HSV-1 | pBjh4034 | pInt5 |
| Circuit integration into HSV-1 | pBjh4577 | pInt2+ (164A) |
| Circuit integration into HSV-1 | pBjh4578 | pInt2+ (EI) |
| Circuit integration into HSV-1 | pBjh4595 | pInt21+ (164A) |
| Circuit integration into HSV-1 | pBjh4596 | pInt21+ (EI) |

TABLE 4

Oligos used for HSV-1 modification

| Oligo ID | Description Sequence |
|---|---|
| JH952F | ctaaatcaggtcgttgtcgtttattgcgtcttcgggtttcgcaagcgcccDeleting ICP4<br>CTCACGTTAAGGGATTTTGG (SEQ ID NO: 4) |
| JH952R | cctcttcgtcctcgtcgtccgacgaggacgaggacgacgacggcaacgacDeleting ICP4<br>TAAATACGGAAGGATCTGAG (SEQ ID NO: 5) |
| JH1009F | gcacatgcttgcctgtcaaactctaccaccccggcacgctctctgtctccDeleting 34.5 ICP0 LAT<br>CTCACGTTAAGGGATTTTGG (SEQ ID NO: 6) |
| JH1009R | cggtgtggttcaacaaagacgccgctttccaggtaggttagacacctgcDeleting 34.5 ICP0 LAT<br>TAAATACGGAAGGATCTGAG (SEQ ID NO: 7) |
| JH1017F | gattttggtcttttatttggggacatacaaggggtcggggcgaccggacDeleting internal repeats<br>CTCACGTTAAGGGATTTTGG (SEQ ID NO: 8) |
| JH1017R | catttcaaacaaatcgccccacgtgttgtccttcttgctcatggccggcDeleting internal repeats<br>TAAATACGGAAGGATCTGAG (SEQ ID NO: 9) |
| JH1023F | cgtttattgcgtcttcgggtttcgcaagcgccccgccccgtccggcccgDeleting US10-ICP4<br>CTCACGTTAAGGGATTTTGG (SEQ ID NO: 10)                region |
| JH1023R | gcgcacgtttgcagcgcacatgcgagacacctcgaccacggttcggaagaDeleting US10-ICP4<br>TAAATACGGAAGGATCTGAG (SEQ ID NO: 11)                region |
| JH1061F | gcgcctccaccgagataacgtcatgctggcctcggggggccgagtaaccgcdeleting luc and inserting<br>CTCACGTTAAGGGATTTTGG (SEQ ID NO: 12)                BFP |
| JH1061R | gacactgaaatgccaccccccctgcgggcggtccattaaagacaacaaacdeleting luc and inserting<br>TAAATACGGAAGGATCTGAG (SEQ ID NO: 13)                BFP |
| JH1080F | ccccaccctcgggttcgtgtatttcctttccctgtccttataaaagccgtDeleting UL43-47<br>CTCACGTTAAGGGATTTTGG (SEQ ID NO: 14) |
| JH1080R | gacatccgataacccgcgtctatcgccaccatgtcggctcgcgaacccgcDeleting UL43-47<br>TAAATACGGAAGGATCTGAG (SEQ ID NO: 15) |
| JH1083F | gcacatgcttgcctgtcaaactctaccaccccggcacgctctctgtctccDeleting gamma34.5-UL4<br>CTCACGTTAAGGGATTTTGG (SEQ ID NO: 16) |
| JH1083R | ctgttggtgattatcgactgtcgcgccgaattttgtgcctaccgctttatDeleting gamma34.5-UL4<br>TAAATACGGAAGGATCTGAG (SEQ ID NO: 17) |
| JH1155F | cgccccaagggggcggggccgccgggtaaaagaagtgagaacgcgaagcgDeleting ICP22<br>CTCACGTTAAGGGATTTTGG (SEQ ID NO: 18) |
| JH1155R | ggcatcggagatttcatcatcgcttgtcgcgctgagatgaatctcgagatDeleting ICP22<br>TAAATACGGAAGGATCTGAG (SEQ ID NO: 19) |
| JH1159F | ccggcggcgaccgttgcgtggaccgcttcctgctcgtcgggcggggagcDeleting ICP47<br>CTCACGTTAAGGGATTTTGG (SEQ ID NO: 20) |
| JH1159R | ccgcccagaaacttgggcgatggtcgtacccgggactcaacgggttaccgDeleting ICP47<br>TAAATACGGAAGGATCTGAG (SEQ ID NO: 21) |

TABLE 4-continued

Oligos used for HSV-1 modification

| Oligo ID | Description | Sequence |
|---|---|---|
| JH1170F | tgctcgtcggcggggggaagccactgtggtcctccgggacgttttctgg CTCACGTTAAGGGATTTTGG (SEQ ID NO: 22) | Deleting ICP22 and replacing GFP |
| JH1185R | cggccgcccgggcccacgggcgccgtcccaaccgcacagtcccaggtaac CTCACGTTAAGGGATTTTGG (SEQ ID NO: 23) | Deleting 34.5 region just outside of packaging site |
| JH1192R | ggttggtcaaaaagggagggacggggccggcagaccgacggcgacaac TAAATACGGAAGGATCTGAG (SEQ ID NO: 24) | Deleting 34.5 region just outside of glyL |
| JH1200F | gcgcctccaccgagataacgtcatgctggcctcgggggccgagtaaccgc CTCACGTTAAGGGATTTTGG (SEQ ID NO: 25) | Deleting Luc |
| JH1200R | gacactgaaatgccaccccccctgcgggcggtccattaaagacaacaaac TAAATACGGAAGGATCTGAG (SEQ ID NO: 26) | Deleting Luc |
| JH1269F | ttattgcgtcttcgggtttcgcaagcgccccgccccgtcccggcccgtta CTCACGTTAAGGGATTTTGG (SEQ ID NO: 27) | Deleting ICP4 right before TAA |
| JH1325F | ggccacgggccccggcgtgccggcgtcggggcgggtcgtgcataatgg CTCACGTTAAGGGATTTTGG (SEQ ID NO: 28) | Deleting IR |
| JH1325R | ttataaccccgggggtcattcccaacgatcacatgcaatctaactggctc TAAATACGGAAGGATCTGAG (SEQ ID NO: 29) | Deleting IR |
| JH1398F | Ccggcggcgaccgttgcgtggaccgcttcctgctcgtcgggcggggagc atgagccagacccaaccc (SEQ ID NO: 30) | scarlessly deleting ICP47 |
| JH1399F | ttattgcgtcttcgggtctcacaagcgccccgccccgtcccggcccgtta CTCACGTTAAGGGATTTTGG (SEQ ID NO: 31) | Deleting ICP4 (17) |
| JH1470F | ggcccgggcggccggggcggcggggccgcgatggcggcggcgggc CTTGTTCTCCGACGCCATC (SEQ ID NO: 32) | deleting ICP4 and PAC and put34.5 under IE4/5 (17) |
| JH1417F | ttattgcgtcttcgggtttcacaagcgccccgccccgtcccggcccgtta CTCACGTTAAGGGATTTTGG (SEQ ID NO: 33) | Deleting ICP4 (KOS) |
| JH1421F | gtgggcccgggcggccggggcggcggggccgcgatggcggcggcgggc CTTGTTCTCCGACGCCATC (SEQ ID NO: 34) | deleting ICP4 and PAC and put34.5 under IE4/5 (KOS) |
| JH1422F | cggccgcccgggcccacgggcgcggtcccaaccgcacagtcccaggtaac CTCACGTTAAGGGATTTTGG (SEQ ID NO: 35) | Deleting 34.5 region just outside of packaging site (KOS) JH1185R counter part |
| HH1422R | tttataaccccgggggtcattcccaacgatcacatgcaatctaactggctc TAAATACGGAAGGATCTGAG (SEQ ID NO: 36) | Deleting IR (KOS) |
| JH1423R | gtggtgtgcagccgtgttccaaccacggtcacgcttcggtgcctctcccc TAAATACGGAAGGATCTGAG (SEQ ID NO: 37) | Deleting ICP27 KOS |
| JH1425R | ccagacaataaagcaccaacaggggttcattcggtgttggcgttgcgtgc TAAATACGGAAGGATCTGAG (SEQ ID NO: 38) | Deleting VP16 KOS |
| JH1438F | cacggcggttctggccgcctcccggtcctcacgcccccttttattgatct CTCACGTTAAGGGATTTTGG (SEQ ID NO: 39) | Deleting up to ICP47 KOS |
| JH1439F | Ccggcggcgaccgttgcgtggaccgcttcctgctcgtcggggggaaaagc atgagccagacccaaccc (SEQ ID NO: 40) | Deleting ICP47 scarlessly KOS |
| JH1439R | ccgcccagagactcgggtgatggtcgtacccgggactcaacgggttaccg TAAATACGGAAGGATCTGAG (SEQ ID NO: 41) | Deleting ICP47 scarlessly KOS |
| JH1441F | ctacgtccgccgtcgcagccgtatccccggaggatcgccccgcatcggcg CTCACGTTAAGGGATTTTGG (SEQ ID NO: 42) | Deleting ICP4 pac34.5 ICP0 LAT right before glyL |
| JH1450R | ccacatataagccccccagccacacgcaagaacagacacgcagaacggctg TAAATACGGAAGGATCTGAG (SEQ ID NO: 43) | Deleting ICP4 pac34.5 ICP0 LAT right before glyL |
| JH1551F | cgcggactcgggaacgtggagccactggcgcagcagcagcgaacaagaag CTCACGTTAAGGGATTTTGG (SEQ ID NO: 44) | Deleting pac |
| JH2197F | TTCATTACATCTGTGTGTTGGTTTTTTGTGTGgtagtgccccaactggggs taac (SEQ ID NO: 45) | SKI_deleting U6-gRNA from MD319 |
| JH2197R | CACAGATGTAATGAAAATAAAGATATTTTATTCCAAAATCCCTTAACGTGs AG (SEQ ID NO: 46) | SKI_deleting U6-gRNA from MD319 |

TABLE 4-continued

Oligos used for HSV-1 modification

| Oligo ID | Description | Sequence |
|---|---|---|
| JH2198F | tggaccgcttcctgctcgtcgggggaaaagcatgagccagacccaacccCTCACGTTAAGGGATTTTGG (SEQ ID NO: 47) | Deleting U6-gRNA from MD319 |
| JH2198R | GTACAAAATACGTGACGTAGAAAGTAATAATTTCTTGGGTAGTTTGCAGTTAAATACGGAAGGATCTGAG (SEQ ID NO: 48) | Deleting U6-gRNA from MD319 |
| JH2309F | cggccggagaaacgtgtcgctgcacggataggggcaggcggtggagaagCTCACGTTAAGGGATTTTGG (SEQ ID NO: 49) | Deleting ICP22 |
| JH2311F | cccaagggccgcccgccgtcccgttggtcccggcgtccggcgggcgggacCTCACGTTAAGGGATTTTGG (SEQ ID NO: 50) | Deleting IE4/5 |
| JH2313F | ccacccagcgcccgaccccccctccccacaaacacgggggcgtcccttaTTAAATTTTAATAGCAGTTG (SEQ ID NO: 51) | Deleting ICP0 |
| JH2313R | cggccgcccgggcccacgggcgcggtcccaaccgcacagtcccaggtaacGTTCGTGGTAACTATGGGTG (SEQ ID NO: 52) | Deleting ICP0 |
| JH2324R | ccacccagcgcccgaccccccctccccacaaacacgggggcgtcccttaTAAATACGGAAGGATCTGAG (SEQ ID NO: 53) | Deleting ICP0 |
| JH2341F | cgaccccagggaccctccgtccgcgaccctccagccgcatacgacccccCTCACGTTAAGGGATTTTGG (SEQ ID NO: 54) | Deleting ICP0 Strain 17 |
| JH2341 | cacccagcgcccgaccccccctccccacaaacacgggggcgtcccttaTAAATACGGAAGGATCTGAG (SEQ ID NO: 55) | Deleting ICP0 Strain 17 |
| JH2343F | cgaccccagggaccctccgtcagcgaccctccagccgcatacgacccccCTCACGTTAAGGGATTTTGG (SEQ ID NO: 56) | Deleting ICP0 Strain KOS |
| JH2626F | gactagcgagttagacaggcaagcactactcgcctctgcagcacatgcttgcctgtcaaactctaccacccggcacgctctctgtctccatggcccgccgccgccgccatcgcggccccgccgccccggccgcccgggcccacgggcgccgtcccaaccgcacagtcccaggtaacCTCACGTTAAGGGATTTTGG (SEQ ID NO: 57) | Deleting joint region from Strain 17 |
| JH2626R | ggccaccgccgcccacccacccacctcgggatacccagcccggtcccccgttccccgggggccgttatctccagcgccccgtccggcgcgccgccccccgccgctaaacccatcccgccccgggacccacatataagcccccagccacacgcaagaacagacacgcagaacggctgTAAATACGGAAGGATCTGAG (SEQ ID NO: 58) | Deleting joint region from Strain 17 |

Mammalian Cell Cultures

HEK293 cell line was purchased from Invitrogen. Vero and U2OS cell line were purchased from ATCC. Vero 2-2 cell line was obtained from Xandra Breakfield laboratory at Massachusetts General Hospital. HEK293, Vero, and Vero 2-2 cell lines were maintained in Dulbecco's modified Eagle medium (DMEM, Cellgro) supplemented with 10% FBS at 37° C., 100% humidity and 5% C02. U2OS cell line was maintained in McCoy's 5A supplemented with 10% FBS at 37° C., 100% humidity and 5% $CO_2$. The packaging cell lines were maintained in McCoy's 5A supplemented with 10%, 0.5 ug/mL of puromycin, and 1 ug/mL of blasticidin at 37° C., 100% humidity and 5% $CO_2$.

Markerless Modification of HSV-1 Genome: Preparation of Markerless Modification Cassette To delete the selected target region of the HSV-1 genome, helper plasmids were constructed that contain ~500-bp homology region followed by kanamycin resistant gene (KanR) and an I-SceI recognition site for I-SecI induced DSB mediated DNA repair or the attP followed by spectinomycin resistant gene (SpecR) and the cognate attB site for serine integrase mediated DNA excision. For insertion, the DNA sequence of interest was placed before 500-bp homology region or attP site. These regions on the helper plasmids were amplified by PCR using primers that have 50-bp homology regions to the target region. The fragment was purified gel electrophoresis followed by column purification (Zymo Research, USA). The purified PCR product was then digested with DpnI (New England BioLabs, USA) and further purified by column purification.

Markerless Modification of HSV-1 Genome: Preparation of Electro-Competent Cells

For Preparation of electro-competent cells, a colony of E. coli DH10B cells harboring pREDI and HSV-1 BAC were inoculated and grown overnight at 30° C. in 3 ml of LB medium supplemented with carbenicillin (Carb, 50 ug/mL) and chloramphenicol (Cm, 12.5 ug/mL). Next day, the overnight culture was diluted 30-fold in 10 mL of LB medium and grown at 30° C. After 3 hours, 200 µL of 16% arabinose and further grown for 1 hour. The cells were harvested by centrifugation at 4000 g for 10 min and washed three times with ice-cold 10% glycerol.

Markerless Modification of HSV-1 Genome: Transformation of the Insert

For replacement of the targeted region of the HSV-1 genome, the prepared markerless modification cassette (400 ng) was electrotransformed into 50 µl of the prepared electro-competent cells. The electrotransformed E. coli cells were incubated in 1 ml of SOC medium at 30° C. for 3 hours, spread onto LB plates containing Carb, Cm, and Kan (25 µg/mL) for I-SecI induced DSB mediated DNA repair or Cm and Spec (100 µg/mL) for serine integrase mediated DNA excision, and incubated at 30° C. for an additional 16 hours. Correct replacement of the target genomic region by the markerless deletion cassette was verified by PCR using a pair of primers that flanked the endpoints of the targeted region and a pair of primers that were specific to genes that reside within the targeted region.

Markerless Modification of HSV-1 Genome: Removal of the Selection Marker Using I-SceI Induced Double Strand Break Mediated DNA Repair The selection marker (KanR_I-SceI) that were introduced into the genome as described above were then excised from the HSV-1 genome by DSB repair mediated by the I-SceI endonuclease expressed from pREDI. Briefly, the *E. coli* cells were grown to $OD_{600}$=0.4 at 30° C. in 3 ml of LB liquid medium containing Carb and Cm, then diluted 30-fold into 3 ml of fresh LB liquid medium containing Carb, Cm, and 10 mM rhamnose and grown to OD600=0.4 at 30° C. After five rounds of serial culture with 30-fold dilution, the cells were plated on LB plates containing Carb, Cm, and 10 mM rhamnose. Then markerless modification mutants (colonies that were Carb and Cm-resistant and Kan-sensitive) were selected. The excision of the selection markers was verified by PCR, followed by sequencing, using a pair of specific primers that flanked the endpoints of the genomic target region. When desired, pREDI was removed by growing *E. coli* at 42° C. overnight without Carb.

Markerless Modification of HSV-1 Genome: Removal of the Selection Marker Using Serine Integrase Mediated DNA Excision The selection marker (attP_SpecR_attB) that were introduced into the genome as described above were then excised from the HSV-1 genome by serine integrase mediate DNA excision. Briefly, the *E. coli* cells were transformed by a cognate helper plasmid and plated on LB agar plate supplemented with Carb and Cm. A colony was then inoculated and grown to $OD_{600}$=0.4 at 30° C. in 3 ml of LB liquid medium containing Carb and Cm, then supplemented with 60 µL of 16% arabinose. After one more round of serial culture with 30-fold dilution with arabinose, the cells were plated on LB plates containing Cm and incubated at 42° C. for an additional 16 hours. Then markerless modification mutants (colonies that were Cm-resistant and Spec-sensitive) were selected. The excision of the selection markers was verified by PCR, followed by sequencing, using a pair of specific primers that flanked the endpoints of the genomic target region.

Rapid Assembly of Circuits: Parts Assembly into Transcription Units (TU)

For assembling parts into TU, Golden gate assembly reaction was used. Briefly, 1 µl of BsaI (New England BioLabs, USA), 0.5 µl of T4 Ligase (New England BioLabs, USA), 0.5 µl of T4 Ligase buffer (New England BioLabs, USA), 2 µl of 100×BSA (NEB), 40 fmol of the backbone, adaptor, TUs, and ddH$_2$O up to a final total volume of 20 µl were placed in a PCR tube. The thermocycler program used for all assemblies was: 1 step of 15 min at 37° C.; then 50 cycles of 2 min at 37° C. then 5 min at 16° C.; 1 step of 15 min at 37° C., 1 step of 20 min at 60° C., 1 step of 5 min at 50° C., and 1 final step of 5 min at 80° C. 1.5 µL of reaction was transformed into 6 µL of Stellar chemically competent cells (Takara Bio USA, USA), rescued in 60 µL of SOC (New England BioLabs, USA), and 30 µL of that was plated on LB agar plates supplemented with Carb followed by incubation at 37° C. overnight. Correct clones were confirmed by restriction digestion mapping.

Rapid Assembly of Circuits: TU Assembly into Circuits

For assembling TUs into circuits, Gibson assembly reactions was used according to the manufacture's protocol (SGI-DNA, USA). 1 µL of reaction was electroporated into TransforMax™ EC100D™ pir+ Electrocompetent *E. coli* (Epicentre, USA). It was then rescued in 1 mL of SOC (New England BioLabs, USA) at 37° C. for 1 hour. 30 µL of that was plated on LB agar plates supplemented with Kan and Spec, and incubated at 30° C. overnight. Correct clones were confirmed by restriction digestion mapping.

Rapid Circuit Integration into HSV-1 Genome Using Serine Integrase Mediated DNA Insertion For integration of circuits into HSV-1 genome, a helper plasmid was transformed into *E. coli* DH10B cells harboring HSV-1 BAC, and the transformants were plated on LB agar plate supplemented with Carb and Cm and incubated at 30° C. overnight. Subsequently, a circuit of interest was electroporated into *E. coli* DH10B cells harboring a helper plasmid and HSV-1 BAC, and the transformants were plated on LB agar plate with Carb, Cm, Kan, and Spec and incubated at 30° C. overnight. A colony was inoculated in LB liquid medium supplemented with Cm, Kan, and Spec, and incubated at 42° C. for 20 minutes followed by overnight at 37° C. The overnight culture was restreaked on LB agar supplemented with Cm, Kan, and Spec, and incubated at 42° C. overnight. A colony was inoculated in LB liquid medium supplemented in Cm, Kan, and Spec, and BAC DNA was purified to be reconstituted in the packaging cell line.

Rapid Construction of Packaging Cell Lines: Integration of the Landing Pad into U2OS Genome by Lentivirus Transduction The gateway system was used to construct the integration vectors. The lentiviral gateway destination vectors contain pFUGW (1) (Addgene) backbone and gateway cassette (comprising chloramphenicol resistance and ccdB genes flanked by attR4 and attR2 recombination sites) followed by blasticidin or puromycin resistance markers constitutively expressed. LR reaction of the destination vectors with entry vectors carrying human elongation factor 1 alpha (hEF1a) promoter and either mKate2 or EBFP2 fluorescent proteins was used to create the following expression vectors: pLV-mKate2-Puromycin and pLV-EBFP2-Blasticidin.

For production of lentiviral particles ~2×10$^6$ HEK293FT cells (Invitrogen) in 3 mL of DMEM complete media were plated into gelatin-coated 60 mm dishes (Corning Incorporated). Three hours later the ~80% confluent cells were co-transfected with the pLV-hEF1a-attP_BxB 1-EYFP-2A-Hygro vector, the packaging plasmid pCMV-dR8.2 (Addgene) and the envelope plasmid pCMV-VSV-G (Addgene), as described previously (1) using Attractene reagent (Qiagen) by following manufacturer's protocol. Media containing viral particles produced from transfected HEK293FT cells were harvested ~48 h post-transfection and filtered through a 0.45-µm syringe filter. MOI of 1 was added to ~50% confluent U2OS cells in 6-well plate seeded immediately before infection. After 48 h, media were changed and supplemented with 200 µg/mL Hygromycin B (InvivoGen). Cells were maintained under selection for 2 weeks.

Rapid Construction of Packaging Cell Lines: BxB1-Mediated Integration of Circuits To integrate circuits, 375 ng of the circuit plasmid with 375 ng of pTU1 BxBlo using attractene (Qiagen) were co-transfected in 6-well format. 72 hours post transfection cells were transferred to 6-well plates and culture medium supplemented with 0.5 µg/mL Puromycin and 2 µg/mL Blasticidin (InvivoGen). Cells were maintained under selection for 2 weeks.

Small-Scale Reconstitution and Harvest of HSV-1::Circuit

A confluent 10 cm plate of U2OS::pBjh3721 was trypsinized with 2 mL of 0.25% Trypsin and neutralized with 10 mL of the fresh complete medium supplemented with 1 μg/mL doxycycline. 2 mL of that was aliquoted in a 6-well plate. While incubating for at least 30-minutes at 37° C. to allow cells to settle down, DNA:Viafect complex was prepared by mixing 3308.8 ng of HSV-1 BAC, 220.6 ng of CAG-Cre, and 220.6 ng of CAG-Flpe with 100 μL of Optimem in a 2 mL microcentrifuge tube. Make sure Optimem is warmed to room temp. Optimem should not be pink. If it is, it will reduce the transfection efficiency significantly. 30 μL of Optimem was added to DNA and the mixture was vortex with three short pulse (volume less than 50 μL might be difficult to vortex well). The total volume of DNA should not exceed 10% of Optimem. 2.25 μL of viafect (vortex well before use) was added and the mixture was immediately vortex with three short pulse, incubated for 5 min at room temperature, and add to the prepared 24 well plate dropwise. The 24 well plate was shaken well and put back in the incubator. After two days, a plaque composed of 3-10 cells is visible under bright field, and it may or may not show fluorescence. Cells should be expressing EYFP by dox.

HSV-1 In Vitro Characterization
Landing Pad Integration Using Zinc Finger Nucleases.

To create pLanding_Pad vector, a 800 bp sequence homologous to the AAVS1 sequence on the left of the ZFN cut site was cloned into the p_TU1 position vector. A 800 bp sequence homologous to the AAVS1 sequence on the right of the ZFN cut site was cloned into the p_TU3 position vector. The following transcription unit was assembled into the p_TU2 position vector with a golden gate reaction containing: double cHS4 core insulator from a p_Insulator, Ubc promoter from a p_Promoter, attP B×B1 from a p_5'UTR, EYFP-2A-HygroR from a p_Gene, inert 3' UTR from a p_3'UTR, and synthetic polyAdenylation signal as well as another copy of double cHS4 core insulator from a p_polyA. The three verified position vectors were then assembled altogether into the Shuttle Vector, deleting the crt red operon cassette.

To create Zinc-Finger Nuclease vector, pLV_CAG_CN-2A-CN, the cDNA encoding the two zinc finger nucleases for the AAVS1 locus[18], separated by a 2A tag was synthesized (GeneArt, Regensburg, Germany) and PCR-amplified with attB1/attB2 tags using the primers oPG608b/oPG609b. Upon gel-extraction, the PCR-product was recombined into a pENTR_L1_L2 vector using BP clonase (Life Technologies, Carlsbad CA), yielding the pENTR_L1_CN-2A-CN_L2 vector. In a next step, pENTR_L1_CN-2A-CN_L2 and pENTR_L1_CAG_L2 were recombined into pLV_R4R2_GTW using the LR clonase II plus (Life Technologies, Carlsbad Calif.), resulting in pLV_CAG_CN-2A-CN.

To integrate the landing pad into the AAVS1 locus, cells were co-transfected with equimolar amount of the Zinc-Finger Nuclease vector pLV_CAG_CN-2A-CN and of the pLanding_pad vector. Clones were created by serial dilutions of the polyclonal surviving population. 72 hours post transfection cell culture medium was supplemented with 200 μg/ml Hygromycin B (Invivogen) and the selection was maintained over a period of 2 weeks. Clonal cell lines were generated by serial dilutions of the surviving population.

Dual Luciferase Assays.

Dual luciferase assays were performed according to the manufacturer's instructions (Promega, cat # N1610, modified protocol listed below)

Plate cells of interest in white walled, clear bottom tissue culture plates (corning cat # xxx) to achieve a density of 80-100%.

Infect cells with HSV-1 control (KOS-LB or 17-LB) or circuit viruses in a total volume of 100 μL of media. Preferably perform a serial titration of each virus to achieve at least several dilution points with visually detectable (on Evos fluorescence microscope) viral plaques. Infection was allowed to proceed in a temperature-constant incubator for at least 24 hours or up to 1 week. The dilution wells that have visually identifiable plaques were noted. The plates were then equilibrated to room temperature and luciferase activity was measured.

A volume of ONE-Glo™ EX Reagent equal to the volume of culture medium was added to the wells. The mixtures were incubated for at least 3 minutes, preferably on an orbital shaker (300-600 rpm). Luminescence was measured with appropriate acquisition times (usually ~1 second) and gain to collect signal in the linear range of detection.

For measuring NanoLuc® luciferase activity, a volume of NanoDLR™ Stop & Glo® Reagent equal to the original culture volume was added to each well and mix thoroughly. preferably on an orbital shaker at 600-900 rpm for at least 3 minutes or by pipetting up and down twice to mix. After at least 10 minutes (including mixing time), NanoLuc® luminescence was measured with appropriate acquisition times (usually ~1 second) and gain to collect signal in the linear range of detection.

Delivery of Engineered Viruses Encoding Genetic Circuits to Tumor-Bearing Mice

Anesthetized (1-4% isoflurane inhalation) female Balb/C mice (6-8 weeks of age) are inoculated with $10^5$ 4T1 breast cancer cells in the $4^{th}$ mammary fat pad (the one closest to the hip and inguinal lymph node). Prior to injection, the site is prepared using a cotton tip applicator soaked in betadine. The injection site is scrubbed in a circular pattern (from center out) with several fresh cotton tips soaked in betadine for a total scrub time of 5 minutes. Finally, the site is rinsed with gauze 3×3 s soaked in 70% isopropyl alcohol and the injection is delivered.

Tumor bearing mice are anesthetized (1-4% isoflurane inhalation), and injected with up to $1 \times 10^7$ pfu of engineered virus. Virus is introduced by intratumoral, subcutaneous, intraperitoneal, or intravenous (retro-orbital or tail vein) injection following surgical skin prep (alternating betadine and alcohol scrubs) of the injection site. This treatment will be repeated up to 3 times at an interval of 48 hours.

Naked nucleic acids (DNA or RNA) encoding additional anti-cancer proteins or circuit components is delivered simultaneously with the viral particles or after a time delay. The viral particles described herein are attenuated through deletion of virulence factors within the viral genome. The naked nucleic acids do not contain any viral sequences. Gene therapy vectors (10-50 μg) are delivered intramuscularly and/or intratumorally up to 5× with an interval of 72 hours (Huang et al, *Cancer Research* (2002) 62:5727-5735). In some instances electroporation is used to enhance delivery of gene therapy vectors. Following anesthesia (1-4% isofluorane inhalation), hair is removed from the injection site (by shaving or using the Nair depilatory cream). The electroporation site is prepared using a cotton tip applicator soaked in betadine. The site is scrubbed in a circular pattern (from center out) with several fresh cotton tips soaked in betadine for a total scrub time of 5 minutes. Finally, the site is rinsed with gauze 3×3s soaked in 70% isopropyl alcohol. Next, a Harvard Apparatus 2-Needle Array (ECM 830) is inserted to a depth of 2-5 mm (depending on the size of the tumor or muscle) to encompass the nucleic acid injection site. The tissue is submitted to electroporation (200V/cm for a period of 60 msec, 100 milliseconds of delay, followed by a second pulse of 200V/cm for a period of 60 msec) using the BTX Caliper electrode system (Nature Materials 12; 367-376 (2013)).

Following injection of virus, mice are monitored every 24 hours for signs of distress. Mice are sacrificed if they exhibit overt weight loss (sacroileac body score of <2), or dyspnea, decreased activity, feeding, or grooming behavior.

The viruses and/or 4T1 cells carry luciferase reporters so that the Caliper Spectrum IVIS optical imaging system can be used to collect longitudinal data on one set of mice (thus reducing the overall number of mice used). Following administration of virus, luminescence is monitored up to 2× per day for 4 days, or up to 1× per day for 9 days, or 1-3× per week for up to 3 months. Prior to bioluminescence imaging, animals are anesthetized (1-4% isoflurane inhalation) and given a saturating dose of luciferin (165 mg/kg). Luciferin (16.5 mg/mL in sterile PBS) is injected subcutaneously at the nape of the neck according to the weight of the mouse (10 µl luciferin/1 g of mouse weight; e.g. a 20 g mouse gets 200 µL). Whole-mouse imaging is performed in the Xenogen bioluminescence and fluorescence cabinet at the Koch Institute.

When necessary, the submandibular method or saphenous vein (without anesthesia) is utilized for weekly blood draws to monitor immune responses. If more frequent collection of smaller amounts of blood is required, it is collected up to 2× per day from the saphenous vein for up to 5 days. The total amount of blood collected is <7.5% of the total blood volume each week (e.g. 100 µL each week for a 20 g mouse) or <15% of the total blood volume if blood collection is performed at 2 week intervals. Blood samples may be assayed for cellular (using flow cytometry) or humoral (by ELISA assay) immune responses.

Necropsies is performed when mice meet criteria requiring euthanasia, when luciferase signal has dropped, or after 3 months, whichever is sooner. Various organs including tumor, brain, eyes, muscle, lung, spleen, lymph nodes, liver, thymus, intestines, and bone marrow may be harvested and removed from the facility to be analyzed by flow cytometry (at the Weiss Lab or at the Koch Institute FACS core facility), or by histology at the Koch Institute Histology Lab. These samples are either fixed in 4% paraformaldehyde to inactivate virus in the animal facility or in a biosafety hood in the Weiss lab. Residual tissue and/or carcasses are bagged for incineration and will be deposited in the carcass refrigerator in the Koch animal facility.

Delivery of Engineered Viruses Encoding Genetic Circuits to Healthy Mice

Since tumors modulate local and systemic immunity, and viral particles elicit anti-viral immune responses it may be useful to characterize the infectivity, persistence and distribution of virus-encoded anti-cancer circuits in healthy, non-tumor bearing mice. In this scenario, healthy mice are anesthetized (1-4% isoflurane inhalation), submitted to surgical skin prep appropriate for the route of virus delivery, and treated with up to $1 \times 10^7$ pfu of engineered virus. Following introduction of virus, the procedure is performed as described above.

In some instances, virus may be introduced by subcutaneous, intraperitoneal, or intravenous (retro-orbital or tail vein) injection following surgical skin prep (alternating betadine and alcohol scrubs) of the injection site. In some instances, virus is introduced by corneal scarification following a sterile PBS wipe of the closed eye area. In some instances, up to $1 \times 10^6$ primary mouse cells (splenocytes or lymph node cells) preinfected in vitro with engineered virus are introduced by subcutaneous, intraperitoneal, or intravenous (retro-orbital or tail vein) injection following surgical skin prep (alternating betadine and alcohol scrubs) of the injection site. In some instances, up to $1 \times 10^4$ 4T1 cancer cells preinfected in vitro with engineered virus are introduced by subcutaneous, intraperitoneal, or intravenous (by tail vein, not by retro-orbital) injection following surgical skin prep (alternating betadine and alcohol scrubs) of the injection site. In some instances, virus is introduced by intracranial injection following surgical skin prep (alternating betadine and alcohol scrubs), a scalp incision, perforation of the skull using a microdrill bit, and injection of virions using a Hamilton syringe.

Delivery of Small Molecule Modulators of Engineered Circuits

The goal is to develop and deliver genetic circuits with therapeutic programs for treatment in mouse models of human disease. The genetic circuits sense their environment, process environmental inputs, and respond with logic-based, controlled expression of therapeutic genes in the correct setting. Following delivery of engineered viruses into mice, mice are treated with a variety of non-hazardous small molecules to inhibit or induce the circuits. These molecules are injected (ABA) or dosed in drinking water (valacyclovir).

Necropsies

Tissues are collected from mice at a humane experimental endpoint according to the NIH guidelines. These tissues can be flash frozen for immunohistochemistry and pathology analysis, prepared for FACS-based analysis of single cell suspensions, prepared for bulk analysis of ex vivo luciferase activity assays, or prepared for ex vivo culture assays for antigen-specific T-cell function. The steps are:

1. harvest tissues, organs, tumors
2. place in 24 well plate in 1 mL of cold PBS on ice
3. dilute collagenase/DNAse 1:200 in RPMI with 10% FBS
4. aliquot 1 ml of diluted collagenase/DNAse into fresh 24 well plate
5. place tissues into plate with collagenase/DNAse
6. use a fine needle syringe to aspirate collagenase/DNAse and inject it into the tissues
7. incubate tissue for 30 min at room temp
8. mince tissue through 40 um strainer
9. wash cells through strainer with 5-10 mL FACS buffer (PBS, 1% BSA, 5 mM EDTA, 0.1% NaN3)
10. centrifuge cells at 300 g for 5 min
11. aspirate sup. Wash pellet in 1 mL FACS buffer
12. centrifuge cells at 300 g for 5 min
13. resuspend cells in 200 µl FACS buffer and transfer into a 5 mL FACS tube with blue cell strainer top All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An engineered Herpes Simplex Virus-1 (HSV-1) vector comprising a modified HSV-1 genome comprising non-functional deletions in both copies of the gene encoding Infected Cell Protein 4 (ICP4), non-functional deletions in both copies of the gene encoding Infected Cell Protein 0 (ICP0), a deletion in the gene encoding Virion Protein 16 (VP16) that results in a truncation of the VP16 protein at amino acid 422, and one or more deletions in one copy of the Latency Associated Transcript (LAT) region,
   wherein a transcript of a LAT region is produced in an infected cell, and
   wherein the HSV-1 genome comprises a nucleotide sequence having 95% sequence identity to the nucleotide sequence of SEQ ID NO: 1.

2. The engineered HSV-1 vector of claim 1, wherein the modified HSV-1 genome further comprises deletions in one or more genes encoding γ34.5, ICP6, ICP8, ICP27, ICP22, or ICP47.

3. The engineered HSV-1 vector of claim 2, wherein one or more deletions render one or more of γ34.5, LAT, ICP27, ICP22, or ICP47 non-functional.

4. The engineered HSV-1 vector of claim 1, wherein the modified HSV-1 genome is from HSV-1 strains F, 17, or KOS.

5. The engineered HSV-1 vector of claim 1, further comprising one or more genetic circuits.

6. The engineered HSV-1 vector of claim 5, wherein the one or more genetic circuits are up to 150 kb in length.

7. The engineered HSV-1 vector of claim 5, wherein the one or more genetic circuits encodes an output molecule.

8. The engineered HSV-1 vector of claim 7, wherein the output molecule is an HSV-1 protein, a therapeutic molecule, a diagnostic molecule, a functional molecule, or an inhibitor of innate immune response.

9. The engineered HSV-1 vector of claim 8, wherein the inhibitor of innate immune response is an RNA interference (RNAi) molecule that targets an innate immune response component.

10. An isolated packaging cell comprising the engineered HSV-1 vector of claim 1.

11. The isolated packaging cell of claim 10, wherein the engineered HSV-1 vector is integrated into the genome of the isolated packaging cell.

12. The isolated packaging cell of claim 10, wherein the isolated packaging cell produces at least 1 plaque forming units of HSV-1 viral particles.

13. The isolated packaging cell of claim 10, wherein the isolated packaging cell is a U2OS cell.

14. An engineered HSV-1 viral particle comprising the engineered HSV-1 vector of claim 1.

15. A method of treating a disease, the method comprising administering an effective amount of the engineered HSV-1 viral particle of claim 14 to a subject in need thereof, wherein the engineered HSV-1 vector of the engineered HSV-1 viral particle comprises a genetic circuit encoding a therapeutic molecule.

16. A method of diagnosing a disease, the method comprising administering an effective amount of the engineered HSV-1 viral particle of claim 14 to a subject in need thereof, wherein the engineered HSV-1 vector of the engineered HSV-1 viral particle comprises a genetic circuit encoding a diagnostic molecule.

17. A method of delivering a genetic circuit into a cell, comprising contacting the cell with the engineered HSV-1 vector of claim 1, wherein the engineered HSV-1 vector comprises a genetic circuit.

18. The engineered HSV-1 vector of claim 1, wherein the modified HSV-1 genome comprises a nucleotide sequence having 99% sequence identity to the nucleotide sequence of SEQ ID NO: 1.

19. The engineered HSV-1 vector of claim 1, wherein the modified HSV-1 genome comprises the nucleotide sequence of SEQ ID NO: 1.

* * * * *

UNITED STATES PATENT AND TRADEMARK OFFICE
CERTIFICATE OF CORRECTION

| | | |
|---|---|---|
| PATENT NO. | : 12,209,250 B2 | Page 1 of 1 |
| APPLICATION NO. | : 16/741827 | |
| DATED | : January 28, 2025 | |
| INVENTOR(S) | : Ron Weiss et al. | |

It is certified that error appears in the above-identified patent and that said Letters Patent is hereby corrected as shown below:

In the Specification

Column 1, Lines 11-16, GOVERNMENT SUPPORT section should read:
This invention was made with Government support under Grant No. GM098792 awarded by the National Institutes of Health. The Government has certain rights in the invention.

Signed and Sealed this
Tenth Day of June, 2025

Coke Morgan Stewart
*Acting Director of the United States Patent and Trademark Office*

```
                              SEQUENCE LISTING

<160> NUMBER OF SEQ ID NOS: 58

<210> SEQ ID NO 1
<211> LENGTH: 32767
<212> TYPE: DNA
<213> ORGANISM: Artificial Sequence
<220> FEATURE:
<223> OTHER INFORMATION: Synthetic

<400> SEQUENCE: 1
gcccgccgcc gccgctttaa agggccgcgc gcgaccccccg gggggtgtgt tttgggggggg    60 gcccgttttc ggggtctggc cgctcctccc cccgctcctc ccccgctcc tccccccgct     120 cctcccccg ctcctccccc cgctcctccc cccgctcctc ccccgctcc tccccccgct     180 cctcccccg ctcctccccc cgctcctccc cccgctcctc ccccgctcc tccccccgct     240 cctcccccg ctcctccccc cgctcctccc cccgctcctc ccccgctcc tccccccgct     300 cccgcggccc cgcccccac gcccgcgcg cgcgcgcacg ccgcccggac cgccgcccgc     360
cttttttgcg cgcgcgcgcg cccgcgggggg gcccgggctg ccacaggtga aaccaacaga    420
gcacggcgca ctccgcacgt cacacgtcac gtcatccacc acacctgccc aacaacacaa    480
ctcacagcga caactcaccg cgcaacaact cctgttcctc atccacacgt caccgcgcac    540
ctcccgctcc tccagacgta ccccggcgca acacaccgct cctgctacac accaccgccc    600
ctccccagcc ccagccctcc ccggcccag ccctccccgg ccccagccct cccggcccc     660 agccctcccc ggcccagcc ctccccggcc cagccctcc ccggcccag ccctcccgg      720 ccccagccct ccccggccgc gtcccgcgct ccctcgggggg ggttcgggca tctctacctc    780
agtgccgcca atctcaggtc agagatccaa acccttccggg ggcgcccgcg caccaccacc    840 gccctcgcc cctcccgcc cctcgccccc tcccgcccct cgccccctcc cgccctcgc      900 cccctcccgc ccctcgcccc ctccccgccc tcgccccctc ccgccctcg ccccctcccg    960 ccctcgccc cctcccgccc ctcgccccct cccgccctc gccccctccc gccctcgcc    1020 ccctcccgcc cctcgccccc tcccgcccct ccgccctcg ccctccccgc             1080 ccctcgcccc ctcccgcccc tcgccccctc ccgccctcg ccccctcccg ccctcgccc    1140 cctcccgccc ctcgcccct ccgccctc gaataaacaa cgctactgca aaacttaatc    1200
aggttgttgc cgtttattgc gtcttcgggt ctcacaagcg ccccgcccg tcccggccg    1260 ttactcacgt taagggattt tgggcttgtt ctccgacgcc atcgccgatg cggggcgatc    1320
ctccggggat acggctgcga cggcggacgt agcacggtag gtcacctacg gactctcgat    1380 gggggggaggg ggcgagaccc acggacccccg acgaccccccg ccgtcgacgc ggaactagcg    1440
cggaccggtc gatgcttggg tgggaaaaag gacagggacg gccgatcccc ctcccgcgct    1500
tcgtccgcgt atcggcgtcc cggcgcggcg agcgtctgac ggtctgtctc tggcggtccc    1560
gcgtcgggtc gtggatccgt gtcggcagcc gcgctccgtg tggacgatcg gggcgtcctc    1620
gggctcatat agtcccaggg gccggcggga aggaggagca gcggaggccg ccggccccc    1680 gcccccccgg cgggccccacc ccgaacggaa ttccattatg cacgaccccg ccccgacgcc    1740
ggcacgccgg gggcccgtgg ccgcggcccg ttggtcgaac ccccggcccc gcccatccgc    1800
gccatctgcc atgggcgggg cgcgagggcg ggtgggtccg cgccccgccc cgcatggcat    1860
```

-continued

```
ctcattaccg cccgatccgg cggtttccgc ttccgttccg catgctaacg aggaacgggc   1920 aggggggcggg gcccgggccc cgacttcccg gttcggcggt aatgagatac gagccccgcg   1980
cgcccgttgg ccgtccccgg gccccccggt cccgcccgcc ggacgccggg accaacggga   2040
cggcgggcgg cccaagggcc gcccgccttg ccgcccccc  attggccggc gggcgggacc   2100
gccccaaggg ggcggggccg ccgggtaaaa gaagtgagaa cgcgaagcgt tcgcacttcg   2160
tcccaatata tatatattat tagggcgaag tgcgagcact ggcgccgtgc ccgactccgc   2220
gccggccccg ggggcgggcc cgggcggcgg ggggcgggtc tctccggcgc acataaaggc   2280
ccggcgcgac cgacgcccgc agacggcgcc ggccacgaac gacgggagcg gctgcggagc   2340
acgcggaccg ggagcgggag tcgcagaggg ccgtcggagc ggacggcgtc ggcatcgcga   2400 cgcccggct cgggatcggg atcgcatcgg aaagggacac gcggacgcgg ggggaaaga   2460 cccgcccacc ccacccacga aacacagggg acgcaccccg ggggcctccg acgacagaaa   2520
cccaccggtc cgccttttttt gcacgggtaa gcaccttggg tgggcggagg aggggggggac  2580 gcgggggcgg aggaggggggg acgcggggggc ggaggagggg ggacgcgggg gcggaggagg   2640
ggggacgcgg gggcggagga gggggacgcg ggggcggag gaggggctc acccgcgttc   2700 gtgccttccc gcaggaggaa cgtcctcgtc gaggcgaccg gcggcgaccg ttgcgtggac   2760
cgcttcctgc tcgtcggggg ggagcatgtc gtgggccctg gaaatggcgg acaccttcct   2820
ggacaccatg cgggttgggc ccaggacgta cgccgacgta cgcgatgaga tcaataaaag   2880
ggggcgtgag gaccgggagg cggccagaac cgccgtgcac gacccggagc gtcccctgct   2940
gcgctctccc gggctgctgc ccgaaatcgc ccccaacgca tccttgggtg tggcacatcg   3000
aagaaccggc gggaccgtga ccgacagtcc ccgtaatccg gtaacccgtt gagtcccggg   3060
tacgaccatc acccgagtct ctgggcggag ggtggttccc ccccgtggct ctcgagatga   3120
gccagaccca accccggcc  ccagttgggc cgggcgaccc agatgtttac ttaaaaggcg   3180
tgccgtccgc cggcatgcac cccagaggtg ttcacgcacc tcgaggacac ccgcgcatga   3240
tctccggacc cccgcaacgg ggtgataatg atcaagcggc ggggcaatgt ggagattcgg   3300
gtctactacg agtcggtgcg gacactacga tctcgaagcc atctgaagcc gtccgaccgc   3360
caacaatccc caggacaccg cgtgttcccc gggagccccg ggttccgcga ccaccccgag   3420
aacctaggga acccagagta ccgcgagctc ccagagaccc cagggtaccg cgtgacccca   3480
gggatccacg acaaccccgg tctcccaggg agccccggtc tccccgggag ccccggtctc   3540
cccgggagcc ccgaccccca cgcacccccc gcgaaccacg tacggctcgc gggtctgtat   3600
agcccgggca agtatgcccc cctggcgagc ccagacccct tctccccaca acatggagca   3660
tacgctcggg cccgcgtcgg gatccacacc gcggttcgcg tcccgcccac cggaagccca   3720
acccacacgc acttgcggca agacccgggc gatgagccaa cctcggatga ctcagggctc   3780
taccctctgg acgccccggg gcttgcgcac ctggtgatgt tgcccgcgga ccaccgggcc   3840
ttctttcgaa ccgtggtcga ggtgtctcgc atgtgcgctg caaacgtgcg cgatcccccg   3900
cccccggcta caggggccat gttgggccgc cacgcgcggc tggtccacac ccagtggctc   3960
cgggccaacc aagagacgtc gcccctgtgg ccctggcgga cggcggccat taactttatc   4020
accaccatgg ccccccgcgt ccaaacccac cgacacatgc acgacctgtt gatggcctgt   4080
gctttctggt gctgtctgac acacgcatcg acgtgttcgt acgcggggct gtactcgacc   4140
cactgcctgc atctgtttgg tgcgtttggg tgtggggacc cggccctaac cccacccctg   4200
```

```
tgctagggca atttgtaccc ttaataaatt ttacaaacag attttatcgc atcgtgtctt    4260
attgcggggg agaaaaccga tgtcggcata gaaaaccgcc atgattctaa gacgtccgaa    4320
cgcgagtggg tggggaacaa cccataccgg acagatgccg atgagccacc cgcacccttg    4380
ggtgcgggtg gtacgggtg gtttgttcat cctatggttc cgaccccaca aacagccccc    4440
agagtcggtt tgggtatggt tacattttct gtctggtggt cgggcttgtt tcttccttgc    4500
cactccccac ccacccactc cccacccacc cactccccac ccacccactc cccacccacc    4560
cactccccac ccacccactc cccacccacc cactccccac ccacccactc cccacccacc    4620
cactccccac ccacccactc cccacccacc caaaaatcaa ccgggagaca acattgccaa    4680
tcgaacccaa tttaatgtag ttaaaggctg ggtgcaaatt gcggggtgat ggggggggaag    4740 agagacgaca agaaggacgc gcgtgtcgat gcggtctttt agcggagcag ccacatcagg    4800
agcgccccaa atccgcccga cagaacggcc acgaggagac aggcgatcac catgccgacg    4860
cagcgggtgc gtctgcgtcg acgccttaat accgactgtt ggcggcccat gcgtacgagg    4920
aagtcgttgg ccgcctcgtc ttcgctttcc gagtagtagg cttcgaccga aactggcgag    4980
gccgtgggat aaagcggcac ggacatgtcg gatcgcgctg aggagttggg atcggagagc    5040
cgggacgtca tcgaggccgg aagaaagctc cgggtgggaa gttgcggtcg ctgtgactca    5100 cgattttaa tttgctgcgg ctaggcggac caccggccct ttatgcgcct cgggcaattg    5160
acgtcacata ccacgcaatc ccacacagga cggcccccag gccggaagcc ccccggagcc    5220
accgagcggc cagccaggcg acaaacaggg aggggggcgtc gacagcctgg agggccatcg    5280
gggagacaac ggccgtgtag cccggggggtc gcgggtgtgg cgagggcgcg gtcgacgtgg    5340 cgagggggcgg gcggtcatgt cgggggggtc cgcgttcgtc ggaaatcgcg attagctcgt    5400
ctccgacgtc cacctcgccg gcggtcgccc agttcggcga ccgacgtggg gcctcgggat    5460
ggggcgcctt accagaagac ggacgaatcg gaggcctggg agtaacggcg atcgggcctt    5520
ccggatccaa aggttgtgag ctggcggcga gattgatgcc catcgctacg ggggtataca    5580
gacggagccg ttggtgataa gatctcaaag ccggatccat ggtggaggg agagtcgggt    5640 ctctccgggg gggccagcca cgggacctgg tcgcgttctc cctcgctgtc cgagctccag    5700
tccgcgtaca gctcgctgtc ggccacgcga atgtacgtgg gccccttacc cgaggccctg    5760
cttttaaccg cccgccaggc acgcctgcgc caacaggtca tacacgccca caccgacaac    5820
cccagtgcag acagcagcag ggcggcccccc atcaccgccc ctaaccgcag ggcgccgtgg    5880 gttggggggcg cgtggggagg ggccccgacg tgcgggtggg tgggctcggc caaatccgcg    5940
ccgcgctgtg ggagggggctg ttccaccacc gcgttccggt actgcgccgc ggtgctgatg    6000
gtaatgtggc cccaggcgtg aatatggtcg ttgacgtaca ccacacacag atacaggccg    6060
gagtgttgtg gggacgcgtc ccggaactcc agattgacgg aggccgcctg ccacgccagc    6120
cccgggacgg gctccatgtg agcctcggcc gaacagcgcg gtgggggggtt tgttctggaa    6180 caccccgcgt agctgcggac ggccaggcga gacgtccacg tactcgcggc gcacggcgcg    6240
tcggccgggg acagacattc tgggagctgc gggtgataca gacacgattc gtatattcgc    6300
atctcggcac acgaggtcgg cacgtcgaac ctcaaccaga cgacgtccat ggagtaggtc    6360
tggtcgtcgt gggcgatggc atggatggag acgttcgtgc tgaacgtctc cccgggggaa    6420
aacaggatag cttccggagt ctccatacgc acggtcaccc cacgcacatg tgagacttcg    6480
ggggcgctgg gccaagacct cgggggggggcg ggggggaggcg ggagccgggg ggtcccgctg    6540
gcgggagtgc cggcgagact ttcgtcctcg ccctcgtcat tgtcatcctc gtcgtaatcg    6600
```

```
gctgrgggtcg ggggtggggt cggaactggg gccggttgca ccaccaggac caccgaggcc    6660
acttggcgag ccgggtcctt tatgtcgccc acggacaggg tatacaggcc gctgtccgtc    6720
tctcggaccc cgtgaataac cagactccgg ttaaccacgg ccgcgcgctc ctgccacacg    6780
aagtccgttc gtagaccccc ggtcgcagat ggggccgggg gggcgtacgc catcgccagc    6840
gggaccggag cgcgcatgca cgccgcatcc acgaccgtct cgggcacctg cttgggggc     6900 atcagcgaga cccacgacgg gtgtaagggg ccgcacccat ccaggggttc cacggcccat    6960
agtagtttct gggtcgggcc gcgccccgta ggccccggag ctggaagcaa cgaaacgtcc    7020
tcgccgacac tcacccgtct ccaggacgtt ttgggcgttc ccgccaagca cgatacaaca    7080
caaacaccga aagaaaccc caccaccgcc ccgcgatcca tgtcccgggg atagcagccg      7140
atcttcgggt aaaatgggag cccaacaaac agcaccgcac caacccgcca gaagaggcaa    7200
agtcaacaca acaacgcctt aaatgcgccg cgggccctct ccccggcttc ctgaactcct    7260
cccatccatt ctttgcttcc ttctttggtt tccggggagg ggggaaaga aatcgacata     7320 cacgatata ggtaaataat accggtttat tcccaactca gggactgcgg tcggttatgt     7380
ggtgctcccg gccagtggcc gtggacctat accaacaggg gaggcgttgg ggtgggtgtc    7440
gtggggtcca cgggggggcgt cggaagccca gccgccccag cgggctccga ctcttcggcg   7500
atggccgtca gggagggcat tggcgtgcgt gacgaccggc gccgggattt gggggggggtg  7560 ctcggatgcg atttgagctc ggctccgagg cgggccatgg ccgcttcgtt caccgcgcat    7620
gagatgcccg tgggcatctg ggggctgtaa atcgggcgac gggagcgtcg gtagcggcgt    7680
tgacatctgt gtataaagca aatacagctc cccagaaaca ccagggctat gatggacgcg    7740
gggatggcta tctggattat ctgggtcacc gttagcgcgt atcgcgagtc gcgggtcgct    7800
cgcgtggcat tagatgggggg ttcgtggttg accccgggag gttgtggttt tggatctccc   7860
gtggggaagg gcgtggtcga tgcttgggga gcggggatgg tggtcgaggg agcggggatg    7920
gtggtcgagg gggtggaggt ggtggtcgag ggggtggagg cctggttagg ggcggggttgg   7980 tatacgctcg ccggggccag acgcggggcc gaagacggaa gcagtttcgg gtcgcaggag    8040
ccataggccg agccgttgta cgccagagtc ccttcggcgg ctatggccat ccccaggaca    8100
aacaggctgg cgtttggcgc gtcaccgacc catacgcgta acacgtacac cccggcatag    8160
tcccgcgttg ccctctggac ccgcaaaagc ggctgttggg ccagattgag ctccaggtg     8220 ggatatgcgg ggctgtgagt gctgtcggtc gcgcgacaca gggcgaatgc cacgcggggg    8280
cgacgtgggc acgcggtcac cgtgacgaca tgcacgaccc gtgggcattt tgtgtcccatg   8340 gggtagtgcc acagctctac gcccccatcg tagtaggtgg tgtggggggac ctggtccccc   8400 acaaagcgaa gctccccgag aataagcagg tcttcctcca ctacgccgtc gggccccaag    8460
gccccggcgt ccacaaatga gtttgatacc agactgaccg tggggccacg gacaaccagg    8520
ctggtggcac agaccagag gcccacgagc caggccct gcaacgggcg gcacggcatc       8580
ccggaacggg acggttcgca aaaaaagctg tgggtgcgac aggcggaaca ggtgcgcgtc    8640
ccccgctacc gacttatcga ctgtccacct ttcccccctt ccagactcgc tttatatgga    8700
gttaaggtcc catcccaacc ccgcagacct gacccccccg cacccattaa gggggggtat    8760
ctagtaaaac aagggctggt gcgaggacgg ctggtcgtct tcccggatgt gggggaggcg    8820
tatgcgcttt ggggcttttt gagtgtgcgc gcgcatccag tacacaattc cgcaaatgac    8880
cagggctgcc aggagactgc cgcccaccgc gccggcgatc aggcccatgt tgttcggggt    8940
```

| | |
|---|---|
| ggccggggga tggtaaggcg tcgcggcgtc ctggatcgac ggtatgtgcc agtttggtgg | 9000 |
| gatttgcggc gccaccgtcc ccacgggtc ctccaagagg gccgaatcct cggggtcttc | 9060 |
| cggggcgagt tctggctgcg tggcgttggg ggtctcggac agctccgggg gcagcagggt | 9120 |
| gctcgtgtat ggggccttgg gcccgtgcca cccggcgatc ttcaagctgt atacggcgac | 9180 |
| ggtgcgctgg ttctcgggga tgaagcgggg cagcatcccg atgctgtcca ccgtcacccc | 9240 |
| ctgctggtag gctgggggg agaggcaggc tgacggggg atgcgcagcg ggagggcgta | 9300 |
| cttacaggag cccttggctc ggtgctccag gataaactgt gtaatctccg tccagtcgtt | 9360 |
| tatcttcacg agccgcaggt acgtgccggc ggtctcaaac gcggggggcgt gcatcaggaa | 9420 |
| ccccaggtta tcctcgctga cggcgctgaa gctgtcatag tagttccagc ggggctgcgt | 9480 |
| tcggatggga caggccccca gagacttgtt gtaggagcat tcggtgtact ccatgaccgt | 9540 |
| gatggggata gcacagttgc ctcccatccg aaaccaagcg atggtcaggt tgtagggttg | 9600 |
| tttccggacg tcttcggagg ccccgcggac aatctggggg gcctccgacg gtgcgtttag | 9660 |
| gagcacgctg cggcaggcgc gctccaacac ggcgtagtaa accgtgatcg ggaggctggg | 9720 |
| gggctggaac gggtccggta ggcccgcctg gatgtggtac acgcgccgga ccccggagg | 9780 |
| gtcggtcagc tggtccagga ccggaaggtc tttgccgcga aagcgattgg ggtcggccat | 9840 |
| cttgagagag gcatccacca aggcatattt gccgcggacc ccatggaggc ccactatgac | 9900 |
| gacaaacaaa atcacggccc ccaacctggc ggcagccccc cccataccgg aacgcaccac | 9960 |
| acaaaagaga ccttaaggat aactgatgat cggggtagtt ggtcgttcgc gctgaagctt | 10020 |
| atgaccgaac aactccctaa cccctgcttt ttaaagacag actttgttat accctcctc | 10080 |
| ctcgtaaaat ggcccctccc ccttggggga ttcgtcggtg tggtcggtat ggacgatagt | 10140 |
| gtcacacggc cgggctaccg cgatctttat tgggggccgg ggccacggat ttcctggtta | 10200 |
| gcccggtgtt gttgggtgcc ctccgcattc gcccccccat cccctgccg gacatggttt | 10260 |
| gggggggcgca ccggtgattt ataccatgcc agctggtggt gtcgggagtt tggacccgac | 10320 |
| atcacccacg cggagaaggg gggggggggg ggaaattata cgacaactgg gtccatgtag | 10380 |
| ggatggtaac gccccccaccc cgcggcacgta cgacgcagga gctcaagcag acatgccgcc | 10440 |
| cccaggacta cggcgcacag cccaccgact acgagggga cggcaaagcc cccaggggg | 10500 |
| ctggggtgag gggacactgg ggcgtgcgtt aaggggtccg ttgtgttggc cgcaggtccc | 10560 |
| cgatgggtgg cggcaagaac agcccccacg aggcttccca aaagccccag atgccagact | 10620 |
| gcgcgcagag acatcgcgac acacagaacg ccaagtcgtg tgctgtttct ccggatagcc | 10680 |
| aggcctggct cagacgtccg ttggccgttt cgggtgggtt ctgaggcccg gaagtcgcgc | 10740 |
| atgcttcatg ggtcccgggc atgtatttaa ctgcaccccg tccaatgacc gcccgcgtc | 10800 |
| cgccacaccc caaaaacacc cagagatgca tatcaactag ataccaccgc ctttattgtt | 10860 |
| cttgctttcc gcatgtgggc tctcccatc ccccgcccca tacccctaccc gcgttcggac | 10920 |
| ggcaggcaca cgtaacgcac gctagggtgt gtgcgtcgcc cgcgtctgga ccaaccgcca | 10980 |
| cacaggtgtg tcgccatcgc accaatacac aaaaacgata aggtgtggat gacggtgctg | 11040 |
| acgacgaaga gggtgtccag ggcggggag gcagtgagga acgagaacag cggggtatgt | 11100 |
| tgaggcgtcg gaaccaaggg tcgtccctt gaggtgagtc gggtcgtggg gcgagttgcc | 11160 |
| agcggcccga taatggtggg gggtgtcttc gggcgactgg tctcggggcg cgcggggag | 11220 |
| ttgttgggat cggggatgg gactacggga cggttgggtt tgtccttctc gacgtcctca | 11280 |
| gccaacggga aggctgggcc cggggactgg ggtagggtgt cacgggtccc atctccccc | 11340 |

```
tcaagatgtt cgccgtcccc ggcccctcc tcctcttcct cctcctccag tccaatactt    11400
ggcatggggg gtgtgtggtc gggcgtggta aggctgatgg cggtgggaga gtcggtggtg    11460
ccggtctggg tcatgttggg ggcttcatgc gagggacgac cggtggtctg gagttggggt    11520
tgggtggtgg aggagacgtt ggtgggaacc cccgatacac cgacaagaac caaaaggaat    11580
gggataatgg gaacaacggc acgcatggcg ccctgcgaca tgatgccaaa acaccacag     11640 acgcggatcg gggtcttttt gtgccaaccc gcaaacagca ccgcccccag ggggcggtca    11700
tttctgttga aacagcggca aacaaagcag ctctgcggcg ctgggcgaa gcgcgccgtc     11760 gaaggtgagg gctttgcaaa ccagatattc gacgtctatg tccatcttgt agtagcgggt    11820
ccaggccggt cggtgtacg gcgggcgatt gttcccggcc gcgcgggagc ggtagcgcga     11880
ggtgaggcgc gattctggat gcggggaaaa ctcgtcaacg tggacctggg cctgtcggat    11940
gatgcgggtg atctgactgt cgcacgggcc ccttttgggg ccgcgggggg ccgagaacaa    12000
ggacgcgttg tggacggcag tctcgaagat caccagaccg cgctccaaa tgtcgacggt     12060 cgtggtatac ggatccccgg ccaggacctc ggggcgttg gtgtcgatgg ttccggcgat     12120
tccgtagggg aaggggcttg atcgggaacc ctgcacgaag cacgcggcgc caaagtcccc    12180
caggcaaatg tcctcggggg tgttaataaa aatatttcg gtcttaatgt cgcggtggat     12240
aatgccctgg cggtgaatgt agtcaacggc gcttaggagc tgccgggaga ccgctgcgat    12300
ctgcgggcgt cccagtgggt tcaggcgcct actcagatag gtatacaggt cggcctggta    12360
cttggggagg accagacacg tgaccccgga cgacacatgc aggtccagga ggggcaggat    12420
cgccgggtgg tccagtcgcc tcagcagtcg cgcctcgtgg ctcgtgctcg tgtaccaccc    12480
cgccttcacg attacccgtt gggggtaatc tggatggctg ctgtcaaaga cacacccctc    12540
cgatcctggg gtgagcgctc cgtggatcgt aaagcccatg ccagtcacca gcttggccat    12600
ggtcgagggg ggcttgccgc cgcggctgat ggctcgagcc gcctccctgt ccatggcgtc    12660
cagctcttcc gcggtaaatc ccgtggcccc aatctcatcc cggctgcgtc gtcgtatacc    12720 gggggagat gcgccacacg ggggagggat gtggtcgttg gccccgataa ggggaccggt    12780
cgcgtccccg ggcagaaaaa gctcctctgc gtattcctcc ggataggcca cgtcgtccgg    12840
ggcgtcctcg tcgacatcgt ccgcggcatc cgcgctgggg tcgtcctcta tggggtagtc    12900
ctggtttccg tacatctggg caaggatctc ctgcagatga cacaggcgct cggcctcgct    12960
gggtggtgtg gtgtgggaag gtttgggggt ctccgggggc ggggagtcca ggcacgcgtc    13020
ctcggctggg gtataaaagg ggccatgagg aaacacccgg gacggctttg tctccggcgg    13080
gacggcctcc tccttcctcc tgccctgtcc cccgtaaacg cgacaaaact tacgacaggc    13140
cattcgccgc accgtgagtg ccaaccaacg agcaccccga acgacgggcc ccggggtttt    13200
aaggagcggc agtttgacga cccacccct gacctacccc cccgtaaatc accctcccct    13260 ccccccggacg cctccgctgc cggtcgctcc aagggccccc ccgggaaggc gggtctgtgg    13320
accgtagggc ccttaaattt ttagagcagc cccgcgtcg gcctgtctcc ccgccgtgcg    13380
tggccttaca aatctgcaag tgccccaaat cggacacggg cctgtaatat accaacatgg    13440
gcgttgttgt cgtcaacgta atgaccctcc ttgaccagaa caacgccctg ccccggactt    13500
ccgtcgacgc aagcccggcc ctgtggagct tcctgcttag gcagtgccgc attttggcat    13560 cagaaccccct gggtacccg gtcgtcgttc gtccggccaa ccttcgacgg ttggccgagc    13620
cgctgatgga cttacccaaa cccacccgcc cgatcgtgcg cactaggtcc tgtcgctgcc    13680
```

```
ccccaaacac caccacgggc ctgtttgcgg aggacagccc cttggagagc accgaggtcg   13740
tggacgccgt ggcgtgcttc cgactgctgc accgagacca acccagcccc cctcgcctct   13800
accacttgtg ggtggtaggc gcggcggatc tgtgtgtgcc gtttctcgaa tacgcccaaa   13860
aaatccggct cggggtaaga tttatcgcca tcaagacccc agacgcgtgg gtgggagaac   13920
cgtgggccgt gccgactcgg ttttttgcccg agtggaccgt ggcgtggacc ccgttccccg   13980
cggcccccaa ccaccccctg gagaccctgc tcagccggta cgaataccag tacggcgtgg   14040
tactgcccgg gacaaacgga cgggagcgcg attgtatgcg ctggctgcgg tccctgattg   14100
ctctgcacaa accccaccca gctacccccag gccccccttac gacgtcccat ccggtgcggc   14160
gtccgtgttg tgcgtgtatg ggcatgcccg aggtcccaga cgagcaaccc acatcgccgg   14220
gccgtggtcc gcaagaaact gaccctctga tcgccgttcg cggcgaacgg ccccgacttc   14280
ctcacatctg ctatccggtt accacccttt agccccccggt gccaataaac cccaaacac   14340 ccccatgtc cgcgtggtct gtttctctcc gcccttcccg ccattaagac gctgggacaa   14400
acgctttgat tttggtcttt tattttgggg acatacaagg gggtcggggc gaccggactc   14460
acggccggag aaacgtgtcg ctgcacggat aggggcaggc ggtggagaag cgcattttcc   14520
ggcagccgtc cagacacttg cggtcttctg cggcgcgacc cgcccagaa tcggatgggc   14580 ccgggcgttc cacggagctg gtatcggcca cgaccgcaga cagccagggc tgggagccct   14640 cctgggggt ccagtcaaac tccccaaact catcctccag acgcacagcg agggacccgc   14700
ggggttctgg ggtttccagc gtaacggggg aggggggcatc ctccgtgtcg gactgggacg   14760
cgagcgtgtg gtccgaaccg gcggcctcca gatcggtggc atcggagatt tcatcatcgc   14820
ttgtcgcgct gagatgaatc tcgagattac taagatcaca ctccgggccg taccgtctgg   14880
tctccaaaca aggaagcttg cacacgggtt ccgcggtggc gtcgaatcga gcctccacct   14940
cccgtatggt gttgcgcagg tgcatgcccc aggttccgcc ggacacctgc agcaaacggc   15000
accacgtgcg cggggccaga cgggctcggc agtatcccat caggtaacag tcgcgtatca   15060
ggtggcgcag gcggttggca ctgccgtggg ggtcccgggc gacccgcagg acccgaaaca   15120
gctgattgat acactggcgc atgtagccca ggtcgggggt ccatcgtgcg ctgctccgcc   15180
tctgggcctg gcgcaccgag cgccgtagca ttgcatttgg gcttggggcc gacggggtgg   15240
gggcccgggg ctgcgtttcc cgggtagacc ggacccgccc catcttagga aaataacccc   15300
catcccgccg atcgggagag ctcgtgagcc gcaggtttac ccgggcccgc ttgggtcgtg   15360
ggggaatgtc gtcataagac cagtcggacg tgtcgtcggg gtcgtccgac accgacgcat   15420
ccgtttccgt ccccgtggtg gattccgccg acatgtccag aaaaaaccgc cccccaagcc   15480 tccgggggc cctacggcca ccgatgcggg gggcttcatc ctggtcccca gactcggtcg   15540
aatccgatgc tgtctcggat tcgacctcag actccaaggc tgtatcggat tctacctcag   15600
actccgatga gaggggcgg gaagggcgct tgcgcttgcg cgtgcccagg ggcgggatc   15660 ggagagcggg acgccgcgct tttacacaag gcgcaaaagc gcctggggaa atgtcggcca   15720
tccagaaaac gtcccggagg accacagtgg cttccccccg cccgacgagc aggaagcggt   15780
ccacgcaacg gtcgccgccg gtcgcctcga cgaggacgtt cctcctgcgg gaaggcacga   15840
acgcgggtga gccccctcct ccgcccccgc gtccccccte ctccgccccc gcgtccccce   15900 tcctccgccc ccgcgtcccc cctctccgc cccgcgtcc ccctcctcc gccccgcgt   15960 cccccctcc tccgcccacc caaggtgctt acccgtgcaa aaaaggcgga ccggtggtt   16020 tctgtcgtcg gaggccccg gggtgcgtcc cctgtgtttc gtgggtgggg tgggcgggtc   16080
```

```
tttcccccc cgtccgcgt gtcccttttcc gatgcgatcc cgatcccgag ccggggcgtc    16140
gcgatgccga cgccgtccgc tccgacggcc ctctgcgact cccgctcccg gtccgcgtgc    16200
tccgcagccg ctcccgtcgt tcgtggccgg cgccgtctgc gggcgtcggt cgcgccgggc    16260
ctttatgtgc gccggagaga cccgcccccc gccgccgggg cccgccccg gggccggcgc    16320
ggagtcgggc acggcgccag tgctcgcact tcgccctaat aatatatata tattgggacg    16380
aagtgcgaac gcttcgcgtt ctcacttctt ttacccggcg gccccgcccc cttggggcg    16440
tcccgcccgc cggccaatgg ggggcggca aggcgggcgg ccttgggcc gcccgccgtc    16500
ccgttggtcc cggcgtccgg cgggcgggac cgggggggccc gggacggcc aacgggcgcg    16560
cggggctcgt atctcattac cgccgaaccg ggaagtcggg gcccgggccc cgccccctgc    16620
ccgttcctcg ttagcatgcg gaacggaagc ggaaaccgcc ggatcgggcg gtaatgagat    16680
gccatgcggg gcgggcgcg gacccacccg ccctcgcgcc ccgcccatgg cagatggcgc    16740
ggatgggcgg ggccggggggt tcgaccaacg ggccgcggcc acgggccccc ggcgtgccgg    16800
cgtcggggcg gggtcgtgca taatggaatt ccgttcgggg tgggcccgcc ggggggggcgg    16860
ggggccggcg gcctccgctg ctcctccttc ccgccggccc ctgggactat atgagcccga    16920
ggacgccccg atcgtccaca cggagcgcgg ctgccgacac ggatccacga cccgacgcgg    16980
gaccgccaga gacagaccgt cagacgctcg ccgcgccggg acgccgatac gcggacgaag    17040
cgcgggaggg ggatcggccg tccctgtcct ttttcccacc caagcatcga ccggtccgcg    17100
ctagttccgc gtcgacggcg ggggtcgtcg gggtccgtgg gtctcgcccc ctcccccat    17160
cgagagtccg taggtgacct accgtgctac gtccgccgtc gcagccgtat ccccggagga    17220
tcgccccgca tcggcgatgg cgtcggagaa caagcccaaa atcccttaac gtgagtaacg    17280
ggccgggacg gggcggggcg cttgtgagac ccgaagacgc aataaacggc aacaacctga    17340
ttaagttttg cagtagcgtt gtttattcga gggggcgggag ggggcgaggg gcgggaggggg    17400
gcgaggggcg ggaggggggcg aggggcggga gggggcgagg ggcgggaggg ggcgaggggc    17460
gggaggggggc gaggggcggg aggggcgag gggcgggagg gggcgagggg cgggaggggg    17520
cgaggggcgg gaggggggcga ggggcgggag gggcgaggg gcgggagggg gcgaggggcg    17580
ggaggggggcg aggggcggga ggggcgagg ggcgggaggg ggcgaggggc gggaggggggc    17640
gaggggcggg aggggcgag gggcgggagg gggcgagggg cgggaggggg cgaggggcgg    17700
tggtggtgcg cgggcgcccc cggagggttt ggatctctga cctgagattg gcggcactga    17760
ggtagagatg cccgaacccc cccgaggag cgcgggacgc ggccggggag ggctggggcc    17820
ggggagggct ggggccgggg agggctgggg ccggggaggg ctgggccggg ggagggctgg    17880
ggccggggag ggctggggcc ggggaggggct ggggccgggg agggctgggg ctggggaggg    17940
gcggtggtgt gtagcaggag cggtgtgttg cgccggggta cgtctggagg agcggggaggt    18000
gcgcggtgac gtgtggatga ggaacaggag ttgttgcgcg gtgagttgtc gctgtgagtt    18060
gtgttgttgg gcaggtgtgg tggatgacgt gacgtgtgac gtgcggagtg cgccgtgctc    18120
tgttggtttc acctgtggca gcccgggccc cccgcgggcg cgcgcgcgcg caaaaaaggc    18180
gggcggcggt ccggcggcg tgcgcgcgcg cggcgggcgt ggggggcggg gccgcggag    18240
cggggggagg agcggggga ggagcgggggg gaggagcggg gggaggagcg ggggggaggag    18300
cggggggagg agcggggga ggagcgggggg gaggagcggg gggaggagcg ggggggaggag    18360
cggggggagg agcggggga ggagcgggggg gaggagcggg gggaggagcg ggggggaggag    18420
```

```
cggggggagg agcgggggga ggagcggggg gaggagcggc cagaccccga aaacgggccc    18480
cccccaaaac acaccccccg ggggtcgcgc gcggcccttt aaagcggcgg cggcgggcag    18540
cccgggcccc ccgcggccga gactagcgag ttagacaggc aagcactact cgcctctgca    18600
cgcacatgct tgcctgtcaa actctaccac cccggcacgc tctctgtctc catggcccgc    18660
cgccgccgcc atcgcggccc ccgccgcccc cggccgcccg ggcccacggg cgccgtccca    18720
accgcacagt cccaggtaac ctcacgttaa gggattttgg agttgaaata tgtttactaa    18780
taagacttta tgggtagggg catctgggaa tctgcaaaat ccatctcaga tccttccgta    18840
tttacagccg ttctgcgtgt ctgttcttgc gtgtggctgg gggcttatat gtggggtccc    18900
gggggcggga tggggtttag cggcggggg cggcgcgccg gacggggcgc tggagataac     18960
ggcccccggg gaacggggga ccgggctgg gtatcccgag gtgggtgggt gggcggcggt     19020
ggccgggccg ggccgggccg ggccgggccg ggtgggcggg gtttggaaaa acgaggagga    19080
ggaggagaag gcggggggg gggagacggg gggaaagcaa ggacacggcc cgggggggtgg    19140 gagcgcgggc cgggccgctc gtaagagccg cgacccggcc gccggggagc gttgtcgccg    19200
tcggtctgcc ggccccgtc cctccctttt ttgaccaacc agcgcccccc ccccctcacc     19260
accattccta ctaccaccac caccaccacc accgacacct cccgcgcacc cccgcccaca    19320 tccccccca acccgcacca ccagcacggg ttgggggtag cagggatca aaggggggca     19380 aagccggcgg ggcggttcgg gggggggggg gggggcggg agaccaagta ggcccgccca    19440
tccgcggccc ctcccggcag ccacgccccc agcgtcgggt gtcacgggga aagagcagag    19500
gggagagggg agaggggggg agaggggaga gggggggaga gggagagggg ggggagagggg  19560 gagaggggg gagaggggag aggggggag aggggagagg ggggagagg ggagaggggg     19620 ggagagggga gagggggga gagggagag gggggggaga gggagagggg gggagagggg     19680
agccagttag attgcatgtg atcgttggga atgaccccccg gggttataaa aggcgcgtcc   19740
cgtggacgcg gccctcggtt gggcgacgca tgccagccca acaaaatccg ccggggtgcc    19800
agtcccattc ccgaaggcgt agcccgttaa cttggctggc ttggatgggg agtagggcct    19860
tttccattac cccaaggacc tagcgcgcgg gagtcgtggc tttggggcgc atccatggct    19920
tcggaggcgg cgcaacccga cgcgggttta tggagcgcgg ggaacgcgtt tgctgatccc    19980
ccgcccccct acgatagctt gtctggtagg aacgagggc cgtttgtcgt tattgatctg     20040
gacaccccca cggacccacc tccaccgtac tctgctgggc ccctgttgtc cgtgccaatt    20100
ccgccaacct cctccggaga gggcgaggcg tcggagcggg gccgctcacg ccaagccgcc    20160
cagcgagccg ctcggcgcgc ccggcgccgc gccgaacgac gtgcgcagcg ccggagtttt    20220
ggccctggcg ggttattggc aaccccctg tttcttccgg aaaccaggct tgtgccccca     20280
cccgacatca caagggacct cttgtcgggc ctcccgacgt acgccgaggc tatgtcggac    20340 cacccccaa cctatgccac tgtcgtggcc gttcgttcga ccgaacagcc gtccggggct    20400
ttggcgcccg acgaccagcg acgaacgcaa aactcgggcg cgtggcggcc tcctagggtc    20460
aattcgcgcg agctgtacag ggcccaacgc gcggcgcgcg gctcgtctga tcatgcccca    20520
taccggcgac agggctgttg tggcgtggt tggcgccatg ctgtatttgg ggtggtcgcg     20580
attgtggtgg tcattattct ggtattcctg tggcggtaag cgcccctgtg agttaataaa    20640
taaaagtatc acggtccata ctggcctgtc gcgttgtctc tgagggcttt gggtccacaa    20700
actcacacca cgcctggttt ggttgggtta cggctctta ttttttttggg gggggttaca    20760 cacattcatg gggggttgg agatcacgcc ttaattttaa tcttgacgcg tcgatgctct     20820
```

```
gccgcgcggg cggccatgcc gctggagctg atggagcgca ggtgctgtag ggccgcggag   20880
gcccccatcc agcatgtttt tgagaacgga taccgacagt ggcagtggta cacgatcccg   20940
tttatcgtgt actctcccgc cgaggacgcg ccggacccag agacgtcctt aatcgtcccg   21000
acgctaaacg gccgcgcaca ccgcagccgc accccgcgct tatcctccag ttcgcgtagg   21060
accggcgggt ggttaaccag gtccgcaaag ttgcggagct cggtaatcag cggaggggtg   21120
tggtgggtgt ccttgtatac cgcaaagaaa agcagtggga ttgtgccgct ggtctcacag   21180
gaggcgcgga ccaggtaact ccgcacggcc acgcaagcgg agtccgtttt gctggtgtgc   21240
atggccgttt cggcctgcca ggtggcgttg aggcagtaag gggggggccac gtgggttatg   21300 tccgggnccc gtaagaacag gttggtgagg ggggtcgctg tcatagtgca aaggggggga   21360
tgcgcccggg cgggaagctc ctaagggcac tatgacaccg gccttggaac ggggacggat   21420
ttatacgttg ggttagttcc ctccgcccac ccaggccgta cgccgggccc accccgcca   21480 tctgccgtga cccacgcccc gccggccatg agcaaagaag gacaaacgga ggggcgattt   21540
gtttgaaatg ttttgttttt attgtaccta aaacagggag ttgcaataaa aatatttgcc   21600
gtgcacgtac ggggggggcga cgatgtgact ggccgtcaac tcgcagacac gactcgaaca   21660
ctcctggcgg tgcgtgtcta ggatttcgat caggcccgcc atgcaggccc ggggaggta   21720 gaaatgcatc ttctctccga ccccgacacc aagggtcgcg tagtcgatct ccgcgacgcc   21780
acgctcgacg cggttggcga gcctggccag aatgacaaac acgaaggatg caatgtcctt   21840
aatgtccgcc agacgccgcc gcgaacacag ttcgtccagg ccgcacaggc ctcgcgcctt   21900
caggtagcac tggagaaagg gccgcaggcg cgtggcgagg ttatccagca cagccgcggc   21960
cgtcccgata atgggggtcct ggggcgcag cggcaggttg tggtggatgc acatcttgca   22020
ccacgccagc gtctcgtcgg cggaggccag cgcctcgatg aaatttttctt ggcgcagcac   22080 gcagtcgcgc atggccttgg cggtcgatgc ggcccgagga ttgccggcaa aagtgcgata   22140
gaggctcggg ccgtgggcga ccaaggtttc ccaggagacc cgtctggtct cggcgtcaaa   22200
gggccctcct tggcccgcca gcaccggggc ccagggcta ttcgcggcgg gaaacggctg   22260 cccccccaaag gggtcgtgca tgacctgtgc gctgcgcca aagctctcgc tgatgcggtc   22320
gaccgccgcg cgctcggaga tggagcgcag gaccaaccgc gtggtggcgt cgatggtgtc   22380
ggcggcgggc gcctttcgct ccggggccgg ggcgcggggg tccgcgggcg ggggggcaat   22440
cgccagcgtc attagcgggg ggggtgcttg gcgcacgccc cgtgtccgct ggcctccggg   22500
tgggtcgggc tgctcactgc cgcgccacgc ctcgccatgg ggggcgccgg ggccgtccgt   22560 ccacccccgcc ccggggcggg gtccccagg gttgcgattg gttctggggg cacgccggcg   22620
ggggtccgac aaaccatcgg cagccccggg accaccgcga ccccgacccc tgcgacgccc   22680
acggcgtccg ccgcgggcag gctgggcttt ggtcggtggg ggttggaggc gggccacctt   22740
gcccccgtgc tgctcggggg agcaagacgg tcgccgggcc ccgaggcgcg accacacact   22800
gtggggcgct ggttgaggat cgttgggcc ctgccgctcc gtcggacgag gcgtctgggt   22860
gctgggtacg ccggggtctt ctggacgaga cgggcggacc gccgggcgag cggcgtcgag   22920
tatcggctcc ggtccgtcct ctccgtgggg gtcttccatg tcctcgtccg acgaggaaca   22980
ctccccgctg ctgtccgatt ccaggtcgtc gcggcggctc tccgccggct cggggggggtc   23040 ctcgtccaga tcgctgtcgg agaggtccag gccgaggtca attagcatat caatgtcagt   23100
cgccatgacc gggctgtcgg ctgccgtcgg ggctggggtg tcggatatgg cctctggtgg   23160
```

```
tggcgcaccg gtagcgagcg accgggcccg aatcggggag aggcaccgaa gcgtgaccgt    23220
ggttggaaca cggctgcaca ccaccaccgg ccgggtggtg gatgtcctta tacccgtggt    23280
gccggggccg gctctcccaa accccteete gttccgcccc ccgggcgggg ccccgcccc     23340 acctccggca cagacaagga ccaatcagac accataagta cgtggcatgt atttaattag    23400
catatcacat accccgttcc gcttccgcgg ggacccgggc gggggtggat acgctggctg    23460
ggttggtctt ggtaacggga cggccaattg ggacccatgg gcggggtcgt tgggatccag    23520
gctacacgtg gcctcggggg accgattttc atttgcatat gacgcgtcgg gtgggtgggc    23580
cccaagacag gacagtttcc aatttgcata tgccgttacg gtttccgccg gcctggatgt    23640
gacgtcatac atcaaacagg cgcctctgga tctcctgctc gtagtgaagc gccacgagca    23700
ccacccgggc caccacggcg atataacaca atcgcactgc gatgcccgag aggatgatgg    23760
aacagcagcg cccgcagacg cccgacagcc ccttggatcg ccccgggggcg gcggccttgt   23820 ctgcgttctt gggggccggg ccccgccgca gaatacaata cagctctgtc aggccgatgg    23880
tggagacaaa acaccaggtg gtgatggtca gaaacagggg gtatgtgatc gcacatgccc    23940
cccgggatat gaaagcggtg ccgacgatga gacccacggc cacaaagcgt agcatcaact    24000
cgcagcctac gatgaccccg atggcggggc ggtggtacaa gaaggtgacc gggtccgtct    24060
caaacaactg aaccaggttt tgccgctgga ccgacagctc gcagagcagg cgggtaattt    24120
tcgtgtaggg gtactgcagg aacacgctcg atacgatgcg gcctgcgtag ttcaagaggt    24180
aggtggccgg ggccaccatc ttgtgggcgg gactcacgac gccaaacata catcggcgtt    24240
ggtggagggc gacgaacgcc agatacagga accaccctac gaccaccaga cgcacccgtg    24300
tgtaccatag ggtctccaga cagttaactg cctcgtggac gttcatgatc cgacgattca    24360
tggcgtcagt tgggacctgg aagggcacga ccctacccgc gataagattg gcgtagcaga    24420
tatgggcgtg gttgcgccag ccccgttgg ggggtgcgt cggggccccc agaaacaata     24480
gggtctggtt cattttcatc cacacgaggg cggtgtcgtt ttggtgccg gtggggcgta     24540 ccgcgtaaat acatcggtgc agcggactgg caccgaagac ggtgtaccac acgagcacga    24600
ggccgtacgc cgttatcaag acgacggttg agaggtgctg cagggaacgg acggcgagca    24660
tggcgtgccg gcgtcaatgg taaacagcgt gtgcaggcgg ttgctgtcgc atttggcggc    24720
aaagcactgc tgacacaagg acacgcacag gcggttgttg gccccgacgc tcagcgcgac    24780
gaatgtccgc gccgtggcgc gactcgcccg gccgtgctta aagcgcagac acgacaggct    24840
ttgctgcagg gtaccgcgaa cggggactag ctgtaggagg acccagtcgt ccttactgac    24900
ggcccgccgg acggatacgg cctgatattc gccggcgtgt tcgggaaagt gggtttcgat    24960
gcacgcgact atccgcccca gcagttccga tgcgaacccc tcgacggtcc ccccgcatc     25020 cggctgtacg ttgtaccgac ccaggacctc cgtcagggtc tcgcgtcgcc caaagtgttc    25080
cagcgcgttg cgggacgcct tcctttcaaa gaagctcaca tagtccccac ccaggctgtg    25140
caggacacgg atctcccggg gggaagcgag ataggtgggc ggggcgtgaa aatggaagcg    25200
ccgcgggtcg gcgtgcgcgg cgacaaacgc cggaacgtct ttgcaggcgg gggggatcac    25260
aaacactggc agcagccttc cgcacgcagg ccgtcggggg gcgattttgg caaaatacgg    25320
caagcgcagg ctgtggccgt gggcgtacac ccccgtatcg atcaacagga agtttttttac   25380 gtagctcccg atggcctcca caaaatctcg gtccaacagc accgcctgct ggatgacccg    25440
tgccaccccc cgcatcgtta gagaaccgtg gacgacgtac ggggcgggga cgggcatgca    25500
cacccgcagt ccgatcttgt cggtgcagga acacacgggc gaatccgttt cgcgaggttc    25560
```

```
cgccgtgggg ccgacttcgt ggcacaggtc aaagtaggca acctcgtcgt ccggggggatc   25620 gtgggatgtg tccatggcgc ccgggtcctc cgcccactcc tcatcaccgg cgtcgtcgta   25680
gcagggaaac cagtccccgt cgtcgtcgtt gccgagtccg ctgccggaac ccacggacgc   25740
cgggccgggc cgacatgcgc ttttgaaaaa ataacaggga tatgcgtcgg ggtccacgcg   25800
ggccgcggga acaggagct  gaaccgcagc cagagccccg cgcctaaagt ggcccagggc   25860
ctcgtggagc cggcgaaagg ggacgggctc cttcagggcg atgtcgagat ccaggatgat   25920
gtttgtgatt gccagcgcgc cgttgaatat ctcgttgcga ttcacgtaca tctgcccccc   25980
ggcatccagg ccgccagggg gcatcacggg gccctgggcg cggatgcgat ccgtgagccg   26040
cctgcccagc gcgccgtggt cggggtgcgc cgccgcttcg gcggacacga ccgcttcggc   26100
caggcgagcg tcccgcgtta tgcgggccca gtcgtcccag gccagcgcgg caaatgcctg   26160
tcccgtgggg accatggata tccggtagac gggcagggga gtctgcaccg ccgcattacg   26220
gataagcgcc gcgatcgccg ggggtgtggg gccctgctgt tccgtggcgg ccagtctcag   26280
gaggcgcttg acaattccgc aggtctgtgg gggcggcgtg ccgcccgccg tgtcctcccc   26340
gggactgggg ggcgcaaacg cgggccaccc gcggggggacc aggagctttt cggcgtccgc   26400
caaacgcccc atcattttgg tggcggagtc cacggccccg caatacgcgg gggcgggcgt   26460
cagggccccg ggcgcgtacg tgcgagcgcg caggtaggcc ttggccgtat cgccatccag   26520
gacggtctcc cgggggggtca cgttgtgttt gacgtactcc ccgatattca gttgggcgcg   26580
cacgtgacaa aaaaattgtt ccacggcctc cctgcccagg ggcgagggct gctccgtgct   26640
ggccgcgggg ttggggtcgt gggtcgtcac ggcccgaaga tgcgtggcta ggcgcggggg   26700
gctgaaacac tcaaaatggg ccaggtagat gtacgtaatg aattcacggt cggacacgcg   26760
caggcaactg cgatcgtggg ttatgaactt ctccagcgca ctggtctcgc ggacgtcggc   26820
cgcaatacgg cgctccacgt aaagcggaaa cccggccgcc gcggcccgc  gggcgtactg   26880 gctcgtgcaa cagaaccgcg tgatggcggc aaacgaggtc agggacgcag cgctgacggt   26940
gtcggggcgg ggggcgtggg gaatcgcgta ggtggcgcag atgtccttga tggcctgcag   27000
gtcgtacgtg gcccccgcgc ccccccagacg ctgggcctga agcaggtagt accgagtggt   27060
gagcaccagg cttttttcgt ccggcccgaa tttgctaaga aaccagaagg gactctgcgc   27120
gcttccataa tacgccctgc ggtacgcggc aagcacgcgc acctcgtggt ggacgtatag   27180
cgtggtaagg ccgcgttgtc ccagggacgt gcgccccacg agcgagcgta gggacgcgcc   27240
ctgatcatac tgccgccgcg gcggcgtcgcg tccggtgcgg gggctggcgt tgttgatggc   27300
cacggtgaga gccaggatca tgttcgcatg cagcgcgaac gtggcctccg cgtccagggt   27360
ggcggcgatg tggtccggtt gtagcggggt cccgtgcgcc agggcgtcct gtagcgcggc   27420
gacgtcgtcc gctcgctcga agcgacagac gaacatgggt cgggttcgcc cgcgggcctg   27480
gtgggtccca cccacttccg tccccaataa acaaaaggtt actcggaagg agtcgccatt   27540
tagcccgccc gacgcttggt agagcgcccg actctcttcg aacctgtctt gctccgtggg   27600
cccgtcggca cggccatcgt gcgtgtatgc gtcgtagctg aatatataaa ccggctcggc   27660
ccccagtaga gagtttgtga ggagggcgat cgaagaggta ataacgcacc cgtcggtcgc   27720
ataaagcgcg gtcacctcca cgggagtccc ggccgcccgc ctctcccgc  ggttcccgtc   27780 ttcctgcccc attgcgtccg cgcgcccaag ggccagtacc cgcccgcgat ggcttctctt   27840
ctcggggcta tatgtggctg gggagcgcgc cccgaggaac aatatgagat gatccgcgcg   27900
```

```
gccgttccgc cctcggaggc ggagccgcgg ctgcaggagg ccctggcggt cgttaacgcg    27960
ctacttcccg cccccatcac gctcgatgac gccctgggt ccctggacga cacccgacgc    28020
ctcgtgaagg cccgcgcctt ggcccgcacg taccacgcct gcatggtgaa cctagaacga    28080
ctggcgcgcc accaccccgg gctcgaggcc cccacgatcg acggggccgt ggcggcccat    28140
caggacaaga tgcggcgcct ggcggacacg tgtatggcca ccatcctgca gatgtacatg    28200
tccgtggggg cggctgacaa gtccgcggat gtgctcgtct cccaggctat tcggagcatg    28260
gccgagagtg acgtggtcat ggaggatgtg gccatcgccg aacgggccct tggcctctcc    28320
gccttcgggg ttgccggggg aacccggtcg gggggattg gggtgaccga ggcgccctcc    28380
ttggggcacc cccacacgcc gcccccggag gttacgctgg cgcctgccgc ccgaaacggc    28440
gacgccctcc cggaccccaa accggaatcg tgtcccgcg tgtccgttcc cagacctaca    28500
gcctccccaa ccgcacctcg ccctggccca tctcgagcag ctccgtgtgt tttgggtcaa    28560
taaatgcgtg ttttcatcca acccgtgtgt tttgtgtttg tgggatggag gggcgggtgt    28620
gatagaccca caggcatcca acataaacaa ctacacacg gaaagatgcg atacaaacgt    28680
tttttattgc ccggaacgaa cccaaagctg tgggctaaat accggtagag ccaaaacccc    28740
cggtcccgcg ctcgctcggg gggcctccg cgtcaaactc gttcgtaaac accaggagcg    28800
gcgggttcct gggttcggcg gttgagtccg gaacacccct ggggtagttt cgaagcgctt    28860
tggtcccgtg aaagttgtcc gggggatcc aaggaagagc gtccgccccc gcaaccagga    28920
gctgggcgac cttggcgccg cctcgaggg tcacaggaac ccccgtaagg ttgtaaacaa    28980
caaacgcaca tacgtgcccg gggagccagc gcgtaggaac gaccaggagg ccgcgggcgt    29040
tgagcgacga ccgccccaac acatagcagg ccgcgggccc ggcgtccgcg tggagcatgc    29100
ggagggatgg ctgcacgacc gtggtgccgt ttgccgggac ggtgaccggg cgacggacga    29160
caatgtcgaa accggcatcc tcctcgcgtt ttggaaggaa ggcgatggct tctcgtacgc    29220
cgtccccgtg ttccgtctga accggcgtca gctcgccggc atagacgagg gaccgccctc    29280
ggcgtcgcgc cggtagggcc gtagtcacgc ttggggcccc gagcgccccc tccaaccaag    29340
gatcttcgcg tatcccggcc ccggttggag ggggggcgc cagttgcggg aactgccgca    29400
gggaaatcgg ctcggtgagg gccgggggg tcgccaggat gtccaggaac gtcacgtcga    29460
cccgcagggt cccgggggca aattcccgcg tccttttagg cgctacgacc acggccataa    29520
cggttccgcg gtaccccgag tcgataagac ccagtattac gtggtgcccg ggctggcta    29580 gcgcgggggc gtgaataatc gcgcaaaagt cagccggcat agccattcgc aggtccagag    29640
agacgcgccc gacggcccat ccggagtccc cgctaacctt cggcataaaa gccaccgcgc    29700
gcctgttgac caggttcagt tgcacgactc cgccccgcg agtagcgacg gccgtgtgcc    29760
agtcgccatc gtaccccga cccaagctgt ccggctggac aaggatcgcc ccggatcccc    29820
actgactcat cttcctgtta gggacgatgg gccccccag aagggtctgt cgggcgggcc    29880
tgttgtttgt cttgctcgtc gccttagcgg cgggagacgc gggcccgcgc ggggagccgc    29940
ccggcgagga gggcgggcgc gatgggatcg ggggcgcgcg gtgcgagacc caaaacactg    30000
gccaaatgtc tgccccgggg gccctggtgc ccttttatgt aggcatggcc tcgatgggcg    30060
tgtgtattat cgcacacgtc tgtcagatct gccagaggct actggctgcc gggcacgcct    30120
gaacccgccc tgtgtggggt gagggtggg ggtggagggt gtcccaggac ttccccttcc    30180
tcgcggaaac cgagaccgtt tggggcgtgt ctgtttcttg gccctggggg attggttaga    30240 cccatggggtt gtggttatat gcacttccta taagactctc ccccaccgcc cacagagggc    30300
```

```
cactcacgca tccccagtgg gttttgcgga ccctctcttc tctcccgggc cgccctatc   30360 gctcgacctc tccacacctg caccaccccc gccgtccgaa cccaggccta attgtccgcg   30420
catccgaccc tagcgtgttc gtggaaccat gacctctcgc cgctccgtga agtcgggtcc   30480
gcgggaggtt ccgcgcgatg agtacgagga tctgtactac accccgtctt caggtatggc   30540
gagtcccgat agtccgcctg acacctcccg ccgtggcgcc ctacagacac gctcgcgcca   30600
gaggggcgag gtccgtttcg tccagtacga cgagtcggat tatgccctct acggggctc    30660 gtcatccgaa gacgacgaac acccggaggt ccccggacg cggcgtcccg tttccggggc     30720
ggttttgtcc ggcccgggc ctgcgcgggc gcctccgcca cccgctgggt ccggagggc      30780 cggacgcaca cccaccaccg ccccccgggc cccccgaacc cagcgggtgg cgactaaggc   30840
ccccgcggcc ccgcggcgg agaccacccg cggcaggaaa tcggcccagc cagaatccgc    30900
cgcactccca gacgccccg cgtcgacggc gccaacccga tccaagacac ccgcgcaggg     30960
gctggccaga aagctgcact ttagcaccgc ccccccaaac cccgacgcgc catggacccc   31020
ccgggtggcc ggctttaaca agcgcgtctt ctgcgccgcg gtcgggcgcc tggcggccat   31080
gcatgcccgg atggcggcgg tccagctctg ggacatgtcg cgtccgcgca cagacgaaga   31140
cctcaacgaa ctccttggca tcaccaccat ccgcgtgacg gtctgcgagg gcaaaaacct   31200
gcttcagcgc gccaacgagt tggtgaatcc agacgtggtg caggacgtcg acgcggccac   31260
ggcgactcga gggcgttctg cggcgtcgcg ccccaccgag cgacctcgag ccccagcccg   31320
ctccgcttct cgccccagac ggcccgtcga gtgaaaactt ccgtacccag acaataaagc   31380
accaacaggg gttcattcgg tgttggcgtt gcgtgccttt gtttcccaat ccgacgggga   31440 ccggactgg gtggcggggg gtgggttgga cagccgccct cggttcgcct tcacgtgaca    31500
ggagccaatg tgggggaag tcacgaggta cggggcggcc cgtgcgggtt gcttaaatgc    31560
gtggtggcga ccacgggctg tcattcctcg ggaacggacg gggttccgc tgcccacttc    31620 cccccataag gtccgtccgg tcctctaacg cgtttggggg ttttctcttc ccgcgccgtc   31680
gggcgtccca cactctctgg gcgggcgggg acgatcgcat caaaagcccg atatcgtctt   31740
tcccgtatca accccaccca atggacctct tggtcgacga gctgtttgcc gacatgaacg    31800
cggacggcgc ttcgccaccg ccccccgcc cggccggggg tcccaaaaac acccggcgg    31860 cccccccgct gtacgcaacg gggcgcctga gccaggccca gctcatgccc tccccaccca   31920
tgcccgtccc ccccgccgcc ctctttaacc gtctcctcga cgacttgggc tttagcgcgg   31980
gccccgcgct atgtaccatg ctcgatacct ggaacgagga tctgtttttcg gcgctaccga   32040 ccaacgccga cctgtaccgg gagtgtaaat cctatcaac gctgcccagc gatgtggtgg    32100 aatggggga cgcgtacgtc cccgaacgca cccaaatcga cattcgcgcc cacggcgacg   32160
tggccttccc tacgcttccg gccacccgcg acggcctcgg gctctactac gaagcgctct   32220
ctcgtttctt ccacgccgag ctacgggcgc gggaggagag ctatcgaacc gtgttggcca   32280
acttctgctc ggccctgtac cggtacctgc gcgccagcgt ccggcagctg caccgccagg   32340
cgcacatgcg cggacgcgat cgcgacctgg gagaaatgct gcgcgccacg atcgcggaca   32400
ggtactaccg agagaccgct cgtctggcgc gtgttttgtt tttgcatttg tatctatttt   32460
tgacccgcga gatcctatgg gccgcgtacg ccgagcagat gatgcggccc gacctgtttg   32520
actgcctctg ttgcgacctg gagagctggc gtcagttggc gggtctgttc cagcccttca   32580
tgttcgtcaa cggagcgctc accgtccggg gagtgccaat cgaggccgc cggctgcggg    32640
```

```
agctaaacca cattcgcgag caccttaacc tcccgctggt gcgcagcgcg gctacggagg    32700
agccaggggc gccgttgacg accccuccca ccctgcatgg caaccaggcc cgcgcctctg    32760
ggtactt                                                              32767
```

```
<210> SEQ ID NO 2
<211> LENGTH: 718
<212> TYPE: PRT
<213> ORGANISM: Artificial Sequence
<220> FEATURE:
<223> OTHER INFORMATION: Synthetic

<400> SEQUENCE: 2
```

```
Met Gln Arg Arg Thr Arg Gly Ala Ser Ser Leu Arg Leu Ala Arg Cys
1               5                   10                  15

Leu Thr Pro Ala Asn Leu Ile Arg Gly Asp Asn Ala Gly Val Pro Glu
            20                  25                  30

Arg Arg Ile Phe Gly Gly Cys Leu Leu Pro Thr Pro Glu Gly Leu Leu
        35                  40                  45

Ser Ala Ala Val Gly Ala Leu Arg Gln Arg Ser Asp Asp Ala Gln Pro
    50                  55                  60

Ala Phe Leu Thr Cys Thr Asp Arg Ser Val Arg Leu Ala Ala Arg Gln
65                  70                  75                  80

His Asn Thr Val Pro Glu Ser Leu Ile Val Asp Gly Leu Ala Ser Asp
                85                  90                  95

Pro His Tyr Glu Tyr Ile Arg His Tyr Ala Ser Ala Ala Thr Gln Ala
            100                 105                 110

Leu Gly Glu Val Glu Leu Pro Gly Gly Gln Leu Ser Arg Ala Ile Leu
        115                 120                 125

Thr Gln Tyr Trp Lys Tyr Leu Gln Thr Val Val Pro Ser Gly Leu Asp
    130                 135                 140

Val Pro Glu Asp Pro Val Gly Asp Cys Asp Pro Ser Leu His Val Leu
145                 150                 155                 160

Leu Arg Pro Thr Leu Ala Pro Lys Leu Leu Ala Arg Thr Pro Phe Lys
                165                 170                 175

Ser Gly Ala Val Ala Ala Lys Tyr Ala Ala Thr Val Ala Gly Leu Arg
            180                 185                 190

Asp Ala Leu His Arg Ile Gln Gln Tyr Met Phe Phe Met Arg Pro Ala
        195                 200                 205

Asp Pro Ser Arg Pro Ser Thr Asp Thr Ala Leu Arg Leu Asn Glu Leu
    210                 215                 220

Leu Ala Tyr Val Ser Val Leu Tyr Arg Trp Ala Ser Trp Met Leu Trp
225                 230                 235                 240

Thr Thr Asp Lys His Val Cys His Arg Leu Ser Pro Ser Asn Arg Arg
                245                 250                 255

Phe Leu Pro Leu Gly Gly Ser Pro Glu Ala Pro Ala Glu Thr Phe Ala
            260                 265                 270

Arg His Leu Asp Arg Gly Pro Ser Gly Thr Thr Gly Ser Met Gln Cys
        275                 280                 285

Met Ala Leu Arg Ala Ala Val Ser Asp Val Leu Gly His Leu Thr Arg
    290                 295                 300

Leu Ala Asn Leu Trp Gln Thr Gly Lys Arg Ser Gly Gly Thr Tyr Gly
305                 310                 315                 320

Thr Val Asp Thr Val Val Ser Thr Val Glu Val Leu Ser Ile Val His
                325                 330                 335
```

His His Ala Gln Tyr Ile Ile Asn Ala Thr Leu Thr Gly Tyr Gly Val
             340                 345                 350

Trp Ala Thr Asp Ser Leu Asn Asn Glu Tyr Leu Arg Ala Ala Val Asp
         355                 360                 365

Ser Gln Glu Arg Phe Cys Arg Thr Thr Ala Pro Leu Phe Pro Thr Met
     370                 375                 380

Thr Ala Pro Ser Trp Ala Arg Met Glu Leu Ser Ile Lys Ala Trp Phe
385                 390                 395                 400

Gly Ala Ala Leu Ala Asp Leu Leu Arg Asn Gly Ala Pro Ser Leu
             405                 410                 415

His Tyr Glu Ser Ile Leu Arg Leu Val Ala Ser Arg Thr Thr Trp
             420                 425                 430

Ser Ala Gly Pro Pro Asp Asp Met Ala Ser Gly Pro Gly Gly His
             435                 440                 445

Arg Ala Gly Gly Gly Thr Cys Arg Glu Lys Ile Gln Arg Ala Arg Arg
         450                 455                 460

Asp Asn Glu Pro Pro Pro Leu Pro Arg Pro Arg Leu His Ser Thr Pro
465                 470                 475                 480

Ala Ser Thr Arg Arg Phe Arg Arg Arg Ala Asp Gly Ala Gly Pro
             485                 490                 495

Pro Leu Pro Asp Ala Asn Asp Pro Val Ala Glu Pro Ala Ala Ala
             500                 505                 510

Thr Gln Pro Ala Thr Tyr Tyr Thr His Met Gly Glu Val Pro Pro Arg
         515                 520                 525

Leu Pro Ala Arg Asn Val Ala Gly Pro Asp Arg Arg Pro Pro Ala Ala
         530                 535                 540

Thr Cys Pro Leu Leu Val Arg Arg Ala Ser Leu Gly Ser Leu Asp Arg
545                 550                 555                 560

Pro Arg Val Trp Gly Pro Ala Pro Glu Gly Glu Pro Asp Gln Met Glu
             565                 570                 575

Ala Thr Tyr Leu Thr Ala Asp Asp Asp Asp Ala Arg Arg Lys
             580                 585                 590

Ala Thr His Ala Ala Ser Ala Arg Glu Arg His Ala Pro Tyr Glu Asp
             595                 600                 605

Asp Glu Ser Ile Tyr Glu Thr Val Ser Glu Asp Gly Gly Arg Val Tyr
             610                 615                 620

Glu Glu Ile Pro Trp Met Arg Val Tyr Glu Asn Val Cys Val Asn Thr
625                 630                 635                 640

Ala Asn Ala Ala Pro Ala Ser Pro Tyr Ile Glu Ala Glu Asn Pro Leu
             645                 650                 655

Tyr Asp Trp Gly Gly Ser Ala Leu Phe Ser Pro Pro Gly Arg Thr Gly
             660                 665                 670

Pro Pro Pro Pro Leu Ser Pro Ser Pro Val Leu Ala Arg His Arg
             675                 680                 685

Ala Asn Ala Leu Thr Asn Asp Gly Pro Thr Asn Val Ala Ala Leu Ser
             690                 695                 700

Ala Leu Leu Thr Lys Leu Lys Arg Glu Gly Arg Arg Ser Arg
705                 710                 715

<210> SEQ ID NO 3
<211> LENGTH: 422
<212> TYPE: PRT
<213> ORGANISM: Artificial Sequence
<220> FEATURE:
<223> OTHER INFORMATION: Synthetic

<400> SEQUENCE: 3

Met Gln Arg Arg Thr Arg Gly Ala Ser Ser Leu Arg Leu Ala Arg Cys
1               5                   10                  15

Leu Thr Pro Ala Asn Leu Ile Arg Gly Asp Asn Ala Gly Val Pro Glu
            20                  25                  30

Arg Arg Ile Phe Gly Gly Cys Leu Leu Pro Thr Pro Glu Gly Leu Leu
        35                  40                  45

Ser Ala Ala Val Gly Ala Leu Arg Gln Arg Ser Asp Asp Ala Gln Pro
    50                  55                  60

Ala Phe Leu Thr Cys Thr Asp Arg Ser Val Arg Leu Ala Ala Arg Gln
65                  70                  75                  80

His Asn Thr Val Pro Glu Ser Leu Ile Val Asp Gly Leu Ala Ser Asp
                85                  90                  95

Pro His Tyr Glu Tyr Ile Arg His Tyr Ala Ser Ala Ala Thr Gln Ala
            100                 105                 110

Leu Gly Glu Val Glu Leu Pro Gly Gly Gln Leu Ser Arg Ala Ile Leu
        115                 120                 125

Thr Gln Tyr Trp Lys Tyr Leu Gln Thr Val Val Pro Ser Gly Leu Asp
130                 135                 140

Val Pro Glu Asp Pro Val Gly Asp Cys Asp Pro Ser Leu His Val Leu
145                 150                 155                 160

Leu Arg Pro Thr Leu Ala Pro Lys Leu Leu Ala Arg Thr Pro Phe Lys
                165                 170                 175

Ser Gly Ala Val Ala Ala Lys Tyr Ala Ala Thr Val Ala Gly Leu Arg
            180                 185                 190

Asp Ala Leu His Arg Ile Gln Gln Tyr Met Phe Phe Met Arg Pro Ala
        195                 200                 205

Asp Pro Ser Arg Pro Ser Thr Asp Thr Ala Leu Arg Leu Asn Glu Leu
210                 215                 220

Leu Ala Tyr Val Ser Val Leu Tyr Arg Trp Ala Ser Trp Met Leu Trp
225                 230                 235                 240

Thr Thr Asp Lys His Val Cys His Arg Leu Ser Pro Ser Asn Arg Arg
                245                 250                 255

Phe Leu Pro Leu Gly Gly Ser Pro Glu Ala Pro Ala Glu Thr Phe Ala
            260                 265                 270

Arg His Leu Asp Arg Gly Pro Ser Gly Thr Thr Gly Ser Met Gln Cys
        275                 280                 285

Met Ala Leu Arg Ala Ala Val Ser Asp Val Leu Gly His Leu Thr Arg
290                 295                 300

Leu Ala Asn Leu Trp Gln Thr Gly Lys Arg Ser Gly Gly Thr Tyr Gly
305                 310                 315                 320

Thr Val Asp Thr Val Val Ser Thr Val Glu Val Leu Ser Ile Val His
                325                 330                 335

His His Ala Gln Tyr Ile Ile Asn Ala Thr Leu Thr Gly Tyr Gly Val
            340                 345                 350

Trp Ala Thr Asp Ser Leu Asn Asn Glu Tyr Leu Arg Ala Ala Val Asp
        355                 360                 365

Ser Gln Glu Arg Phe Cys Arg Thr Thr Ala Pro Leu Phe Pro Thr Met
370                 375                 380

Thr Ala Pro Ser Trp Ala Arg Met Glu Leu Ser Ile Lys Ala Trp Phe
385                 390                 395                 400

Gly Ala Ala Leu Ala Ala Asp Leu Leu Arg Asn Gly Ala Pro Ser Leu

His Tyr Glu Ser Ile Leu
        420

<210> SEQ ID NO 4
<211> LENGTH: 70
<212> TYPE: DNA
<213> ORGANISM: Artificial Sequence
<220> FEATURE:
<223> OTHER INFORMATION: Synthetic

<400> SEQUENCE: 4
ctaaatcagg tcgttgtcgt ttattgcgtc ttcgggtttc gcaagcgccc ctcacgttaa     60
gggattttgg     70

<210> SEQ ID NO 5
<211> LENGTH: 70
<212> TYPE: DNA
<213> ORGANISM: Artificial Sequence
<220> FEATURE:
<223> OTHER INFORMATION: Synthetic

<400> SEQUENCE: 5
cctcttcgtc ctcgtcgtcc gacgaggacg aggacgacga cggcaacgac taaatacgga     60
aggatctgag     70

<210> SEQ ID NO 6
<211> LENGTH: 70
<212> TYPE: DNA
<213> ORGANISM: Artificial Sequence
<220> FEATURE:
<223> OTHER INFORMATION: Synthetic

<400> SEQUENCE: 6
gcacatgctt gcctgtcaaa ctctaccacc ccggcacgct ctctgtctcc ctcacgttaa     60
gggattttgg     70

<210> SEQ ID NO 7
<211> LENGTH: 70
<212> TYPE: DNA
<213> ORGANISM: Artificial Sequence
<220> FEATURE:
<223> OTHER INFORMATION: Synthetic

<400> SEQUENCE: 7
cggtgtggtt caacaaagac gccgcgtttc caggtaggtt agacacctgc taaatacgga     60
aggatctgag     70

<210> SEQ ID NO 8
<211> LENGTH: 70
<212> TYPE: DNA
<213> ORGANISM: Artificial Sequence
<220> FEATURE:
<223> OTHER INFORMATION: Synthetic

<400> SEQUENCE: 8
gattttggtc ttttatttgg ggacatacaa gggggtcggg gcgaccggac ctcacgttaa     60
gggattttgg     70

<210> SEQ ID NO 9
<211> LENGTH: 70
<212> TYPE: DNA

```
<213> ORGANISM: Artificial Sequence
<220> FEATURE:
<223> OTHER INFORMATION: Synthetic

<400> SEQUENCE: 9
catttcaaac aaatcgcccc acgtgttgtc cttctttgct catggccggc taaatacgga      60
aggatctgag                                                            70

<210> SEQ ID NO 10
<211> LENGTH: 70
<212> TYPE: DNA
<213> ORGANISM: Artificial Sequence
<220> FEATURE:
<223> OTHER INFORMATION: Synthetic

<400> SEQUENCE: 10
cgtttattgc gtcttcgggt ttcgcaagcg ccccgccccg tcccggcccg ctcacgttaa      60
gggattttgg                                                            70

<210> SEQ ID NO 11
<211> LENGTH: 70
<212> TYPE: DNA
<213> ORGANISM: Artificial Sequence
<220> FEATURE:
<223> OTHER INFORMATION: Synthetic

<400> SEQUENCE: 11
gcgcacgttt gcagcgcaca tgcgagacac ctcgaccacg gttcggaaga taaatacgga      60
aggatctgag                                                            70

<210> SEQ ID NO 12
<211> LENGTH: 70
<212> TYPE: DNA
<213> ORGANISM: Artificial Sequence
<220> FEATURE:
<223> OTHER INFORMATION: Synthetic

<400> SEQUENCE: 12
gcgcctccac cgagataacg tcatgctggc ctcgggggcc gagtaaccgc ctcacgttaa      60
gggattttgg                                                            70

<210> SEQ ID NO 13
<211> LENGTH: 70
<212> TYPE: DNA
<213> ORGANISM: Artificial Sequence
<220> FEATURE:
<223> OTHER INFORMATION: Synthetic

<400> SEQUENCE: 13
gacactgaaa tgccaccccc cctgcgggcg gtccattaaa gacaacaaac taaatacgga      60
aggatctgag                                                            70

<210> SEQ ID NO 14
<211> LENGTH: 70
<212> TYPE: DNA
<213> ORGANISM: Artificial Sequence
<220> FEATURE:
<223> OTHER INFORMATION: Synthetic

<400> SEQUENCE: 14 ccccacccctc gggttcgtgt atttcctttc cctgtcctta taaagccgt ctcacgttaa      60 gggattttgg                                                            70
```

<210> SEQ ID NO 15
<211> LENGTH: 70
<212> TYPE: DNA
<213> ORGANISM: Artificial Sequence
<220> FEATURE:
<223> OTHER INFORMATION: Synthetic

<400> SEQUENCE: 15
gacatccgat aacccgcgtc tatcgccacc atgtcggctc gcgaacccgc taaatacgga    60
aggatctgag                                                          70

<210> SEQ ID NO 16
<211> LENGTH: 70
<212> TYPE: DNA
<213> ORGANISM: Artificial Sequence
<220> FEATURE:
<223> OTHER INFORMATION: Synthetic

<400> SEQUENCE: 16
gcacatgctt gcctgtcaaa ctctaccacc ccggcacgct ctctgtctcc ctcacgttaa    60
gggattttgg                                                          70

<210> SEQ ID NO 17
<211> LENGTH: 70
<212> TYPE: DNA
<213> ORGANISM: Artificial Sequence
<220> FEATURE:
<223> OTHER INFORMATION: Synthetic

<400> SEQUENCE: 17
ctgttggtga ttatcgactg tcgcgccgaa ttttgtgcct accgctttat taaatacgga    60
aggatctgag                                                          70

<210> SEQ ID NO 18
<211> LENGTH: 70
<212> TYPE: DNA
<213> ORGANISM: Artificial Sequence
<220> FEATURE:
<223> OTHER INFORMATION: Synthetic

<400> SEQUENCE: 18
cgccccaagg gggcggggcc gccgggtaaa agaagtgaga acgcgaagcg ctcacgttaa    60
gggattttgg                                                          70

<210> SEQ ID NO 19
<211> LENGTH: 70
<212> TYPE: DNA
<213> ORGANISM: Artificial Sequence
<220> FEATURE:
<223> OTHER INFORMATION: Synthetic

<400> SEQUENCE: 19
ggcatcggag atttcatcat cgcttgtcgc gctgagatga atctcgagat taaatacgga    60
aggatctgag                                                          70

<210> SEQ ID NO 20
<211> LENGTH: 70
<212> TYPE: DNA
<213> ORGANISM: Artificial Sequence
<220> FEATURE:
<223> OTHER INFORMATION: Synthetic -continued

<400> SEQUENCE: 20
ccggcggcga ccgttgcgtg gaccgcttcc tgctcgtcgg gcgggggagc ctcacgttaa    60
gggattttgg    70

<210> SEQ ID NO 21
<211> LENGTH: 70
<212> TYPE: DNA
<213> ORGANISM: Artificial Sequence
<220> FEATURE:
<223> OTHER INFORMATION: Synthetic

<400> SEQUENCE: 21
ccgcccagaa acttgggcga tggtcgtacc cgggactcaa cgggttaccg taaatacgga    60
aggatctgag    70

<210> SEQ ID NO 22
<211> LENGTH: 70
<212> TYPE: DNA
<213> ORGANISM: Artificial Sequence
<220> FEATURE:
<223> OTHER INFORMATION: Synthetic

<400> SEQUENCE: 22
tgctcgtcgg gcgggggaa gccactgtgg tcctccggga cgttttctgg ctcacgttaa    60
gggattttgg    70

<210> SEQ ID NO 23
<211> LENGTH: 70
<212> TYPE: DNA
<213> ORGANISM: Artificial Sequence
<220> FEATURE:
<223> OTHER INFORMATION: Synthetic

<400> SEQUENCE: 23
cggccgcccg ggcccacggg cgccgtccca accgcacagt cccaggtaac ctcacgttaa    60
gggattttgg    70

<210> SEQ ID NO 24
<211> LENGTH: 70
<212> TYPE: DNA
<213> ORGANISM: Artificial Sequence
<220> FEATURE:
<223> OTHER INFORMATION: Synthetic

<400> SEQUENCE: 24
ggttggtcaa aaagggagg acgggggcc ggcagaccga cggcgacaac taaatacgga    60
aggatctgag    70

<210> SEQ ID NO 25
<211> LENGTH: 70
<212> TYPE: DNA
<213> ORGANISM: Artificial Sequence
<220> FEATURE:
<223> OTHER INFORMATION: Synthetic

<400> SEQUENCE: 25
gcgcctccac cgagataacg tcatgctggc ctcggggggcc gagtaaccgc ctcacgttaa    60
gggattttgg    70

<210> SEQ ID NO 26
<211> LENGTH: 70

```
<212> TYPE: DNA
<213> ORGANISM: Artificial Sequence
<220> FEATURE:
<223> OTHER INFORMATION: Synthetic

<400> SEQUENCE: 26
gacactgaaa tgccaccccc cctgcgggcg gtccattaaa gacaacaaac taaatacgga    60
aggatctgag                                                          70

<210> SEQ ID NO 27
<211> LENGTH: 70
<212> TYPE: DNA
<213> ORGANISM: Artificial Sequence
<220> FEATURE:
<223> OTHER INFORMATION: Synthetic

<400> SEQUENCE: 27
ttattgcgtc ttcgggtttc gcaagcgccc cgccccgtcc cggcccgtta ctcacgttaa    60
gggattttgg                                                          70

<210> SEQ ID NO 28
<211> LENGTH: 70
<212> TYPE: DNA
<213> ORGANISM: Artificial Sequence
<220> FEATURE:
<223> OTHER INFORMATION: Synthetic

<400> SEQUENCE: 28
ggccacgggc ccccggcgtg ccggcgtcgg ggcggggtcg tgcataatgg ctcacgttaa    60
gggattttgg                                                          70

<210> SEQ ID NO 29
<211> LENGTH: 70
<212> TYPE: DNA
<213> ORGANISM: Artificial Sequence
<220> FEATURE:
<223> OTHER INFORMATION: Synthetic

<400> SEQUENCE: 29
ttataacccc gggggtcatt cccaacgatc acatgcaatc taactggctc taaatacgga    60
aggatctgag                                                          70

<210> SEQ ID NO 30
<211> LENGTH: 68
<212> TYPE: DNA
<213> ORGANISM: Artificial Sequence
<220> FEATURE:
<223> OTHER INFORMATION: Synthetic

<400> SEQUENCE: 30
ccggcggcga ccgttgcgtg gaccgcttcc tgctcgtcgg gcgggggagc atgagccaga    60
cccaaccc                                                            68

<210> SEQ ID NO 31
<211> LENGTH: 70
<212> TYPE: DNA
<213> ORGANISM: Artificial Sequence
<220> FEATURE:
<223> OTHER INFORMATION: Synthetic

<400> SEQUENCE: 31
ttattgcgtc ttcgggtctc acaagcgccc cgccccgtcc cggcccgtta ctcacgttaa    60
```
gggattttgg     70

<210> SEQ ID NO 32
<211> LENGTH: 69
<212> TYPE: DNA
<213> ORGANISM: Artificial Sequence
<220> FEATURE:
<223> OTHER INFORMATION: Synthetic

<400> SEQUENCE: 32
ggcccgggcg gccgggggcg gcggggccg cgatggcggc ggcggcgggc cttgttctcc     60
gacgccatc     69

<210> SEQ ID NO 33
<211> LENGTH: 70
<212> TYPE: DNA
<213> ORGANISM: Artificial Sequence
<220> FEATURE:
<223> OTHER INFORMATION: Synthetic

<400> SEQUENCE: 33
ttattgcgtc ttcgggtttc acaagcgccc cgccccgtcc cggcccgtta ctcacgttaa     60
gggattttgg     70

<210> SEQ ID NO 34
<211> LENGTH: 69
<212> TYPE: DNA
<213> ORGANISM: Artificial Sequence
<220> FEATURE:
<223> OTHER INFORMATION: Synthetic

<400> SEQUENCE: 34
gtgggcccgg gcggccgggg gcggcggggg ccgcgatggc ggcggcgggc cttgttctcc     60
gacgccatc     69

<210> SEQ ID NO 35
<211> LENGTH: 70
<212> TYPE: DNA
<213> ORGANISM: Artificial Sequence
<220> FEATURE:
<223> OTHER INFORMATION: Synthetic

<400> SEQUENCE: 35
cggccgcccg ggcccacggg cgcggtccca accgcacagt cccaggtaac ctcacgttaa     60
gggattttgg     70

<210> SEQ ID NO 36
<211> LENGTH: 70
<212> TYPE: DNA
<213> ORGANISM: Artificial Sequence
<220> FEATURE:
<223> OTHER INFORMATION: Synthetic

<400> SEQUENCE: 36
tttataaccc cggggtcatt cccaacgatc acatgcaatc taactggctc taaatacgga     60
aggatctgag     70

<210> SEQ ID NO 37
<211> LENGTH: 70
<212> TYPE: DNA
<213> ORGANISM: Artificial Sequence
<220> FEATURE:
<223> OTHER INFORMATION: Synthetic

<400> SEQUENCE: 37
gtggtgtgca gccgtgttcc aaccacggtc acgcttcggt gcctctcccc taaatacgga    60
aggatctgag                                                          70

<210> SEQ ID NO 38
<211> LENGTH: 70
<212> TYPE: DNA
<213> ORGANISM: Artificial Sequence
<220> FEATURE:
<223> OTHER INFORMATION: Synthetic

<400> SEQUENCE: 38
ccagacaata aagcaccaac aggggttcat tcggtgttgg cgttgcgtgc taaatacgga    60
aggatctgag                                                          70

<210> SEQ ID NO 39
<211> LENGTH: 70
<212> TYPE: DNA
<213> ORGANISM: Artificial Sequence
<220> FEATURE:
<223> OTHER INFORMATION: Synthetic

<400> SEQUENCE: 39
cacggcggtt ctggccgcct cccggtcctc acgcccccctt ttattgatct ctcacgttaa   60
gggattttgg                                                          70

<210> SEQ ID NO 40
<211> LENGTH: 68
<212> TYPE: DNA
<213> ORGANISM: Artificial Sequence
<220> FEATURE:
<223> OTHER INFORMATION: Synthetic

<400> SEQUENCE: 40
ccggcggcga ccgttgcgtg gaccgcttcc tgctcgtcgg ggggaaaagc atgagccaga    60
cccaaccc                                                            68

<210> SEQ ID NO 41
<211> LENGTH: 70
<212> TYPE: DNA
<213> ORGANISM: Artificial Sequence
<220> FEATURE:
<223> OTHER INFORMATION: Synthetic

<400> SEQUENCE: 41
ccgcccagag actcgggtga tggtcgtacc cgggactcaa cgggttaccg taaatacgga    60
aggatctgag                                                          70

<210> SEQ ID NO 42
<211> LENGTH: 70
<212> TYPE: DNA
<213> ORGANISM: Artificial Sequence
<220> FEATURE:
<223> OTHER INFORMATION: Synthetic

<400> SEQUENCE: 42
ctacgtccgc cgtcgcagcc gtatcccgg aggatcgccc cgcatcggcg ctcacgttaa     60
gggattttgg                                                          70

<210> SEQ ID NO 43

```
<211> LENGTH: 70
<212> TYPE: DNA
<213> ORGANISM: Artificial Sequence
<220> FEATURE:
<223> OTHER INFORMATION: Synthetic

<400> SEQUENCE: 43
ccacatataa gcccccagcc acacgcaaga acagacacgc agaacggctg taaatacgga     60
aggatctgag                                                           70

<210> SEQ ID NO 44
<211> LENGTH: 70
<212> TYPE: DNA
<213> ORGANISM: Artificial Sequence
<220> FEATURE:
<223> OTHER INFORMATION: Synthetic

<400> SEQUENCE: 44
cgcggactcg ggaacgtgga gccactggcg cagcagcagc gaacaagaag ctcacgttaa     60
gggattttgg                                                           70

<210> SEQ ID NO 45
<211> LENGTH: 54
<212> TYPE: DNA
<213> ORGANISM: Artificial Sequence
<220> FEATURE:
<223> OTHER INFORMATION: Synthetic

<400> SEQUENCE: 45
ttcattacat ctgtgtgttg gttttttgtg tggtagtgcc ccaactgggg taac           54

<210> SEQ ID NO 46
<211> LENGTH: 52
<212> TYPE: DNA
<213> ORGANISM: Artificial Sequence
<220> FEATURE:
<223> OTHER INFORMATION: Synthetic

<400> SEQUENCE: 46
cacagatgta atgaaaataa agatatttta ttccaaaatc ccttaacgtg ag             52

<210> SEQ ID NO 47
<211> LENGTH: 70
<212> TYPE: DNA
<213> ORGANISM: Artificial Sequence
<220> FEATURE:
<223> OTHER INFORMATION: Synthetic

<400> SEQUENCE: 47
tggaccgctt cctgctcgtc gggggggaaaa gcatgagcca gacccaaccc ctcacgttaa    60
gggattttgg                                                           70

<210> SEQ ID NO 48
<211> LENGTH: 70
<212> TYPE: DNA
<213> ORGANISM: Artificial Sequence
<220> FEATURE:
<223> OTHER INFORMATION: Synthetic

<400> SEQUENCE: 48
gtacaaaata cgtgacgtag aaagtaataa tttcttgggt agtttgcagt taaatacgga     60
aggatctgag                                                           70
```

```
<210> SEQ ID NO 49
<211> LENGTH: 70
<212> TYPE: DNA
<213> ORGANISM: Artificial Sequence
<220> FEATURE:
<223> OTHER INFORMATION: Synthetic

<400> SEQUENCE: 49
cggccggaga aacgtgtcgc tgcacggata ggggcaggcg gtggagaagc ctcacgttaa    60
gggattttgg                                                          70

<210> SEQ ID NO 50
<211> LENGTH: 70
<212> TYPE: DNA
<213> ORGANISM: Artificial Sequence
<220> FEATURE:
<223> OTHER INFORMATION: Synthetic

<400> SEQUENCE: 50
cccaagggcc gcccgccgtc ccgttggtcc cggcgtccgg cgggcgggac ctcacgttaa    60
gggattttgg                                                          70

<210> SEQ ID NO 51
<211> LENGTH: 70
<212> TYPE: DNA
<213> ORGANISM: Artificial Sequence
<220> FEATURE:
<223> OTHER INFORMATION: Synthetic

<400> SEQUENCE: 51
ccacccagcg cccgaccccc ccctccccac aaacacgggg gcgtccctta ttaaatttta    60
atagcagttg                                                          70

<210> SEQ ID NO 52
<211> LENGTH: 70
<212> TYPE: DNA
<213> ORGANISM: Artificial Sequence
<220> FEATURE:
<223> OTHER INFORMATION: Synthetic

<400> SEQUENCE: 52
cggccgcccg ggcccacggg cgcggtccca accgcacagt cccaggtaac gttcgtggta    60
actatgggtg                                                          70

<210> SEQ ID NO 53
<211> LENGTH: 70
<212> TYPE: DNA
<213> ORGANISM: Artificial Sequence
<220> FEATURE:
<223> OTHER INFORMATION: Synthetic

<400> SEQUENCE: 53
ccacccagcg cccgaccccc ccctccccac aaacacgggg gcgtccctta taaatacgga    60
aggatctgag                                                          70

<210> SEQ ID NO 54
<211> LENGTH: 70
<212> TYPE: DNA
<213> ORGANISM: Artificial Sequence
<220> FEATURE:
<223> OTHER INFORMATION: Synthetic

<400> SEQUENCE: 54
```

-continued cgaccccag ggaccctccg tccgcgaccc tccagccgca tacgaccccc ctcacgttaa    60
gggattttgg                                                          70

<210> SEQ ID NO 55
<211> LENGTH: 70
<212> TYPE: DNA
<213> ORGANISM: Artificial Sequence
<220> FEATURE:
<223> OTHER INFORMATION: Synthetic

<400> SEQUENCE: 55
cacccagcgc ccgaccccc cctccccaca aacacggggg gcgtccctta taaatacgga    60
aggatctgag                                                          70

<210> SEQ ID NO 56
<211> LENGTH: 70
<212> TYPE: DNA
<213> ORGANISM: Artificial Sequence
<220> FEATURE:
<223> OTHER INFORMATION: Synthetic

<400> SEQUENCE: 56 cgaccccag ggaccctccg tcagcgaccc tccagccgca tacgaccccc ctcacgttaa    60
gggattttgg                                                          70

<210> SEQ ID NO 57
<211> LENGTH: 200
<212> TYPE: DNA
<213> ORGANISM: Artificial Sequence
<220> FEATURE:
<223> OTHER INFORMATION: Synthetic

<400> SEQUENCE: 57
gactagcgag ttagacaggc aagcactact cgcctctgca cgcacatgct tgcctgtcaa    60
actctaccac cccggcacgc tctctgtctc catggcccgc cgccgccgcc atcgcggccc   120
ccgccgcccc cggccgcccg ggcccacggg cgccgtccca accgcacagt cccaggtaac   180
ctcacgttaa gggattttgg                                               200

<210> SEQ ID NO 58
<211> LENGTH: 200
<212> TYPE: DNA
<213> ORGANISM: Artificial Sequence
<220> FEATURE:
<223> OTHER INFORMATION: Synthetic

<400> SEQUENCE: 58
ggccaccgcc gcccacccac ccacctcggg atacccagcc ccggtccccc gttcccgggg    60
ggccgttatc tccagcgccc cgtccggcgc gccgcccccc gccgctaaac cccatcccgc   120
ccccgggacc ccacatataa gccccagcc acacgcaaga acagacacgc agaacggctg   180
taaatacgga aggatctgag                                               200